US008420607B2

(12) United States Patent
Carlson et al.

(10) Patent No.: US 8,420,607 B2

(45) Date of Patent: Apr. 16, 2013

(54) ANTHRAX CARBOHYDRATES, SYNTHESIS AND USES THEREOF

(75) Inventors: Russell W. Carlson, Athens, GA (US); Geert-Jan Boons, Athens, GA (US); Conrad Quinn, Lilburn, GA (US); Mahalakshmi Vasan, Athens, GA (US); Margreet A. Wolfert, Athens, GA (US); Therese Buskas, Athens, GA (US); Alex J. Harvey, legal representative, Athens, GA (US); Biswa Choudhury, Athens, GA (US); Elmar Kannenberg, Athens, GA (US); Christine Leoff, Athens, GA (US); Alok Mehta, Athens, GA (US); Elke Saile, Athens, GA (US); Jana Rauvolfova, Braselton, GA (US); Patricia Wilkins, Duluth, GA (US)

(73) Assignees: University of Georgia Research Foundation, Inc., Athens, GA (US); The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 623 days.

(21) Appl. No.: 12/317,693

(22) Filed: Dec. 24, 2008

(65) Prior Publication Data

US 2010/0233174 A9 Sep. 16, 2010

Related U.S. Application Data

(63) Continuation-in-part of application No. PCT/US2007/015196, filed on Jun. 29, 2007.

(60) Provisional application No. 60/817,929, filed on Jun. 30, 2006, provisional application No. 60/933,937, filed on Jun. 8, 2007, provisional application No. 61/056,204, filed on May 27, 2008, provisional application No. 61/132, 515, filed on Jun. 19, 2008.

(51) Int. Cl.

| | |
|---|---|
| ***A01N 43/04*** | (2006.01) |
| ***A61K 31/70*** | (2006.01) |
| ***A61K 39/02*** | (2006.01) |
| ***A61K 39/00*** | (2006.01) |
| ***A61K 39/38*** | (2006.01) |
| ***C07G 3/00*** | (2006.01) |
| ***C07G 11/00*** | (2006.01) |
| ***C07H 15/00*** | (2006.01) |
| ***C07H 17/00*** | (2006.01) |

(52) U.S. Cl.

USPC ......... 514/25; 424/234.1; 424/184.1; 536/4.1

(58) Field of Classification Search .................... 514/25; 424/234.1, 184.1; 536/4.1

See application file for complete search history.

(56) References Cited

U.S. PATENT DOCUMENTS

| | | | |
|---|---|---|---|
| 5,591,631 | A | 1/1997 | Leppla et al. |
| 5,677,274 | A | 10/1997 | Leppla et al. |
| 5,952,454 | A | 9/1999 | Kovac et al. |
| 6,323,339 | B1 | 11/2001 | Seeberger et al. |
| 6,426,421 | B1 | 7/2002 | Buchwald et al. |
| 6,573,245 | B1 | 6/2003 | Marciani |
| 6,579,725 | B1 | 6/2003 | Seeberger et al. |
| 6,592,872 | B1 | 7/2003 | Klimpel et al. |
| 6,693,178 | B2 | 2/2004 | Buchwald et al. |
| 6,828,110 | B2 | 12/2004 | Lee et al. |
| 6,846,917 | B2 | 1/2005 | Seeberger et al. |
| 6,913,756 | B1 | 7/2005 | Kearney |
| 6,916,474 | B2 | 7/2005 | Harvey et al. |
| 7,097,965 | B2 | 8/2006 | Klimpel et al. |
| 7,102,023 | B2 | 9/2006 | Buchwald et al. |
| 7,160,517 | B2 | 1/2007 | Seeberger et al. |
| 7,211,663 | B2 | 5/2007 | Seeberger |
| 7,329,513 | B2 | 2/2008 | Bhatnagar et al. |
| 7,329,738 | B1 | 2/2008 | Lee et al. |
| 7,446,182 | B1 | 11/2008 | Georgiou et al. |
| 2002/0048590 | A1 | 4/2002 | Klimpel et al. |
| 2002/0082386 | A1 | 6/2002 | Mangold et al. |
| 2002/0085964 | A1 | 7/2002 | Seeberger et al. |
| 2003/0004322 | A1 | 1/2003 | Seeberger et al. |
| 2003/0013862 | A1 | 1/2003 | Seeberger et al. |
| 2003/0181690 | A1 | 9/2003 | Buchwald et al. |
| 2003/0198651 | A1 | 10/2003 | Klimpel et al. |
| 2003/0232452 | A1 | 12/2003 | Seeberger et al. |
| 2004/0014715 | A1 | 1/2004 | Ostroff |
| 2004/0033546 | A1 | 2/2004 | Wang |

(Continued)

FOREIGN PATENT DOCUMENTS

| | | | |
|---|---|---|---|
| EP | 1 706 417 | B1 | 5/2008 |
| WO | WO 03/040179 | A1 | 5/2003 |

(Continued)

OTHER PUBLICATIONS

Bhatacharjee et al. Bioconjugate Chem. 1990, 1,375-380.*

Sutton et al. Journal of Immunological Mehtods vol. 82, issue 2, 1985, pp. 215-224.*

Definition of Kit—Oxford Dictionaries Online. http://oxforddictionaries.com/search?q=kit&view=uk retrieved Dec. 11, 2010.*

Wong, C.-H., Haynie, S.L., Whitesides, G.M. (1982) Enzyme-Catalyzed Synthesis of N-Acetyllactosamine with in Situ Regeneration of uridine 5'-Diphosphate Glucose and Uridine 5'-Diphosphate Glucose and Uridine 5'-Diphosphate Galactose. The Journal of Organic Chemistry, vol. 74, p. 5416-5418.*

(Continued)

*Primary Examiner* — Scarlett Goon

(74) *Attorney, Agent, or Firm* — Mueting Raasch & Gebhardt, P.A.

(57) ABSTRACT

The present invention presents the isolation, characterization and synthesis of oligosaccharides of *Bacillus anthracis*. Also presented are antibodies that bind to such saccharide moieties and various methods of use for such saccharide moieties and antibodies.

14 Claims, 45 Drawing Sheets

U.S. PATENT DOCUMENTS

| | | | | |
|---|---|---|---|---|
| 2004/0115214 | A1* | 6/2004 | Gu et al. | 424/184.1 |
| 2004/0170967 | A1 | 9/2004 | Lee et al. | |
| 2004/0220389 | A1 | 11/2004 | Buchwald et al. | |
| 2005/0054038 | A1 | 3/2005 | Bhatnagar et al. | |
| 2005/0106647 | A1 | 5/2005 | Harvey et al. | |
| 2005/0107295 | A1 | 5/2005 | Arora et al. | |
| 2005/0187381 | A1 | 8/2005 | Seeberger et al. | |
| 2005/0221337 | A1 | 10/2005 | Seeberger et al. | |
| 2005/0267294 | A1 | 12/2005 | Harvey et al. | |
| 2005/0281830 | A1 | 12/2005 | Morrow et al. | |
| 2006/0127929 | A1 | 6/2006 | Swager et al. | |
| 2007/0264273 | A1 | 11/2007 | Barenholz et al. | |
| 2007/0265441 | A1 | 11/2007 | Seeberger et al. | |
| 2008/0020410 | A1 | 1/2008 | Lee et al. | |
| 2008/0262204 | A1 | 10/2008 | Georgiou et al. | |
| 2009/0004218 | A1 | 1/2009 | Hacohen et al. | |
| 2009/0010928 | A1 | 1/2009 | Casey | |
| 2009/0155299 | A1 | 6/2009 | Werz et al. | |

FOREIGN PATENT DOCUMENTS

| | | | |
|---|---|---|---|
| WO | WO 2005/007804 | A2 | 1/2005 |
| WO | WO 2005/012339 | A2 | 2/2005 |
| WO | WO 2005/048918 | A2 | 6/2005 |
| WO | WO 2005/056588 | A1 | 6/2005 |
| WO | WO 2005/012339 | A3 | 7/2005 |
| WO | WO 2005/007804 | A3 | 9/2005 |
| WO | WO 2006/055925 | A2 | 5/2006 |
| WO | WO 2006/068758 | A2 * | 6/2006 |
| WO | WO 2006/055925 | A3 | 11/2006 |
| WO | WO 2007/044607 | A2 | 4/2007 |
| WO | WO 2005/048918 | A3 | 5/2007 |
| WO | WO 2007/044607 | A3 | 8/2007 |
| WO | WO 2007/099392 | A2 | 9/2007 |
| WO | 2007/125089 | A2 | 11/2007 |
| WO | WO 2008/042261 | A2 | 4/2008 |
| WO | WO 2008/042261 | A3 | 5/2008 |
| WO | WO 2007/099392 | A3 | 5/2009 |

OTHER PUBLICATIONS

Kenjo, A., Takahashi, M., Matsushita, M., Endo, Y., Nakata, M., Mizuochi, T., Fujita, T. (2001) Cloning and Characterization of Novel Ficolins from the Solitary Ascidian, Halocynthia roretzi. The Journal of Biochemistry, vol. 276, No. 23, p. 19959-19965.*

Tanemura, M., Yin, D., Chong, A.S. Galili, U. (2000) Differential immune responses to α-gal epitopes on xenografts and allografts: implications for accommodation in xenotransplantation. Journal of Clinical Investigation, vol. 105, p. 301-310.*

Jobron, L., Sujino, K., Hummel, G., Palcic, M.M. (2003) Glycosyltransferase assays utilizing N-acetyllactosamine acceptor immobolized on a cellulose membrane. Analytical Biochemistry, vol. 323, p. 1-6.*

Minor, P.D. Problems in the development of new vaccines. Microbiology Today, vol. 27, p. 74-75.*

Feizi, T., Chai, W. (2004) Oligosaccharide microarrays to decipher the glyco code. Nature Reviews. Molecular Cell Biology, vol. 5, p. 582-588.*

Chemical Abstracts Database, CAS Registry No. 377090-70-5, entered on Dec. 20, 2001.*

Stangier, K., Palcic, M., Bundle, D.R., Hindsgaul, O., Thiem, J. (1998) Fucosyltransferase-catalyzed formation of -galactosylated Lewis structures. Carbohydrate Research, vol. 305, p. 511-515.*

Bhattacharjee, A.K., Sadoff, J.C., Collins, H., Cross, A.S., Khalil, A.H., Bieber, M.M., Wright, C., Teng, N.N.H. (1990) Synthesis and Characterization of Gentiobiose Heptaacetate Conjugate Vaccines That Produce Endotoxin-Neutralizing Antibodies. Bioconjugate Chemistry, vol. 1, p. 375-380.*

Halkes, K.M., Lefeber, D.J., Fransen, C.T.M., Kamerling, J.P., Vliegenthart, J.F.G. (1998) Synthesis of the spacer-containing β-GalpNAc-(1→4)-β-D-GlcpNAc-(1→3)-α-Galp moiety, representing the non-fucosylated backbone trisaccharide of the glycocalyx glycan of the parasite *Schistosoma mansoni*. Carbohydrate Research, vol. 308, p. 329-338.*

Hermanson, G.T. (1996) Bioconjugate Techniques, p. 421-429, Academic Press, Elsevier.*

Definition of “compound” and “composition” from the Grant & Hackh’s Chemical Dictionary (1987) p. 148, McGraw-Hill, Inc.*

“Anthrax” from the Department of Molecular Virology and Microbiology at Baylor College of Medicine [online], [retrieved May 15, 2012]. Retrieved from the Internet <http://www.bcm.edu/molvir/anthrax>.*

Chu, “Elusys’ anthrax drug enters clinical trials,” Oct. 4, 2005. Available online [retrieved on Jun. 23, 2009]. Retrieved from the Internet: <http://www.drugresearcher.com/content/view/print/27586>; 1 page.

Chu, “New discovery in the lab halts anthrax,” Dec. 2, 2005. Available online [retrieved on Jun. 23, 2009]. Retrieved from the Internet: <http://www.labtechnologist.com/content/view/print/153801>; 1 page.

“Elusys’ Anthrax Anti-Toxin, Anthrim(TM), Enters Second Phase I Clinical Study,” Apr. 20, 2009. Available online [retrieved on Jun. 23, 2009]. Retrieved from the Internet: <http://reuters.com/articlePrint?articleId=US170129%2B20-Apr-2009%2BPRN20090...>; 2 pages.

Macdonald, “Lonza’s GS system wins Elusys anthrax Ab contract,” Jun. 16, 2009. Available online [retrieved on Jun. 23, 2009]. Retrieved from the Internet: <http://www.outsourcing-pharma.com/content/view/print/250638>; 1 page.

Maynard et al., “Protection against anthrax toxin by recombinant antibody fragments correlates with antigen affinity,” Jun. 1, 2002 *Nat. Biotechnol*. 20(6):597-601.

Megget, “Two pharma gets US anthrax biodefense contracts,” Sep. 26, 2007. Available online [retrieved on Jun. 23, 2009]. Retrieved from the Internet: <http:www.in-phrmatechnologist.com/content/view/print/212973>; 1 page.

*Product Pipeline*— ANTHIM™ Anthrax Anti-Toxin datasheet. Elusys Therapeutics, Inc.; Pine Brook, NJ. Copyright 2009 Available online [retrieved on Jun. 23, 2009]. Retrieved from the Internet: <http://www.elusys.com/anthim-anthrax.html>; 2 pages.

Torrents et al., “Efficient growth inhibition of *Bacillus anthracis* by knocking out the ribonucleotide reductase tyrosyl radical,” Dec. 13, 2005 *Proc. Nat. Acad. Sci. USA* 102(50):17946-17951. Available online on Dec. 1, 2005.

Abshire et al., “Production and validation of the use of gamma phage for identification of *Bacillus anthracis*,” Sep. 2005 *J. Clin. Microbiol*. 43:4780-4788.

Amano et al., “Isolation and characterization of structural components of *Bacillus cereus* AHU 1356 cell walls,” May 16, 1977 *Eur. J Biochem*. 75:513-522.

American Type Culture Collection, “ATTC No. 10987,” organism: *Bacillus cereus* Frankland and Frankland; designation: NRS 248 [online]; Manassas, VA [retrieved on May 11, 2009] from the Internet. Retrieved from the Internet: <http://www.atcc.org/ATCCAdvancedCatalogSearch/ProductDetails/tabid/452/Default.aspx?ATCCNum=10987&Template=bacteria>; 2 pgs.

American Type Culture Collection, “ATTC No. 14579,” organism: *Bacillus cereus* Frankland and Frankland; designation: [BCRC 10603, CXM 2010, CCUG 7414, CIP 66.24, DSM 31, HAMBI 1887, HAMBI 1905, IAM 12605, JCM 2152, LMG 6923, NBRC 15305, NCCB 75008, NCIMB 9373, NCTC 2599, NRRL B-3711, VKM B-504] [online]; Manassas, VA [retrieved on May 11, 2009] from the Internet. Retrieved from the Internet: <http://www.atcc.org/ATCCAdvancedCatalogSearch/ProductDetails/tabid/452/Default.aspx?ATCCNum=14579&Template=bacteria>; 2 pgs.

American Type Culture Collection, “ATTC No. 33679,” organism: *Bacillus thruingiensis* Berliner deposited as *Bacillus thruingiensis* subsp. *kurstaki* de Barjac and Lemille; designation: NRRL B-3792 [online]; Manassas, VA [retrieved on May 11, 2009] from the Internet. Retrieved from the Internet: http://www.atcc.org/ATCCAdvancedCatalogSearch/ProductDetails/tabid/452/Default.aspx?ATCCNum=33679&Template=bacteria>; 1 pg.

American Type Culture Collection, “ATTC No. 35646,” organism: *Bacillus thuringiensis* Berliner; designation: USDA HD522 [online]; Manassas, VA [retrieved on May 11, 2009] from the Internet. Retrieved from the Internet: http://www.atcc.org/ATCCAdvancedCatalogSearch/ProductDetails/tabid/452/Default.aspx?ATCCNum=35646&Template=bacteria>; 1 pg.

Anderson et al., "D-configuration peptides that bind with high-affinities to carbohydrate binding proteins," Poster Abstract No. 83, Abstract No. 139 in "Session II: Glycan Biosynthesis, Processing and Recognition" of the *Annual Conference of the Society for Glycobiology*. Universal City, CA; Nov. 15-19, 2006. Proceedings published in: Nov. 2006 *Glycobiology* 16(11):1130.

"Aphton and VaxGen's joint venture Celltrion announce commercialization and manufacturing agreements for IGN311," Jul. 25, 2005 *VaxGen Press Release* Available online [retrieved Jul. 14, 2009]. Retrieved from the Internet: <http://www.b2i.us/profiles/investor/NewsPDF.asp?b=923&ID=10832&m=rl>; 2 pgs.

Ausubel et al., eds., *Current Protocols in Molecular Biology*, vols. 1-4, John Wiley & Sons, Inc., New York, NY, 1994; title page, publisher's page and table of contents only (19 pages).

Avashia et al., "Fatal pneumonia among metal workers due to inhalation exposure to *Bacillus cereus* containing *Bacillus anthracis* toxin genes," Feb. 1, 2007 *Clin. Infect. Dis.* 44:414-416. Available online on Dec. 27, 2006.

Baillie, "*Bacillus anthracis*, a story of nature subverted by man," 2005 *Lett. Appl. Microbiol.* 41:227-229.

Beaman et al., "Paracrystalline sheets reaggregated from solubilized exosporium of *Bacillus cereus*," Jul. 1971 *J. Bacteriol.* 107(1):320-324.

Bhat et al., "Structure of lipid A component of *Rhizobium leguminosarum* by. phaseoli lipopolysaccharide. Unique nonphosphorylated lipid A containing 2-amino-2-deoxygluconate, galacturonate, and glucosamine," May 20, 1994 *J. Biol. Chem.* 269(20):14402-14410.

Bhaysar et al., "Teichoic acid is an essential polymer in *Bacillus subtilis* that is functionally distinct from teichuronic acid," Dec. 2004 *J. Bacteriol.* 186(23):7865-7873.

"BioThrax® (Anthrax Vaccine Adsorbed)," product website [online]. Emergent BioSolutions Inc.: Rockville, MD. Copyright 2009 [retrieved on May 11, 2009]. Retrieved from the Internet: <http://www.biothrax.com/whatisbiothrax/>; 1 pg.

Boons, Geert-Jan "Cellular Activation Induced by Multivalent Ligands," Grant Abstract, Grant No. 1RO1GM065248-01A2 [online]. National Institute of General Medical Sciences, National Institutes of Health. Project dates Jan. 1, 2004 to Dec. 31, 2007 [retrieved on May 11, 2009]. Retrieved from the Internet: <http://crisp.cit.nih.gov/crisp/CRISP_LIB.getdoc?textkey=6723322&p_grant_num=1R01GM065248-01A2&p_query=&ticket=94045649&p_audit_session_id=464258258&p_keywords=>; 2 pgs.

Boons, Geert-Jan "Cellular Activation Induced by Multivalent Ligands," Grant Abstract, Grant No. 5RO1GM065248-02 [online] National Institute of General Medical Sciences, National Institutes of Health. Project dates Jan. 1, 2004 to Dec. 31, 2007 [retrieved on May 11, 2009]. Retrieved from the Internet: <http://crisp.cit.nih.gov/crisp/CRISP_LIB.getdoc?textkey=6839445&p_grant_num=5R01GM065248-02&p_query=&ticket=94045649&p_audit_session_id=464258258&p_key words=>; 2 pgs.

Boons, Geert-Jan "Cellular Activation Induced by Multivalent Ligands," Grant Abstract, Grant No. 5RO1GM065248-03 [online]. National Institute of General Medical Sciences, National Institutes of Health. Project dates Jan. 1, 2004 to Dec. 31, 2007 [retrieved on May 11, 2009]. Retrieved from the Internet: <http://crisp.cit.nih.gov/crisp/CRISP_LIB.getdoc?textkey=7002679&p_grant_num=5R01GM065248-03&p_query=&ticket=94045649&p_audit_session_id=464258258&p_keywords=>; 2 pgs.

Boons, Geert-Jan "Cellular Activation Induced by Multivalent Ligands," Grant Abstract, Grant No. 3RO1GM065248-03S1 [online]. National Institute of General Medical Sciences, National Institutes of Health. Project dates Jan. 1, 2004 to Dec. 31, 2007 [retrieved on May 11, 2009]. Retrieved from the Internet: <http://crisp.cit.nih.gov/crisp/CRISP_LLB.getdoc?textkey=7178347&p_grant_num=3R01GM065248-03 S1&p_query=&ticket=94045649&p_audit_session_id=464258258&p_keywords=>; 2 pgs.

Boons, Geert-Jan "Cellular Activation Induced by Multivalent Ligands," Grant Abstract, Grant No. 5RO1GM065248-04 [online]. National Institute of General Medical Sciences, National Institutes of Health. Project dates Jan. 1, 2004 to Aug. 18, 2008 [retrieved on May 11, 2009]. Retrieved from the Internet: <http://crisp.cit.nih.gov/crisp/CRISP_LIB.getdoc?textkey=7162501&p_grant_num=5R01GM065248-04&p_query=&ticket=94045649&p_audit_session_id=464258258&p_keywords=>; 2 pgs.

Boons, Geert-Jan "New synthetic methods for the preparation of carbohydrate-based vaccines," Grant Abstract, Grant No. 2RO1GM065248-05 [online]. National Institute of General Medical Sciences, National Institutes of Health. Project dates Jan. 1, 2004 to Jul. 31, 2012 [retrieved on May 11, 2009]. Retrieved from the Internet: <http://crisp.cit.nih.gov/crisp/CRISP_LIB.getdoc?textkey=7461340&p_grant_num=2R01GM065248-05&p_query=&ticket=94045649&p_audit_session_id=464258258&p_keywords=>; 2 pgs.

Borman, "Anthrax antigen synthesized," Oct. 3, 2005 *Chem. Eng. News* 83(40):10. Available online [retrieved on May 19, 2009]. Retrieved from the Internet: <http://pubs.acs.org/cen/news/83/i40/8340notw2.html>; 1 pg.

Bourgogne et al., "Global effects of virulance gene regulators in a *Bacillus anthracis* strain with both virulence plasmids," May 2003 *Infect. Innnun.* 71(5):2736-2743.

Brechtel and Bahl, "In Thermoanaerobacterium thermosulfurigenes EM1 S-layer homology domains to not attach to peptidoglycan," Aug. 1999 *J. Bacteriol.* 181(16):5017-5023.

Brossier et al., "Anthrax spores make an essential contribution to vaccine efficacy," Feb. 2002 *Infect. Immun.* 70(2):661-664.

Brown, "Rapid methods for extracting autolysins from *Bacillus subtilis*," Feb. 1973 *J. Bacteriol.* 25(2):295-300.

"Carbohydrates as Vaccine Candidates," Apr. 2007 *Collaboration and Licensing Opportunities*. National Institute of Diabetes and Digestive and Kidney Diseases; National Institutes of Health. Available online [retrieved on May 19, 2009]. Retrieved from the Internet: <http://techdev.niddk.nih.gov/_PDFs/CarbsVaccines.pdf>; 3 pgs.

Carlson, Russell "*Bacillus anthracis* cell surface carbohydrates," Grant Abstract, Grant No. 1R21AI056061-01 [online]. National Institute of Allergy and Infectious Diseases, National Institutes of Health. Project dates Sep. 30, 2003 to Sep. 29, 2005 [retrieved on May 11, 2009]. Retrieved from the Internet: <http://crisp.cit.nih.gov/crisp/CRISP_LIB.getdoc?textkey=6673663&p_grant_num=1R21AI056061-01&p_query=&ticket=94044092&p_audit_session_id=464256078&p_keywords=>; 2 pgs.

Carlson, Russell "*Bacillus anthracis* cell surface carbohydrates," Grant Abstract, Grant No. 5R21AI056061-02 [online]. National Institute of Allergy and Infectious Diseases, National Institutes of Health. Project dates Sep. 30, 2003 to Sep. 330, 2006 [retrieved on May 11, 2009]. Retrieved from the Internet: <http://crisp.cit.nih.gov/crisp/CRISP_LIB.getdoc?textkey=6803538&p_grant_num=5R21AI056061-02&p_query=&ticket=94044092&p_audit_session_id=464256078&p_keywords=>; 2 pgs.

Choudhury et al., "The structure of the major cell wall polysaccharide of *Bacillus anthracis* is species-specific," Sep. 22, 2006 *J. Biol. Chem.* 281(31):27932-27941. Available online on Jul. 26, 2006.

Clements et al., "Antibacterial activities and characterization of novel inhibitors of LpxC," Jun. 2002 *Antimicrob. Agents Chemother.* 46(6):1793-1799.

Daubenspeck et al., "Novel oligosaccharide side chains of the collagen-like region of Bc1A, the major glycoprotein of the *Bacillus anthracis* exosporium," Jul. 23, 2004 *J. Biol. Chem.* 279(30):30945-30953. Available online on May 19, 2004.

De et al., "A two-component direct fluorescent-antibody assay for rapid identification of *Bacillus anthracis*," Oct. 2002 *Emerg. Infect. Dis.* 8(10):1060-1065.

DelVecchio et al., "Proteomic profiling and identification of immunodominant spore antigens of *Bacillus anthracis, Bacillus cereus,* and *Bacillus thuringiensis*," Sep. 2006 *Appl. Environ. Microbiol.* 72(9):6355-6363.

Doolan et al., "The US capitol bioterrorism anthrax exposures: clinical epidemiological and immunological characteristics," Jan. 15, 2007 *J. Infect. Dis.* 195(2):174-184. Available online on Dec. 6, 2006.

Drysdale et al., "atx.A. controls *Bacillus anthracis* capsule synthesis via acpA and a newly discovered regulator, acpB," Jan. 2004 *J. Bacteriol.* 186(2):307-315.

Duesbery and VandeWoude, "Anthrax toxins," Sep. 1999 *Cell. Mol. Life Sci.* 55(12):1599-1609.

Forsberg et al., "Structural characterization of the O-antigenic polysaccharide of the lipopolysaccharide from *Rhizobium etli* strain CE3. A unique O-acetylated glycan of discrete size, containing 3-O-methyl-6-deoxy-L-talose and 2,3,4-tri-O-,methyl-I fucose," Jun. 23, 2000 *J. Biol. Chem.* 275(25):18851-18863.

Fox et al., "Determination of carbohydrate profiles of *Bacillus anthracis* and *Bacillus cereus* including identification of O-methyl methylpentoses by using gas chromatography-mass spectrometry," Apr. 1993 *J. Clin. Microbiol.* 31(4):887-894.

Freymond et al., "Poly(glucosyl-N-acetylgalactosamine 1-phosphate), a wall teichoic acid of *Bacillus subtilis* 168: its biosynthetic pathway and mode of attachment to peptidoglycan," Jun. 2006 *Microbiology* 152(Pt 6):1709-1718.

Friedlander et al., "Anthrax vaccine: evidence for safety and efficacy against inhalational anthrax," Dec. 8, 1999 *JAMA* 282(22):2104-2106.

Gerhardt and Ribi, "Ultrastructure of the exosporium enveloping spores of *Bacillus cereus*," Dec. 1964 *J. Bacteriol.* 88:1774-1789.

Green et al., "Demonstration of a capsule plasmid in *Bacillus anthracis*," Aug. 1985 *Infect. Immun.* 49(2):291-297.

Gudlavelleti et al., "Structural characterization of the lipid A component of *Sinorhizobium* sp. NGR234 rough and smooth form lipopolysaccharide. Demonstration that the distal amide-linked acyloxyacyl residue containing the long chain fatty acid is conserved in *Rhizobium* and *Sinorhizobium* sp.," Feb. 7, 2003 *J. Biol. Chem.* 278(6):3957-3968. Available online on Nov. 26, 2002.

Gudlavaletti et al., "The *Neisseria meningitidis* serogroup A capsular polysaccharide O-3 and O-4 acetyltransferase," Oct. 8, 2004. *J. Biol. Chem.* 279(41):42765-42773. Available online on Aug. 4, 2004.

Hachisuka et al., "Fine filaments on the outside of the exosporium of *Bacillus anthracis* spores," Jun. 1966 *J. Bacteriol.* 91(6):2382-2384.

Han et al., "Pathogenic sequence analysis of *Bacillus cereus* and *Bacillus thuringiensis* isolates closely related to *Bacillus anthracis*," May 2006 *J. Bacteriol.* 188(9):3382-3390.

Helgason et al., "Genetic diversity of *Bacillus cereus/B. Thuringiensis* isolates from natural sources," Aug. 1998 *Cur. Microbiol.* 37(2):80-87.

Helgason et al., "Multilocus sequence typing scheme for bacteria of the *Bacillus cereus* group," Jan. 2004 *Appl. Environ. Microbiol.* 70(1):191-201.

Hoffmaster et al., "Identification of anthrax toxin genes in a *Bacillus cereus* associated with an illness resembling inhalation anthrax," Jun. 1, 2004 *PNAS* 101(22):8449-8454. Available online on May 21, 2004.

Hoffmaster et al., "Characterization of *Bacillus cereus* isolates associated with fatal pneumonias: strains are closely related to *Bacillus anthracis* and harbor *B. anthracis* virulence genes," Sep. 2006 *J. Clin. Microbiol.* 44(9):3352-3360.

Hoffmaster et al., "Genetic diversity of clinical isolates of *Bacillus cereus* using multilocus sequence typing," Nov. 6, 2008 *BMC Microbiol.* 8:191-200.

"Human Genome Sciences reports on progress of clinical trials and announces goals for 2005 at JP Morgan healthcare conference," Jan. 10, 2005 *Human Genome Sciences Press Release* Available online [retrieved Jul. 14, 2009]. Retrieved from the Internet: <http://www.hgsi.com/index2.php?option=com_content&task=view&id=225&pop=l&page=0&Itemid=232>; 7 pgs.

International Preliminary Report on Patentability issued in PCT/US2007/015196; issued on Jan. 6, 2009.

International Search Report issued in PCT/US2007/015196; issued on Sep. 4, 2008.

Iwasaki et al., "Structural studies on the neutral polysaccharide of *Bacillus subtilis* AHU 1219 cell walls," Jan. 2, 1989 *Eur J. Biochem.* 178(3):635-641.

Jernigan et al., "Bioterrorism-related inhalational anthrax: the first 10 cases reported in the United States," Nov.-Dec. 2001 *Emerg. Infect. Dis.* 7(6):933-944.

Jernigan et al., "Investigation of bioterrorism-related anthrax, United States, 2001: epidemiologic findings," Oct. 2002 *Emerg. Infect. Dis.* 8(10):1019-1028.

Joellenbeck et al. (Eds), *The Anthrax Vaccine: Is it safe: does it work?* National Academies Press: Washington DC; 2002. Available online [retrieved on May 12, 2009]. Retrieved from the Internet: <http://www.nap.edu/catalog/10310.html>; Cover page, publishers page, and table of contents (5 of 289 pages).

Kahler et al., "O-acetylation of the terminal N-acetylglucosamine of the lipooligosaccharide inner core in *Neisseria meningitidis*. Influence on inner core structure and assembly," Jul. 21, 2006 *J. Biol. Chem.* 281(29):19939-19948. Available online on May 9, 2006.

Keim et al., "Multiple-locus variable-number tandem repeat analysis reveals genetic relationships within *Bacillus anthracis*," May. 2000 *J. Bacteriol.* 182(10):2928-2936.

Klee et al., "Characterization of *Bacillus anthracis*-like bacteria isolated from wild great apes for Cote d'Ivoire and Cameroon," Aug. 2006 *J. Bacteriol.* 188(15):5333-5344.

Ko et al., "Population structure of the *Bacillus cereus* group as determined by sequence analysis of six housekeeping genes and the plcR gene," Sep. 2004 *Infect. Immun.* 7(9)2:5253-5261.

Kojima et al., "Structural studies on the acidic polysaccharide of *Bacillus cereus* AHU 1356 cell walls," May 2, 1985 *Eur. J. Biochem.* 148(3):479-484.

Kojima et al., "Pyruvic-acid-containing polysaccharide in the cell wall of *Bacillus polymyxa* AHU 1385," Jun. 1, 1988 *Eur. J. Biochem.* 174(2):255-260.

Kubler-Kielb et al., "Saccharides cross-reactive with *Bacillus anthracis* spore glycoprotein as an anthrax vaccine component," Jun. 24, 2008 *PNAS* 105(25):8709-8712. Available online on Jun. 18, 2008.

Lawrence and Ford, "Aerobic spore-bearing bacteria in milk," May 1916 *J. Bacteriol.* 1(3):277-320.

Leendertz et al., "A new *Bacillus anthracis* round in wild chimpanzees and a gorilla from West and Central Africa," Jan. 27, 2006 *PloS Pathogens* 2(1):1-4.

Leoff et al., "Secondary non-classical cell wall polymer structures are specific to strains of the *Bacillus cereus* group," Poster, *Bacillus—ACT 2007* (*Bacillus anthracis, B. cereus,* and *B. thuringiensis* International Conference). Oslo, Norway; Jun. 21-17, 2007.

Leoff et al., "Cell wall carbohydrate compositions of strains from the *Bacillus cereus* group of species correlate with phylogenetic relatedness," Jan. 2008 *J. Bacteriol.* 190(1):112-121. Available online on Nov. 2, 2007.

Le Quere et al., "Structural characterization of a K-antigen capsular polysaccharide essential for normal symbiotic infection in *Rhizobium* sp. NGR234: deletion of the rkpMNO locus prevents synthesis of 5,7-diacetamido-3,5,7,9-tetradeoxy-non-2-ulosonic acid," Sep. 29, 2006 *J. Biol. Chem.* 281(39):28981-28992. Available online on Jun. 12, 2006.

Little et al., "Production and characterization of monoclonal antibodies to the protective antigen component of *Bacillus anthracis* toxin," Jul. 1988 *Infect. Immun.* 56(7):1807-1813.

Lyons et al., "Murine model of pulmonary anthrax: kinetics of dissemination, histopathology, and mouse strain susceptibility," Aug. 2004 *Infect. Immun.* 72(8):4801-4809.

Ma et al., "Drug targeting *Mycobacterium tuberculosis* cell wall synthesis: genetics of dTDP-rhamnose synthetic enzymes and development of a microtiter plate-based screen for inhibitors of conversion of dTDP-glucose to dTDP-rhamnose," May 2001 *Antimicrob. Agents Chemother.* 45(5):1407-1416.

Makino et al., "Molecular characterization and protein analysis of the cap region, which is essential for encapsulation in *Bacillus anthracis*," Feb. 1989 *J Bacteriol.* 171(2):722-730.

Mayer-Scholl et al., "Human neutrophils kill *Bacillus anthracis*," Nov. 11, 2005 *PloS Pathogens.* 1(3):179-186.

Mehta et al., "Synthesis and immunological studies of an oligosaccharide derived from *Bacillus anthracis*," Poster Abstract No. CARB-40. *231$^{st}$ National Meeting of the American Chemical Society.* Atlanta, GA; Mar. 26-30, 2006. Available online [retrieved on May 19, 2009]. Retrieved from the Internet: <http://oasys2.confex.com/acs/231nm/techprogram/>; 1pg.

Mehta et al., "Synthesis and antigenic analysis of the BclA glycoprotein oligosaccharide from the *Bacillus anthracis* exosporium," Dec. 13, 2006 *Chem. Eur. J.* 12(36):9136-9149.

Merrill et al., "Fluorescent heteroduplex assay for monitoring *Bacillus anthracis* and close relatives in environmental samples," Jun. 2003 *Appl. Environ. Microbiol.* 69(6):3317-3326.

Mesnage et al., "Bacterial SLH domain proteins are non-covalently anchored to the cell surface via a conserved mechanism involving wall polysaccharide pyruvylation," Sep. 1, 2000 *EMBO J.* 19(17):4473-4484.
Miceika et al., "Detection of group a *streptococcal* antigen directly from throat swabs with a ten-minute latex agglutination test," Mar. 1985 *J. Clin. Microbiol.* 21(3):467-469.
"Michigan lands $75 million large-scale anthrax vaccine plant, an industrial info news alert" Aug. 1, 2006 Business Wire. Available online [retrieved on May 19, 2009]. Retrieved from the Internet: <http://www.thefreelibrary.com/_/print/PrintArticle.aspx?id=148891064>; 1 pg.
Mohamed et al., "Enhancement of anthrax lethal toxin cytotoxicity: a subset of monoclonal antibodies against protective antigen increases lethal toxin-mediated killing of murine macrophages," Jun. 2004 *Infect. Immun.* 72(6):3276-3283.0
Mohamed et al., "A high-affinity monoclonal antibody to anthrax protective antigen passively protects rabbits before and after aerosolized *Bacillus anthracis* spore challenge," Feb. 2005 *Infect. Immun.* 73(2):795-802.
Mong et al., "Reactivity-based one-pot total synthesis of fucose $GM6_1$ oligosaccharide: a sialylated antigenic epitope of small-cell lung cancer," Feb. 4, 2003 *PNAS* 100(3):797-802. Available online on Jan. 27, 2003.
Murazumi et al., "Biosynthesis of the wall neutral polysaccharide in *Bacillus cereus* AHU 1356," Nov. 17, 1986 *Eur. J Biochem.* 161(1):51-59.
Orlandi et al., "Cloning immunoglobulin variable domains for expression by the polymerase chain reaction," May 1989 *PNAS* 86(10):3833-3837.
Park "Synthesis of biosynthetic precursors of anthrax- and cholera-related antigenic carbohydrates," Poster Abstract No. CARB-81. *231st National Meeting of the American Chemical Society*. Atlanta, GA; Mar. 26-30, 2006. Available online [retrieved on May 19, 2009]. Retrieved from the Internet: <http://oasys2.confex.com/acs/231nm/techprogram/>; 1 pg.
"Ph.D.™ -7 Phage Display Peptide Library Kit," NEB Catalog # E8100S. Product Manual [online]. New England Biolabs: Ipswich, MA. Jan. 2006. [retrieved on May 11, 2009]. Retrieved from the Internet: <http://www.neb.com/nebecomm/ManualFiles/manualE8100.pdf>; 28 pgs.
"Ph.D.™ -12 Phage Display Peptide Library Kit," NEB Catalog # E8110S. Product Manual [online]. New England Biolabs: Ipswich, MA. Nov. 2007. [retrieved on May 11, 2009]. Retrieved from the Internet: <http://www.neb.com/nebecomm/ManualFiles/manualE8110.pdf>; 28 pgs.
Priest et al., "Population structure and evolution of the *Bacillus cereus* group," Dec. 2004 *J Bacteriol.* 186(23):7959-7970.
Quinn et al., "Specific, sensitive, and quantitative enzyme-linked immunosorbent assay for human immunoglobulin G antibodies to anthrax toxin protective antigen," Oct. 2002 *Emerg. Infect. Dis.* 8(10):1103-1110.
Radnedge et al., "Genome differences that distinguish *Bacillus anthraces* from *Bacillus cereus* and *Bacillus thuringiensis*," May 2003 *Appl. Environ. Microbiol.* 69(5):2755-2764.
Rahman et al., "The structure of the lipooligosaccharide (LOS) from the alpha-1,2-N-acetyl glucosamine transferase (rfaK(NMB)) mutant strain CMK1 of *Neisseria meningitidis*: implications for LOS inner core assembly and LOS-based vaccines," Aug. 2001 *Glycobiology* 11(8):703-709.
Rasko et al., "The genome sequence of *Bacillus cereus* ATCC 10987 reveals metabolic adaptations and a large plasmid related to *Bacillus anthracis* pX01," Feb. 11, 2004 *Nucl. Acids Res.* 32(3):977-988.
Read et al., "The genome sequence of *Bacillus anthracis* Ames and comparison to closely related bacteria," May 1, 2003 *Nature* 423(6935):81-86.
Romero-Steiner et al., "Standardization of an opsonophagocytic assay for the measurement of functional antibody activity against *Streptococcus pneumoniae* using differentiated HL-60 cells," Jul. 1997 *Clin. Diagn. Lab. Immunol.* 4(4):415-422.
Saile et al., "*Bacillus anthracis* spore carbohydrates as markers of exposure and infection," Poster, *Bacillus—ACT 2007* (*Bacillus anthracis, B. cereus,* and *B. thuringiensis* International Conference). Oslo, Norway; Jun. 21-27, 2007.
Saile et al., "Novel carbohydrate determinants in *Bacillus anthracis*—exposure zone markers and diagnostic tools," Poster, *Bacillus—ACT 2009* (*Bacillus anthracis, B. cereus*, and *B. thuringiensis* International Conference). Santa Fe, New Mexico; Aug. 30-Sep. 3, 2009.
Schaffer and Messner, "The structure of secondary cell wall polymers: how gram-positive bacteria stick their cell walls together," Mar. 2005 *Microbiology* 151(Pt 3):643-651.
Schneerson et al., "Poly(gamma-D-glutamic acid) protein conjugates induce IgG antibodies in mice to the capsule of *Bacillus anthracis*: a potential addition to the anthrax vaccine," Jul. 22, 2003 *PNAS* 100(15):8945-4950. Available online on Jul. 11, 2003.
Seeberger et al., "Synthetic oligosaccharides and glycolipids as tools and vaccine candidates: malaria and bacteria as examples," Meeting Abstract. *Carbohydrate moieties as Vaccine Candidates Workshop* (National Institute of Allergy and Infectious Disease; National Institutes of Health). Bethesda, MD; Sep. 10-11, 2007. Meeting Program cover page, meeting schedule, and p. 23.
Adamo et al., "Synthesis of the βanomer of the spacer-equipped tetrasaccharide side chain of the major glycoprotein of the *Bacillus anthracis* exosporium," Dec. 12, 2005 *Carbohydr. Res.* 340:2579-2582. Available online on Oct. 10, 2005.
Adamo et al., "Studies towards a conjugate vaccine for anthrax: synthesis of the tetrasaccharide side chain of the *Bacillus anthracis* exosporium," 2006 *Helv. Chim. Acta* 89(6):1075-1089.
Allison and Verma, "Serotype-converting bacteriophages and 0-antigen modification of *Shigella flexneri*," Jan. 2000 *Trends Microbiol.* 8(1):17-23.
Alper et al., "Probing the specificity of aminoglycoside-ribosomal RNA interactions with designed synthetic analogs," Mar. 11, 1998 *J. Am. Chem. Soc.* 120(9):1965-1978. Available online on Feb. 24, 1998.
Barker et al., "Multilocus sequence typing reveals that *Bacillus cereus* strains isolated from clinical infections have distinct phylogenetic origins," Apr. 1, 2005 *FEMS Microbiol. Lett.* 245(1):179-184. Available online on Mar. 19, 2005.
Borin et al., "Single strand conformation polymorphism analysis of PCR-tDNA fingerprinting to address the identification of *Bacillus* species," Dec. 1, 1997 *FEMS Microbiol. Lett.* 157(1):87-93.
Braccini et al., "Conformational analysis of nitrilium intennediates in glycosylation reactions" Aug. 17, 1993 *Carbohydr. Res.* 246(1):23-41.
Buskas et al., "The immunogenicity of the tumor-associated antigen $Lewis^Y$ may be suppressed by a bifunctional cross-linker required for coupling to a carrier protein," Jul. 19, 2004 *Chemistry* 10(14):3517-3524. Available online on May 26, 2004.
Bystricky et al., "Conjugation of yeast mannans with protein employing cyanopyridinium agent (CDAP)—an effective route of antifungal vaccine preparation," Oct. 2000 *Glycoconjugate J.* 17(10):677-680.
Carlson et al., "Structure of the oligosaccharides obtained from the core regions of the lipopolysaccharides of *Bradyhizobium japonicum* 61A101c and its symbiotically defective lipopolysaccharide mutant, JS314," Jul. 2, 1992 *Carbohydr. Res.* 231:205-219.
Castanha et al., "Strain discrimination among *B. anthracis* and related organisms by characterization of *bclA* polymorphisms using PCR coupled with agarose gel or microchannel fluidics electrophoresis," Jan. 2006 *J Microbiol. Meth.* 64(1):27-45. Available online on Jul. 1, 2005.
Castanha et al., "Rapid discrimination of *Bacillus anthracis* from other members of the *B. cereus* group by mass and sequence of 'intact' small acid soluble proteins (SASPs) using mass spectrometry," Nov. 2006 *J Microbiol. Meth.* 67(2):230-240. Available online on May 26, 2006.
Castanha et al., "*Bacillus cereus* strains fall into two clusters (one closely and one more distantly related) to *Bacillus anthracis* according to amino acid substitutions in small acid-soluble proteins as determined by tandem mass spectrometry," Jun. 2007 *Mol. Cell. Probes* 21(3):190-201. Available online on Nov. 16, 2006.

Cataldi et al., "Construction and characterization of a protective antigen-deficient *Bacillus anthracis* strain," Jul. 1990 *Mol. Microbiol.* 4(7):1111-1117.
Chabot et al., "Anthrax capsule vaccine protects against experimental infection," Nov. 2004 *Vaccine* 23(1):43-47. Available online on Jul. 13, 2004.
Choudhury et al., "The structure of the lipopolysaccharide from a *galU* mutant of *Pseudomonas aeruginosa* serogroup-O11," Dec. 30, 2005 *Carbohydr. Res.* 340(18):2761-2772. Available online on Oct. 17, 2005.
Ciucanu and Kerek, "A simple and rapid method for the permethylation of carbohydrates," Aug. 15, 1984 *Carbohydr. Res.* 131(2):209-217.
Classon et al., "Synthesis of an artificial antigen that corresponds to a disaccharide repeating unit of the capsular polysaccharide of *Haemophilus influenzae* type d. A facile synthesis of methyl 2-acetamido-2-deoxy-β-D-mannopyranoside," Sep. 2, 1991 *Carbohydr. Res.* 216:187-196.
Crich and Vinogradova, "Synthesis of the antigenic tetrasaccharide side chain from the major glycoprotein of *Bacillus anthracis* exosporium," Aug. 17, 2007 *J. Org. Chem.* 72(17):6513-6520. Available online on Jul. 28, 2007.
Dai et al., "The *atxA* gene product activates transcription of the anthrax toxin genes and is essential for virulence," Jun. 1995 *Mol. Microbiol.* 16(6):1171-1181.
deBarjec and Lemille, "Presence of flagellar antigenic subfactors in serotype 3 of *Bacillus thuringiensis*," Jan. 1970 *J Invertebr. Pathol.* 15(1):139-140.
Elchert et al., "Application of the synthetic aminosugars for glycodiversification: synthesis and antimicrobial studies of pyranmycin," Mar. 5, 2004 *J. Org. Chem.* 69(5):1513-1523. Available online on Jan. 28, 2004.
Fox et al., "Carbohydrates and glycoproteins of *Bacillus anthracis* and related bacilli: targets for biodetection," Aug. 2003 *J. Microbiol. Methods* 54(2):143-152.
Gaunt et al., "Rational design of benzyl-type protecting groups allows sequential deprotection of hydroxyl groups by catalytic hydrogenolysis," 1998 *J Org. Chem.* 63(13):4172-4173. Available online on Jun. 26, 1998.
Ginsberg et al., "In vitro reconstruction of two essential steps in wall teichoic acid biosynthesis," Feb. 17, 2006 *ACS Chem. Biol.* 1(1):25-28. Available online on Jan. 24, 2006.
Gridley and Osborn, "Recent advances in the construction of β-D-mannose and β-D-mannosamine linkages," 2000 *J. Chem. Soc. Perkin Transactions 1* 10:1471-1491. Available online on Apr. 25, 2000.
Guo et al., "De novo asymmetric synthesis of the anthrax tetrasaccharide by a palladium-catalyzed glycosylation reaction," Jul. 2, 2007 *Angew. Chem. Int. Ed.* 46(27):5206-5208. Available online on May 30, 2007.
Hilleman, "Overview: cause and prevention in biowarfare and bioterrorism," Aug. 19, 2002 *Vaccine* 20(25-26):3055-3067. Available online on Jul. 12, 2002.
Jentoft, "Why are proteins O-glycosylated?" Aug. 1990 *Trends Biochem Sci.* 15(8):291-294.
Jiang et al., "Expanding the pyrimidine diphosphosugar repertoire: the chemoenzymatic synthesis of amino- and acetamidoglucopyranosyl derivatives," Apr. 17, 2001 *Angew. Chem. Int. Ed.* 40(8):1502-1505.
Katsuki et al., "Improved direct method for determination of keto acids by 2,4-dinitrophenylhydrazine," Oct. 1971 *Anal. Biochem.* 43(2):349-356.
Kern and Schneewind, "BslA, a pXO1-encoded adhesin of *Bacillus anthracis*,"Apr. 2008 *Mol. Microbiol.* 68(2):504-515.
Kim et al., "Genetic relationships of *Bacillus anthracis* and closely related species based on variable-number tandem repeat analysis and BOX-PCR genomic fmgerprinting," Jan. 22, 2002 *FEMS Microbiol. Lett.* 207(1):21-27. Available online on Dec. 13, 2001.
Kim et al., "A general strategy for stereoselective glycosylations," Aug. 31, 2005 *J. Am. Chem. Soc.* 127(34):12090-12097. Available online on Aug. 5, 2005.
Kim et al., "Stereoselective glycosylation reactions with chiral auxiliaries," Jan. 28, 2005 *Angew. Chem. Int. Ed.* 44(6):947-949. Available online on Jan. 3, 2005.
Klinman et al., "CpG oligonucleotides improve the protective immune response induced by the anthrax vaccination of rhesus macaques," Jul. 29, 2004 *Vaccine* 22(21-22):2881-2886. Available online on Jan. 28, 2004.
Kuo et al., "Decontamination of bacterial spores by a microwave plasma torch," Meeting Abstract. 32$^{nd}$ *IEEE International Conference on Plasma Science* (Institution of Electrical and Electronic Engineers). Monterey, CA; Jun. 18-23, 2005. Published in *Plasma Science, 2005 IEEE Conference Record—Abstracts*, p. 257. Available online [retrieved Jul. 16, 2009]. Retrieved from the Internet: <http://ieeexplore.ieee.org/xpl/absprintf.jsp?arnumber=4198597 &page=Free>; 1 pg.
Leoff et al., "Structural elucidation of the nonclassical secondary cell wall polysaccharide from *Bacillus cereus* ATCC 10987. Comparison with the polysaccharides from *Bacillus anthracis* and *B. cereus* type strain ATCC 14579 reveals both unique and common structural features," Oct. 31, 2008 *J. Bacteriol.* 283(44):29812-29821. Available online on Aug. 29, 2008.
Leoff et al., "Secondary cell wall polysaccharides of *Bacillus anthracis* are antigens that contain specific epitopes which cross-react with three pathogenic *Bacillus cereus* strains that caused severe disease, and other epitopes common to all the *Bacillus cereus* strains tested," Jun. 2009 *Glycobiology* 19(6):665-673. Available online on Mar. 6, 2009.
Lindberg, "Glycoprotein conjugate vaccines," Oct. 1999 *Vaccine* 17(Supp. 2):S28-S36.
Liu et al., "Synthesis of (25R)-ruscogenin-1-y1-β-D-xylopyranosyl-(1,3)-[β-D-glucopyranosul-(1,2)]β-D-fucopyranoside," Dec. 1, 2000 *Carbohydr. Res.* 329(4):745-754.
Messner, "Bacterial glycoproteins," Jan. 1997 *Glycoconjugate J.* 14(1):3-11.
Mieszala et al., "Conjugation of meningococcal lipooligosaccharides through their lipid A terminus conserves their inner epitopes and results in conjugate vaccines having improved immunological properties," Jan. 20, 2003 *Carbohydr. Res.* 338(2):167-175.
Misra and Roy, "Synthesis of the tetrasaccharide repeating unit of the antigen from *Escherichia coli* O126 as its methyl glycoside," Sep. 1998 *J. Carbohydr. Chem.* 17(7):1047-1056. Available online on Sep. 1, 1998.
Mock and Fouet, "Anthrax," 2001 *Ann. Rev. Microbiol.* 55:647-671.
Oberli et al., "Synthesis of a hexasaccharide repeating unit from *Bacillus anthracis* vegetative cell walls," Mar. 6, 2008 *Org. Lett.* 10(5):905-908. Available online on Jan. 31, 2008.
Parthasarathy et al., "Application of carbohydrate miccroarray technology for the detection of *Burkolderia pseudomallei, Bacillus anthracis* and *Francisella tularensis* antibodies," Nov. 3, 2008 *Carbohydrate Res.* 343(16):2783-2788. Available online on Jun. 14, 2008.
Pitt et al., "In vitro correlate of immunity in a rabbit model of inhalational anthrax," Sep. 14, 2001 *Vaccine* 19(23):4768-4773.
Pozsgay, "Synthesis of glycoconjugate vaccines against *Shigella dysenteriae* type 1," Aug. 21, 1998 *J. Org. Chem.* 63(17):5983-5999. Available online on Jul. 29, 1998.
Rasko et al., "Genomics of the *Bacillus cereus* group of organisms," Apr. 2005 *FEMS Microbiol. Rev.* 29(2):303-329. Available online on Jan. 28, 2005.
Rigden et al., "The PA14 domain, a conserved all-β domain in bacterial toxins, enzymes, adhesins and signaling molecules," Jul. 2004 *Trends Biochem. Sci.* 29(7):335-339. Available online on Jun. 7, 2004.
Sakagami and Hamana, "A selective ring opening reaction of 4,6-*O*-benzylidene acetals in carbohydrates using trialkylsilane derivatives," Jul. 15, 2000 *Tetrahedron Lett.* 41(29):5547-5551.
Saksena et al., "Studies toward a conjugate vaccine for anthrax. Synthesis and characterization of anthrose [4,6-dideoxy-4-(3-hydroxy-3-methylbutanamido)-2-*O*- methyl-D-glucopyranose] and its methyl glycosides," Jul. 4, 2005 *Carbohydr. Res.* 340(9):1591-1600.

Saksena et al., "Synthesis of the tetrasaccharide side chain of the major glycoprotein of the *Bacillus anthracis* exosporium," Feb. 1, 2006 *Bioorg. Med. Chem. Lett.* 16(3):615-617. Available online on Nov. 4, 2005.
Saksena et al., "Immunogens related to the synthetic tetrasaccharide side chain of the *Bacillus anthracis* exosporium," Jun. 15, 2007 *Bioorg. Med. Chem.* 15(12):4283-4310. Available online on Mar. 23, 2007.
Schaffer et al., "A pyrohposphate bridge links the pyruvate-containing secondary cell wall polymer of *Paenibacillus alvei* CCM 2051 to muramic acid," Oct. 2000 *Glycoconj. J.* 17(10):681-690.
Schmidt et al., "Sweet new world: glycoproteins in bacterial pathogens," Dec. 2003 *Trends Microbiol.* 11(12):554-561.
Ezzell, Jr. et al., "Identification of *Bacillus anthracis* by using monoclonal antibody to cell wall galactose-*N*-acetylglucosamine polysaccharide," Feb. 1990 *J Clin. Microbiol.* 28:223-231.
Kern et al., "*Bacillus anthracis* surface-layer proteins assemble by binding to the secondary cell wall polysaccharide in a manner that requires *csaB* and *tagO*," Sep. 3, 2010 *J. Mol. Biol.* 401:757-775. Available online on Jul. 13, 2010.
Oberli et al., "Molecular analysis of carbohydrate-antibody interactions: case study using a *Bacillus anthracis* tetrasaccharide," Aug. 4, 2010 *J Am. Chem. Soc.* 132:10239-10241. Available online on Jul. 8, 2010.
Tamborrini et al., "Immuno-detection of anthrose containing tetrasaccharide in the exosporium of *Bacillus anthracis* and *Bacillus cereus* strains," May 2009 *J. Appl. Microbiol.* 106:1618-1628. Available online on Feb. 16, 2009.
Carlson et al., "Structural and antigenic analyses of *Bacillus anthracis* carbohydrates," Meeting Abstract. FASEB Summer Research Conference; Microbial Polysaccharides of Medical, Agricultural, and Industrial Importance. Carefree, AZ; Jun. 15-20, 2008.
David et al., "A mild procedure for the regiospecific benzylation and allylation of polyhydroxy-compounds *via* their stannylene derivatives in non-polar solvents," 1981 *J. Chem. Soc. Perkin Transactions 1* pp. 1796-1801.
Des membres et des correspondants de L'academie, "Memoires et communications," *CR Acad. Sci. Agr. Bulg.* Jan.-Jun. 1881 92(9):429-435.
Ekwunife et al., "Isolation and purification of cell wall polysaccharide of *Bacillus anthracis* (ΔSteme)," Aug. 15, 1991 *FEMS Microbiol. Lett.* 82(3):257-262.
Gerhardt, "Cytology of *Bacillus anthracis*," Sep.-Oct. 1967 *Fed. Proc.* 26(5):1504-1517.
Guo and Jennings, "Protein-polysaccharide conjugation," in *Methods in Molecular Medicine—Meningococcal Vaccines: Methods and Protocols*, vol. 66 (Pollard and Maiden, Eds.) Humana Press: Totowa, NJ; 2001. Cover page, publisher's page and pp. 49-54.
Hardy and Townsend, "High-pH anion-exchange chromatography of glycoprotein-derived carbohydrates," 1994 *Methods in Enzymol.* vol. 230. pp. 208-225.
Keppie and Harris-Smith, "The chemical basis of the virulence of *Bacillus anthracis6*. II: Some biological properties of bacterial products," Oct. 1953 *Br. J. Exp. Pathol.* 34(5):486-496.
Kramer and Roth, "Ultrastructural differences in the exosporium of the Sterne and Vollum strains of *Bacillus anthracis*," Dec. 1968 *Can J. Microbiol.* 14(12):1297-1299.
Molnar and Pragai, "Attempts to detect the presence of teichoic acid in *Bacillus anthracis*," 1971 *Acta Microbiol. Acad. Sci. Hung.* 18(2):105-108.
Moxon and Kroll, "The role of bacterial polysaccharide capsules as virulence factors," 1990 *Curr. Top. Microbiol. Immunol.* 150:65-85.
Novak et al., "Unusual clinical isolates of *Bacillus cereus*: correlatoin of multilocus sequence types with severity of disease," Meeting Abstract. 105$^{th}$ *General Meeting of the American Society for Microbiology*. Atlanta, GA; Jun. 5-9, 2005.
Peters, "Synthesis and conformational analysis of methyl 2-*O*-(α-D-mannopyranosyl)-αD-mannopyranodise," Feb. 12, 1991 *Liebigs Ann. Chem.* 2:135-141.
Priest, "Systemics and Ecology of *Bacillus*," in *Bacillus subtilis and other Gram-Positive Bacteria* (Hoch et al., Eds.) American Society for Microbiology, Washington, DC. Copyright 1993. Cover page and pp. 3-16.
Qin and Grindley, "Improvements in the regioselectivity of alkylation reactions of stannylene acetals," Jan. 1996 *J Carbohydr. Chem.* 15(1):95-108.
Ratcliffe and Fraser-Reid, "Generation of α-D-glucopyranosylacetonitrilium ions. Concerning the reverse anomeric effect," 1990 *J. Chem. Soc. Perkins Transactions 1* 3:747-750.
Schaffer et al., "The diacetamidodideoxyuronic-acid-containing glycan chain of *Bacillus stearothermophilus* NRS 2004/3a represents the secondary cell-wall polymer of wild-type *B. stearothermophilus* strains," Jul. 1999 *Microbiology* 145(Pt. 7):1575-1583.
Schmidt, "New methods for the synthesis of glycosides and oligosaccharides—are there alternatives to the Koenigs-Knorr method?" Mar. 1986 *Angew. Chem. Int. Ed.* 25(3):212-235.
Schmidt and Kinzy, "Anomeric activation for glycoside synthesis: the trichloroacetimidate method," 1994 *Adv. Carbohydr. Chem. Biochem.* 50:21-123.
Schuch et al., "A bacteriolytic agent that detects and kills *Bacillus anthracis*," Aug. 22, 2002 *Nature* 418(6900):884-889.
Seeberger and Werz, "Synthesis and medical applications of oligosaccharides," Apr. 26, 2007 *Nature* 446(7139):1046-1051.
Shafer et al., "Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides," Jan. 18, 2000 *Vaccine* 18(13):1273-1281.
Shemyakin et al., "Preventative and therapeutic effects of $\alpha_1$-acid glycoprotein in mice infected with *B. anthracis*," Oct. 2005 *Bull. Exp. Biol. Med.* 140(4):439-444.
Singh et al., "Targeting the methyl erythritol phosphate (MEP) pathway for novel antimalarial, antibacterial and herbicidal drug discovery inhibition of 1-deoxy-D-xylulose-5-phosphate reductoisomerase (DXR) enzyme," 2007 *Curr. Pharm. Design* 13(11):1161-1177.
Smith et al., *Aerobic Sporeforming Bacteria* Agriculture Monograph 16: United States Department of Agriculture. Issued Nov. 1952.
Steichen et al., "Identification of the immunodominant protein and other proteins of the *Bacillus anthracis* exosporium," Mar. 2003 *J. Bacteriol.* 185(6):1903-1910.
Steindl et al., "The secondary cell wall polymer of *Geobacillus tepidamans* GS5-97$^T$: structure of different glycoforms," Oct. 17, 2005 *Carbohydr. Res.* 340(14):2290-2296. Available online on Aug. 10, 2005.
Sterne, "Variation in *Bacillus anthracis*," Apr. 1937 *Ond. J. Vet. Sci. Anim. Indust.* 8(2):271-349.
Sterne, "The effects of different carbon dioxide concentrations on the growth of virulent anthrax strains: pathogenicity and immunity tests on guinea-pigs and sheep with anthrax variants derived from virulent strains," Jul. 1937 *Ond. J. Vet. Sci. Anim. Indust.* 9(1):49-67.
Sylvestre et al., "A collagen-like surface glycoprotein is a structural component of the *Bacillus anthracis* exosporium," Jul. 2002 *Mol. Microbiol.* 45(1):169-178.
Tamborrini et al., "Anti-carbohydrate antibodies for the detection of anthrax spores," Oct. 6, 2006 *Angew. Chem. Int. Ed.* 45(39):6581-6582. Available online on Aug. 17, 2006.
Tanaka et al., "Efficient stereoselective synthesis of γ-*N*-glycosyl asparagines by N-glycosylation of primary amide groups," Feb. 16, 2005 *J. Am. Chem. Soc.* 127(6):1630-1631. Available online on Jan. 22, 2005.
Tarasenko et al., "Glycoconjugates as inhibitors of *Bacillus* spores," Meeting Abstract 323.8. *35$^{th}$ International Congress of Physiological Sciences—Experimental Biology 2005®* . San Diego, CA; Mar. 31-Apr. 6, 2005. *FASEB J.* 19(4 Supp. S Pt 1):A546.
Tarasenko et al., "Inhibition of sporeforming pathogens using glycoconjugates," Meeting Abstract 533.5. *35$^{th}$ International Congress of Physiological Sciences—Experimental Biology 2005®* . San Diego, CA; Mar. 31-Apr. 6, 2005. *FASEB J.* 19(4 Supp. S Pt 1):A871.
Bouzianas, "Potential biological targets of *Bacillus anthracis* in anti-infective approaches against the threat of bioterrorism," Aug. 2007 *Expert Rev. Anti-Infective Ther.* 5(4):665-684.
Lees et al., "Activation of soluble polysaccharides with 1-cyano-4-dimetylaminopyridinium tetrafluoroborate for use in protein-polysaccharide conjugate vaccines and immunological reagents," Feb. 1996 *Vaccine* 14(3):190-198.

Leoff et al., "Cell wall carbohydrates in strain of the *Bacillus cereus* group," Poster and Abstract, *Bacillus—Act 2005* (*Bacillus anthracis, B. cereus, and B. thuringiensis* International Conference). Santa Fe, New Mexico; Sep. 25-29, 2005.
Leoff et al., "Secondary cell wall polysaccharide structures from pathogenic bacilli (i.e. *B. anthracis and B. cereus*) are closely related," POSTER presented at the University of Georgia; May 2007.
Leoff et al., "The immune response to the secondary cell wall polysaccharide of *Bacillus anthracis* is specific to these bacteria," POSTER presented at the University of Georgia; May 2007.
"Swiss scientists find new testing system for anthrax," Aug. 23, 2006 Xinhua News Agency. Available online [retrieved on May 19, 2009]. Retrieved from the Internet <http://english.people.com.cn/200608/24/print20060824_296222.html>; 1 pg.
Temeyer, "Larvicidal activity of *Bacillus thuringiensis* subsp. *israelensis* in the dipteran *Haematobia irritans*," May 1984 *Appl. Environ. Microbiol*. 47(5):952-955.
Ticknor et al., "Fluorescent amplified fragment length polymorphism analysis of Norwegian *Bacillus cereus* and *Bacillus thuringiensis* soil isolates," Oct. 2001 *Appl. Environ. Microbiol*. 67(10):4863-4873.
Turnbull, "Anthrax vaccines: past, present and future," Aug. 1991 *Vaccine* 9(8):533-539.
Tzeng et al., "The MisR/MisS two-component regulatory system influences inner core structure and immunotype of lipooligosaccharide in *Neisseria meningitidis*," Aug. 13, 2004 *J. Biol. Chem*. 279(33):35053-35062. Available online on Jun. 1, 2004.
"Vaccines preserved with AVANT Immunotherapeutics' VitriLife technology show good stability at room temperature and above," May 12, 2004 *AVANT Therapeutics Press Release* Available online [retrieved 2009-07-14]. Retrieved from the Internet: <http://ir.celldextherapeutics.com/phoenix.zhtml?c=93243&p=irol-newsArticle_pf&ID= 525982&highlight=>; 2 pgs.
VanErt et al., "Strain-specific single-nucleotide polymorphism assays for the *Bacillus anthracis* Ames strain," Jan. 2007 *J. Clin. Microbio*. 45(1):47-53. Available online on Nov. 8, 2006.
Vankar et al., "Synthesis of β-O-glycosides using enol ether and imidate derived leaving groups. Emphasis on the use of nitriles as a solvent," 1991 *Tetrahedron* 47(48):9985-9992.
Vasan et al., "Chemical synthesis and immunological properties of oligosaccharides derived from the vegetative cell wall of *Bacillus anthracis*," Jul. 21, 2008 *ChemBioChem* 9(11):1716-1720. Available online on Jun. 18, 2008.
"VaxGen and EndoBiologics form collaboration to pursue early stage research for meningitis B vaccine," May 4, 2005 *VaxGen Press Release* Available online [retrieved Jul. 14, 2009]. Retrieved from the Internet: <http://www.b2i.us/profiles/investor/NewsPDF.asp?b=923&ID=9428&m=rl>; 2 pgs.
Veeneman et al., "Iodonium ion promoted reactions at the anomeric centre. II. An efficient thioglycoside mediated approach toward the formation of 1,2-*trans* linked glycosides and glycosidic esters," 1990 *Tetrahedron Lett*. 31(9):1331-1334. Available online on Mar. 7, 1990.
Venezia et al., "Evaluation of a rapid method for the detection of streptococcal group A antigen directly from throat swabs," Mar. 1985 *J. Clin. Microbiol*. 21(3):395-398.
Venot et al., "Disaccharide mimetics of the aminoglycoside antibiotic neamine," Sep. 6, 2004 *ChemBioChem* 5(9):1228-1236. Available online on Sep. 2, 2004.
Wang et al., "Activity of alpha- and theta-defensins against primary isolates of HIV-1," Jul. 1, 2004 *J. Immunol*. 173:515-520.
Wang and Roehrl, "Anthrax vaccine design: strategies to achieve comprehensive protection against spore, bacillus, and toxin," Mar. 24, 2005 *Med. Immunol*. 4(1):4.
Wang et al., "Photogenerated glycan arrays identify immunogenic sugar moieties of *Bacillus anthracis* exosporium," Jan. 2007 *Proteomics* 7(2):180-184.
Wang et al., "Photo-generated arrays for probing immunogenic sugard moieties of microbial pathogens (*B. anthracis*)," Meeting Abstract. *Carbohydrate moieties as Vaccine Candidates Workshop* (National Institute of Allergy and Infectious Disease; National Institutes of Health). Bethesda, MD; Sep. 10-11, 2007. Meeting Program cover page, meeting schedule, and p. 21.
Watt and Boons, "A convergent strategy for the preparation of N-glycan core di-, tri-, and pentasaccharide thioaldoses for the site-specific glycosylation of peptides and proteins bearing free cysteines," Jan. 22, 2004 *Carbohydr. Res*. 339(2):181-193.
Webb, "A silent bomb: the risk of anthrax as a weapon of mass destruction," Apr. 15, 2003 *PNAS* 100(8):4355-4356. Available online on Apr. 7, 2003.
Weintraub, "Immunology of bacterial polysaccharide antigens," Nov. 14, 2003 *Carbohydr. Res*. 338(23):2539-2547.
Werz and Seeberger, "Total synthesis of antigen *Bacillus anthracis* tetrasaccharide—creation of an anthrax vaccine candidate," Oct. 31, 2005 *Angew. Chem. Int. Ed* 44(39):6315-6318. Available online on Sep. 19, 2005.
Williams, "A newly discovered carbohydrate structure unique to anthrax," Winter 2007 *University of Georgia Research Magazine* 36(1):3. Available online [retrieved on Aug. 24, 2009]. Retrieved from the Internet: <http://researchmagazine.uga.edu/winter2007/printanewly.htm>; 1 pg.
Winans et al., "A chemically synthesized version of the insect antibacterial glycopeptide, diptericin, disrupts bacterial membrane integrity," Sep. 7, 1999 *Biochemistry* 38(36):11700-11710. Available online on Aug. 14, 1999.
Xia et al., "Use of 1,2-dichloro 4,5-dicyanoquinone (DDQ) for cleavage of the 2- naphthylmethyl (NAP) group," Jan. 8, 2000 *Tetrahedron Lett*. 41(2):169-173.
York et al., "Isolation and characterization of plant cell walls and cell wall components," 1985 *Meth. Enzymol*. 118:3-40.
Yu and Tao, "Glycosyl trifluoroacetimidates. Part 1: Preparation and application as new glycosyl donors," Mar. 18, 2001 *Tetrahedron Lett*. 42(12):2405-2407. Available online on Apr. 10, 2001.
Yu and Tao, "Glycosyl triflouroacetimidates. 2. Synthesis of dioscin and xiebai saponin I," Dec. 13, 2002 *J. Org. Chem*. 67(25):9099-9102. Available online on Nov. 16, 2002.
Zhu and Boons, "A highly efficient synthetic strategy for polymeric support synthesis of $Le^x$, $Le^y$, and H-type 2 oligosaccharides," Jun. 1, 2001 *Chemistry Eur. J*. 7(11):2382-2389.
Zona and Janecek, "Relationships between SLH motifs from different glycoside hydrolase families," 2005 *Biologia* (*Bratislava*) 60(Supp. 16):115-121.
Fouet et al., "*Bacillus anthracis* cell envelope components", 2002. *Current Topics in Microbiology and Immunology*. 271:87-113.
Longchamp et al., "Molecular recognition specificity of*Bacillus anthracis* spore antibodies", 1999. *Journ. of Applied Microbiology*. 87:246-249.
Sasaki et al., "Structure of Teichoic-Acid—Glycopeptide Complexes from Cell Walls of *Bacillus cereus* AHU 1030", 1983. *Eur. J. Biochem*. 132:207-213.
Swiecki et al., "Monoclonal Antibodies for *Bacillus anthracis* Spore Detection and Functional Analyses of Spore Germination and Outgrowth", 2006. *Journ. of Immunology*. pp. 6076-6084 and Table II (2 pgs).
Extended European Search Report (including Search Report and Search Opinion) for related EP Divisional Patent Application 10 17 5743.3. Dated Feb. 2, 2012.

* cited by examiner

F
β-Gal-(1→4)
→6)-α-GlcNAc-(1→4)-β-ManNAc-(1→4)-β-GlcNAc-(1→
C D E
α-Gal-(1→3) α-Gal-(1→3)
B A

1: $R^1$ = Me, $R^2$ =

2: $R^1$ = H, $R^2$ =

3: $R^1$ = Me, $R^2$ =

4: $R^1$ = Me, $R^2$ =

16

14: R = H

15: R = Lev

17: R = Lev

18: R = H

19: R = Lev

20: R = H

21: R = Me

22: $R^1$ = Me, $R^2$ =

23: $R^1$ = H, $R^2$ =

24: $R^1$ = Me, $R^2$ =

25: $R^1$ = Me, $R^2$=

1, 2, 3, and 4

B. anthracis

β-Gal-(1→4)
|
[→6)-α-GlcNAc-(1→4)-β-ManNAc-(1→4)-β-GlcNAc-(1→6)-α-GlcNAc-(1→]ₙ-6)-α-GlcNAc-(1→4)-β-ManNAc-(1→4)-β-GlcNAc
                                                                              |                                              |
                                                                     *β-Gal-(1→4)                              α-Gal-(1→3)
|                                                                                    |
α-Gal-(1→3)                                                              *α-Gal-(1→3)

B. cereus G9241

β-Gal-(1→4)
|
[→6)-α-GlcNAc-(1→4)-β-ManNAc-(1→4)-β-GlcNAc-(1→6)-α-GlcNAc-(1→]ₙ-6)-α-GlcNAc-(1→4)-β-ManNAc-(1→4)-β-GlcNAc
            (when n 1)                                                        |                                              |
              **α-Gal-(1→6)                                          *β-Gal-(1→4)                         **α-Gal-(1→6)
|                                                                                    |
α-Gal-(1→3)                                                              *α-Gal-(1→3)
*(when n>2)

A.

B.

$R_1$-$R_4$ = Gal or H

A
β-D-Gal-1→4┐
α-D-GlcNAc-1→4-β-D-ManNAc-1→4-β-D-GlcNAc-1→spacer
α-D-Gal-1→3┘ α-D-Gal-1→3┘
B C

Structures

| A | B | C |
|---|---|---|
| - | - | - |
| + | - | - |
| - | + | - |
| - | - | + |
| + | + | - |
| + | - | + |
| - | + | + |
| + | + | + |

Fig. 30

5
6
7. R = Me, $X_1$ = OC(NH)$CCl_3$, $X_2$ = H
8. R = Lev, $X_1$ = H, $X_2$ = SEt
9. R = Lev
10. R = H
11. R = Lev
12. R = H
13. R = Me
14. R = Lev
15. R = H
16. R = Me, $R_1$ = H
17. R = Me, $R_1$ =
18. R = Me, $R_1$ =
19. R = Me, $R_1$ =
20. R = H, $R_1$ =
21. R = Me, $R_1$ =
22. R = Me, $R_1$ =
23. R = Me, $R_1$ =
24. R = H, $R_1$ =

1

2

1S + 2S 3S 4

A.

B.

X $\rightarrow$-6-$\alpha$-(GlcNAc or GalNAc)-1$\rightarrow$4-$\beta$-ManNAc-1$\rightarrow$4-$\beta$-GlcNAc-1$\rightarrow$

C.

ANTHRAX CARBOHYDRATES, SYNTHESIS AND USES THEREOF

CONTINUING APPLICATION DATA

This application is a continuation-in-part of International Application No. PCT/US2007/015196, filed Jun. 29, 2007, which claims the benefit of U.S. Provisional Application Ser. No. 60/817,929, filed Jun. 30, 2006, and U.S. Provisional Application Ser. No. 60/933,937, filed Jun. 8, 2007; further this application claims the benefit of U.S. Provisional Application Ser. No. 61/056,204, filed May 27, 2008, and U.S. Provisional Application Ser. No. 61/132,515, filed Jun. 19, 2008; all of which are incorporated herein by reference in their entireties.

GOVERNMENT FUNDING

The present invention was made with government support under Grant Nos. AI 056061, R21 AI 059577, and GM 065248 warded by the National Institutes Health, and Grant No. DE-FG09-93ER20097, awarded by the Department of Energy. The Government has certain rights in this invention.

BACKGROUND

*Bacillus anthracis* is a gram-positive, spore-forming bacterium that causes anthrax in humans and other mammals. Because of the high resilience of *B. anthracis* spores to extremes of their environment they can persist for many years until encountering a signal to germinate. When spores of *B. anthracis* are inhaled or ingested they may germinate and establish populations of vegetative cells which release anthrax toxins often resulting in the death of the host. The relative ease by which *B. anthracis* may be weaponized and the difficulty in early recognition of inhalation anthrax due to the non-specific nature of its symptoms were demonstrated by the death of four people who inhaled spores from contaminated mail (Jernigan et al., 2002, *Emerg Infect Dis;* 8:1019-1028; Jernigan et al., 2001, *Emerg Infect Dis,* 7:933-944; Webb, 2003, *Proc Natl Acad Sci;* 100:4355-4356). Consequently, considerable efforts are being directed towards the development of early disease diagnostics and improved anthrax vaccines.

*B. anthracis* belongs to the *Bacillus cereus* group which includes the closely related *B. cereus, B. anthracis*, and *B. thuringiensis* species. *Bacillus cereus* strains can be potent food-borne pathogens, while *B. thuringiensis* are insect pathogens, and *B. anthracis* is the causative organism of anthrax. Although differentiation amongst *B. cereus, B. thuringiensis* and *B. anthracis* in practice is not difficult, the speed and specificity of confirmatory identification of virulent *B. anthracis* are of great importance in the context of bioterrorism preparedness and emergency response. This need is all the more pressing as the existence of non-pathogenic *B. anthracis* strains is well established and recent studies have shown the potential for *B. cereus* strains to harbor functional *B. anthracis* virulence genes (Hoffmaster et al., 2004, *Proc Natl Acad Sci* 101:8449-8454).

Thus, there is a need for improved diagnostic assays that can reliably identify anthrax in its early stages and quickly distinguish it from other flu-like or febrile illnesses. And, in view of the potential use of *B. anthracis* as a weapon in a bioterrorism attack, there is a need for improved vaccines.

SUMMARY OF THE INVENTION

The present invention includes a method of identifying *Bacillus anthracis*, the method including determining the glycosyl composition of a cell wall carbohydrate preparation, wherein a cell wall carbohydrate preparation from *B. anthracis* includes glucose (Glc), galactose (Gal), N-acetyl mannose (ManNAc), N-acetyl glucosamine (GlcNAc) and does not include N-acetylgalactosamine (GalNAc). The present invention includes a method of identifying *Bacillus anthracis*, the method including determining the glycosyl composition of a phosphate bound cell wall polysaccharide preparation, wherein a phosphate bound cell wall polysaccharide preparation from *B. anthracis* includes galactose (Gal), N-acetyl mannose (ManNAc) and N-acetyl glucosamine (GlcNAc) in a ratio of about 3:1:2. In some embodiments, the phosphate bound cell wall polysaccharide preparation is released from the cell wall by treatment with aqueous hydrogen fluoride (HF). The present invention includes a method of identifying a pathogenic *Bacillus cereus* strain, the method including determining the glycosyl composition of a phosphate bound cell wall polysaccharide preparation, wherein a phosphate bound cell wall polysaccharide preparation from a pathogenic strain of *B. cereus* includes galactose (Gal), N-acetyl mannose (ManNAc) and N-acetyl glucosamine (GlcNAc) in a ratio of about 3:1:1. In some embodiments, the phosphate bound cell wall polysaccharide preparation is released from the cell wall by treatment with aqueous hydrogen fluoride (HF).

The present invention includes a method of identifying *Bacillus anthracis* wherein a hydrogen fluoride released polysaccharide (HF-PS) from the vegetative cell wall of *B. anthracis* includes an amino sugar backbone of →6)-α-GlcNAc-(1→4)-β-ManNAc-(1→4)-β-GlcNAc-(1→. The present invention includes a method of identifying *B. anthracis* wherein a hydrogen fluoride released polysaccharide (HF-PS) from the vegetative cell wall of *B. anthracis* includes an amino sugar backbone of →6)-α-GlcNAc-(1→4)-β-ManNAc-(1→4)-β-GlcNAc-(1→, wherein the α-GlcNAc residue is substituted with α-Gal at O3, the α-GlcNAc residue is substituted with β-Gal at O4, and/or the β-GlcNAc is substituted with α-Gal at O3. The present invention includes a method of identifying *B. anthracis* wherein a hydrogen fluoride released polysaccharide (HF-PS) from the vegetative cell wall of *B. anthracis* includes one or more of the HF-PS related saccharide moieties as described herein.

The present invention includes an isolated oligosaccharide having the amino sugar backbone of →6)-α-GlcNAc-(1→4)-β-ManNAc-(1→4)-β-GlcNAc-(1→, wherein the α-GlcNAc residue is substituted with α-Gal at O3, the α-GlcNAc residue is substituted with 1-Gal at O4, and/or the β-GlcNAc is substituted with α-Gal at O3. Such an oligosaccharide may include a trisaccharide having a β-Gal-(1→4)-α-GlcNAc-(1→O) disaccharide, wherein the α-GlcNAc residue is substituted at O3 with an α-Gal residue and/or a trisaccharide having a β-ManNAc-(1→4)-β-GlcNAc-(1→O) disaccharide, wherein the β-GlcNAc is substituted at O3 with an α-Gal residue. The present invention includes a HF-PS oligosaccharide or HF-PS-related saccharide moiety as described herein. The present invention includes such an isolated oligosaccharide or saccharide moiety conjugated to a polypeptide. In some embodiments, the polypeptide is selected from the group consisting of keyhole limpet hemacyanin (KLH), protective antigen (PA), tetanus toxoid (TT), and bovine serum albumin (BSA).

The present invention includes an isolated oligosaccharide of HF-PS of *B. anthracis*. The present invention includes such an isolated oligosaccharide conjugated to a polypeptide. In some embodiments, the polypeptide is selected from the group consisting of keyhole limpet hemacyanin (KLH), protective antigen (PA), tetanus toxoid (TT), and bovine serum albumin (BSA).

The present invention includes an isolated oligosaccharide of HF-PS of *B. cereus* strain G9241. The present invention includes such an isolated oligosaccharide conjugated to a polypeptide. In some embodiments, the polypeptide is selected from the group consisting of keyhole limpet hemacyanin (KLH), protective antigen (PA), tetanus toxoid (TT), and bovine serum albumin (BSA).

The present invention includes diagnostic kits that included one or more isolated oligosaccharides, including an isolated oligosaccharides having the amino sugar backbone of →6)-α-GlcNAc-(1→4)-β-ManNAc-(1→4)-β-GlcNAc-(1→, wherein the α-GlcNAc residue is substituted with α-Gal at O3, the α-GlcNAc residue is substituted with β-Gal at O4, and/or the β-GlcNAc is substituted with O-Gal at O3; an isolated oligosaccharide of HF-PS of *B. anthracis*, related saccharide moieties thereof, and structurally related analogs thereof and/or an isolated oligosaccharide of HF-PS of *B. cereus* strain G9241, related saccharide moieties thereof, and structurally related analogs thereof.

The present invention includes an antibody that binds to the oligosaccharide →6)-α-GlcNAc-(1→4)-β-ManNAc-(1→4)-β-GlcNAc-(1→, wherein the α-GlcNAc residue is substituted with α-Gal at O3, the α-GlcNAc residue is substituted with β-Gal at O4, and/or the β-GlcNAc is substituted with α-Gal at O3.

The present invention includes a polyclonal antibody that binds to an isolated HF-PS oligosaccharide of *B. anthracis*, related saccharide moieties thereof, or structurally related analogs thereof, wherein the polyclonal antibody does not bind to vegetative cells or spores of *B. cereus* strain 10987.

The present invention includes a polyclonal antibody that binds to an isolated oligosaccharide of HF-PS of *B. anthracis*, related saccharide moieties thereof, or structurally related analogs thereof, wherein the polyclonal antibody does not bind to vegetative cells or spores of *B. cereus* strain 10987.

The present invention includes a monoclonal antibody that binds to an isolated oligosaccharide of HF-PS of *B. anthracis*, related saccharide moieties thereof, or structurally related analogs thereof.

The present invention includes a method of detecting *Bacillus anthracis* in a sample, the method including contacting the sample with one or more antibodies, wherein one or more antibodies includes an antibody that binds to the oligosaccharide →6)-α-GlcNAc-(1→4)-β-ManNAc-(1→4)-β-GlcNAc-(1→, wherein the α-GlcNAc residue is substituted with α-Gal at O3, the α-GlcNAc residue is substituted with β-Gal at O4, and/or the β-GlcNAc is substituted with α-Gal at O3; a polyclonal antibody that binds to an isolated HF-PS of *B. anthracis*, wherein the polyclonal antibody does not bind to vegetative cells or spores of *B. cereus* strain 10987; a polyclonal antibody that binds to an isolated oligosaccharide of HF-PS of *B. anthracis*, wherein the polyclonal antibody does not bind to vegetative cells or spores of *B. cereus* strain 10987; and/or a monoclonal antibody that binds to an isolated oligosaccharide of HF-PS of *B. anthracis*.

The present invention includes a method of treating or preventing anthrax in a subject, the method including administering one or more antibodies, wherein one or more antibodies includes an antibody that binds to the oligosaccharide →6)-α-GlcNAc-(1→4)-β-ManNAc-(1→4)-β-GlcNAc-(1→, wherein the α-GlcNAc residue is substituted with α-Gal at O3, the α-GlcNAc residue is substituted with β-Gal at O4, and/or the β-GlcNAc is substituted with α-Gal at O3; a polyclonal antibody that binds to an isolated HF-PS of *B. anthracis*, wherein the polyclonal antibody does not bind to vegetative cells or spores of *B. cereus* strain 10987; a polyclonal antibody that binds to an isolated oligosaccharide of HF-PS of *B. anthracis*, wherein the polyclonal antibody does not bind to vegetative cells or spores of *B. cereus* strain 10987; and/or a monoclonal antibody that binds to an isolated oligosaccharide of HF-PS of *B. anthracis*.

The present invention includes a diagnostic kit including one or more antibodies, wherein one or more antibodies includes an antibody that binds to the oligosaccharide →6)-α-GlcNAc-(1→4)-β-ManNAc-(1→4)-β-GlcNAc-(1→, wherein the α-GlcNAc residue is substituted with α-Gal at O3, the α-GlcNAc residue is substituted with β-Gal at O4, and/or the β-GlcNAc is substituted with α-Gal at O3; a polyclonal antibody that binds to an isolated HF-PS of *B. anthracis*, wherein the polyclonal antibody does not bind to vegetative cells or spores of *B. cereus* strain 10987; a polyclonal antibody that binds to an isolated oligosaccharide of HF-PS of *B. anthracis*, wherein the polyclonal antibody does not bind to vegetative cells or spores of *B. cereus* strain 10987; and/or a monoclonal antibody that binds to an isolated oligosaccharide of HF-PS of *B. anthracis*.

The present invention includes a method of detecting exposure to or infection with *Bacillus anthracis* in a subject, the method including detecting the presence of an antibody that binds to the oligosaccharide →6)-α-GlcNAc-(1→4)-β-ManNAc-(1→4)-β-GlcNAc-(1→, wherein the α-GlcNAc residue is substituted with α-Gal at O3, the α-GlcNAc residue is substituted with 3-Gal at O4, and/or the β-GlcNAc is substituted with α-Gal at O3.

The present invention includes a vaccine including an isolated oligosaccharide having the amino sugar backbone of →6)-α-GlcNAc-(1→4)-β-ManNAc-(1→4)-β-GlcNAc-(1→, wherein the α-GlcNAc residue is substituted with α-Gal at O3, the α-GlcNAc residue is substituted with e-Gal at O4, and/or the β-GlcNAc is substituted with α-Gal at O3. The present invention includes a vaccine including an isolated oligosaccharide having the amino sugar backbone of →6)-α-GlcNAc-(1→4)-β-ManNAc-(1→4)-β-GlcNAc-(1→, wherein the α-GlcNAc residue is substituted with α-Gal at O3, the α-GlcNAc residue is substituted with β-Gal at O4, and/or the β-GlcNAc is substituted with α-Gal at O3, and wherein the isolated oligosaccharide conjugated to a polypeptide. In some embodiments the polypeptide is selected from the group consisting of keyhole limpet hemacyanin (KLH), protective antigen (PA), tetanus toxoid (TT), and bovine serum albumin (BSA).

The present invention includes a method of treating or preventing anthrax, the method including administering an agent that inhibits the synthesis of the oligosaccharide →6)-α-GlcNAc-(1→4)-β-ManNAc-(1→4)-β-GlcNAc-(1→, wherein the α-GlcNAc residue is substituted with α-Gal at O3, the α-GlcNAc residue is substituted with β-Gal at O4, and/or the β-GlcNAc is substituted with α-Gal at O3. The present invention includes a method of synthesizing a HF-PS-related oligosaccharide, HF-PS-related saccharide moiety, or structurally related analogs thereof. The present invention includes an agent that inhibits the synthesis of a HF-PS-related oligosaccharide, HF-PS-related saccharide moiety, or structurally related analogs thereof. The present invention includes methods of treating or preventing anthrax, the method including administering an agent that inhibits the synthesis of a HF-PS-related oligosaccharide, HF-PS-related saccharide moiety, or structurally related analogs thereof.

The present invention includes an isolated trisaccharide having a β-Gal-(1→4)-α-GlcNAc-(1→O) disaccharide, wherein the α-GlcNAc residue is substituted at O3 with an α-Gal residue. The present invention includes an isolated trisaccharide having a β-ManNAc-(1→4)-β-GlcNAc-(1→O) disaccharide, wherein the β-GlcNAc is substituted at O3 with an α-Gal residue. Such trisaccharides may further have an aminopentyl spacer at the anomeric position. The present invention includes such isolated trisaccharides conjugated to a polypeptide. In some embodiments, the polypeptide is selected from the group consisting of keyhole limpet hemacyanin (KLH), protective antigen (PA), tetanus toxoid (TT), and bovine serum albumin (BSA). In some embodiments, the polypeptide may be conjugated to the trisaccharide via an aminopentyl spacer at the anomeric position. The present invention includes diagnostic kits that include one or more such isolated trisaccharides.

The present invention includes a vaccine including an isolated trisaccharide having a β-Gal-(1→4)-α-GlcNAc-(1→O) disaccharide, wherein the α-GlcNAc residue is substituted at O3 with an α-Gal residue, and/or an isolated trisaccharide having a β-ManNAc-(1→4)-β-GlcNAc-(1→O) disaccharide, wherein the β-GlcNAc is substituted at O3 with an α-Gal residue.

The present invention includes an antibody that binds to an isolated trisaccharide having a β-Gal-(1→4)-α-GlcNAc-(1→O) disaccharide, wherein the α-GlcNAc residue is substituted at O3 with an α-Gal residue. The present invention includes an antibody that binds to an isolated trisaccharide having a β-ManNAc-(1→4)-β-GlcNAc-(1→O) disaccharide, wherein the β-GlcNAc is substituted at O3 with an α-Gal residue. In some embodiments, the antibody is a polyclonal antibody. In some embodiments, the antibody is a monoclonal antibody.

The present invention includes a method of detecting *Bacillus anthracis* in a sample, the method including contacting the sample with an antibody that binds to an isolated trisaccharide having a β-Gal-(1→4)-α-GlcNAc-(1→O) disaccharide, wherein the α-GlcNAc residue is substituted at O3 with an α-Gal residue, and/or contacting the sample with an antibody that binds to an isolated trisaccharide having a β-ManNAc-(1→4)-β-GlcNAc-(1→O) disaccharide, wherein the β-GlcNAc is substituted at O3 with an α-Gal residue.

The present invention includes a method of treating or preventing anthrax in a subject, the method including administering an antibody that binds to an isolated trisaccharide having a β-Gal-(1→4)-α-GlcNAc-(1→O) disaccharide, wherein the α-GlcNAc residue is substituted at O3 with an α-Gal residue, and/or administering an antibody that binds to an isolated trisaccharide having a β-ManNAc-(1→4)-β-GlcNAc-(1→O) disaccharide, wherein the β-GlcNAc is substituted at O3 with an α-Gal residue.

The present invention includes a method of detecting exposure to or infection with *Bacillus anthracis* in a subject, the method including detecting the presence of an antibody that binds to an isolated trisaccharide having a β-Gal-(1→4)-α-GlcNAc-(1→O) disaccharide, wherein the α-GlcNAc residue is substituted at O3 with an α-Gal residue, and/or detecting the presence of an antibody that binds to an isolated trisaccharide having a β-ManNAc-(1→4)-β-GlcNAc-(1→O) disaccharide, wherein the β-GlcNAc is substituted at O3 with an α-Gal residue.

The present invention includes a method of treating or preventing anthrax, the method including administering an agent that inhibits the synthesis of an isolated trisaccharide having a β-Gal-(1→4)-α-GlcNAc-(1→O) disaccharide, wherein the α-GlcNAc residue is substituted at O3 with an α-Gal residue, and/or inhibits the synthesis of an isolated trisaccharide having a β-ManNAc-(1→4)-β-GlcNAc-(1→O) disaccharide, wherein the β-GlcNAc is substituted at O3 with an α-Gal residue.

The present invention includes a method of synthesizing an isolated trisaccharide having a β-Gal-(1→4)-α-GlcNAc-(1→O) disaccharide, wherein the α-GlcNAc residue is substituted at O3 with an α-Gal residue, and/or methods of synthesizing an isolated trisaccharide having a β-ManNAc-(1→4)-β-GlcNAc-(1→O) disaccharide, wherein the β-GlcNAc is substituted at O3 with an α-Gal residue.

The present invention includes an isolated anthrose oligosaccharide including 2-O-methyl-4-N-β-hydroxyisovaleryl-4,6-dideoxyglucose, anthrose variant 2, anthrose variant 3, or anthrose variant 4, related saccharide moieties thereof, and structurally-related analogs thereof. The present invention includes such isolated anthrose oligosaccharides conjugated to a polypeptide. In some embodiments, the polypeptide is selected from the group consisting of keyhole limpet hemacyanin (KLH), protective antigen (PA), tetanus toxoid (TT), and bovine serum albumin (BSA).

The present invention includes an anthrose trisaccharide including 2-O-methyl-4-N-β-hydroxyisovaleryl-4,6-dideoxyglucose, anthrose variant 2, anthrose variant 3, or anthrose variant 4. The present invention includes such isolated trisaccharides conjugated to a polypeptide. In some embodiments, the polypeptide is selected from the group consisting of keyhole limpet hemacyanin (KLH), protective antigen (PA), tetanus toxoid (TT), and bovine serum albumin (BSA).

The present invention includes an isolated anthrose monosaccharide including the isovaleryl portion of 2-O-methyl-4-N-β-hydroxyisovaleryl-4,6-dideoxyglucose, and variants thereof. The present invention includes such isolated monosaccharides conjugated to a polypeptide. In some embodiments, the polypeptide is selected from the group consisting of keyhole limpet hemacyanin (KLH), protective antigen (PA), tetanus toxoid (TT), and bovine serum albumin (BSA).

The present invention includes an isolated anthrose disaccharide including the isovaleryl portion of 2-O-methyl-4-(3-hydroxy-3-methylbutamido)-4,6-dideoxy-D-glucopyranose and variants thereof. The present invention includes such isolated disaccharides conjugated to a polypeptide. In some embodiments, the polypeptide is selected from the group consisting of keyhole limpet hemacyanin (KLH), protective antigen (PA), tetanus toxoid (TT), and bovine serum albumin (BSA).

The present invention includes an isolated BclA-OS oligosaccharide of *B. anthracis*, BclA-OS-related related saccharide moieties, structurally-related analogs thereof, and synthetic variants thereof. The present invention includes such isolated saccharide moieties conjugated to a polypeptide. In some embodiments, the polypeptide is selected from the group consisting of keyhole limpet hemacyanin (KLH), protective antigen (PA), tetanus toxoid (TT), and bovine serum albumin (BSA). The present invention includes a vaccine including one or more such conjugated oligosaccharides.

The present invention includes a diagnostic kit including one or more isolated oligosaccharides selected from an isolated anthrose oligosaccharide including 2-O-methyl-4-N-β-O-hydroxyisovaleryl-4,6-dideoxyglucose, anthrose variant 2, anthrose variant 3, or anthrose variant 4; an anthrose trisaccharide including 2-O-methyl-4-N-β-hydroxyisovaleryl-4,6-dideoxyglucose, anthrose variant 2, anthrose variant 3, or anthrose variant 4; an isolated anthrose monosaccharide including the isovaleryl portion of 2-O-methyl-4-N-β-hydroxyisovaleryl-4,6-dideoxyglucose, and variants thereof; an isolated anthrose disaccharide including the isovaleryl portion of 2-O-methyl-4-(3-hydroxy-3-methylbutamido)-4,6-dideoxy-D-glucopyranose and variants thereof; an isolated BclA-OS oligosaccharide of *B. anthracis* and synthetic variants thereof; and/or BclA-OS-related saccharide moieties, and synthetic variants thereof.

The present invention includes a vaccine including one or more of the isolated BclA-OS oligosaccharides and/or BclA-OS related saccharide moieties, and synthetic variants thereof.

The present invention includes an antibody that binds to an isolated oligosaccharide selected from an isolated anthrose oligosaccharide including 2-O-methyl-4-N-β-hydroxyisovaleryl-4,6-dideoxyglucose, anthrose variant 2, anthrose variant 3, or anthrose variant 4; an anthrose trisaccharide including 2-O-methyl-4-N-β-hydroxyisovaleryl-4,6-dideoxyglucose, anthrose variant 2, anthrose variant 3, or anthrose variant 4; an isolated anthrose monosaccharide including the isovaleryl portion of 2-O-methyl-4-N-β-hydroxyisovaleryl-4,6-dideoxyglucose, and variants thereof; an isolated anthrose disaccharide including the isovaleryl portion of 2-O-methyl-4-(3-hydroxy-3-methylbutamido)-4,6-dideoxy-D-glucopyranose and variants thereof; an isolated BclA-OS oligosaccharide of *B. anthracis* and synthetic variants thereof; and/or BclA-OS related saccharide moieties, and synthetic variants thereof. The present invention includes a method of detecting *Bacillus anthracis* spores in a sample, the method including contacting the sample with one or more such antibodies. The present invention includes a diagnostic kit including one or more such antibodies. The present invention includes a method of treating or preventing anthrax in a subject, the method including administering one or more such antibodies to the subject.

The present invention includes a polyclonal antibody that binds to an isolated BclA-OS of *B. anthracis*, wherein the polyclonal antibody does not bind to vegetative cells or spores of *B. cereus* strain 10987. The present invention includes a method of detecting *Bacillus anthracis* spores in a sample, the method including contacting the sample with one or more such antibodies. The present invention includes a diagnostic kit including one or more such antibodies. The present invention includes a method of treating or preventing anthrax in a subject, the method including administering one or more such antibodies to the subject.

The present invention includes a polyclonal antibody that binds to an isolated oligosaccharide of BclA-OS of *B. anthracis*, wherein the polyclonal antibody does not bind to vegetative cells or spores of *B. cereus* strain 10987. The present invention includes a method of detecting *Bacillus anthracis* spores in a sample, the method including contacting the sample with one or more such antibodies. The present invention includes a diagnostic kit including one or more such antibodies. The present invention includes a method of treating or preventing anthrax in a subject, the method including administering one or more such antibodies to the subject.

The present invention includes a monoclonal antibody that binds to an isolated oligosaccharide of BclA-OS of *B. anthracis*. The present invention includes a method of detecting *Bacillus anthracis* spores in a sample, the method including contacting the sample with one or more such antibodies. The present invention includes a diagnostic kit including one or more such antibodies. The present invention includes a method of treating or preventing anthrax in a subject, the method including administering one or more such antibodies to the subject.

The present invention includes a method of detecting exposure of a subject to *Bacillus anthracis*, the method including detecting the presence of an antibody that binds to binds to an isolated anthrose-containing saccharide, anthrose-related saccharide moiety, or structurally related analog thereof.

The present invention includes a method of synthesizing an anthrose-containing saccharide, anthrose-related saccharide moiety, and structurally related analogs thereof. The present invention includes an agent that inhibits the synthesis of an anthrose-containing saccharide, anthrose-related saccharide moiety, or structurally related analog thereof. The present invention includes methods of treating or preventing anthrax, the method including administering such an agent.

The present invention includes a diagnostic kit including as one element an isolated HF-PS-related oligosaccharide, saccharide-related moiety, or structurally related analog thereof, and as a second element an isolated an anthrose-containing saccharide, anthrose-related saccharide moiety, or structurally related analog thereof.

The present invention includes a diagnostic kit including as one element an antibody that binds to an isolated HF-PS-related oligosaccharide, saccharide-related moiety, or structurally related analog, and as a second element an antibody that binds to an anthrose-containing saccharide, anthrose-related saccharide moiety, or structurally related analog thereof.

The terms "comprises" and variations thereof do not have a limiting meaning where these terms appear in the description and claims. Unless otherwise specified, "a," "an," "the," and "at least one" are used interchangeably and mean one or more than one.

BRIEF DESCRIPTION OF THE FIGURES

FIG. 1A is a GC-MS sugar profile obtained from a *B. anthracis* Sterne cell wall sample. FIG. 1B is a GC-MS sugar profile obtained from a *B. anthracis* Sterne purified sample released from cell walls through HF treatment and purified on BioGel P2 columns. "1" identifies Gal; "2" identifies Glc; "3" identifies ManNAc; "4" identifies GlcNAc; "6" identifies Inositol (internal standard); and "7" identifies N-acetylmuramic acid.

FIG. 2A is a GC-MS sugar profile obtained from a *B. cereus* ATCC 10987 cell wall sample. FIG. 2B is a GC-MS sugar profile obtained from a *B. cereus* ATCC 10987 purified sample released from cell walls through HF treatment and purified on BioGel P2 columns. "1" identifies Gal; "2" identifies Glc; "3" identifies ManNAc; "4" identifies GlcNAc; "5" identifies GalNAc; "6" identifies Inositol (internal standard); and "7" identifies N-acetylmuramic acid.

FIG. 19A demonstrates that anti-live sterne spore serum recognizes *B. anthracis* HF-PS. FIG. 19B demonstrates that anti-*B. anthracis* Ames HF-PS-KLH serum recognizes *B. anthracis* Pasteur HF-PS-BSA.

FIG. 26A is a NMR spectra from Ba-Ames. FIG. 26B is a NMR spectra from Bc-G9241. FIG. 26C is a NMR spectra from Bc-BB87. FIG. 26D is a NMR spectra from Bc-BB102. The square blocks show conserved anomeric peaks present in both Ba and Bc strains, in respect to the Ba-Ames. The oval boundaries show peaks which are present in Bc strains but are not found in Ba-Ames HF-PS. All the Ba strains studied represent the same spectra as Ba-Ames shown here.

FIG. 27A is a MALDI-TOF mass spectra from Ba-Ames. FIG. 27B is a MALDI-TOF mass spectra from Bc-G9241. FIG. 27C is a MALDI-TOF mass spectra from Bc-BB87. FIG. 27D is a MALDI-TOF mass spectra from Bc-BB102. The samples were dissolved in water (10 μg/μl) and mixed with Super-DHB (1:1 v/v) and spotted on Stainless steel MALDI plate. The spectra were acquired on positive and reflectron mode.

FIG. 30 shows the synthetic HF-PS oligosaccharide structures that will be evaluated by ELISA inhibition. The tetrasaccharide backbone (in grey) will remain constant for all structures. Variation will occur in the terminal Gal residues (A, B, and C) as indicated.

FIGS. 42A-42C present an immuno-dot blot assay shown the binding of antiserum to *B. anthracis* HF-PS-KLH conjugate to the indicated amount (μg) of: (FIG. 42A) BSA, maltoheptaose, chemically synthesized AntRha$_2$ trisaccharide (labeled as Anthrose), and *B. anthracis* Sterne spores; (FIG. 42B) unconjugated and BSA-conjugated HF-PS from the indicated *B. anthracis* and *B. cereus* strains; and (FIG. 42C) cells and cell walls from the indicated *B. anthracis* and *B. cereus* strains.

DETAILED DESCRIPTION OF ILLUSTRATIVE EMBODIMENTS OF THE INVENTION

Figure 1:
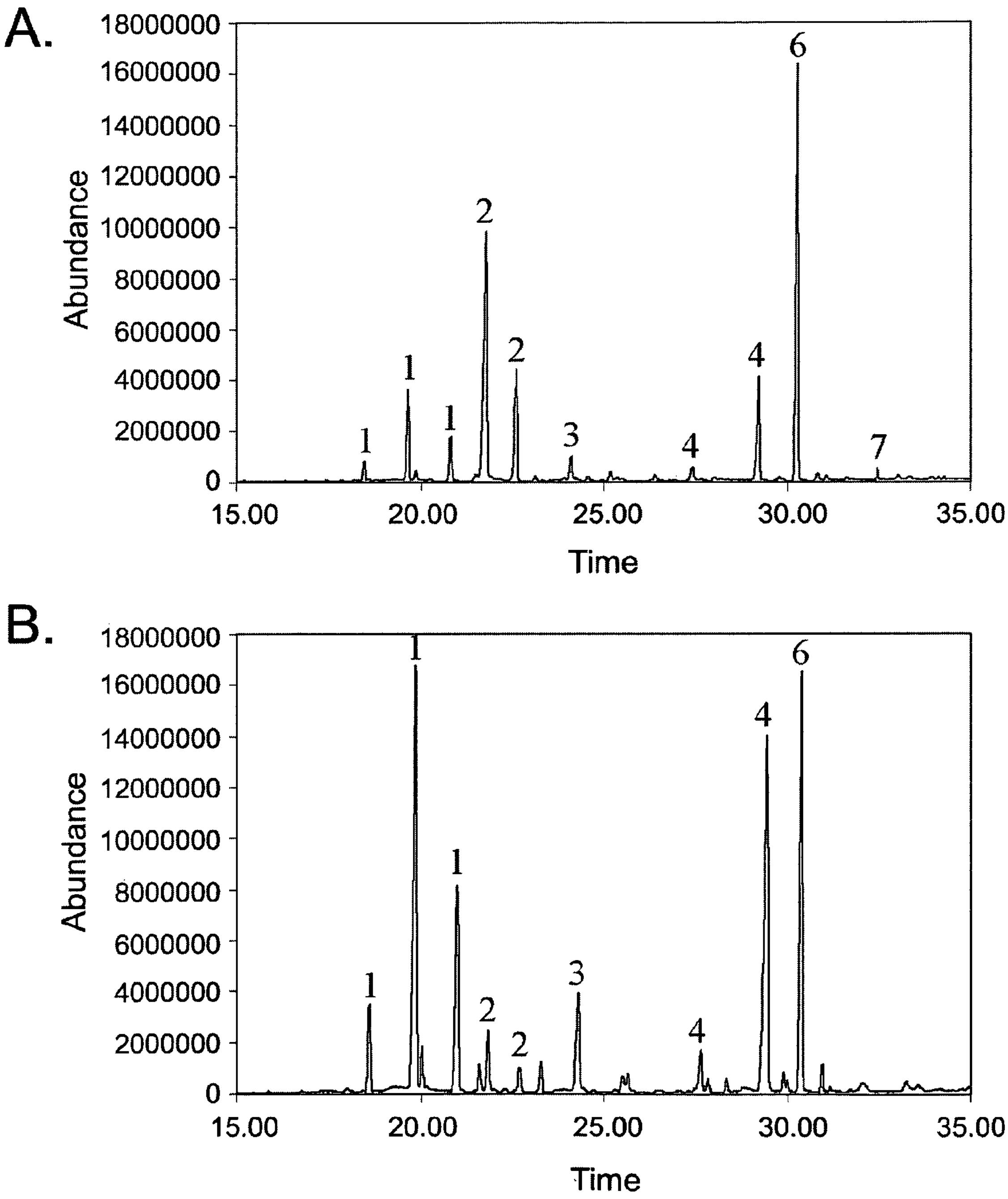
FIGS. 1A-1B show gas chromatographic-mass spectrometric (GC-MS) sugar profiles obtained from *B. anthracis* Sterne $34F_2$ vegetative cell walls after hydrolysis of the total cell wall preparations and derivatisation into trimethylsilyl (TMS) methylglycosides.

Anthrax is a disease of caused by the spore-forming bacterium *Bacillus anthracis*. The present invention includes the isolation, characterization, and synthesis of *B. anthracis* carbohydrates and various diagnostic and therapeutic applications.

The present invention includes methods of identifying *B. anthracis* by determining the glycosyl composition of a cell wall carbohydrate preparation. For example, the present invention includes methods of identifying *B. anthracis* by determining the glycosyl composition of a cell wall carbohydrate preparation, wherein a cell wall carbohydrate preparation from *B. anthracis* includes glucose (Glc), galactose (Gal), N-acetyl mannose (ManNAc), N-acetyl glucosamine (GlcNAc) and does not includes N-acetylgalactosamine (GalNAc). The present invention include methods of identifying *B. anthracis* by determining the glycosyl composition of a phosphate bound cell wall polysaccharide preparation, wherein a phosphate bound cell wall polysaccharide preparation from *B. anthracis* includes galactose (Gal), N-acetyl mannose (ManNAc) and N-acetyl glucosamine (GlcNAc) in a ratio of about 3:1:2. In some aspects, the phosphate bound cell wall polysaccharide preparation is released from the cell wall by treatment with aqueous hydrogen fluoride (HF). Determinations of the glycosyl composition of a cell wall carbohydrate preparation and/or a phosphate bound cell wall polysaccharide preparation, and ratios thereof, can be used in methods of determining the clade and/or lineage of a member the *B. cereus* group of species and in methods of identifying pathogenic members of the *Bacillus cereus* group.

The present invention describes the isolation, characterization, and synthesis of novel oligosaccharide structures that are present in vegetative cells of *B. anthracis*. These structures are specific to *B. anthracis* and differ from that of other closely related *Bacillus* species. These structures can be conjugated to protein carriers or chemically synthesized and conjugated to protein carriers, to be used as a vaccine antigen for the prevention of anthrax, as a moiety for the distinction of *B. anthracis* from other bacteria, and as a diagnostic tool to detect *B. anthracis* infections. This novel oligosaccharide is a hydrogen fluoride released polysaccharide (also referred to herein as "HF-PS") released from the vegetative cell wall of *B. anthracis* and has an amino sugar backbone of →6)-α-GlcNAc-(1→4)-β-ManNAc-(1→4)-β-GlcNAc-(1→. In some embodiments, the α-GlcNAc residue is substituted with α-Gal at O3, the α-GlcNAc residue is substituted with β-Gal at O4, and/or the β-GlcNAc is substituted with α-Gal at O3. The present invention includes an isolated oligosaccharide having the amino sugar backbone of →6)-α-GlcNAc-(1→4)-β-ManNAc-(1→4)-β-GlcNAc-(1→, wherein the α-GlcNAc residue is substituted with α-Gal at O3, the α-GlcNAc residue is substituted with β-Gal at O4, and/or the β-GlcNAc is substituted with α-Gal at O3. The present invention includes, but is no limited to, isolated monosaccharides, disaccharides, trisaccharides, and tetrasaccharides of this oligosaccharide, and synthetic analogs thereof. The present invention also includes polysaccharides that include repeating units such oligosaccharides, monosaccharides, disaccharides, trisaccharides, tetrasaccharides, or synthetic analogs.

For example, a saccharide moiety of the present invention includes, but is not limited to, any of the saccharide moieties presented in FIG. 9, FIG. 15, FIG. 16, FIG. 28, FIG. 30, FIG. 33, FIG. 34, FIG. 37, and FIG. 38, and any of the saccharide moieties described in Example 1, Example 2, Example 4, Example 5, and Examples 8-10.

The present invention includes isolated HF-PS saccharide moieties present on *B. anthracis*, including, but not limited to HF-PS saccharide moieties present on *B. anthracis* Ames, *B. anthracis* Pasteur, and/or *B. anthracis* Sterne, but not present on *B. cereus* strain ATCC 14579 and/or *B. cereus* strain ATCC 10987. As used herein, ATCC is the American Type American Type Culture Collection, P.O. Box 1549, Manassas, Va. 20108, USA. The present invention includes HF-PS saccharide moieties present on *B. anthracis*, for example, *B. anthracis* and present on pathogenic *B. cereus* strains G9241, BB87, and/or BB102, but not present on *B. cereus* strain ATCC 14579 and/or *B. cereus* ATCC strain 10987. The present invention includes HF-PS saccharide moieties present on *B. anthracis*, but not present on *B. cereus* strain G9241, and not present on *B. cereus* strain ATCC 14579 and/or *B. cereus* ATCC strain 10987. The present invention includes HF-PS saccharide moieties present on *B. cereus* strain G9241, but not present on present on *B. anthracis*, and not present on *B. cereus* strain ATCC 14579 and/or *B. cereus* ATCC strain 10987.

As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state. Preferably, a saccharide moiety of the present invention is purified, i.e., essentially free from any other carbohydrates or associated cellular products or other impurities.

Figure 33:
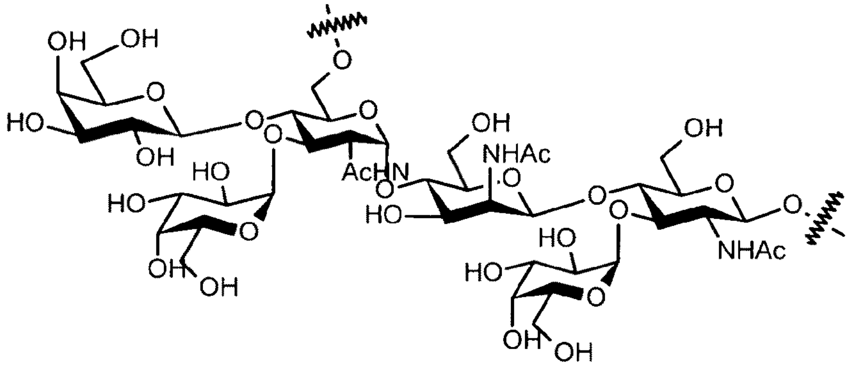
FIG. 33 presents the structure of the secondary cell wall polysaccharide of *B. anthracis* and synthetic compounds 1 and 2 of Example 10. Compound 1 is a trisaccharide having a β-Gal-(1→4)-α-GlcNAc-(1→O) disaccharide, wherein the α-GlcNAc residue is substituted at O3 with an α-Gal residue. Compound 2 is a trisaccharide having a β-ManNAc-(1→4)-β-GlcNAc-(1→O) disaccharide, wherein the β-GlcNAc is substituted at O3 with an α-Gal residue.
Figure 33:
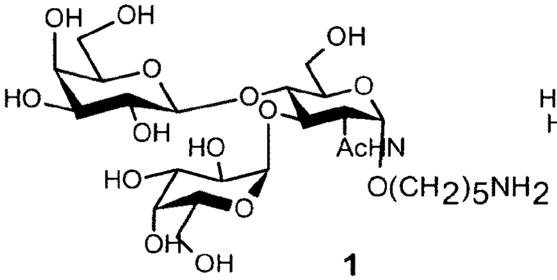
Figure 33:
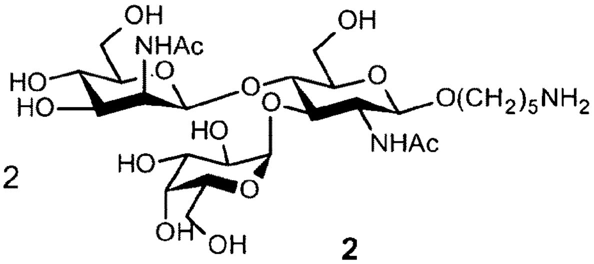

The present invention includes an isolated trisaccharide having a β-Gal-(1→4)-α-GlcNAc-(1→O) disaccharide, wherein the α-GlcNAc residue is substituted at O3 with an α-Gal residue. The present invention also includes an isolated trisaccharide having a β-ManNAc-(1→4)-β-GlcNAc-(1→O)

disaccharide, wherein the β-GlcNAc is substituted at O3 with an α-Gal residue. Such trisaccharides include, but are not limited to, compound 1 and compound 2, as shown in FIG. 33 (with or without the aminopentyl spacer at the anomeric position) and as described in Example 10. Such trisaccharides may further have an aminopentyl spacer at the anomeric position. The present invention includes such isolated trisaccharides conjugated to a polypeptide. In some embodiments, the polypeptide is selected from the group consisting of keyhole limpet hemacyanin (KLH), protective antigen (PA), tetanus toxoid (TT), and bovine serum albumin (BSA). In some embodiments, the polypeptide may be conjugated to the trisaccharide via an aminopentyl spacer at the anomeric position.

The present invention describes the isolation, characterization, and synthesis of a novel oligosaccharide structure from the *B. anthracis* spore exosporium coat, an oligosaccharide that is present on a collagen-like protein present in the exosporium, also referred to herein as "BclA-OS." This structure is specific to *B. anthracis* and different from that of other closely related *Bacillus* species. It can be conjugated to protein carriers or chemically synthesized and conjugated to protein carriers, to be used as a vaccine antigen for the prevention of anthrax, as a moiety for the distinction of *B. anthracis* from other bacteria, and as a diagnostic tool to detect *B. anthracis* infections.

The present invention includes the isolated oligosaccharide having 2-O-methyl-4-(3-hydroxy-3-methylbutamido)-4,6-dideoxy-D-glucopyranose (also called anthrose and also referred to herein as 2-O-methyl-4-N-β-hydroxyisovaleryl-4,6-dideoxyglucose and 4-N-β-hydroxyisovaleryl-4,6-dideoxyglucose) and isolated monosaccharides, disaccharides, trisaccharides, and tetrasaccharides of this oligosaccharide, and synthetic analogs thereof. The present invention includes isolated trisaccharides, disaccharides, and monosaccharides containing the antigenic terminal 4"-(3-methylbutyryl)-moiety of BclA-OS of *B. anthracis.*

The present invention also includes polysaccharides that include more than one repeating units of such oligosaccharides, monosaccharides, disaccharides, trisaccharides, tetrasaccharides, or synthetic analogs.

For example, a BclA-OS saccharide moiety of the present invention includes, but is not limited to, any of the saccharide moieties presented in FIG. 10, FIG. 12, FIG. 29, and FIG. 31, including the synthetic variants, and any of the saccharide moieties described in Example 3, Example 6, Example 7, and Example 9.

The present invention includes isolated BclA-OS saccharide moieties present on *B. anthracis*, including, but not limited to BclA-OS saccharide moieties present on *B. anthracis* Ames, *B. anthracis* Pasteur, and/or *B. anthracis* Sterne, and not present on *B. cereus* strain ATCC 14579 and/or *B. cereus* strain ATCC 10987.

As used herein, a carbohydrate contains one or more saccharide monomers. A carbohydrate may be a monosaccharide, an oligosaccharide, or a polysaccharide. As used herein, a monosaccharide is a single saccharide monomer. As used herein, an oligosaccharide is a polymeric saccharide that contains two or more saccharides and is characterized by a well-defined structure. A well-defined structure is characterized by the particular identity, order, linkage positions (including branch points), and linkage stereochemistry (α, β) of the monomers, and as a result has a defined molecular weight and composition. An oligosaccharide typically may contain about 2 to about 20 or more saccharide monomers. An oligosaccharide of the present invention includes, but is not limited to, a disaccharide, a trisaccharide, and a tetrasaccharide. The present invention includes any of the saccharide moieties described herein, including any of the monosaccharides, disaccharides, trisaccharides, tetrasaccharides, and oligosaccharides described herein.

The present invention also includes an isolated saccharide moiety, including, but not limited to, monosaccharide, disaccharide, trisaccharide, and tetrasaccharide moieties, and oligosaccharide structures as described herein conjugated to a carrier, such as, for example, a polypeptide carrier. Examples of polypeptide carriers include, but are not limited to, keyhole limpet hemacyanin (KLH), protective antigen (PA), tetanus toxoid (TT), bovine serum albumin (BSA), outer membrane protein complex of *Neiserria meningitides*, diptheria toxoid, Hepatitis B surface antigen, and/or Hepatitis B core antigen. Many such methods for conjugation are available to the skilled artisan. Such conjugates may be used, for example, in vaccines and as reagents in diagnostic kits. The present invention also includes an isolated saccharide moiety, including, but not limited to, monosaccharide, disaccharide, trisaccharide, and tetrasaccharide moieties, and oligosaccharide structures as described herein conjugated to an artificial spacer, such as, for example, an artificial aminopropyl spacer. Such an artificial spacer may be used to facilitate the conjugation to a carrier or other support substrate.

The present invention includes compositions including one or more of the isolated saccharide moieties as described herein, including, but not limited to, monosaccharide, disaccharide, trisaccharide, and tetrasaccharide moieties, and oligosaccharide structures as described herein. The present invention includes compositions including one or more of the saccharide moiety carrier conjugates, as described herein. The present invention includes compositions including one or more of the saccharide moieties conjugated to an artificial spacer, as describe herein.

The present invention includes vaccines including one or more of the isolated saccharide moieties and isolated oligosaccharides described herein. As used herein, the term a "vaccine" or "vaccine composition" refers to a pharmaceutical composition containing an antigen, such as one or more of the saccharide moieties described herein, where the composition can be used to prevent or treat a disease or condition in a subject. A vaccine of the present invention may include one or more isolated saccharide moieties of *B. anthracis* HF-PS, as described herein. A vaccine of the present invention may include one or more isolated saccharide moieties of a pathogenic strain of *B. cereus* HF-PS, such as, for example, *B. cereus* strain G9241, as described herein. A vaccine of the present invention may include isolated trisaccharides having a β-Gal-(1→4)-α-GlcNAc-(1→O) disaccharide, wherein the α-GlcNAc residue is substituted at O3 with an α-Gal residue and/or isolated trisaccharides having a β-ManNAc-(1→4)-β-GlcNAc-(1→O) disaccharide, wherein the β-GlcNAc is substituted at O3 with an α-Gal residue. A vaccine of the present invention may include one or more isolated saccharide moieties of *B. anthracis* BclA-OS, as described herein. A vaccine of the present invention may include a combination of two, three, four, five, six, seven, eight, nine, ten, or more of the various HF-PS and BclA-OS saccharide moieties described herein.

A vaccine of the present invention includes one or more of the isolated saccharide moieties described herein conjugated to a carrier, such as, for example, a polypeptide carrier. Examples of polypeptide carriers include, but are not limited to, keyhole limpet hemacyanin (KLH), protective antigen (PA), tetanus toxoid (TT), bovine serum albumin (BSA), outer membrane protein complex of *Neiserria meningitides*, diptheria toxoid, Hepatitis B surface antigen, and/or Hepatitis B core antigen. Many such methods for conjugation are available to the skilled artisan.

In one embodiment of the present invention, one or more saccharide moieties as described herein may be conjugated to PA. PA is part of the anthrax toxin complex and is a potent antigen. Combining PA with the saccharides and oligosaccharides of the present invention will be useful in directing the immune response to the toxin (via the PA antigen), the spores (via the BclA-OS saccharide moiety) and the cells (via the HF-PS saccharide moiety) of *B. anthracis*. This association with PA will make carbohydrates more immunogenic and provide an enhanced synergistic immune response to the PA antigen. The conjugate as a vaccine will provide an earlier and better immune response to *B. anthracis* spores and cells than do current vaccines. Conjugation to PA may offer a divalent vaccine that will protect against both the spore and vegetative forms of *B. anthracis*. A PA-carbohydrate conjugate antigen may act in concert against both the toxemia of anthrax and the spore or vegetative organism. Such a vaccine construct, when administered by a route that induces an IgA anti-spore response at the mucosal surface will provide an earlier immune intervention against inhalation anthrax. Likewise, such PA conjugates may also be used as diagnostic tools for the detection of both spores and vegetative cells.

Although capsular polysaccharides (CPSs) are often very poor immunogens, they have proven to be excellent molecules for the production of vaccines that are effective against many encapsulated strains of *Haemophilus influenzae, Neisseria meningitidis*, and *Streptococcus pneumoniae*. Current vaccines are conjugate vaccines, produced by coupling these polysaccharides to proteins, such as diphtheria toxoid, tetanus toxoid, or the outer membrane protein of non-typeable *Haemophilus influenzae*. Conjugate vaccines induce strong IgG antibody and memory responses and have proven very effective in preventing infections caused by these pathogens. Such vaccines often consist of multiple polysaccharide-protein conjugates forming a multivalent vaccine that covers the largest percentage of environmental serotypes. The *B. anthracis* saccharide-carrier conjugate vaccines of the present invention include, but are not limited to, monovalent, divalent, and multivalent conjugates.

The present invention includes saccharide moieties that represent synthetic oligosaccharide epitopes. Organic synthesis can provide carbohydrate epitopes in high purity and in relatively large amounts for controlled conjugation to a carrier protein. In this approach, synthetic saccharides may be equipped with an artificial spacer to facilitate the conjugation. A range of synthetic oligosaccharides can be used to determine the minimal epitope for a protective antibody response. These synthetic saccharides can also be employed to map ligand requirements of monoclonal antibodies raised against natural polysaccharides. Such synthetic carbohydrate-protein conjugates will allow the preparation of vaccine antigens without the complicating problems of chemical lability and structural heterogeneity of the natural polysaccharide projects. In addition chemical synthesis allows for the determination of the precise epitopes needed for the optimal immune response, and helps sort out the details of the structure/function relationships of the carbohydrate antigens.

The vaccines of the present invention may also include an adjuvant, including, but not limited to, an aluminum based adjuvant, such as, for example, aluminum phosphate, aluminum hydroxide, aluminum hydroxyl-phosphate, and aluminum hydroxyl-phosphate-sulfate, and non-aluminum adjuvants, such as, for example, QS21, Lipid-A, Freund's complete adjuvant, Freund's incomplete adjuvant, neutral liposomes, microparticles, cytokines, chemokines, and synthetic oligodeoxynucleotide (ODN) containing CpG motifs (CpG ODN) (Life Technologies, Grand Island, N.Y.).

A vaccine of the present invention may also include one or more additional antigens, for example, an additional *B. anthracis* antigen (such as, for example, PA), or an antigen from *Haemopholis influenza*, hepatitis virus A, B, or C, influenza virus types A or B, including, for example, the M2, hemaglutinin, and/or neuraminidase proteins of an influenza virus, human papilloma virus, measles, rubella, varicella, rotavirus, polio, *Streptococcus pneumonia*, and *Staphylococcus aureus*. Such additional antigens may be conjugated to any of the saccharides and oligosaccharides described herein.

The vaccines of the present invention may be formulated according to methods known and used in the art. The vaccines of the present invention may include salts, buffers, preservatives, or other substances designed to improve or stabilize the composition. The vaccines of the present invention may include a pharmaceutically acceptable excipient. The vaccine of the present invention may be administered to a subject by any of many different routes. For example, the vaccine may be administered intravenously, intraperitonealy, subcutaneously, intranasally, orally, transdermally, and/or intramuscularly. Suitable dosing regimes may be determined by taking into account factors well known in the art including, for example, the age, weight, sex, and medical condition of the subject; the route of administration; the desired effect; and the particular conjugate and formulation employed. The vaccine may be administered as either a single does or multiple doses. When administered in a multi-dose vaccination format, the timing of the doses may follow schedules known in the art. For example, after an initial administration, one or more booster doses may subsequently be administered to maintain antibody titers and/or immunologic memory.

The present invention includes methods of detecting or determining exposure of a subject to *B. anthracis*, to a pathogenic strain of *B. cereus*, and/or a nonpathogenic strain of *B. cereus*, the method including detecting the presence of an antibody that binds to a saccharide moiety as described herein. The present invention includes methods of distinguishing exposure to *B. anthracis* from exposure to a pathogenic strain of *B. cereus* or exposure to a nonpathogenic strain of *B. cereus*. The present invention includes methods of distinguishing exposure to a pathogenic strain of *B. cereus* from exposure to a nonpathogenic strain of *B. cereus*, the method including detecting the presence of an antibody that binds to a saccharide moiety as described herein. Antibodies may be detected in samples obtained from the subject, including a biological sample, such as, for example, a tissue or fluid sample isolated from a subject, including but not limited to, for example, blood, plasma, serum, fecal matter, urine, bone marrow, bile, spinal fluid, lymph tissue and lymph fluid, samples of the skin, external secretions of the skin, respiratory, intestinal, and genitourinary tracts, tears, saliva, milk, blood cells, organs, and biopsies. The present invention includes diagnostic kits containing one or more of the isolated saccharide moieties described herein. The saccharides moieties may be labeled with one or more of the detectable markers known to the skilled artisan. In some aspects, a saccharide moiety may be bound to a solid substrate. A saccharide moiety may be included as positive and/or negative controls in antibody based detection methods and kits. Saccharide moieties include, but are not limited to, one or more isolated saccharide moieties of *B. anthracis* HF-PS as described herein, one or more isolated saccharide moieties of a pathogenic strain of *B. cereus* HF-PS as described herein, such as, for example, *B. cereus* strain G9241, and/or one or more isolated saccharide moieties of *B. anthracis* BclA-OS as described herein. A combination of two, three, four, five, six, seven, eight, nine, ten, or more of the various HF-PS and BclA-OS saccharide moieties described herein, may be included in a diagnostic methods or kit of the present invention.

The present invention includes antibodies that bind to the isolated saccharide moieties described herein. Antibodies of the present invention may be, for example, polyclonal, monoclonal, humanized, chimeric, or single chain. As used herein the terms "antibodies" or "antibody" are used interchangeably.

The present invention includes polyclonal antibodies that are generated by immunization with one of the isolated *B. anthracis* HF-PS or BclA-OS saccharide moieties, as described herein. Such a saccharide moiety may be conjugated to a carrier polypeptide. Such a polyclonal antibody will demonstrate a binding specificity to the immunizing *B. anthracis* HF-PS or BclA-OS saccharide moiety but will not bind to the HF-PS or BclA-OS saccharide moiety, spores or vegetative cells of a nonpathogenic *B. cereus* strain, such as, for example, *B. cereus* strain ATCC 14579 or *B. cereus* strain ATCC 10987.

In some embodiments, an antibody preparation may bind to vegetative cells of *B. anthracis* Ames. In some embodiments, an antibody preparation may not bind to vegetative cells of *B. anthracis* Ames. In some embodiments, an antibody preparation may bind to spores of *B. anthracis* Ames. In some embodiments, an antibody preparation may not bind to spores of *B. anthracis* Ames. As used herein, "spores" includes both ungerminated and ungerminated spores.

An antibody the binds to spores may bind to both ungerminated and germinated spores, may bind to ungerminated spores but not bind to germinated spores, or may bind to germinated spores and not bind to ungerminated spores. In some embodiments, an antibody preparation may bind to both vegetative cells of *B. anthracis* Ames and spores of *B. anthracis* Ames. In some embodiments, an antibody preparation may bind to vegetative cells of *B. anthracis* Ames, but not bind to spores of *B. anthracis* Ames. In some embodiments, an antibody preparation may not bind to vegetative cells of *B. anthracis* Ames, but bind to spores of *B. anthracis* Ames.

The present invention includes monoclonal antibodies that bind to an isolated *B. anthracis* HF-PS or BclA-OS saccharide moiety as described herein. In some embodiments, such a monoclonal antibody may bind to an isolated HF-PS saccharide moiety from *B. anthracis*, including, but not limited to the isolated HF-PS saccharide moiety from *B. anthracis* Ames, *B. anthracis* Pasteur, and/or *B. anthracis* Stern. In some embodiments, such a monoclonal antibody may bind to intact *B. anthracis* vegetative cells or spores. In some embodiments, such a monoclonal antibody may not bind to intact *B. anthracis* vegetative cells or spores. In some embodiments, such a monoclonal antibody does not bind to intact *B. cereus* strain ATCC 14579 or *B. cereus* strain ATCC 10987 vegetative cells or spores and does not bind isolated HF-PS from *B. cereus* strains ATCC 14579 or ATCC 10987. In some embodiments, such a monoclonal antibody also binds to intact *B. cereus* strain G9241, BB87, and/or BB102 vegetative cells or spores or binds to isolated HF-PS from the pathogenic *B. cereus* strains G9241, BB87, and/or BB102. In some embodiments, such a monoclonal antibody does not bind to intact *B. cereus* strain G9241, BB87, and/or BB102 vegetative cells or spores or does not bind to isolated HF-PS from *B. cereus* strains G9241, BB87, and/or BB102.

The present invention includes monoclonal antibodies that bind to an isolated HF-PS saccharide moiety from the pathogenic *B. cereus* strains that cause severe or fatal pneumonia, including, for example, *B. cereus* strains G9241, BB87, and/or BB102. Such a monoclonal antibody may or may not bind intact *B. cereus* strain G9241, BB87, and/or BB102 vegetative cells or spores. Such an antibody does not bind to an isolated HF-PS saccharide moiety from *B. anthracis* Ames, *B. anthracis* Pasteur, and/or *B. anthracis* Sterne and does not bind to intact *B. anthracis* vegetative cells or spores.

The present invention includes an antibody that binds to an isolated trisaccharide having a β-Gal-(1→4)-α-GlcNAc-(1→O) disaccharide, wherein the α-GlcNAc residue is substituted at O3 with an α-Gal residue. The present invention includes an antibody that binds to an isolated trisaccharide having a β-ManNAc-(1→4)-β-GlcNAc-(1→O) disaccharide, wherein the β-GlcNAc is substituted at O3 with an α-Gal residue. In some embodiments, the antibody is a polyclonal antibody. In some embodiments, the antibody is a monoclonal antibody.

The present invention includes monoclonal antibodies that bind to an isolated BclA-OS saccharide moiety as described herein. In some embodiments, such a monoclonal antibody may bind to an isolated BclA-OS saccharide moiety from *B. anthracis*, including, but not limited to the isolated BclA-OS saccharide moiety from *B. anthracis* Ames, *B. anthracis* Pasteur, and/or *B. anthracis* Sterne. Such an antibody may or may not bind to intact *B. anthracis* vegetative cells or spores. In some embodiments, such a monoclonal antibody does not bind to intact *B. cereus* strain ATCC 14579 or *B. cereus* strain ATCC 10987 vegetative cells or spores. In some embodiments, such a monoclonal antibody does not bind the BclA-OS saccharide moiety isolated from *B. cereus* strains ATCC 14579 or ATCC 10987.

The antibodies of the present invention include various antibody fragments, also referred to as antigen binding fragments, which include only a portion of an intact antibody, generally including an antigen binding site of the intact antibody and thus retaining the ability to bind antigen. Examples of antibody fragments include, for example, Fab, Fab', Fd, Fd', Fv, dAB, and $F(ab')_2$ fragments produced by proteolytic digestion and/or reducing disulfide bridges and fragments produced from an Fab expression library. Such antibody fragments can be generated by techniques well known in the art. Antibodies of the present invention can include the variable region(s) alone or in combination with the entirety or a portion of the hinge region, CH1 domain, CH2 domain, CH3 domain and/or Fc domain(s).

Antibodies include, but are not limited to, polyclonal antibodies, affinity-purified polyclonal antibodies, monoclonal antibodies, human antibodies, humanized antibodies, chimeric antibodies, anti-idiotypic antibodies, multispecific antibodies, single chain antibodies, single-chain Fvs (scFv), disulfide-linked Fvs (sdFv), Fab fragments, F(ab') fragments, $F(ab')_2$ fragments, Fv fragments, diabodies, linear antibodies fragments produced by a Fab expression library, fragments comprising either a VL or VH domain, intracellularly-made antibodies (i.e., intrabodies), and antigen-binding antibody fragments thereof.

The antibodies of the present invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Immunoglobulins can have both heavy and light chains. An array of IgG, IgE, IgM, IgD, IgA, and IgY heavy chains can be paired with a light chain of the kappa or lambda form.

The antibodies of the invention can be from any animal origin, including birds and mammals. In some embodiments, the antibodies are human, murine, rat, donkey, sheep, rabbit, goat, guinea pig, camel, horse, or chicken antibodies. As used herein, “human” antibodies include antibodies having the amino acid sequence of a human immunoglobulin and include antibodies isolated from human immunoglobulin libraries or from animals transgenic for one or more human immunoglobulins.

The term “polyclonal antibody” refers to an antibody produced from more than a single clone of plasma cells. In contrast “monoclonal antibody” refers to an antibody produced from a single clone of plasma cells. The preparation of polyclonal antibodies is well known. Polyclonal antibodies may be obtained by immunizing a variety of warm-blooded animals such as horses, cows, goats, sheep, dogs, chickens, rabbits, mice, hamsters, guinea pigs and rats as well as transgenic animals such as transgenic sheep, cows, goats or pigs, with an immunogen. The resulting antibodies may be isolated from other proteins by using an affinity column having an Fc binding moiety, such as protein A, or the like.

Monoclonal antibodies can be obtained by various techniques familiar to those skilled in the art. For example, spleen cells from an animal immunized with a desired antigen are immortalized, commonly by fusion with a myeloma cell. Monoclonal antibodies can be isolated and purified from hybridoma cultures by techniques well known in the art. Other known methods of producing transformed B cell lines that produce monoclonal antibodies may also be used. In some embodiments, the antibody can be recombinantly produced, for example, produced by phage display or by combinatorial methods. Such methods can be used to generate human monoclonal antibodies.

A therapeutically useful antibody may be derived from a “humanized” monoclonal antibody. Humanized monoclonal antibodies are produced by transferring one or more CDRs from the heavy and light variable chains of a mouse (or other species) immunoglobulin into a human variable domain, then substituting human residues into the framework regions of the murine counterparts. The use of antibody components derived from humanized monoclonal antibodies obviates potential problems associated with immunogenicity of murine constant regions. The present invention includes, for example, antibodies with all of the CDR regions of an anti-saccharide antibody, all of the heavy chain CDRs of an anti-saccharide antibody, or all of the CDR regions of the light chain of an anti-saccharide antibody, wherein the humanized antibody retains the anti-saccharide binding specificity. The constant region of a humanized monoclonal antibody of the present invention can be that from human immunoglobulin belonging to any isotype. It may be, for example, the constant region of human IgG.

Antibodies of the present invention include chimeric antibodies. A chimeric antibody is one in which different portions are derived from different animal species. For example, chimeric antibodies can be obtained by splicing the genes from a mouse antibody molecule with appropriate antigen specificity together with genes from a human antibody molecule of appropriate biological specificity.

Antibodies of the present invention can be produced by an animal, chemically synthesized, or recombinantly expressed. Antibodies of the present invention can be purified by any method known in the art for purification of an immunoglobulin molecule, for example, by chromatography (e.g., ion exchange, affinity, and sizing column chromatography), centrifugation, differential solubility, or by any other standard technique for the purification of proteins.

Antibodies of the present invention can be assayed for immunospecific binding by the methods described herein and by any suitable method known in the art. The immunoassays that can be used include but are not limited to competitive and non-competitive assay systems using techniques such as BIAcore analysis, FACS (Fluorescence activated cell sorter) analysis, immunofluorescence, immunocytochemistry, Western blots, radio-immunoassays, ELISA (enzyme linked immunosorbent assay), “sandwich” immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see e.g., Ausubel et al, Eds, 1994, *Current Protocols in Molecular Biology, Vol.* 1, John Wiley & Sons, Inc., N.Y.).

Also included in the present invention are hybridoma cell lines, transformed B cell lines, and host cells that produce the monoclonal antibodies of the present invention; the progeny or derivatives of these hybridomas, transformed B cell lines, and host cells; and equivalent or similar hybridomas, transformed B cell lines, and host cells.

The present invention further provides an isolated polynucleotide molecule having a nucleotide sequence encoding a monoclonal antibody of the invention. The present invention is further directed to an isolated polynucleotide molecule having a nucleotide sequence that has at least 75%, at least 80%, at least 85%, at least 90%, at least 95%, at least 96%, at least 97%, at least 98%, or at least 99% sequence identity to nucleotide sequence encoding a monoclonal antibody of the invention. The invention also encompasses polynucleotides that hybridize under high stringency to a nucleotide sequence encoding an antibody of the invention, or a complement thereof. As used herein “stringent conditions” refer to the ability of a first polynucleotide molecule to hybridize, and remain bound to, a second, filter-bound polynucleotide molecule in 0.5 M $NaHPO_4$, 7% sodium dodecyl sulfate (SDS), and 1 mM EDTA at 65° C., followed by washing in 0.2×SSC/0.1% SDS at 42° C. (see Ausubel et al. (eds.), Current Protocols in Molecular Biology, Vol. 1, Green Publishing Associates, Inc., and John Wiley & Sons, Inc., N.Y. (1989), at p. 2.10.3). Also included in the present invention are polynucleotides that encode one or more of the CDR regions or the heavy and/or light chains of a monoclonal antibody of the present invention. General techniques for cloning and sequencing immunoglobulin variable domains and constant regions are well known. See, for example, Orlandi et al., 1989*, Proc. Nat'l Acad. Sci. USA* 86: 3833.

The present invention also includes recombinant vectors including an isolated polynucleotide of the present invention. The vector can be, for example, in the form of a plasmid, a viral particle, or a phage. The appropriate DNA sequence can be inserted into a vector by a variety of procedures. In general, the DNA sequence is inserted into an appropriate restriction endonuclease site(s) in a vector by procedures known in the art. Such procedures are deemed to be within the scope of those skilled in the art. Large numbers of suitable vectors and promoters are known to those of skill in the art, and are commercially available. The following vectors are provided by way of example. Bacterial vectors include, for example, pQE70, pQE60, pQE-9, pBS, pD10, phagescript, psiX174, pbluescript SK, pbsks, pNH8A, pNH16a, pNH18A, pNH46A, ptrc99a, pKK223-3, pKK233-3, pDR540, and pRIT5. Eukaryotic vectors include, for example, pWLNEO, pSV2CAT, pOG44, pXT1, pSG, pSVK3, pBPV, pMSG, and pSVL. However, any other plasmid or vector can be used.

The present invention also includes host cells containing the above-described vectors. The host cell can be a higher eukaryotic cell, such as a mammalian or insect cell, or a lower eukaryotic cell, such as a yeast cell. Or, the host cell can be a prokaryotic cell, such as a bacterial cell, or a plant cell. Introduction of a vector construct into the host cell can be effected by any suitable techniques, such as, for example, calcium phosphate transfection, DEAE-Dextran mediated transfection, or electroporation.

Also included in the present invention are phage display libraries expressing one or more hypervariable regions from a monoclonal antibody of the present invention, and clones obtained from such a phage display library. A phage display library is used to produce antibody derived molecules. Gene segments encoding the antigen-binding variable domains of antibodies are fused to genes encoding the coat protein of a bacteriophage. Bacteriophage containing such gene fusions are used to infect bacteria, and the resulting phage particles have coats that express the antibody-fusion protein, with the antigen-binding domain displayed on the outside of the bacteriophage. Phage display libraries can be prepared, for example, using the Ph.D.™-7 Phage Display Peptide Library Kit (Catalog #E8100S) or the Ph.D.™-12 Phage Display Peptide Library Kit (Catalog #E8110S) available from New England Biolabs Inc., Ipswich, Mass.

The monoclonal antibodies of the present invention may be coupled directly or indirectly to a detectable marker by techniques well known in the art. A detectable marker is an agent detectable, for example, by spectroscopic, photochemical, biochemical, immunochemical, or chemical means. Useful detectable markers include, but are not limited to, fluorescent dyes, chemiluminescent compounds, radioisotopes, electron-dense reagents, enzymes, colored particles, biotin, or dioxigenin. A detectable marker often generates a measurable signal, such as radioactivity, fluorescent light, color, or enzyme activity. Antibodies conjugated to detectable agents may be used for diagnostic or therapeutic purposes. Examples of detectable agents include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody or indirectly, through an intermediate such as, for example, a linker known in the art, using techniques known in the art. Examples of suitable enzymes include horseradish peroxidase, alkaline phosphatase, beta-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferin, and aequorin; and examples of suitable radioactive material include iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{131}$mIn, $^{115}$mIn), technetium ($^{99}$Tc, $^{99}$mTc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru. Techniques for conjugating such therapeutic moieties to antibodies are well-known.

Included in the present invention are compositions of one or more of the antibodies of the present invention. A composition may also include, for example, buffering agents to help to maintain the pH in an acceptable range or preservatives to retard microbial growth. Such compositions may also include a pharmaceutically acceptable carrier. The compositions of the present invention are formulated in pharmaceutical preparations in a variety of forms adapted to the chosen route of administration. Formulations include those suitable for parental administration or for perfusion. The term "pharmaceutically acceptable," as used herein, means that the compositions or components thereof so described are suitable for administration to a subject without undue toxicity, incompatibility, instability, allergic response, and the like.

The present invention includes methods of treating or preventing anthrax in a subject by the administration of one or more of the antibodies described herein. Such methods for the passive administration of antibodies are well known. Such antibodies may be polyclonal and/or monoclonal. In some applications, a cocktail of antibodies may be administered; a cocktail of more than one of the antibodies described herein and/or other available antibodies. As used herein "treating" or "treatment" can include both therapeutic and prophylactic treatments. Desirable effects of treatment include preventing occurrence or recurrence of disease, alleviation of symptoms, diminishing any direct or indirect pathological consequences of the disease, decreasing the rate of disease progression, amelioration or palliation of the disease state, and remission or improved prognosis. A subject or patient, as used herein, can be either human or nonhuman, including for example, a human, a higher primate, a non-human primate, domestic livestock and domestic pets (such as dogs, cats, cattle, horses, pigs, sheep, goats, mules, and donkeys) laboratory animals (such as mice, rats, hamsters, guinea pigs, and rabbits), and wild life.

The present invention includes methods of detecting *B. anthracis* and/or *B. cereus* vegetative cells or spores in a biological or environmental sample by contacting the sample with one or more of the antibodies described herein. As used herein, a biological sample refers to a sample of tissue or fluid isolated from a subject, including but not limited to, for example, blood, plasma, serum, fecal matter, urine, bone marrow, bile, spinal fluid, lymph tissue and lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

Such a method may distinguish between *B. anthracis*, and other *Bacillus* species. Such a method may distinguish between *B. anthracis* and *B. cereus*. Such a method may distinguish between *B. anthracis* and a nonpathogenic strain of *B. cereus*. Such a method may distinguish between *B. anthracis* and a pathogenic strain of *B. cereus*. Such a method may distinguish between a pathogenic strain of *B. cereus* and a nonpathogenic strain of *B. cereus*. A single antibody as described herein may be used. A combination of two, three, four, five, six, seven, eight, nine, ten, or more of the various antibodies as described herein may be used in a diagnostic methods or kit of the present invention. A combination may be a cocktail of antibodies. A combination may be the use of several antibodies, each with a unique binding specificity, each used in a separate step or compartment of a detection assay. A combination includes a combination of different monoclonal antibodies, a combination of polyclonal antibodies, and a combination of monoclonal antibodies and polyclonal antibodies.

The present invention includes diagnostic kits containing one or more of the antibodies described herein. The antibodies may be labeled with one or more of the detectable markers known to the skilled artisan. In some aspects, the antibodies may be bound to a solid substrate.

The present invention includes diagnostic kits containing one or more of the isolated saccharide or oligosaccharide moieties described herein, and one or more of the antibodies described herein. The antibodies and/or saccharide moieties may be labeled with one or more of the detectable markers known to the skilled artisan. In some aspects, the antibodies and/or saccharide moieties may be bound to a solid substrate.

Diagnostic kits of the present invention may include other reagents such as buffers and solutions needed to practice the invention are also included. Optionally associated with such container(s) can be a notice or printed instructions. As used herein, the phrase "packaging material" refers to one or more physical structures used to house the contents of the kit. The packaging material is constructed by well known methods, preferably to provide a sterile, contaminant-free environment. As used herein, the term "package" refers to a solid matrix or material such as glass, plastic, paper, foil, and the like, capable of holding within fixed limits a polypeptide. Diagnostic kits of the present invention may also include instructions for use. Instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

The present invention includes the methods of synthesizing the *B. anthracis* HF-PS and BclA-OS saccharides, as described herein. The present invention also includes agents that inhibit such synthesis of the *B. anthracis* HF-PS and BclA-OS saccharides described herein. Antibiotics are the current therapeutic treatment for *B. anthracis*. Other types of therapeutic agents, including antibodies and antitoxin agents, are being investigated. The biosynthetic pathways of bacterial cell wall components that are crucial for the viability or virulence of a bacterium are also useful targets for the development of therapeutics (Clements et al., 2002, *Antimicrob Agents Chemother* 46:1793-1799; Ma et al., 2001, *Antimicrob Agents Chemother* 45:1407-1416). The present invention includes inhibitors of the biosynthesis of such cell wall carbohydrates of *B. anthracis* for use as therapeutics agents. The present invention includes agents that modulate the synthesis of the saccharide moieties and oligosaccharides described herein. In some aspects, modulation includes the inhibition of the rate or the yield of synthesis. In some aspect, modulation includes an enhanced rate or yield of synthesis. The present invention includes methods of treating or preventing anthrax by the administration of one or more such agents.

The present invention is illustrated by the following examples. It is to be understood that the particular examples, materials, amounts, and procedures are to be interpreted broadly in accordance with the scope and spirit of the invention as set forth herein.

EXAMPLES

Example 1

Cell Wall Carbohydrate Compositions of Strains from the *B. cereus* Group of Species Correlate with Phylogenetic Relatedness The *Bacillus cereus* group of bacteria is comprised of the closely related species *B. cereus, B. anthracis*, and *B. thuringiensis. Bacillus cereus* strains can be potent opportunistic pathogens, while *B. thuringiensis* is an insect pathogen, and *B. anthracis* is the causative organism of anthrax. The distribution of *B. anthracis* spores in the US mail system in 2001 demonstrated their potential as a bioterrorist weapon. Although differentiation amongst *B. cereus, B. thuringiensis* and *B. anthracis* in practice is not difficult, the speed and specificity of confirmatory identification of virulent *B. anthracis* are of great importance in the context of bioterrorism preparedness and emergency response. In particular, there is a need for diagnostic tools based on the immunological response since this response has potential for great clinical sensitivity by virtue of amplifying the host systemic response to a low level of infection. This need is all the more pressing as the existence of non-pathogenic *B. anthracis* strains is well established and recent studies have shown the potential for *B. cereus* strains to harbor functional *B. anthracis* virulence genes (Hoffmaster, et al., 2004, *Proc. Natl. Acad. Sci.,* 101: 8449-8454).

Traditionally, *Bacillus* species have been differentiated based on their phenotypic and biochemical characteristics. Recently, molecular methods of classification have become more prevalent. These methods include fluorescent heteroduplex analysis (Merrill et al., 2003, *Appl Environ. Microbiol.,* 69:3317-3326), single-strand conformational polymorphism analysis (Borin and Daffonchio, 1997, *FEMS Microbiol. Lett.,* 157:87-93), multilocus enzyme electrophoresis (Helgason et al., 1998, *Curr. Microbiol.,* 37:80-87), variable-number tandem repeat analysis (Keim et al., 2000, *J. Bacteriol.,* 182: 2928-2936; Kim et al., 2002, *FEMS Microbiol. Lett.,* 207:21-27), multi-locus sequence typing (MLST) analysis (Barker et al., 2005, *FEMS Microbiol. Lett.,* 245:179-184; Helgason et al., 2004, *Appl. Environ. Microbiol.,* 70:191-201; Ko et al., 2004, *Infect. Immun.,* 72:5253-5261; Priest et al., 2004, *J. Bacteriol.,* 186:7959-7970), and amplified fragment length polymorphism (Han et al., 2006, *J. Bacteriol.,* 188:3382-3390; Ticknor et al., 2001, *Appl. Environ. Microbiol.,* 67:4863-4873). These classification methods have been used to re-group *Bacillus* strains. The phylogenetic picture that is emerging from these studies for strains of *B. cereus* is only partially in accordance with the more traditional classification scheme. For example, the *B. cereus* group strains have traditionally been classified as three species; *B. cereus, B. thuringiensis*, and *B. anthracis* whereas fluorescent heteroduplex analysis places these species in only two subgroups (Merrill et al., 2003, *Appl. Environ. Microbiol.,* 69:3317-3326). These recent findings, as well as those based on comparative *Bacillus* species genome analyses, have altered the more traditional *Bacillus* taxonomic groupings (Read et al., 2003, *Nature,* 423:81-86).

A study published in 2005 (Barker et al., 2005, *FEMS Microbiol. Lett.,* 245:179-184) used MLST analyses to evaluate the phylogeny of invasive *B. cereus* isolated from clinical infections. The study showed that pathogenic strains were not restricted to a single clonal group or lineage but were genomically diverse and related to strains traditionally grouped as *B. anthracis, B. cereus*, or *B. thuringiensis*. Also using MLST, the same laboratory reported separately that a collection of *B. cereus* group strains representing 59 sequence types could be assigned to 3 clades and 9 lineages (Priest et al., 2004, *J. Bacteriol.,* 186:7959-7970). This grouping was particularly interesting since it showed that all *B. cereus* group strains obtained from human or animal infections, including anthrax and bacterial pneumonia, are closely related to each other. Although it is possible to readily differentiate *B. anthracis* from *B. cereus* using phenotypic and biochemical test systems (Ticknor et al., 2001, *Appl. Environ. Microbio;* 67:4863-4873), most of the tests, including modern techniques, fail to recognize the pathogenic potential and rely on advanced systemic infection (culture isolation, immunohistochemistry, and PCR). Since current methods used for rapid identification of *B. anthracis* rely on detection of plasmid encoded genetic elements that can distinguish *B. anthracis* from other members of the *B. cereus* group (Hoffmaster, et al., 2004, *Proc. Natl. Acad. Sci;* 101:8449-8454), the observation of *B. cereus* strains causing severe pneumonias showed that, for an effective response in a disease outbreak, there is a need for an additional, independent, rapid, and robust detection method that allows for an unambiguous detection and identification of the agents involved while infection levels are low. The immune response to a cell wall carbohydrate offers a route to such a detection method. Acknowledging this demand, a number of recent reports explored new routes of strain typing and identification, using e.g. amplified fragment length polymorphism (Radnedge et al., 2003, *Appl. Environ. Microbiol;* 69:2755-2764), single-nucleotide genome polymorphisms (Van Ert et al., 2007, *J. Clin. Microbiol.,* 45:47-53), monoclonal antibodies to cell wall and spore components (De et al., 2002, *Emerg. Infect. Dis.,* 8:1060; Tamborrini et al., 2006, *Angew. Chem. Int. Ed.,* 45:1-3), tandem mass spectrometry on small acid-soluble proteins (Castanha et al., 2006, *J. Microbiol. Meth.,* 67:230-240; Castanha et al., 2007, *Mol. Cell. Probes,* 21:190-201), gamma phage specificity to *Bacillus* cell (Abshire et al., 2005, *J. Clin. Microbiol.,* 43:4780-4788), and a glycan array derived from a spore protein carbohydrate component (Wang et al., 2007, *Proteomics,* 7:180-184).

Despite this variety of approaches to strain identification and typing, *Bacillus* cell wall carbohydrates have not been adequately investigated with regard to taxonomic classification and strain identification. Infection by pathogenic strains of the *B. cereus* group likely involves multiple components of the cell wall that interact with the host. These include the capsule, the S-layer and various cell wall glycoconjugates. During an infection, these cell wall components may function in bacterial adhesion to host cells and also as barriers to the host defense mechanism, thereby acting as virulence factors. The functional importance of the cell wall carbohydrate ensures its structural conservation and, thus, makes it a good candidate for identification and classification of *Bacillus* species, as well as for development into a vaccine antigen. Carbohydrates are a common feature of the bacilli cell wall, e.g. as capsules, or as S-layer protein components, etc. In many bacterial genera the cell walls are well established as diagnostic targets (Allison and Verma, 2000, *Trends Microbiol.,* 8:17-23; Miceika et al., 1985, *J. Clin. Microbiol.,* 21:467-469; Venezia et al., 1985, *J. Clin. Microbiol.,* 21:395-398; and Weintraub, 2003, *Carbohydr. Res.,* 338:2539-2547), carbohydrate-based vaccine antigens (Lindberg, 1999, *Vaccine,* 17:S28-S36; Weintraub, 2003, *Carbohydr. Res.,* 338:2539-2547), and virulence factors (Moxon and Kroll, 1990, *Curr. Topics Microbiol. Immunol.,* 150:65-86). Therefore, the characterization of cell walls of *B. anthracis* and other strains of the *B. cereus* group could be important for identifying potential vaccine antigens, diagnostics, and to elucidate the molecular basis for their virulence and pathogenicity.

Previous studies have established a precedent for distinctive glycosyl compositions of the total cell walls of representative strains from *B. anthracis, B. cereus*, and *B. thuringiensis*. For example, galactose (Gal) was found only in *B. anthracis* cell walls, while glucose (Glc) and N-acetylgalactosamine (GalNAc) were present in *B. cereus* cell walls (Fox et al., 2003, *J. Microbiol. Methods,* 54:143-152; Wunschel et al., 1994, *Sys. Appl. Microbiol.,* 17:625-635). These published data suggest that there could be cell wall carbohydrates that are specific to each of these three *Bacillus* species. However, a systematic comparison of the cell wall compositions/structures from members of the *B. cereus* group of bacteria as a function of the more detailed MLST phylogenetic classification has not been reported. In this example, the glycosyl compositions of the cell walls from a collection of strains of the *B. cereus* group with characterized phylogenetic relatedness based on the MLST method was examined. In addition, since recent sequencing projects of whole genomes from *B. cereus* group strains showed that genes involved in carbohydrate biosynthesis and metabolism are localized not only on the chromosome, but can also be encoded on plasmids (Rasko et al., 2005, *Microbiol. Rev.,* 29:303-329), it was investigated whether cell wall composition is influenced by the virulence plasmid content in selected *B. anthracis* strains. The data demonstrate that there is variation in the glycosyl compositions of cell walls among even closely related *B. cereus* group strains and that this compositional variation correlates with differences in phylogenetic relatedness. Further, this example shows that at standard laboratory growth conditions the types of carbohydrates found in the cell walls of *B. anthracis* strains may depend, to some extent, on their virulence plasmid content.

Briefly, with this example it was determined that members of the *Bacillus cereus* group contain cell wall carbohydrates that vary in their glycosyl compositions. Recent multi-locus sequence typing (MLST) refined the relatedness of *B. cereus* members by separating them into clades and lineages. Based on MLST, several *B. anthracis, B. cereus* and *B. thuringiensis* strains were selected and compared their cell wall carbohydrates. The cell walls of different *B. anthracis* strains (Clade 1/Anthracis) were composed of glucose (Glc), galactose (Gal), N-acetyl mannosamine (ManNAc), and N-acetyl glucosamine (GlcNAc). In contrast, the cell walls from Clade 2 strains (*B. cereus* type strain ATCC 14579, and of *B. thuringiensis* strains) lacked Gal, and contained N-acetylgalactosamine (GalNAc). The *B. cereus* Clade 1 strains had cell walls that were similar in composition to *B. anthracis* in that they all contained Gal. However, the cell walls from some Clade 1 strains also contained GalNAc which was not present in *B. anthracis* cell walls. Three recently identified Clade 1 strains of *B. cereus* that cause severe pneumonia, i.e. strains BB102, BB87, and G9241, had cell walls compositions that closely resembled those of *B. anthracis*. It was also observed that *B. anthracis* strains cell wall glycosyl compositions differed from one another in a plasmid-dependent manner. When plasmid pXO2 was absent, the ManNAc/Gal ratio decreased while the Glc/Gal ratio increased. Also, deletion of atxA, a global regulatory gene, from a pXO2-minus strain resulted in cell walls with an even greater level of Glc.

Materials and Methods

Bacterial strains and culture conditions. Most *B. anthracis* strains were obtained from the CDC culture collection. The strains *B. anthracis* 7702 and UT-60 strain were obtained from T. Koehler, University of Texas/Houston Health Science Center. A list of bacterial strains used in this study and their sources are given in Table 1. Cells cultured over night in brain heart infusion medium (BHI) (BD BBL, Sparks, Md.) containing 0.5% glycerol were used to inoculate four 250-ml volumes of BHI medium in 2-L Erlenmeyer flasks the next morning. Cultures were grown at 37° C. (*B. anthracis*) or 30° C. (*B. cereus, B. thuringiensis*) shaking at 200 rpm. Growth was monitored by measuring the optical density of the cultures at 600 nm. In mid-log phase, cells were harvested by centrifugation (8,000×g, 4° C., 15 min), washed two times in sterile saline, enumerated by dilution plating on BHI agar plates, and then autoclaved for 1 h at 121° C. before further processing.

Preparation of bacterial cell walls. The bacterial cell walls were prepared by modification of a previously described procedure (Brown, 1973 *J. Bacteriol* 25:295-300). The autoclaved bacterial cells ($3\times10^8$ to $3\times10^9$ CFU/ml) were disrupted in 40 ml sterile saline on ice by four 10-minute sonication cycles. The complete or near complete disruption of cells was checked microscopically. Unbroken cells were removed by a low speed centrifugation run (8,000×g, 4° C., 15 min). The separated pellet and supernatant fractions were stored at −70° C. The cell walls were separated from the low speed supernatants by ultracentrifugation at 100,000×g, 4° C. for 4 hours. The resulting cell wall pellets were washed by suspension in cold, deionized water followed by an additional ultracentrifugation at 100,000×g, 4° C. for four hours, and lyophilized.

Release of phosphate-bound polysaccharides from the cell wall. Phosphate-bound polysaccharides were released from the cell walls by treatment with aqueous HF according to a modification of the procedure described by Ekwunife et al. (Ekwunife et al., 1991, *FEMS Microbiol. Lett.,* 82:257-262). Briefly, the cell walls are subjected to 47% hydrogen fluoride (HF) under stirring at 4° C. for 48 hours. The reaction mixture was neutralized with $NH_4OH$, subjected to a 10 minute low speed centrifugation, and the supernatant with the released polysaccharides lyophilized, redissolved in deionized water and subjected to a chromatographic size separation on a Bio-Gel P2 column (Bio-Rad). The fractions eluting from the BioGel P2 column were monitored using a refractive index detector. Polysaccharide-containing peaks were pooled, lyophilized and analyzed by gas chromatography-mass spectrometry as described below. These HF-released polysaccharides are referred to as HF-PSs.

Glycosyl composition analysis. The carbohydrate profiles were determined by gas chromatography-mass spectrometry (GC-MS) analysis of the trimethylsilyl (TMS) methylglycosides as previously described by York et al. (York et al., 1985, *Meth. Enzymol.,* 118:3-40). The cell walls and HF-PSs were subjected to methanolysis at 80° C. for 18 hours in methanolic HCl (1 M). The resulting methyl glycosides were N-acetylated, trimethylsilylated, and then analyzed by GC-MS analysis (5890A GC-MS; Agilent Technologies, Palo Alto, Calif.) using a 30-m DB-1 fused silica capillary column (J&W Scientific, Folsom, Calif.). Inositol was used as an internal standard, and retention times were compared to authentic standards. Composition analysis was done on samples obtained from at least two independent cultures of each strain, and each sample was also analyzed at least two times.

Results

Glycosyl composition analysis for members of the *B. cereus* group. The strains investigated in this study and their classification are listed in Table 1. The glycosyl composition for the cell wall samples from each strain is shown in Table 2. Also, the glycosyl composition of cell pellets was initially analyzed from a number of strains shown in Tables 1 and 2. Findings showed that they all contained the same glycosyl residues found in the isolated cell walls with the exception that cell pellets invariably contained some ribose, presumably due to RNA. The glycosyl composition of the cell walls from all the *B. anthracis* strains contained Glc, Gal, ManNAc, and GlcNAc. Qualitatively, *B. cereus* strains belonging to Clade 1/Cereus IV had the same cell wall glycosyl components as strains belonging to Clade 1/Anthracis. The cell walls from strains of Clade 1/*Cereus* III differed from those of Clade 1/Anthracis in that they contained additional Man, while strains belonging to Clade 1/*Cereus* I differed in that their cell walls additionally contained GalNAc, and the cell walls from all strains belonging to Clade 2 lacked Gal and contained GalNAc.

There were some notable differences with regard to the relative amounts of certain glycosyl residues even among strains belonging to the same clade and lineage. For example, strain *B. anthracis* Sterne $34F_2$ had cell walls with notably decreased levels of ManNAc compared to *B. anthracis* Ames and *B. anthracis* Pasteur 4229, while *B. anthracis* 7702 and its atxA deletion mutant UT-60 showed an increase in cell wall Glc levels compared to the other *B. anthracis* strains. Quantitative differences in various glycosyl components were also present between *B. cereus* Clade 1/*Cereus* I strains F666 and ATCC 10987. Relative to strain *B. cereus* ATCC 10987, strain *B. cereus* F666 contained significantly increased amounts of Glc and decreased amounts of Gal. Differences were also noticeable in strains *B. cereus* B5780 and BB102 cell walls, both belonging to Clade 1/*Cereus* III. Strain B5780 had a much higher level of Glc and lower levels of both Gal and ManNAc compared to strain BB102.

Effects of plasmid content on the glycosyl composition in *B. anthracis* cell walls. In order to determine whether the plasmid content has an effect on glycosyl composition of cell walls in the different *B. anthracis* strains, the glycosyl residue percentages were normalized, as shown in Table 2, to the amount of Gal for each sample. The reason for normalizing to Gal is that, as will be described below, Gal is the major glycosyl residue found in the HF-PSs for each of the *B. anthracis* strains, and the HF-PSs of these strains all have the same structure as reported by Choudhury et al. (Example 2 and Choudhury et al., 2006, *J. Biol. Chem.,* 281:27932-27941). These Gal-normalized values are given in Table 3 together with the plasmid content in the different strains. Qualitatively, the sugar profiles of the different cell walls were not affected by the plasmid content. Quantitatively, the glycosyl composition of the cell wall from *B. anthracis* Pasteur which lacks pXO1 was the same as that of *B. anthracis* Ames which contains both pXO1 and pXO2. This finding argues that the plasmid pXO1 has no impact on sugar composition of the cell wall. In contrast, pXO2-minus *B. anthracis* strains (Sterne $34F_2$ and 7702), have cell walls with reduced amounts of ManNAc relative to Gal suggesting that the absence of the pXO2 plasmid impacts cell wall glycosyl composition.

TABLE 1

Strains investigated: MLST groupings, clinical manifestation, and source.

| Strain | MLST Clade, Lineage[1,2] | Clinical Information[3] | Source/ Provider[4] | Reference[5] |
|---|---|---|---|---|
| *B. anthracis* Ames | Clade 1 | Veterinary isolate | Cow (1981, Texas) | Van Ert 2007 |
| *B. anthracis* 4229 Pasteur | Anthracis | Veterinary vaccine strain (Italy) | Unknown, 1880's | CR Acad Sci Agr Bulg 1881; 92: 429 |
| *B. anthracis* $34F_2$ Sterne | | Veterinary vaccine strain | Cow (1930s, South Africa) | Sterne 1937 |
| *B. anthracis* 7702 | | n/a | Koehler, Univ. of Texas Houston | Cataldi and Mock, 1990 |

TABLE 1-continued

Strains investigated: MLST groupings, clinical manifestation, and source.

| Strain | MLST Clade, Lineage[1,2] | Clinical Information[3] | Source/ Provider[4] | Reference[5] |
|---|---|---|---|---|
| *B. anthracis* UT-60 (strain 7702 Δ atxA) | | n/a | Laboratory derived deletion mutant | Dai 1995 |
| *B. cereus* F666 (ST-92) | Clade 1, Cereus I | Gastrointestinal illness | Human stool isolate, (1981, North Carolina) | Novak 2005 |
| *B. cereus* ATCC 10987 | | n/a | dairy isolate (1930) | Smith 1952 |
| *B. cereus* B5780 (ST-76) | Clade 1, Cereus III | unknown | Human blood isolate (1970, Texas) | Novak 2005 |
| *B. cereus* BB102 | | fatal pneumonia | Human blood isolate (2003, Texas) | Hoffmaster 2006 |
| *B. cereus* G9241 | Clade 1, Cereus IV | Severe pneumonia | Human blood isolate (1994, Louisiana) | Hoffmaster 2004 |
| *B. cereus* BB87 | | fatal pneumonia | Human blood isolate (2003, Texas) | Hoffmaster 2006 |
| *B. cereus* ATCC 14579 | Clade 2 Tolworthi | n/a | *B. cereus* type strain; possibly dairy isolate (1916) | Lawrence 1916 |
| *B. thuringiensis* ATCC 33679 | Clade 2 Kurstaki | entomocidal | ATCC; originally isolated from diseased insect larvae | De Barjee 1970 |
| *B. thuringiensis* ATCC 35646 | Clade 2 Sotto | larvicidal to horn flies | CDC; originally isolated from sewage in Israel | Temeyer 1984 |

[1]The phylogenetic relatedness of strains on the basis of multi locus sequence typing (MLST) was adopted from Priest et al. (Priest et al., 2004, J. Bacteriol. 186: 7959-7970).

[2]The classification of these strains in Cereus IV is proposed (Novak et al., 2005. Presented at the 105th American Society for Microbiology Meeting, Atlanta, GA.).

[3]Abbreviation: n/a, not available.

[4]Strains *B. anthracis* 7702 and *B. anthracis* UT-60 were kindly provided by Theresa Koehler, University of Texas-Houston Health Science Center, Houston.

[5]Van Ert et al, 2007, J. Clin. Microbiol. 45: 47-53; Sterne, 1937, Ond. J. Vet. Sci. An. Ind. 9: 49-67; Cataldi and Mock, 1990, Mol. Microbiol. 4: 1111-1117; Dai et al., 1995, Mol. Microbiol. 16: 1171-1181; Novak et al., 2005. Presented at the 105th American Society for Microbiology Meeting, Atlanta, GA; Smith, 1952, U.S. Dep. Agric. Monogr. 16: 1-148; Hoffmaster et al., 2006, J. Clin. Microbiol. 44: 3352-3360; Hoffmaster et al., 2004, Proc. Natl. Acad. Sci. 101: 8449-8454; Lawrence, 1916, J. Bacteriol. 1: 277-320; de Barjee, 1970, J. Invertebr. Pathol. 15: 139-140; and Temeyer, 1984, Appl. Environ. Microbiol. 47: 952-955.

TABLE 2

Sugar composition of cell walls from members of the *B. cereus* group.

| MLST Clade, Lineage | Strain | Sugar composition* | | | | | |
|---|---|---|---|---|---|---|---|
| | | Man | Glc | Gal | ManNAc | GlcNAc | GalNAc |
| Clade 1 | *B. anthracis* Ames | n.d. | 6.2 ± 1.1 | 54.2 ± 7.4 | 13.2 ± 4.3 | 26.2 ± 4.2 | n.d. |
| Anthracis | *B. anthracis* Pasteur 4229 | n.d. | 5.6 ± 1.2 | 52.3 ± 7.7 | 13.2 ± 3.6 | 28.6 ± 4.9 | n.d. |
| | *B. anthracis* Sterne 34$F_2$ | n.d. | 8.5 ± 1.7 | 61.3 ± 6.7 | 4.7 ± 2.1 | 25.4 ± 5.0 | n.d. |
| | *B. anthracis* 7702 | n.d. | 15.0 ± 1.6 | 54.5 ± 8.6 | 8.1 ± 5.8 | 21.3 ± 2.4 | n.d. |
| | *B. anthracis* UT-60 (atxA deletion mutant of 7702) | n.d. | 23.0 ± 1.1 | 49.3 ± 3.1 | 7.2 ± 0.9 | 20.2 ± 3.0 | n.d. |
| Clade 1 | *B. cereus* F666 | n.d. | 24.5 ± 7.9 | 13.2 ± 5.8 | 12.8 ± 3.6 | 32.3 ± 6.5 | 16.8 ± 3.7 |
| Cereus I | *B. cereus* ATCC 10987 | n.d. | 2.6 ± 1.3 | 31.8 ± 6.2 | 15.4 ± 0.2 | 25.7 ± 3.0 | 24.5 ± 4.2 |
| Clade1 | *B. cereus* B5780 | 2.7 ± 1.4 | 68.3 ± 2.7 | 1.2 ± 0.2 | 2.9 ± 1.5 | 24.9 ± 3.2 | n.d. |
| CereusIII | *B. cereus* BB102 | 0.9 ± 0.5 | 5.1 ± 0.8 | 61.7 ± 5.8 | 9.5 ± 3.9 | 22.9 ± 2.7 | n.d. |
| Clade 1 | *B. cereus* G9241 | n.d. | 5.2 ± 0.7 | 63.4 ± 2.1 | 9.5 ± 1.9 | 21.7 ± 1.0 | n.d. |
| Cereus IV | *B. cereus* BB87 | n.d. | 2.5 ± 0.9 | 57.4 ± 9.2 | 11.4 ± 6.6 | 28.0 ± 3.2 | n.d. |
| Clade2 Tolworthi | *B. cereus* ATCC 14579 | n.d. | 27.7 ± 2.2 | n.d. | 14.5 ± 4.5 | 45.2 ± 2.5 | 12.2 ± 3.1 |
| Clade 2 Kurstaki | *B. thuringiensis* ATCC 33679 | n.d. | 55 | n.d. | 7.2 | 30 | 7.7 |
| Clade 2 Sotto | *B. thuringiensis* ATCC 35646 | n.d. | 20 | n.d. | 15 | 49 | 17 |

Values are given in percent (+/− one standard deviation) of total carbohydrate before HF treatment.

*For the strains *B. anthracis* Sterne 34$F_2$ and *B. cereus* ATCC10987, high Glc content was occasionally observed in cell wall preparations. The sugar compostions given here are from cell wall preparations confirmed in independent culturing experiments.

n.d. = none detected;

Man = mannose;

Glc = glucose;

Gal = galactose;

ManNAc = N-acetylmannosamine;

GlcNAc = N-acetylglucosamine;

GalNAc = N-acetylgalactosamine.

N-acetylmuramic acid was also detected in the cell wall preparations, but not quantified.

For MLST classification see Table 1.

In addition, *B. anthracis* 7702 cell walls displayed a three-fold increase (relative to Gal) in Glc levels compared to the cell wall from *B. anthracis* Ames (Table 3). The increase in the amounts of cell wall Glc was even more pronounced in *B. anthracis* UT-60; a derivative of *B. anthracis* 7702 that has a deletion mutation in the atxA regulatory gene on pXO1 in addition to lacking pXO2 (Dai et al., 1995, *Mol. Microbiol.*, 16:1171-1181). In this strain an approximately a 5-fold increase in Glc compared to the cell wall from *B. anthracis* Ames was observed and about a 60% increase in Glc as compared to the amounts in the parent strain *B. anthracis* 7702. These data indicate that the absence of pXO2 and the deletion of the regulatory gene atxA from pXO1 both result in detectable changes in the cell wall glycosyl composition of *B. anthracis*.

TABLE 3

Effect of different plasmid combinations on the sugar composition of the *B. anthracis* cell walls [relative to the amounts of Gal]:

| | | Relative sugar composition | | | |
|---|---|---|---|---|---|
| Strain | Plasmid content | Glc | Gal | ManNAc | GlcNAc |
| *B. anthracis* Ames | ($pXO1^+$, $pXO2^+$) | 0.1 | 1.0 | 0.25 | 0.5 |
| *B. anthracis* Pasteur 4229 | ($pXO1^-$, $pXO2^+$) | 0.1 | 1.0 | 0.3 | 0.5 |
| *B. anthracis* Sterne $34F_2$ | ($pXO1^+$, $pXO2^-$) | 0.1 | 1.0 | 0.1 | 0.4 |
| *B. anthracis* 7702 | ($pXO1^+$, $pXO2^-$) | 0.3 | 1.0 | 0.15 | 0.4 |
| *B. anthracis* UT-60 (atxA deletion mutant of strain 7702) | ($pXO1^+$ ΔatxA, $pXO2^-$) | 0.5 | 1.0 | 0.15 | 0.5 |

Figure 2:
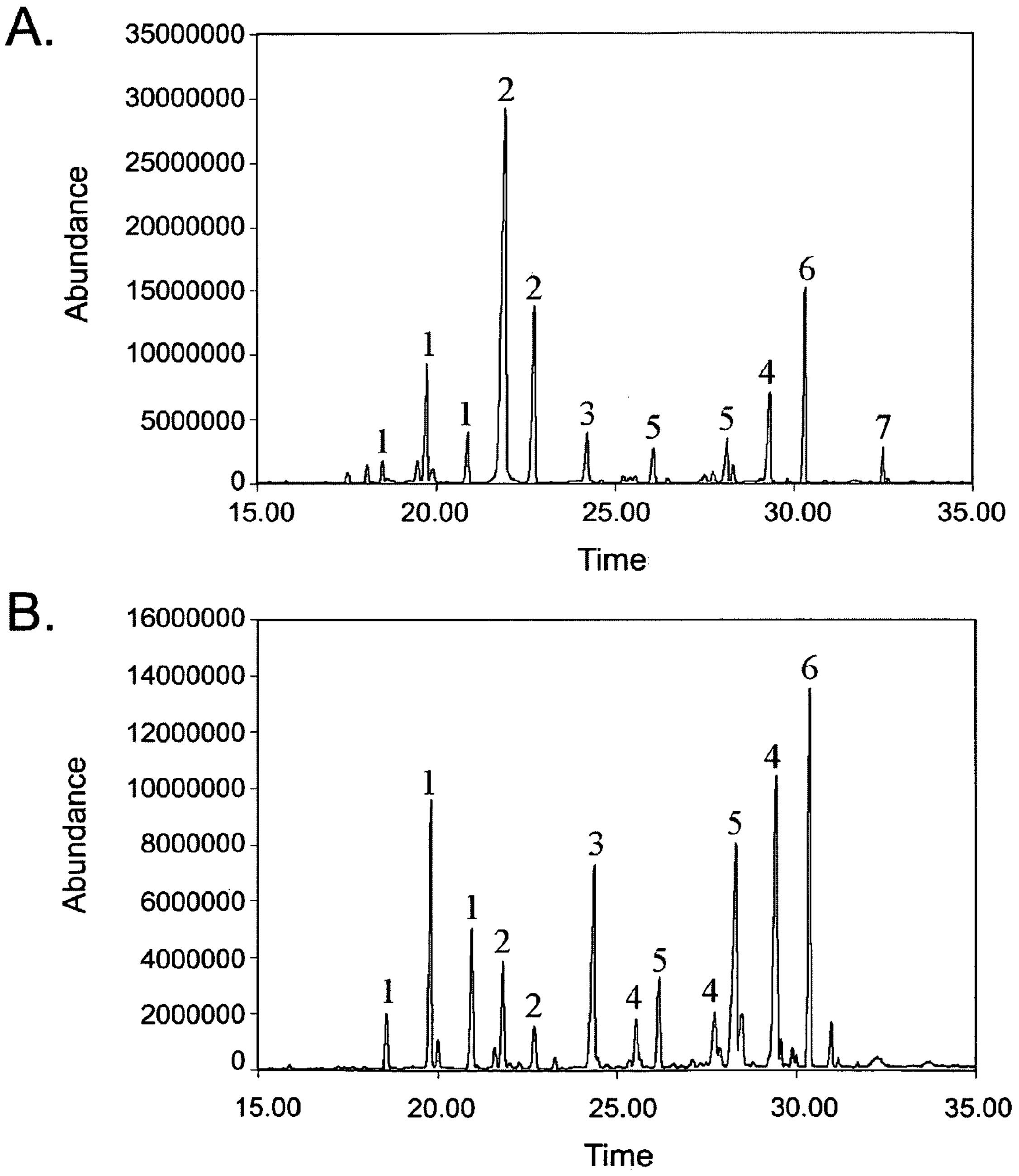
FIGS. 2A-2B show gas chromatographic-mass spectrometric (GC-MS) sugar profiles obtained from *B. cereus* ATCC 10987 vegetative cell walls after hydrolysis of the total cell wall preparations and derivatisation into trimethylsilyl (TMS) methylglycosides.

Composition of HF released polysaccharides. Polysaccharides that are attached to the bacterial cell walls through phosphate bonds can be released through HF treatment (Kojima et al., 1985, *Eur. J. Biochem.*, 148:479-484). This procedure was used in other studies to obtain the cell wall polysaccharide from *B. anthracis* which is thought to anchor the S-layer protein to the peptidoglycan (Ekwunife et al., 1991, *FEMS Microbiol. Lett.*, 82:257-262; Mesnage et al., 2000, *EMBO J.*, 19:4473-4484). The glycosyl residue compositions of the HF-PSs from the investigated strains of *B. anthracis* (Clade 1/Anthracis), and *B. cereus* (Clade 1/*Cereus* I, III, IV, and Clade 2/Tolworthi) are presented in Table 4, and GC-MS profiles of the cell wall compositions compared with the HF-PSs of pXO2-minus *B. anthracis* strains and *B. cereus* ATCC 10987 are shown in FIGS. 1 and 2. *B. anthracis* 7702 was not analyzed by this method.

These results show that the HF-PSs from *B. anthracis* Ames, *B. anthracis* Pasteur, *B. anthracis* Sterne $34F_2$, and *B. anthracis* UT-60 all have the same glycosyl residue composition, both qualitatively and quantitatively; they all contain Gal, ManNAc, and GlcNAc in approximately a 3:1:2 ratio as shown in Example 2 (see, also, Choudhury et al., 2006, *J. Biol. Chem.*, 281:27932-27941). Each of these polysaccharides has a small amount of Glc, but further structural analysis has shown that this is due to contamination by a Glc-rich component that is not part of this polysaccharide. The presence of a Glc-rich polysaccharide in *B. anthracis* cell walls that is not part of the HF-PS was most obvious for one culture of *B. anthracis* Sterne $34F_2$ in which the cell wall had a relative Glc content of 52% while its HF-PS contained only 4.2% Glc (see Table 4 and FIGS. 1A and 1B). The "missing" Glc was found in the cell wall debris after HF-treatment and, therefore, *B. anthracis* Sterne $34F_2$ apparently has a Glc-rich component in the cell wall that is not released by HF-treatment. However, this Glc-rich cell wall component was only observed in one of three *B. anthracis* Sterne $34F_2$ cultures. At this point it is not clear what actually governs the different levels of the Glc-rich cell wall component observed in the various Sterne $34F_2$ cell wall preparations. The increased cell wall Glc level, even though variable from different Sterne $34F_2$, cultures, was observed only in pXO2-minus *B. anthracis* strains.

TABLE 4

Sugar composition of isolated polysaccharides released from the *Bacillus* cell walls through HF treatment.

| MLST Clade, | | Sugar Composition | | | | | |
|---|---|---|---|---|---|---|---|
| Lineage | Strain | Man | Glc | Gal | ManNAc | GlcNAc | GalNAc |
| Clade 1 | *B. anthracis* Ames | n.d. | 2.7 ± 0.1 | 57.0 ± 2.8 | 19.3 ± 1.0 | 21.1 ± 2.1 | n.d. |
| Anthracis | *B. anthracis* Pasteur 4229 | n.d. | 0.5 | 53.4 | 15.7 | 30.4 | n.d. |
| | *B. anthracis* Sterne $34F_2$ | n.d. | 4.2 | 52.7 | 13.7 | 29.5 | n.d. |
| | *B. anthracis* UT-60 | n.d. | 3.8 | 56.5 | 18.1 | 21.7 | n.d. |
| Clade1 | *B. cereus* F666 | n.d. | 25.9 | 21.4 | 19.1 | 18.0 | 15.7 |
| Cereus I | *B. cereus* ATCC 10987 | n.d. | 8.6 | 26.7 | 25.3 | 16.4 | 23.0 |
| Clade 1 | *B. cereus* B5780 | 1.1 | 65.6 | 0.9 | 3.6 | 28.8 | n.d. |
| Cereus III | *B. cereus* BB102 | 2.2 | 3.1 | 65.5 | 11.4 | 17.8 | n.d. |
| Clade 1 | *B. cereus* G9241 | n.d. | 1.3 | 55.8 | 19.3 | 23.6 | n.d. |
| Cereus IV | *B. cereus* BB87 | n.d. | 0.9 | 61.8 | 14.2 | 23.2 | |
| Clade2 Tolworthi | *B. cereus* ATCC 14579 | n.d. | 25.3 | n.d. | 15.4 | 44.9 | 14.4 |

Compositions are given as relative percent of total carbohydrate after HF treatment.

For abbreviations and MLST classification, see Table 2.

The only *B. anthracis* strains which, for multiple culture preparations, had cell walls that consistently contained increased amounts of Glc were strains UT-60 and, to a lesser extent, its parent strain 7702. Since there are no indications of structural differences in the purified HF-PS polysaccharides from these strains compared to the other *B. anthracis* strains, it is likely that a non-HF-PS Glc-rich component is synthesized by strain *B. anthracis* 7702, and, to an even greater amount, by its derived atxA deletion mutant, UT-60. The most plausible explanation for this observed increase in Glc levels in strain *B. anthracis* UT-60 is that the inactivation of the atxA gene somehow affects (i.e. increases) the amount of a Glc-rich component.

The finding that the cell walls of several pXO2-minus *B. anthracis* strains apparently contain a Glc-rich component that is not solubilized by treatment with aqueous HF was also observed for *B. cereus* ATCC 10987. The cell wall from this strain contained 60% Glc while the HF-PS contained only 8.6% Glc (see Table 4 and FIGS. 2A and 2B). This result, as with results for extracts from pXO2-minus *B. anthracis* strains, indicates that *B. cereus* ATCC 10987 contains a Glc-rich polysaccharide that is not released by HF-treatment and, in fact, Glc was found in the cell wall debris after HF-treatment. As with the *B. anthracis* HF-PSs, further structural analysis shows that the relative small amount of Glc found in the *B. cereus* 10987 HF-PS is due to residual contamination by a 4-linked glucose-containing component. Thus, the *B. cereus* ATCC 10987 HF-PS consists of Gal, ManNAc, GlcNAc and GalNAc in a 1:1:1:1 ratio, and clearly has a different structure than the *B. anthracis* HF-PS. This structural difference was also supported by a comparison of the proton NMR spectra of these HF-PSs as shown in Example 2. The HF-PS isolated from strain *B. cereus* F666 (this strain is in the same Clade 1/*Cereus* I lineage as strain *B. cereus* ATCC 10987) has a glycosyl composition that resembles the HF-PS of strain *B. cereus* ATCC 10987 but with a significantly increased amount of Glc. In fact, the HF-PS from strain F666 showed three times the amounts of Glc compared to the HF-PS from *B. cereus* ATCC 10987. This result suggests that Glc is a part of the F666 HF-PS and, therefore, this HF-PS likely consists of Glc, Gal, ManNAc, GlcNAc, and GalNAc in a 1:1:1:1:1 ratio. However, further structural investigation is required to determine whether the Glc is a component of its HF-PS or whether it is due to a mixture of different polysaccharides in this HF-PS preparation.

The strains that belong to the *B. cereus* group Clade 1/*Cereus* III, strains B5780 and BB102, showed more pronounced differences from one another in their HF-PS sugar compositions. Both strains contained a small amount of Man in their isolated HF-PS fractions, which was not observed in the other HF-PSs examined. In addition, strain B5780 HF-PS contained larger amounts of Glc and lower amounts of Gal and ManNAc compared to the HF-PS from strain BB102 HF-PS which contained a small amount of Glc and larger amounts of Gal and ManNAc (Table 4). It is possible that the glycosyl residues present in small amounts are due to low levels of contaminating carbohydrates that are not part of the HF-PS structures. If that is the case, then the HF-PS of strain *B. cereus* B5780 would be composed of Glc and GlcNAc in a 2:1 ratio, and the HF-PS of *B. cereus* BB102 would be composed of Gal, ManNAc, and GlcNAc in a 6:1:2 ratio.

The HF-PS preparations that were most similar to the *B. anthracis* HF-PSs were from the *B. cereus* group strains that belong to the Clade 1/*Cereus* IV lineage, G9241 and BB87. These strains, as with strain BB102, are pathogens that caused severe pneumonia (Hoffmaster et al., 2006, *J. Clin. Microbiol.,* 44:3352-3360). The HF-PSs from in these strains consisted of Gal, ManNAc, and GlcNAc in a 3:1:1 (or 3:1:2) ratio. The ratio of these glycosyl residues in the *B. anthracis* HF-PS is 3:1:2. The structures of the BB87 and G9241 HF-PSs will be determined, to determine if they are the same or different from the *B. anthracis* HF-PS structure.

The HF-PS from the type strain *B. cereus* 14579 (Clade 2/Tolworthi) also had a decrease in Glc content compared to its cell wall (compare Tables 2 and 4). This result indicates that this *B. cereus* type strain also contains some Glc-rich component that was not released from the cell wall by HF-treatment. Unlike the HF-PSs from the *B. anthracis* strains and from *B. cereus* ATCC 10987, Glc is also a major glycosyl residue in the *B. cereus* ATCC 14579 HF-PS and, therefore it is likely that Glc is a component of this polysaccharide. This was verified by further structural analysis of this HF-PS. The components of the HF-PS from *B. cereus* ATCC 14579 are Glc, ManNAc, GlcNAc, and GalNAc in approximately a 1:1:2:1 ratio.

Discussion

Cell wall compositions were examined from a selection of strains belonging to the *B. cereus* group species, *B. anthracis, B. cereus*, and *B. thuringiensis*. Recent investigations into the phylogenetic relatedness of these *B. cereus* group strains, e.g. multilocus sequence typing, offer a more differentiated picture than previous classification schemes and resulted in separating these strains into two clades and several lineages (Table 1) (Priest et al., 2004, *J. Bacteriol.,* 186:7959-7970). This example showed that the glycosyl residue composition of the cell walls varied significantly both qualitatively and quantitatively among the investigated strains in a manner that reveal possible correlations with their phylogenetic relatedness.

In summary, *B. cereus* strains that are closely related could be differentiated in a clade/lineage-specific manner through qualitative analysis of their cell wall glycosyl components; quantitative glycosyl analysis showed that strains belonging to the same lineage vary from one another in the amounts of various glycosyl residues indicating the presence of strain-specific cell wall carbohydrates; analysis of the cell walls from recently discovered pathogenic *B. cereus* strains that caused severe pneumonia, i.e. strains BB102, BB87, and G9241 (Hoffmaster et al., 2006, *J. Clin. Microbiol.,* 44:3352-3360; Hoffmaster, et al., 2004, *Proc. Natl. Acad. Sci.,* 101: 8449-8454), showed that they have glycosyl compositions that were most similar to the cell walls of the *B. anthracis* strains; the plasmid content of *B. anthracis* strains appeared to affect cell wall glycosyl compositions, i.e. the amounts of ManNAc and the amount of Glc were lower and higher, respectively, in the cell walls from strains that lacked the pXO2 virulence plasmid, and the amount of a possible Glc-rich non-HF-PS cell wall was particularly increased in an atxA mutant of *B. anthracis*; the HF-PSs released from the cell walls of the different *B. anthracis* strains all had the same Gal:ManNAc:GlcNAc ratio, 3:1:2, as shown in Example 2; consistent with the fact that they have the same structure; and the HF-PSs from strains of the *B. cereus* group Clade 1/*Cereus* I (i.e. *B. cereus* ATCC 10987 and F666), Clade 1/*Cereus* III (i.e. *B. cereus* B5780 and BB102), and Clade 2/Tolworthi (i.e. the type strain *B. cereus* ATCC 14579), each had a unique glycosyl composition that was different from the *B. anthracis* HF-PSs indicating that they had different structures from one another and from the *B. anthracis* HF-PS structure.

This is the first report that compares, in a systematic manner, the cell wall carbohydrates of several pathogenic and nonpathogenic members of the *B. cereus* based on the MLST phylogenetic grouping of Priest et al. (Priest et al., 2004, *J. Bacteriol.,* 186:7959-7970). Earlier studies by Fox et al. (Fox et al., 1993, *J. Clin. Microbiol.*, 31:887-894; Wunschel et al., 1994, *Sys. Appl. Microbiol.*, 17:625-635) determined carbohydrate profiles from vegetative cells and spores of a number of *B. cereus* and *B. anthracis* strains that had less clearly defined relationships. In that study the carbohydrate content of intact vegetative cells and spores was investigated. As expected, the present findings corroborate some of those reported by Fox et al., but there are also some differences. For example, rhamnose, ribose or methylated sugars were not detected in any of the cell wall preparations of this example. Since rhamnose and methyl rhamnose are components of the exosporium glycoprotein BclA (Daubenspeck et al., 2004, *J. Biol. Chem.*, 279:30945-30953), it may be that the vegetative cell preparations described in these earlier reports contained some spore material.

This comparative analysis of the cell walls from MLST-defined *Bacillus* strains provides new information that correlates with their phylogenetic relatedness. Even though our study involved a limited number of strains, the qualitative glycosyl residue differences suggest that cell wall compositions may be used to distinguish between *B. cereus* clades and also between lineages within a single clade. In addition, comparison of two *B. cereus* strains, B5780 and BB102, both belonging to linage *Cereus* III of Clade 1 showed that, while they contain the same glycosyl residues, these residues are present at very different levels (Table 2). This result suggests the possibility of strain-specific quantitative differences that could, in some cases, allow identification for strains within a single *B. cereus* lineage. However, a larger sample of *Bacillus* strains is needed to determine breadth and consistency of these qualitative and quantitative differences.

Glycosyl compositions of the cell walls of *B. anthracis* strains before and after treatment with HF revealed that the absence of plasmid pXO2 may have some impact on cell wall glycosyl composition. This example observed consistently decreased relative amounts of ManNAc (relative to the amounts of Gal) in the cell walls of all *B. anthracis* strains missing pXO2. The fact that the HF-PS from all the pXO1-minus *B. anthracis* strains had the same glycosyl composition and structure (Example 2 and Choudhury et al., 2006, *J. Biol. Chem.*, 281:27932-27941) as the HF-PSs from *B. anthracis* Ames, Pasteur, suggests that the lower level of ManNAc in the cell wall could reflect an increase in a Gal-containing component that is not part of the HF-PS. An additional effect on cell wall glycosyl composition was detected in *B. anthracis* UT-60; namely the deletion of atxA from pXO1 results in higher levels of Glc in the cell wall (as compared to its parent strain, 7702), presumably due to larger amounts of the Glc-rich non-HF-PS component in its cell wall. Taken together, these results indicate that the pXO1 and pXO2 plasmids may have a role in determining the presence or absence of a Glc-rich component in some cell walls even though there are no known carbohydrate synthesis-related genes on pXO1 or pXO2 that could easily explain the observed glycosyl changes. The gene products of the majority of open reading frames (ORFs) predicted on the virulence plasmids pXO1 and pXO2 are still unidentified (Rasko et al., 2005, *Microbiol. Rev.*, 29:303-329). It may well be that there are ORFs that encode as yet unidentified carbohydrate synthesis-related genes. In the case of *B. anthracis* UT-60, the deleted atxA gene located on virulence plasmid pXO1 encodes a global regulator and the major transcriptional activator of the pXO1-borne anthrax toxin genes (Bourgogne et al., 2003, *Infect. Immun.*, 71:2736-2743). In a genetically complete strain, containing both pXO1 and pXO2, atxA has also been shown to be indirectly involved in the regulation of the capsule biosynthesis operon capBCAD located on pXO2 (Drysdale et al., 2004, *J. Bacteriol.*, 186:307-315). The cap genes are essential for the encapsulation of *B. anthracis* cells by a poly-γ-D-glutamic acid, one of the identified *B. anthracis* virulence factors necessary for the protection of *B. anthracis* cells inside the host (Keppie et al., 1953, *Br. J. Exp. Pathol.*, 34:486-496; Miceika et al., 1985, *J. Clin. Microbiol.*, 21:467-469). The stimulating effect on the Glc level and the relatively lower amount of ManNAc in *B. anthracis* UT-60 (and the other pXO1 minus *B. anthracis* strains) may indicate additional and previously unknown regulatory roles of atxA and of pXO2 in cell wall polysaccharide biosynthesis.

As a first approach to determine the cell wall polysaccharide structures that are underlying the observed sugar composition profiles, phosphate-bound cell wall polysaccharides were released by HF treatment of the cell walls and purified. This procedure was used to purify the cell wall from *B. anthracis* that is thought to anchor the S-layer protein to the peptidoglycan (Mesnage et al., 2000, *EMBO J.*, 19:4473-4484). Composition analysis of these HF-PSs from the different *B. anthracis* strains revealed that all had the same 3:1:2 Gal:ManNAc:GlcNAc ratio, reflecting the identical structures of these polysaccharides (see Example 2 and Choudhury et al., 2006, *J. Biol. Chem.*, 281:27932-27941). Since the HF-PS compositions from all the *B. anthracis* strains were same, it is likely that their structures are independent of the presence of absence of the virulence plasmids, pXO1 or pXO2. On the other hand, the *B. anthracis* HF-PSs were clearly different from the HF-PSs from the cell walls of other *B. cereus* group members, e.g. in strain ATCC 14579 (a Clade 2 *B. cereus* strain) it was composed of Glc:ManNAc:GlcNAc:GalNAc in a ratio of approximately 1:1:2:1, and in strain *B. cereus* ATCC 10987 (a Clade 1/*Cereus* 1 strain) of a Gal:ManAc:GlcNAc:GalNAc ratio of 1:1:1:1 (Table 4), in strain *B. cereus* BB102 (Clade 1/*Cereus* III) of Gal, ManNAc and GlcNAc in a ratio of 6:1:2, and in strains *B. cereus* G9241 and BB87 (Clade 1/*Cereus* IV) of Gal, ManNAc and GlcNAc in approximately a 3:1:1 ratio. Thus, it is quite possible that the HF-PSs from the *B. cereus* strains vary in a manner that correlates with clade or lineage.

An interesting observation is the similarity of glycosyl compositions among the cell walls of *B. cereus* strains that have recently been shown to cause severe pneumonia in humans (Hoffmaster et al., 2006, *J. Clin. Microbiol.*, 44:3352-3360; Hoffmaster, et al., 2004, *Proc. Natl. Acad. Sci.*, 101:8449-8454) with those of *B. anthracis* (Table 2). These clinical strains, namely *B. cereus* G9241, BB102, and BB87 belong to Clade 1, lineage *Cereus* III or IV (Novak, Hoffmaster, and Wilkins, 2005, presented at the 105th American Society for Microbiology Meeting, Atlanta, Ga.). This result indicates that the cell walls of these pathogenic *B. cereus* strains may contain carbohydrates that have common structural features with each other and with those of *B. anthracis*. The HF-PS preparations of these *B. cereus* strains also displayed glycosyl compositions that were relatively similar to one another and to the HF-PSs from the *B. anthracis* strains (Table 4).

An interesting feature of *B. cereus* strains G9241, BB87 and BB102 is that they all contain at least considerable numbers of genes with high similarity to genes of the virulence plasmid pXO1 of *B. anthracis* (e.g. *B. cereus* G9241 carries a plasmid that is almost identical to *B. anthracis* pXO1) (Hoffmaster et al., 2006, *J. Clin. Microbiol.*, 44:3352-3360; Hoffmaster, et al., 2004, *Proc. Natl. Acad. Sci.*, 101:8449-8454). Recently "*Bacillus anthracis*-like" isolates were obtained from chimpanzees and gorillas from Cote d'Ivoire and Cameroon that were thought to have died from anthrax-like disease (Leendertz et al., 2006, *PLoS Pathogens*, 2:1-4; Silke et al., 2006, *J. Bacteriol.*, 188:5333-5344). Interestingly, based on molecular analysis (MLST and others), these strains fell outside the well-supported cluster of classic *B. anthracis* strains and instead clustered with *B. cereus* and *B. thuringiensis* strains, most closely with a recently described atypical and pathogenic *B. thuringiensis*. These *B. anthracis*-like isolates from great apes reportedly contain both pXO1 and pXO2 plasmids, while the pathogenic *Bacillus cereus* strains BB102, G9241, BB87 all contain only a pXO1-like plasmid, but not pXO2 (Hoffmaster et al., 2006, *J. Clin. Microbiol.*, 44:3352-3360). The similarity of the HF-PS compositions for strains BB87, BB102, and G9241 with those observed for the *B. anthracis* HF-PSs suggested that the underlying HF-PSs in these strains are structurally related. Perhaps, the HF-PS structure found in *B. anthracis* and, possibly, the related HF-PS structures of the pathogenic *B. cereus* strains are necessary for virulence and/or are a characteristic of *B. cereus* strains that are able to pick up one or both of the *B. anthracis* virulence plasmids. It is not known whether the African gorilla isolates contain HF-PSs that corroborate these suspicions. To date, these bacteria have not yet been characterized with regard to their cell wall carbohydrates.

The results of this example indicate that cell wall carbohydrates of the *B. cereus* group strains will be useful for strain classification and have applications such as diagnostics and vaccines. The results of this example can now also be found in Leoff et al., 2008, *J Bacteriol;* 190(1):112-121.

Example 2

The Structure of the Cell Wall Polysaccharide of *Bacillus Anthracis* is Species Specific

*Bacillus anthracis* contains only a few known carbohydrates as part of its vegetative cell wall and spore. In this example the structure of the polysaccharide released from the cell wall of the vegetative cell by aqueous hydrogen fluoride (HF) is described. This HF-released polysaccharide (HF-PS) was isolated and structurally characterized from the Ames, Sterne and Pasteur strains of *B. anthracis*. The HF-PSs were also isolated from the closely related *B. cereus* ATCC 10987 strain, and from the *B. cereus* ATCC 14579 type strain and compared to those of *B. anthracis*. The structure of the *B. anthracis* HF-PS was determined by glycosyl composition and linkage analyses, matrix assisted laser desorption time of flight mass spectrometry (MALDI-TOF MS), and one- and two-dimensional nuclear magnetic resonance (NMR) spectroscopy. The HF-PSs from all of the *B. anthracis* isolates had an identical structure consisting of an amino sugar backbone of →6)-α-GlcNAc-(1→4)-β-ManNAc-(1→4)-β-GlcNAc-(1→ in which the α-GlcNAc residue is substituted with α-Gal and β-Gal at O3 and O4, respectively, and the β-GlcNAc substituted with α-Gal at O3. There is some variability in the presence of two of these three Gal substitutions. Comparison with the HF-PSs from *B. cereus* 10987 and *B. cereus* 14579 via glycosyl composition analysis and proton NMR spectroscopy showed that the *B. anthracis* structure was clearly different from each of these HF-PSs and, further, that the *B. cereus* 10987 HF-PS structure was different from that of *B. cereus* 14579. The presence of a *B. anthracis*-specific polysaccharide structure in its vegetative cell wall is discussed with regard to its relationship to those of other bacilli and to the possible functions of this molecule.

*Bacillus anthracis* is a gram-positive, spore-forming bacterium that causes anthrax (Mock and Fouet, 2001, *Ann. Rev. Microbiol.*, 55, 647-671). Cell wall carbohydrates such as capsular polysaccharides are well known virulence factors with regard to numerous bacterial pathogens, both gram-negative and gram-positive. However, relatively little is known about the carbohydrates in the vegetative cell walls of *B. anthracis* as well as other members of the *B. cereus* group of bacteria. While there have been some glycosyl composition analyses, there have been no reported structures for carbohydrates from the vegetative cell wall of *B. anthracis*.

Generally, the carbohydrate-containing components of the vegetative cell walls of gram-positive bacteria consist of the extensive peptidoglycan layer, teichoic acids, lipoteichoic acids, capsular polysaccharides, and crystalline cell surface proteins known as S-layer proteins that are often glycosylated (Messner, 1997, *Glycoconjugate J.*, 14(1): 3-11). However, the *B. anthracis*' cell wall differs in several aspects from this generalized description. First, *B. anthracis* cells are surrounded by a poly-δ-D-glutamic capsule and not by a polysaccharide capsule. Second, their cell walls do not contain teichoic acid (Molnar, 1971, *Acta Microbiol. Acad. Sci. Hung.*, 18(2): 105-108), and lastly, their S-layer proteins are not glycosylated (Mock and Fouet, 2001, *Ann. Rev. Microbiol.*, 55: 647-671; Mesnage et al., 2000, *EMBO J.*, 19:4473-4484). However, glycosyl composition comparisons of the cell walls of *B. anthracis, B. cereus*, and *B. thuringiensis* show that they do contain glycosyl residues and that they differ from one another in their glycosyl compositions (Fox et al., 2003, *J. Microbiol. Methods*, 54:143-152).

To date, cell wall carbohydrates from the vegetative cells of members of the *B. cereus* group have been addressed only to a limited extent (Ekwunife et al., 1991, *FEMS Microbiol. Lett.*, 82:257-262; Fox et al., 1993, *J. Clin. Microbiol.*, 31:887-894; Amano et al., 1977, *Eur. J. Biochem.*, 75:513-522). All of these carbohydrates are rich in amino glycosyl residues but have variations in the type and amounts of these residues. The study of Ekwunife et al. focused on the sugar composition of a carbohydrate polymer released from the cell wall through HF-treatment (the HF-treatment releases wall polysaccharides covalently bound via a phosphate bond to the peptidoglycan) of strain *B. anthracis* (Δ Sterne) and found that the HF-released polysaccharide (HF-PS) contained Gal, GlcNAc, and ManNAc in an approximate ratio of 3:2:1. This HF-PS was also further investigated by Mesnage et al. who reported the importance of a pyruvyl substituent with regard to the function of this polysaccharide in anchoring the S-layer proteins to the cell wall.

Fox et al. investigated a number of *B. anthracis* and *B. cereus* strains for their total cell glycosyl compositions, which showed interesting differences between the different strains (Fox et al., 1993, *J. Clin. Microbiol.*, 31:887-894). For example, in contrast to the *B. anthracis* strains, all *B. cereus* strains investigated contained GalN, suggesting possible differences in cell wall architecture in the different bacilli cell walls and, possibly, the occurrence of strain- or species-specific carbohydrates. The possibility of species/strain-specific structures is of interest for at least two reasons: the taxonomy within the *B. cereus* group has recently become a matter of debate (Priest et al., 2004, *J. Bacteriol*, 186(23):7959-7970; Han et al., 2006, *J. Bacteriol.*, 188(9):3382-3390 and investigations into cell wall carbohydrates of *B. cereus* group members may hold additional clues to their phylogenetic relatedness. In addition, the identification of specific cell wall carbohydrate structures could provide valuable leads in the elucidation of their functional importance in pathogenic interactions.

The function of one *B. anthracis* cell wall polysaccharide has been addressed in the literature. This function is its role for anchoring the S-layer proteins to the vegetative cell wall (Mesnage et al., 2000, *EMBO J.*, 19:4473-4484). The S-layer proteins contain a S-layer homology domain, which is found also in other S-layer proteins from Gram-positive bacteria and in cell wall enzymes, such as xylanase and pullanase from *Thermoanaerobacterium thermohydrosulfurigenes* (*Clostridium thermosulfurogenes*) (Brechtel and Bahl, 1999, *J. Bacteriol.,* 181(16):5017-5023). It is thought that S-layer homology domains bind to secondary cell wall carbohydrates that are covalently linked to the cell wall peptidoglycan via HF-labile phosphate bridges (Mesnage et al., 2000, *EMBO J.,* 19:4473-4484) and thus anchor the S-layer proteins to the bacterial cell walls. This function has been investigated in greatest detail for *B. anthracis* (Mesnage et al., 2000, *EMBO J.,* 19:4473-4484).

Thus far only a series of older reports about an isolated strain, namely *B. cereus* AHU 1356, addressed the question of a cell wall carbohydrate structure directly. The structures of neutral and acidic cell wall carbohydrates have been described for that strain. The neutral carbohydrate was composed of GlcNAc, ManNAc, GalNAc, and Glc in ratios of 4:1:1:1 (Amano et al., 1977, *Eur. J. Biochem.,* 75:513-522; Kojima et al., 1985, *Eur. J. Biochem.,* 148(3):479-484; Murazumi et al., 1986, *Eur. J. Biochem.,* 161(1):51-59), whereas the acidic carbohydrate was composed of GlcNAc, Gal, Rha, glycerol and phosphorus in ratios of 1:1:2:1:1 (Kojima et al., 1985, *Eur. J. Biochem.,* 148(3), 479-484).

As a first step in addressing cell wall carbohydrate structure/function relationships within members of the *B. cereus* group, this examples reports the structures of the HF-PSs of a number of *B. anthracis* and *B. cereus* strains. Structures were determined for these polysaccharides from *B. anthracis* Ames, *B. anthracis* Pasteur, and *B. anthracis* Sterne $34F_2$. These structures were compared with those from a closely related *B. cereus* strain, ATCC 10987, and from the *B. cereus* type strain, ATCC 14579. The results showed that all three *B. anthracis* strains contained the same HF-PS structure that differed from that of *B. cereus* 10987, which, in turn, differed from that of *B. cereus* ATTC 14579.

Experimental Methods

Bacterial Strains and Cultural Conditions. *B. anthracis* Ames, *B. anthracis* Pasteur, *B. anthracis* Sterne $34F_2$, and *B. cereus* strains ATCC 10987, and ATCC 14579 were provided from the Center for Disease Control culture collection. The mutant UT60 (i.e. Sterne 7702 ΔatxA) was provided by Dr. Theresa Kohler, University of Texas, Houston. Cultures were grown overnight (16 hours, 37° C.) in 100 ml of brain heart infusion medium (BD BBL, Sparks, Md.) containing 0.5% glycerol at 37° C., 200 rpm. In the morning, 4×1.5 ml of the overnight cultures were pelleted (10,000×g at room temperature for 5 minutes), the supernatants were discarded, the pellets resuspended in 500 liters of brain heart infusion and these four cell suspensions used to inoculate four 250-ml volumes of brain heart infusion medium in 1-liter Erlenmeyer flasks. Incubation was carried out at 37° C. (*B. anthracis*) or 30° C. (*B. cereus* and *B. thuringiensis*) on a shaker at 200 rpm. Growth was monitored by measuring the optical density at 600 nm. Cells were harvested in mid-log phase by centrifugation (8,000×g at 4° C. for 15 minutes), washed two times in sterile saline and enumerated by serial dilution and surface spread counts on brain heart infusion agar plates. Cultures were sterilized by autoclaving for 1 hour at 121° C. prior to further processing and carbohydrate analysis.

Preparation of Cell Wall Extract. The bacterial cells were grown as described above and cell walls were prepared by modification of a previously described procedure (Brown, 1973, *J. Bacteriol.,* 25, 295-300). Briefly, the autoclaved bacterial cells ($1\times10^{10}$ to $1\times10^{11}$ CFU) were disrupted in 40-ml sterile saline on ice by four 10-minute sonication cycles, using a Branson Sonifier (Type 450, Branson Ultrasonics Corp., Danbury, Conn.) with a ½ inch probe, operating at a frequency of 20 kHz. The complete or near complete disruption of cells was checked microscopically. Unbroken cells were removed by centrifugation (8,000×g, 4° C., 15 minutes). The separated pellet and supernatant fractions were stored at 80° C. Cell wall materials were sedimented by ultracentrifugation at 100,000×g at 4° C. for 4 hours (Optima L-90K Ultracentrifuge, Beckman). The resulting cell wall pellets were washed by suspension in cold, deionized water followed by an additional ultracentrifugation as above and lyophilization.

Isolation and Purification of the Cell Surface Polysaccharide. Cell wall materials from the *B. anthracis* Ames, *B. anthracis* Pasteur, *B. anthracis* Sterne 34F2 and UT60, the ΔatxA deletion mutant of *B. anthracis* Sterne 7702, were treated with 48% HFat 4° C. for 48 hours. The HF-treated material was neutralized by ice cold ammonium hydroxide solution (~30%) in an ice-water bath. The neutralized material was desalted by gel permeation chromatography using fine grade Bio-Gel P2 (Bio-Rad). Water was used as the eluent and an online refractive index detector was used to monitor the sample eluting from the column. The fractions that gave a positive response in the refractive index detector were collected, pooled, lyophilized, and used for further analysis.

Composition Analysis. Glycosyl composition analysis was done by the preparation and gas-chromatography mass-spectrometric (GC-MS) analysis of trimethylsilyl (TMS) methylglycosides (York et al., 1985, *Meth Enzymol,* 118:3-40). The TMS methylglycosides were identified and were quantified by comparison to authentic standards. In brief, the samples were methanolyzed using 1 molar (M) methanolic HCl at 80° C. for 18 hours to form the monomeric methylglycosides, followed by N-acetylation using pyridine and acetic anhydride (1:1) in presence of methanol at 100° C. for 1 hour. After removing the reagents by flushing with dry nitrogen the methyl glycosides were treated with Tri-Sil (Pierce) reagent at 80° C. for 30 minutes to form TMS methyl glycosides. The TMS methylglycosides were dissolved in hexane and analyzed on a GC-MS using HP-1MS column (30 m×0.25 mm×0.25 μm). Pyruvic acid content was measured according to the method of Hestrin. This method can detect less than 2 μg of pyruvic acid, and 200 μg of the isolated polysaccharides were assayed.

Glycosyl Linkage Analysis. The linkage analysis was performed according to a modification of the method of Ciucanu and Kerek (Ciucanu and Kerek, 1984, *Carbohydr. Res.,* 131: 209-217). Briefly, the samples were dissolved in dry dimethylsulfoxide (DMSO) (0.250 μl) overnight with stirring, followed by addition of $Me_2SO$/sodium hydroxide slurry and stirring for 2 hours at room temperature. Methyl iodide was added to the sample and stirred for 40 minutes. Another aliquot of methyl iodide was added and stirred for another 30 minutes. The reaction was cooled on an ice-bath and the partially methylated polysaccharide was extracted by partitioning between chloroform and water. The partially methylated sample in the chloroform layer was dried and used for the preparation of partially methylated alditol acetates (PMAAs). The partially methylated polysaccharide was methanolyzed to monomers using methanolic 1 M HCl at 80° C. for 16 hours followed by hydrolysis with 4 M trifluoroacetic acid (TFA) at 100° C. for 4 hours. The aldoses were reduced to their corresponding alditols by sodium borodeuteride ($NaBD_4$) overnight at room temperature. The excess borodeuteride was neutralized using 30% acetic acid solution and boric acid was removed as methyl borates by repeated refluxing and evaporation with acidified methanol and methanol respectively. The partially methylated alditols were then acetylated using a pyridine:acetic anhydride (1:1) solution at 100° C. for 1 hour. Pyridine and acetic anhydride were removed by flushing with dry nitrogen and the partially PMAAs were dissolved in dichloromethane and analyzed by GC-MS using a HP-1 MS column. The linkage positions of each monosaccharide were identified from its mass fragmentation pattern and by matching its retention time to that of authentic PMAA standards.

NMR Analysis. The polysaccharide samples (2-3 mg) were dissolved in 0.5 mL of regular grade deuterium oxide ($D_2O$) (99.8% Aldrich), and lyophilized; this process was repeated to exchange the hydroxyl and amide protons with deuterium. The sample was finally dissolved in 0.5 mL 100% $D_2O$ (100% D; Cambridge Isotope Laboratories) and transferred to a 5 mm NMR tube. All one- and two-dimensional NMR spectra were acquired at 25° C. on a 600 MHz Varian Inova instrument using the standard software supplied by Varian. Proton NMR spectra were measured using a spectral width of 8 kHz and the data were processed with HOD signal referenced to δ 4.78 ppm (the chemical shift of HOD relative to that of acetone at 25° C.). Gradient correlated spectra (gCOSY) were measured over a spectral width of 2.25 kHz in both dimensions using a dataset of ($t_1$x$t_2$) of 256×1024 points with 16 scans. Homonuclear total correlated spectra (TOCSY) and through space nuclear Overhauser effect correlation spectra (NOESY) were collected using a dataset of ($t_1$x$t_2$) of 256×1024 points and acquired over 32 scans. The mixing time used for TOCSY and NOESY experiments were 80 and 300 msec, respectively. To determine the carbon chemical shift a gradient $^1H$-$^{13}C$ single quantum coherence experiment (gHSQC) was done. Spectral widths with proton and carbon dimensions of 2.25 and 13.9 kHz, respectively, and a dataset of ($t_1$x$t_2$) 128×512 with of 96 scans were used in collecting the gHSQC spectra. All the NMR data were processed and analyzed using an NMR processing software Mest-Rec version 4.7.5 on Windows.

Mass Spectroscopy. Matrix-assisted laser desorption ionization time of flight (MALDI-TOF) mass spectrometer model Voyager-DE BioSpectrometry Work station (Applied Biosystems, Foster City, Calif.) was used to obtain the mass spectrum for each polysaccharide sample. Each sample was dissolved in 1:1 mixture of methanol:water and mixed at equal proportion (v/v) with 0.5 M 2, 5-dihydroxy benzoic acid (DHB) as the matrix. About 0.7 µl of this mixture was loaded on each spot on a stainless steel MALDI plate and air-dried. The spectra were acquired in delayed, linear and positive mode using 337 nm N2 laser with acceleration voltage of 20 kV.

Results

Isolation and initial analysis. Glycosyl composition analysis, as described in Example 1, showed that the HF-PSs from *B. anthracis* strains Ames, *B. anthracis* Pasteur, *B. anthracis* Sterne $34F_2$, and *B. anthracis* UT60, all had the same composition; namely, galactose (Gal), N-acetylglucosamine (GlcNAc), and N-acetylmannose (ManNAc) in an approximate 3:2:1 ratio, respectively. The composition of the HF-PS from *B. cereus* ATCC 10987 consisted of Gal, ManNAc, GlcNAc and GalNAc in a 1:1:1:1 ratio, and that of *B. cereus* ATCC 14579 of Glc, ManNAc, GlcNAc, and GalNAc in approximately a 1:1:2:1 ratio. None of the *B. anthracis* HF-PSs contained detectable levels (above 0.5% of the sample mass) pyruvic acid as determined by the colorimetric method of Katsuki (Katsuki et al., 1971, *Anal. Biochem,* 43(2):349-356). Methylation analysis of the *B. anthracis* HF-PSs showed that all of these polysaccharides contained the same glycosyl linkages; namely, terminally linked Gal, 4-linked GlcNAc, 6-linked GlcNAc, 4,6-linked GlcNAc, 3,4-linked GlcNAc, 3,4,6-linked GlcNAc, and 4-linked ManNAc. The variation in the GlcNAc linkages in these polysaccharides indicated that there is heterogeneity in the substitution of the GlcNAc residues.

Figure 3:
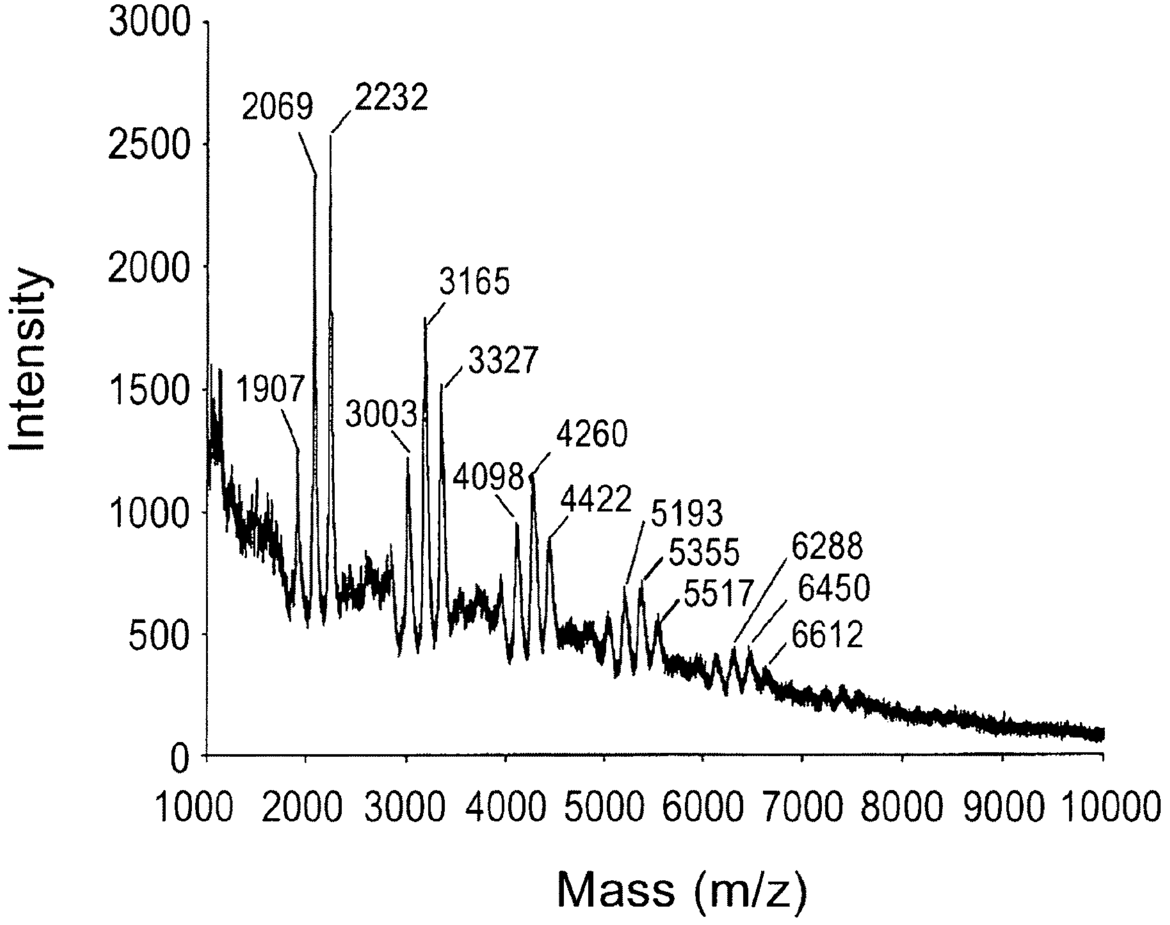
FIG. 3 is a matrix-assisted laser desorption ionization-time of flight mass spectrum (MALDI-TOF MS) (positive mode) of the HF-PS from *B. anthracis* Ames. The spectra of the HF-PSs from *B. anthracis* Sterne, UT60, and Pasteur were all identical to this spectrum.

Mass spectrometric analysis using MALDI-TOF MS confirmed that the *B. anthracis* HF-PSs where heterogeneous in the number of hexosyl (in this case, Gal) residues. The mass spectrum of the *B. anthracis* Ames polysaccharide is shown in FIG. 3 and the proposed compositions for the various ions are shown in Table 5. The mass spectrum shows a series of ion clusters. The mass observed for each ion cluster differs from that in the adjacent cluster by m/z 1095, a mass that is consistent a hexasaccharide repeating oligosaccharide comprised of three hexosyl and three N-acetylhexosaminosyl resides; e.g. $Gal_3GlcNAc_2ManNAc$. Each ion cluster contains three major ions that differ from one another by a single hexosyl unit, which, in this case, would be Gal. For example, m/z 2232 is consistent with a composition of $Gal_6GlcNAc_4ManNAc_2$, 2069 contains one less Gal residue, and m/z 1907 contains two less Gal residues (see Table 5). This heterogeneity in Gal residues, together with the variation in substitution pattern of the GlcNAc residues, suggests that the molecular heterogeneity in these polysaccharides is due to variation in substitution of one or more of the GlcNAc residues by Gal residues. The fact that each ion cluster contains variation in only one or two less Gal residues indicates that these changes may occur in only one of the multiple oligosaccharide repeating units for each ion cluster; e.g. the m/z ions 6612, 6450, and 6288 are due to $[Gal_3GlcNAc_2ManNAc_2]_5Gal_3GlcNAc_2ManNAc_1$, $[Gal_3GlcNAc_2ManNAc_1]_5Gal_2GlcNAc_2ManNAc_1$, and $[Gal_3GlcNAc_2ManNAc_1]_5Gal_1GlcNAc_2ManNAc_1$, respectively.

Figure 4:
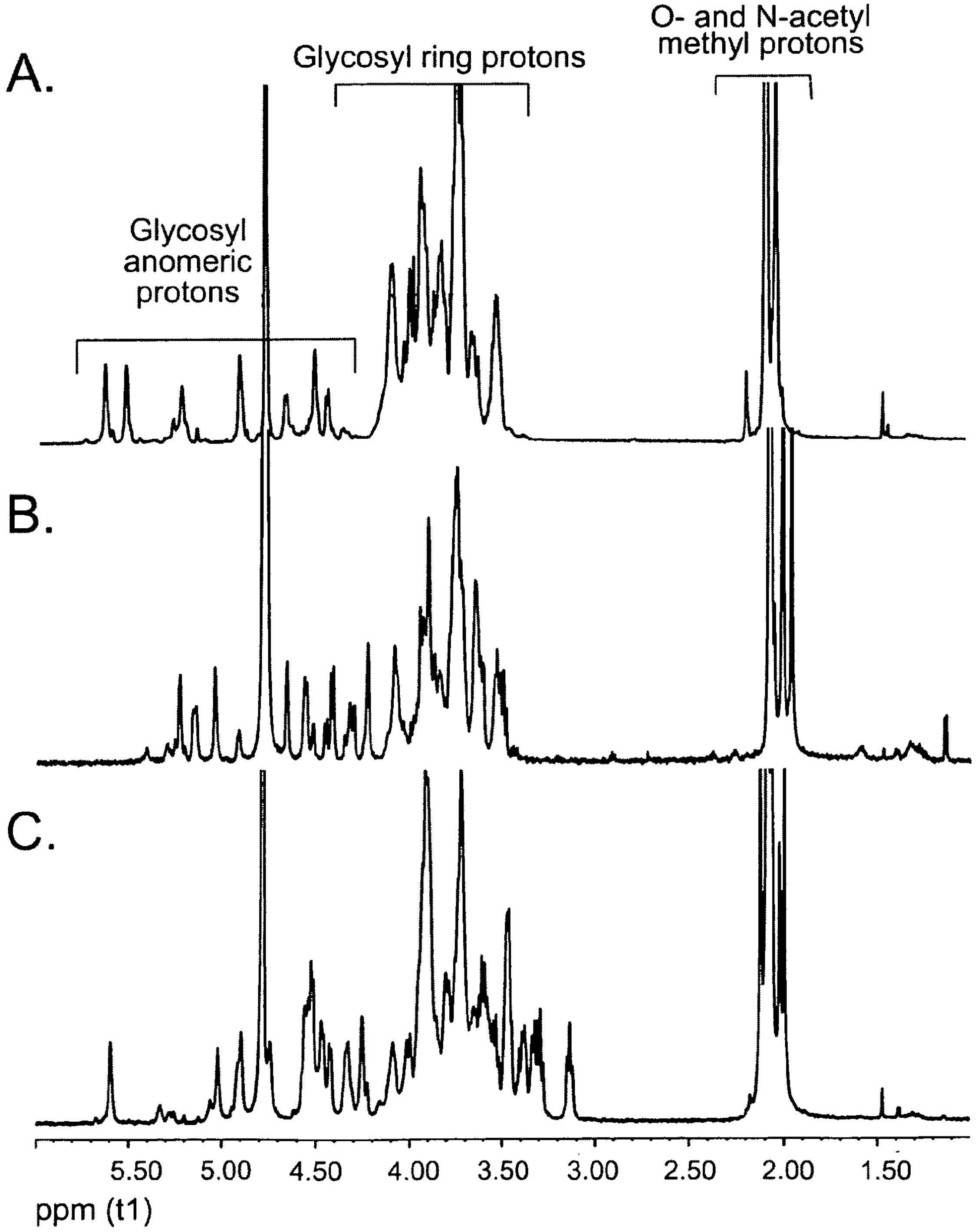
FIGS. 4A-4C present proton NMR spectra for the HF-PSs. The spectra for the HF-PSs are shown for *B. anthracis* Ames (FIG. 4A), *B. cereus* ATCC 10987 (FIG. 4B), and *B. cereus* ATCC 14579 (FIG. 4C).

NMR Analysis of the *B. anthracis* Polysaccharides. As reported in Example 1, the glycosyl residue compositions of the HF-PSs from the *B. anthracis* strains are different from those for *B. cereus* ATCC 10987, and the *B. cereus* type strain ATTC 14579. The proton NMR spectra comparing HF-PS from *B. anthracis* Ames with the two *B. cereus* strains is shown in FIGS. 4A-4C. Each spectrum clearly differs from the other in the pattern of resonances for their glycosyl anomeric and ring protons. These results show, as is indicated by the composition differences, that the structure of the HF-PS from the *B. anthracis* is different from those of *B. cereus* ATCC 10987 and ATCC 14579 and, furthermore, that the *B. cereus* ATCC 10987 structure differs from that of strain ATCC 14579. The spectra comparing the HF-PSs of *B. anthracis* Ames, *B. anthracis* Sterne, and *B. anthracis* Pasteur are shown in FIGS. 5A-5C. These spectra are identical to one another and support the conclusion that these polysaccharides all have the same structure. Further NMR analyses (gCOSY, TOCSY, NOESY, and gHSQC) also gave identical spectra for the HF-PSs from the *B. anthracis* strains. Because of the identical nature of these NMR analyses of the *B. anthracis* HF-PSs, the structural details are described below for the HF-PS isolated from *B. anthracis* Ames.

Figure 5:
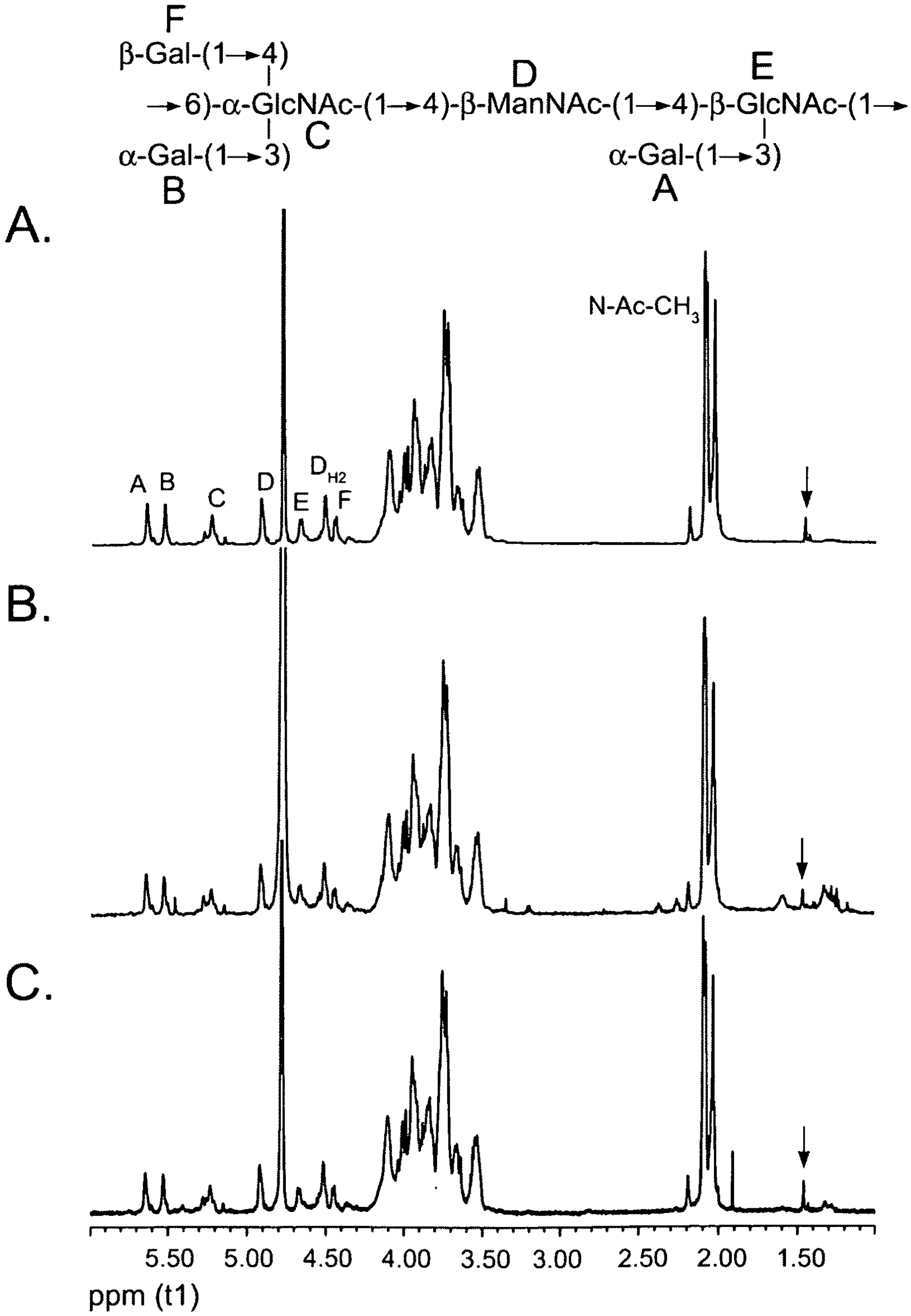
FIGS. 5A-5C present proton NMR spectra for the HF-PSs from the various *B. anthracis* strains. The spectra are shown for the HF-PSs from *B. anthracis* Ames (FIG. 5A), *B. anthracis* Sterne (FIG. 5B), *B. anthracis* Pasteur (FIG. 5C). The spectrum for *B. anthracis* UT60 was identical to those shown in this figure.

The proton spectrum given in FIG. 5A for the *B. anthracis* Ames polysaccharide shows it contains six anomeric signals at δ 5.64, δ 5.53, δ 5.22, δ 4.91, δ 4.67 ($J_{1,2}$=7.2 Hz), δ 4.44 (J1,2=7.8 Hz) supporting the conclusion that this polysaccharide consists of a hexasaccharide repeat unit; a result that is consistent with the composition and mass spectrometric data described above. Furthermore, the chemical shifts and $J_{1,2}$ coupling constants of these anomeric protons indicate that three of these glycosyl residues are α-anomers, and at least two are β-anomers, while the anomeric configuration of the remaining glycosyl residue (i.e. the glycosyl residue with H1 at δ 4.91) can not be deduced from the 1-D proton spectrum due to its small $J_{1,2}$ coupling, which indicates that this residue is in the manno configuration. The presence of a repeating unit of six glycosyl residues is also supported by the HSQC spectrum (FIG. 6) which clearly shows six anomeric proton/carbon resonances. A resonance at δ 1.48 was observed (FIG. 5, arrows), that is consistent with the methyl protons of a pyruvyl substituent as reported by Mesnage et al. (Mesnage et al., 2000, *EMBO J.,* 19:4473-4484). However, the relatively low intensity of this resonance indicates that the putative pyruvyl component is present in non-stoichiometric, and low, amounts. Pyruvate is an acid labile component and it is very likely that the majority of this component was removed during the aqueous HF treatment of the cell walls.

The assignments of the proton and carbon resonances for the polysaccharides were determined by a series of two-dimensional NMR experiments; COSY, TOCSY (FIG. 7), NOESY (FIG. 8), and HSQC (FIG. 6) analyses. The rationale for these assignments (given in Table 6) is described in the following paragraphs.

Figure 6:
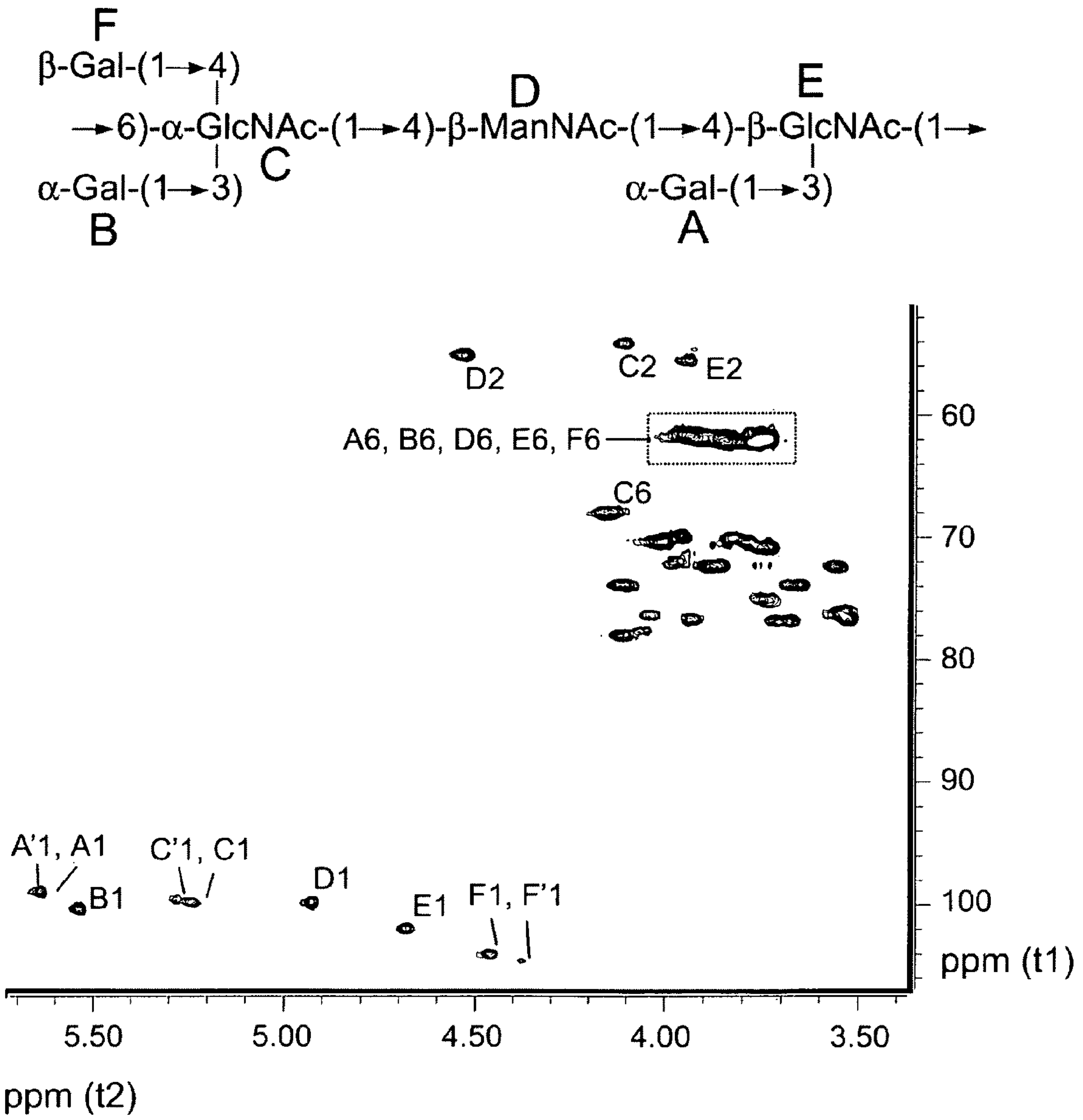
FIG. 6 shows the HSQC spectrum of the HF-PS from *B. anthracis* Ames. The structure and the assigned proton/carbon correlations are as shown. The complete NMR assignments are given in Table 6. The HSQC spectra of the HF-PSs from *B. anthracis* Sterne, UT60, and Pasteur are identical to this spectrum.
Figure 7:
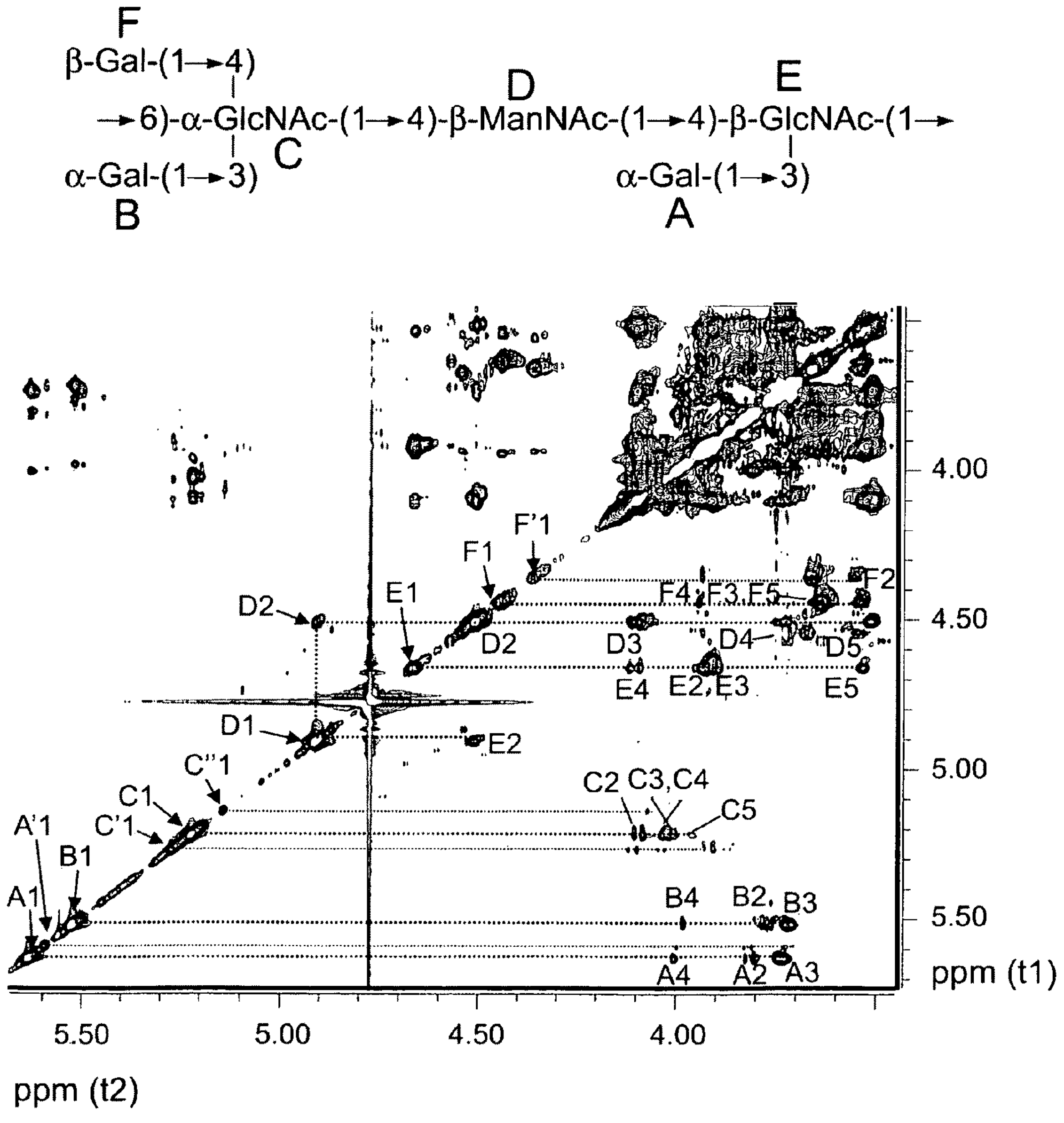
FIG. 7 shows the TOCSY spectrum of the HF-PS from *B. anthracis* Ames. The structure and the assigned proton resonances are as shown. The complete NMR assignment is given in Table 6. The TOCSY spectra of the HF-PSs from *B. anthracis* Sterne, UT60, and Pasteur are identical to this spectrum.

Residue A contains an anomeric proton, H1, resonating at δ 5.64. The H1 through H4 assignments are readily assigned from the COSY and TOCSY (FIG. 7) data. It is apparent from the TOCSY spectrum that the H4 resonance at δ 4.00 has a small overall coupling to the adjacent H3 and H5 protons (i.e. $J_{3,4}+J_{4,5}<9.6$ Hz) supporting the conclusion that A has a galacto configuration, and, therefore, is an α-Gal residue. In order to assign H5 and the H6 protons, it was necessary to determine, using the TOCSY data, the resonances of the protons coupled to H4. This analysis showed that H4 is coupled to protons at δ 3.74 (H3), δ 3.82 (H2), and another proton at δ 3.84 which was assigned as H5. The H5 resonance was, in turn coupled to protons in the δ 3.76 range which are likely the H6 protons. The HSQC spectrum (FIG. 6) shows that protons at δ 3.76 are coupled to a C-6 at δ 62, which supports the presence of H6 protons at this chemical shift. The remaining carbon chemical shifts for this residue, and for the following residues, were also obtained from the HSQC spectrum (FIG. 6).

Residue B has an anomeric H1 at δ 5.53. As with residue A, the H1 through H4 resonances are readily assigned from the COSY and TOCSY data, and the small overall $J_{3,4}$ and $J_{4,5}$ coupling constants of H4 (<9.6 Hz) show that residue B has a galacto configuration and is a second α-Gal residue. Further analysis of the TOCSY data show that H4 (δ 3.98) is coupled to H3 (δ3.72), H2 (δ 3.77), and a proton resonating at δ 3.87 which was assigned to H5. This proton was coupled to H6 protons with chemical shifts in the δ 3.73 range. As with residue A, due to overlapping resonances in this range, it was not possible to determine the exact chemical shifts of the H6 protons. However, the protons in this range are coupled to C-6 carbons that resonate at about δ 62 (the HSQC spectrum, FIG. 6) supporting that these are H6 protons.

The anomeric proton of residue C has a chemical shift of δ 5.22. The H1 through H5 assignments were made from the COSY and TOCSY data. Further analysis of the TOCSY data showed that H3 (δ 4.02) was coupled to H4 (δ 4.03), H5 (δ 3.94) and to protons at δ 4.07-4.12 which were assigned as the H6 protons. The HSQC spectrum (FIG. 6) showed that protons at δ 4.07-4.12 were coupled to a carbon at δ 68.1 which is consistent with a glycosyl residue that is substituted at position C6. The HSQC spectrum also showed that H2 (δ 4.09) was coupled to a carbon at δ 54.1 consistent with this carbon having an attached nitrogen and, therefore, supporting the conclusion that this is a glycosaminosyl residue. Since composition analysis shows the presence of only GlcNAc and ManNAc residues, the TOCSY proton interactions from H1 through H5 supports the conclusion that this residue has proton-proton coupling constants that are consistent with it having a gluco configuration and, therefore, residue C is identified as an α-GlcNAc residue.

The anomeric H1 of residue D has a chemical shift of δ 4.91. The COSY and TOCSY data (FIG. 7) show that H1 is coupled to H2 at δ 4.51. The TOCSY spectrum shows that only H2 can be observed via H1 indicating that residue D has a very small $J_{1,2}$ coupling and, therefore, has a manno configuration. The HSQC spectrum shows that H2 is coupled to a nitrogen-bearing carbon at δ 55.0 supporting the conclusion that residue D is a glycosaminosyl residue. Examination of the protons coupled to H2 from the TOCSY data allowed assignment of H3 (δ 4.09), H4 (δ 3.74), and H5 (δ 3.51). The TOCSY spectrum also showed that H5 is coupled to H3, H4, and to protons with chemical shifts at δ 3.84/3.77 which were assigned as H6 protons. These protons were coupled to a carbon resonating at δ 62.2 consistent with a C6 carbon. The anomeric configuration of a manno residue is difficult to determine since both α- and β-anomers have small $J_{1,2}$ coupling constants. However, the NOESY spectrum (FIG. 8) shows NOEs between H1, H3, and H5 supporting the conclusion that these protons are all in axial position and, therefore, that this residue has a r-configuration. Thus, D is a β-ManNAc residue.

The H1 of residue E has a chemical shift of δ 4.67 and, as described above, both this chemical shift and the $J_{1,2}$ value of 7.2 Hz show that it has a β-configuration. The COSY and TOCSY data show that H1 is coupled to H2 at δ 3.92, H3 also at δ 3.92, H4 at δ 4.10, and H5 at δ 3.54. Further analysis of the TOCSY data showed that H5 is coupled to protons at δ 3.77 and 3.84 which were assigned as H6 protons, and, which HSQC analysis show are coupled to a C-6 with a chemical shift of δ 61.6 (HSQC analysis, FIG. 6). The HSQC spectrum also shows that H2 (δ 3.92) is coupled to a nitrogen-bearing carbon at δ 55.3. These results show that residue E is the remaining glycoaminosyl residue, a β-GlcNAc residue.

Residue F has an anomeric H1 with a chemical shift of δ 4.44 and a $J_{1,2}$ coupling of 7.8 Hz showing that it has a β-configuration. The COSY and TOCSY data (FIG. 7) allow assignment from H1 to H2 (δ 3.54), H3 (δ 3.64), and H4 (δ 3.94). The TOCSY data also revealed that H4 has a small total $J_{3,4}$ plus $J_{4,5}$ coupling of less than 9.6 Hz showing that residue F has a galacto configuration. The TOCSY data also shows that H4 is coupled to H2 and H3 as expected, and also to a proton with a chemical shift of δ 3.63 which was assigned to H5. This H5 was, in turn coupled to protons at δ 3.77 to 3.84 which were assigned as the H6 protons. The HSQC spectrum (FIG. 6) showed that these protons are coupled to a C6 carbon at δ 61.9. Thus, F is a β-galactose residue.

The COSY and TOCSY spectra, as with the methylation and mass spectrometric data, also suggest heterogeneity in the polysaccharide. There are multiple versions of residue C (the α-GlcNAc residue) as evidenced by an additional minor glycosyl ring system connected to an anomeric proton at δ 5.27 (residue C'), and another minor glycosyl ring system at δ 5.14 (residue C"), FIG. 6. Similarly, there is an additional version of residue A, A', as evidenced by another ring system through an H1 at δ 5.60, and an additional version of residue F, F', via a ring system through H1 at δ 4.36. These additional terminal α- and β-Gal glycosyl ring systems (A' and F') as well as the additional α-GlcNAc residues (C' and C") support the above methylation and mass spectrometric data that show heterogeneity in the GlcNAc substitution pattern, and heterogeneity in the level of hexose (i.e. in this case, Gal) addition; likely due to variable substitutions of the α-GlcNac residue C by the Gal residues A and F.

Figure 8:
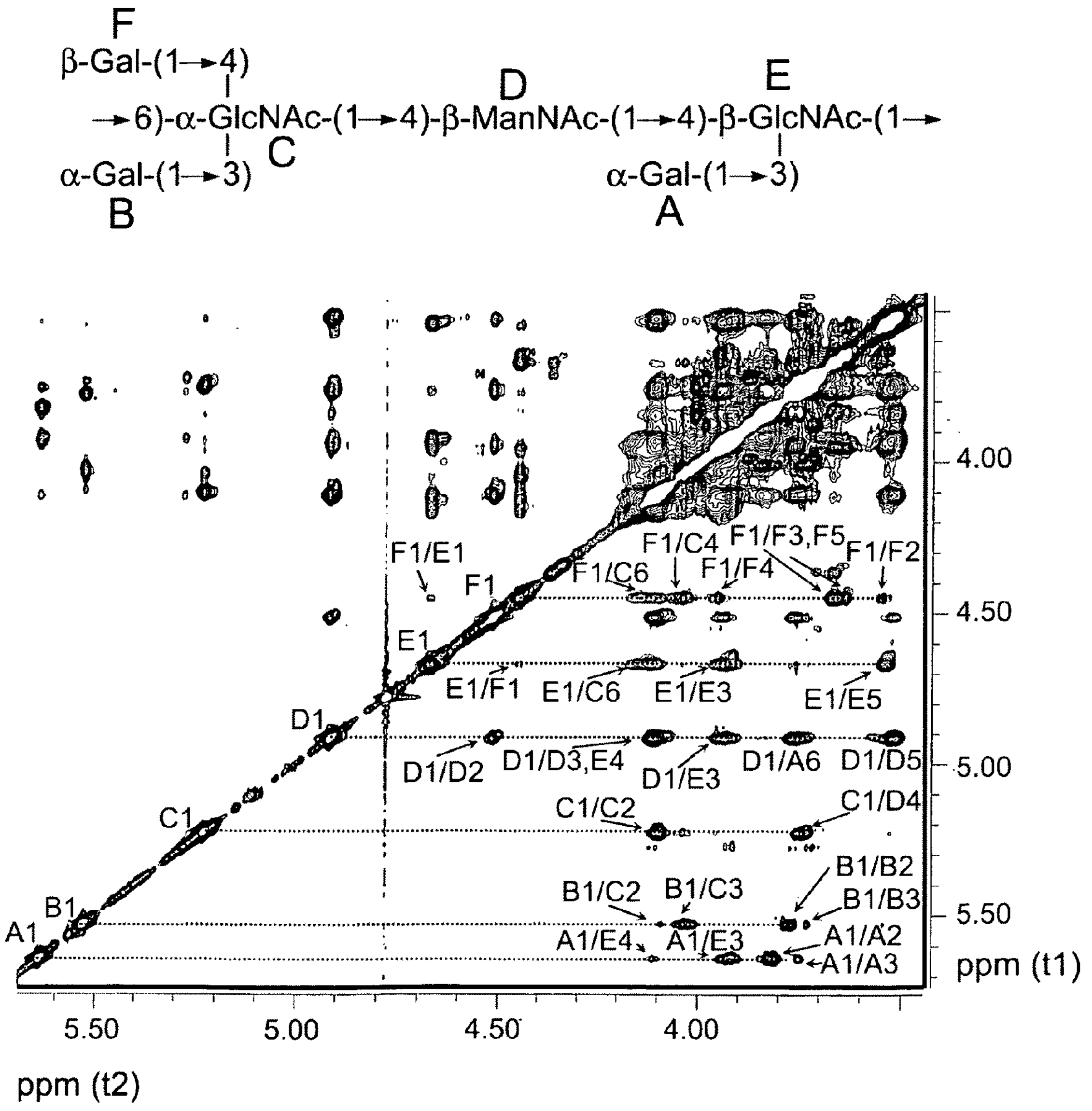
FIG. 8 shows the NOESY spectrum of the HF-PS from *B. anthracis* Ames. The structure and the inter- and intra-residue NOEs are indicated. The NOESY spectra of the HF-PSs from *B. anthracis* Sterne, UT60, and Pasteur are identical to this spectrum.

The sequence of the glycosyl residues was determined from by NOESY analysis, FIG. 8. Residue A, α-galactose, has a strong inter-residue nuclear Overhauser effect (NOE) from H1 at δ 5.64 to H3 (δ 3.92) of residue E, β-GlcNAc, supporting a α-Gal-(1→3)-β-GlcNAc sequence. There is also a weak inter-residue NOE to H4 (δ 4.10) of the β-GlcNAc residue, and strong and weak intra-residue NOEs to H2 at δ 3.82 and H3 at δ 3.74, respectively.

Residue B, the second α-galactose, has a strong inter-residue NOE from H1 at δ 5.53 to H3 (δ 4.02) of residue C, α-GlcNAc, supporting a α-Gal-(1→3)-α-GlcNAc sequence. A weak inter-residue NOE to H2 (δ 4.09) of residue C was also present. Strong and weak intra-residue NOEs to H2 and H3 at δ 3.77 and 3.72, respectively, were also observed.

Residue C, α-GlcNAc, has a strong inter-residue NOE from H1 (δ 5.22) to the H4 (δ 3.74) of residue D, β-ManNAc, which supports a α-GlcNAc-(1→4)-β-ManNAc sequence. This information combined with inter-residue NOE for residue A described above shows that the oligosaccharide repeating unit has a partial sequence (Structure 1). There is also a strong intra-residue NOE from the H1 of residue C to its H2 at δ 4.09.

Structure 1

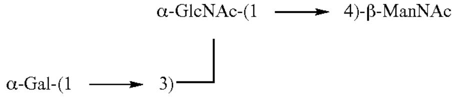

Residue D, β-ManNAc, has NOEs to protons at δ 4.51, 4.10, 3.92, 3.74, and 3.51. The NOEs at δ 4.51 and 3.51 are due to intra-residue interactions with H2 and H5, respectively, as expected for a β-linked ManNAc residue. The NOE to the proton at δ 3.92 is an inter-residue NOE to H3 of residue E, β-GlcNAc. However, it is unlikely that the ManNAc residue is attached to this position of β-GlcNAc since, as described above, it is already occupied by a α-galactose residue (residue A). However, there is also a strong NOE to a proton at V 4.10. It is likely that this NOE is due to a combination of an intra-residue NOE to H3 (δ 4.10) and an inter-residue NOE to H4 (δ 4.10) of residue E, β-GlcNAc. The placement of β-ManNAc at this position on the β-GlcNAc likely results in a close spatial arrangement the β-ManNAc H1 to the H3 of the β-GlcNAc residue accounting for the NOE between these two protons. These data indicate the presence of a β3-ManNAc-(1→4)-β-GlcNAc sequence and, together with the inter-residue NOEs described above for residues A, B and C indicate that the polysaccharide contains a partial sequence (Structure 2).

Structure 2

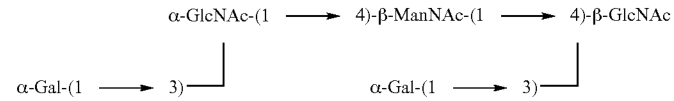

The presence of a 3,4-linked GlcNAc residue is also consistent with the methylation data described earlier. The β-ManNAc residue also has an NOE from H1 to a proton at δ 3.74. Because this residue is a β-linked ManNAc, it is unlikely that this proton is the intra-residue H4 as that proton would not be in close proximity to H1. However, it is possible that one of the H6 protons of the α-Gal residue (A) (in the δ 3.74 to δ 3.77 range) linked to position C3 of this same β-GlcNAc residue is in close enough proximity to the ManNAc H1 to account for this NOE.

Residue E, the β-GlcNAc residue, has NOEs to protons at δ 4.12, 3.92, and 3.54. The NOEs to δ 3.92 and 3.54 are intra-residue contacts to H3 and H5, respectively which would be expected for a W-linked GlcNAc residue. The contact at δ 4.12 is due to an inter-residue NOE to H6 of residue C, the α-GlcNAc residue. Thus, residue E, the β-GlcNAc residue is attached to position 6 of residue C, the α-GlcNAc residue, indicating a partial sequence for this repeating oligosaccharide (Structure 3). An inter-residue NOE with the H1 (δ 4.44) of residue F, β-Gal, was also observed indicating that the anomeric protons of residues E and F are in close proximity.

Structure 3

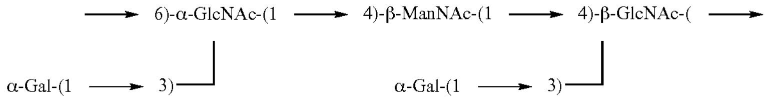

Figure 9:
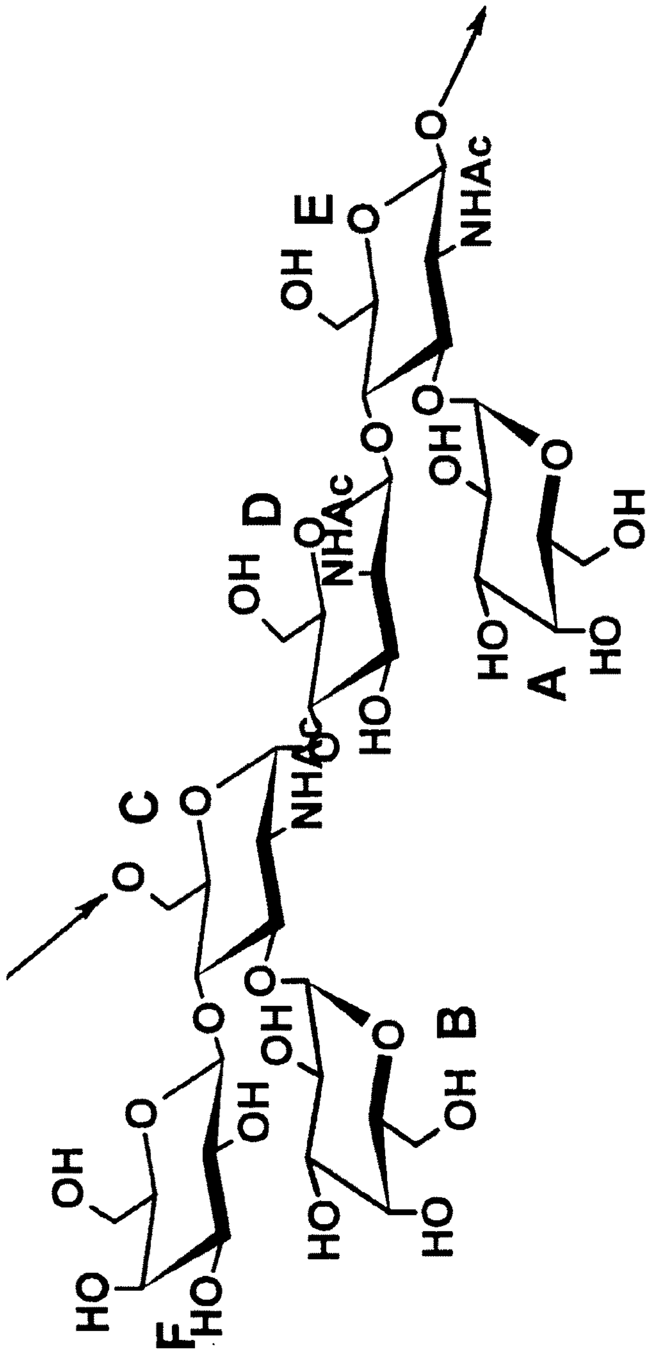
FIG. 9 shows the structure of the HF-PS repeating oligosaccharide from *B. anthracis.*

The remaining residue, F (β-galactose), has a strong inter-residue NOE to H4 (δ 4.03) of residue C as well as intra-residue NOEs to H2, H3, and H4 at δ 3.54, 3.64, and 3.94, respectively. The NOE at δ 3.64 could also overlap somewhat with an intra-residue NOE to H5 at δ 3.63. These results indicate that the β-Gal residue F is attached to the α-GlcNAc residue C at C4. As described above for residue E, a NOE between the anomeric protons of residues F and E were also observed supporting that the anomeric protons of these two residues are in close proximity. Therefore, these NMR data together with the mass spectrometer, glycosyl composition, and linkage data show that the polysaccharide contains an overall repeating unit sequence (Structure 4).

due is substituted with a pyruvyl residue at the O-4/O-6 positions (Kojima et al., 1988, *Eur. J. Biochem,* 174(2):255-260). A major *B. cereus* cell wall polysaccharide from strain AHU 1356 is reported to have a →3)-α-GalNAc-(1→4)-β-ManNAc-(1→3)-α-GlcNAc-(1→ backbone in which the GalNAc residue is substituted with an α-Glc at O-6, the ManNAc with a β-GlcNAc at O-3, and the GlcNAc residue with a →6)-β-GlcNAc-(1→6)-β-GlcNAc-(1→ disaccharide at O-6 (Amano et al., 1977, *Eur. J. Biochem.,* 75, 513-522). The structure reported in this example for the HF-PS from the *B. anthracis*, as shown in FIG. 9, also consists of an amino sugar backbone of →6)-α-GlcNAc-(1→4)-β-ManNAc-(1→4)-β-GlcNAc-(1→ in which the α-GlcNAc residue is Structure 4

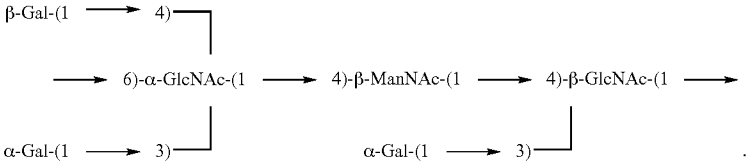

Discussion

This example reports the structure of the HF-PS from *B. anthracis* (FIG. 9) and demonstrates that this structure is the same for *B. anthracis* Ames, *B. anthracis* Sterne, *B. anthracis* UT60, and *B. anthracis* Pasteur. In addition, a proton NMR comparison, as well as composition analysis, shows that this structure is different from the HF-PS from a strain of *B. cereus* ATCC 10987 that is closely related to *B. anthracis* (Rasko et al., 2004, *Nucl. Acids Res.,* 32(3), 977-988), and from the HF-PS of *B. cereus* ATCC 14597 (the type strain). Earlier publications (Mesnage et al., 2000, *EMBO J.,* 19, 4473-4484; Ekwunife et al., 1991, *FEMS Microbiol. Lett.,* 82:257-262) reported the composition of the cell wall polysaccharide from *B. anthracis* and that of the major polysaccharide released from the cell wall by treatment with aqueous HF. This HF treatment disrupts the phosphate bridge of the polysaccharide to the cell wall peptidoglycan. The composition of the HF-PS was reported to consist of Gal, ManNAc, and GlcNAc in a 3:1:2 ratio (Ekwunife et al., 1991, *FEMS Microbiol. Lett.,* 82:257-262), or in a 10:3:1 ratio (Mesnage et al., 2000, *EMBO J.,* 19, 4473-4484). The work of this example is consistent with the earlier report of Ekwunife et al. (showing that the *B. anthracis* HF-PS consists of these glycosyl residues in a 3:1:2 ratio. It was also reported that the HF-PS was pyruvylated (Mesnage et al., 2000, *EMBO J.,* 19, 4473-4484), and that the pyruvyl substituent is required for the function of the HF-PS; acting as the ligand for the S-layer homology domain of S-layer proteins (Mesnage et al., 2000, *EMBO J.,* 19, 4473-4484). From the results of this example, the presence of a pyruvyl substituent is uncertain (described further below).

It is worth noticing that a number of reported polysaccharide structures from related bacilli strains have the common feature of an amino sugar backbone substituted by branching glycosyl residues and non-carbohydrate substitutents. The major polysaccharide from *B. subtilis* AHU 1219 cell walls consists of a →6)-α-GalNAc-(1→4)-β-ManNAc-(1→4)-β-GlcNAc-(1→ backbone in which the GalNAc residue is substituted at O-3 with a β-Glc residue and the ManNAc residue is substituted at O-3 with a β-GlcNAc residue (Iwasaki et al., 1989, *Eur. J. Biochem.,* 178(3):635-641). The major polysaccharide for the cell walls of *Paenibacillus polymyxa* AHU 1385 (formerly *B. polymyxa*) consists of →3)-β-ManNAc-(1→4)-β-GlcNAc-(1→ backbone in which the ManNAc resisubstituted with α-galactose and β-galactose at O-3 and O-4, respectively, and the β-GlcNAc substituted with -galactosidase at O-3. The data also suggest that there is variability in the presence of the two Gal substitutions on the α-GlcNAc residue. A common feature in the backbone structure of all of these polysaccharides, including the *B. anthracis* structure, seems to be the presence of a ManNAc-GlcNAc disaccharide component. The commonality of the amino sugar backbone in all of these bacilli cell wall polysaccharides may indicate that this molecule has an essential function for the viability of *Bacillus* species.

That the HF-PS from *B. anthracis* Sterne had essential functions is supported in a report by Mesnage et al. (Mesnage et al., 2000, *EMBO J.,* 19:4473-4484). Whereas Mesnage et al. did not determine the structure of this polysaccharide, the proton NMR spectrum they show of the HF-PS for *B. anthracis* Sterne is identical to the spectra in FIG. 5 of the present example for the HF-PSs isolated from *B. anthracis* Ames, *B. anthracis* Sterne, and *B. anthracis* Pasteur. Mesnage et al. state that pyruvate is a component of the HF-PS; however, whereas the NMR spectra of the present example showed a resonance consistent with a pyruvyl methyl group (the resonance at δ 1.48, see FIG. 4) as reported by Mesnage et al., colorimetric analysis failed to detect pyruvate in any of the *B. anthracis* HF-PSs. The reason for this discrepancy is unknown at this time. However, because pyruvate substitutents are labile to mild acid, it is possible that the majority of these substituents were removed by HF treatment and, in the present example, resulted in lowering the pyruvate content below detectable levels when using the calorimetric assay. Mesnage et al. reported that a csaB mutant was affected in the addition of the pyruvyl substituent to the polysaccharide in that it lacked the resonance at δ 1.48. The csaB mutant was shown to be defective in locating the S-layer proteins, EA1 and Sap, to its surface. The mutant also showed an increase in sedimentation when grown in liquid medium, formation of aberrant colonies on solid medium, and, on microscopic examination, a defect in cell separation. Furthermore, the csaB mutant failed to undergo autolysis. Because all of these effects were produced by the failure to substitute the otherwise normal HF-PS with pyruvate it seems likely that the ability to produce the entire polysaccharide is essential for the viability of *B. anthracis* and, therefore, its synthetic mechanism is a potential target for novel therapeutics.

In addition to the function of the HF-PS in *B. anthracis* autolysis and cell division just described, a recent report by Mayer-Scholl et al. (Mayer-Scholl et al., 2005, *PLoS Path.*, 1(3):179-186) present data that indirectly indicate a role for a cell wall polysaccharide in the defense response of the host. They showed that the active component from the neutrophil granule that killed vegetative *B. anthracis* cells were α-defensins. The α-defensins are cationic peptides that are part of the innate immune system and are involved in the resistance of a host toward both Gram-negative and Gram-positive infections. Because α-defensins are lectin-like and likely function by binding to carbohydrate components on the surface of the pathogen (Wang et al., 2004, *J. Immunol.*, 173: 515-520), it seems quite possible that the ability of neutrophils to kill vegetative *B. anthracis* cells depends on the binding of α-defensins to a carbohydrate component of the vegetative cell wall. It is possible that the α-defensin ligand may be the HF-PS.

As described above, previous composition analysis and structural determination have shown that the major polysaccharide from *Bacillus* species cell walls varies depending on the species being examined. This example shows that this variation is even more refined in that glycosyl compositions vary among *B. cereus* clades, and also among lineages within a single clade (as shown in Example 1). These composition differences reflect structural variation in the *B. cereus* group as demonstrated by the different NMR spectra (FIG. 4) of the HF-PSs from *B. anthracis, B. cereus* ATCC 10987, and *B. cereus* ATCC 14579. The *B. cereus* ATCC 10987 strain is quite closely related to *B. anthracis* strains as reported by Rasko et al. (Rasko et al., 2004, *Nucl. Acids Res.*, 32(3):977-988) in that it contains a plasmid that is similar to pXO1, but lacks the pathogenicity island that encodes for the toxin components. In fact, the genome of *B. cereus* ATCC 10987 is 93.7% similar to *B. anthracis*, whereas it is 90.9% similar to *B. cereus* ATCC14579 (Rasko et al., 2004, *Nucl. Acids Res.*, 32(3):977-988). Thus, these results support the conclusion that the *B. anthracis* structure reported in this example is specific to *B. anthracis* and different from that of even closely related *B. cereus* strains. An exception to this conclusion may be several pathogenic isolates of *B. cereus*, which are able to cause pneumonia in humans (Hoffmaster et al. M., 2004, *Proc. Natl. Acad. Sci.*, 101(22):8449-8454). Ongoing work shows that in these *B. cereus* strains, the cell wall polysaccharide compositions are very close to those of the *B. anthracis* strains (see Example 1). These results suggest that the major cell wall polysaccharide may have a function in determining the virulence of *B. anthracis* as well as of these pathogenic *B. cereus* strains. More detailed structural comparisons of the HF-PSs from the pathogenic *B. cereus* strains that are closely related to *B. anthracis* are currently underway.

In conclusion, this example describes the structure of the predominant cell wall carbohydrate of *B. anthracis* and proposes that this cell wall carbohydrate is critical for viability, and for pathogenicity of *B. anthracis*, and, therefore, is a target for development of specific antimicrobials against anthrax. See, also, Choudhury et al., Sep. 22, 2006, *J Biol Chem* 281, (38):27932-27941; published, JBC Papers in Press, Jul. 26, 2006, DOI 10.1074/jbc.M605768200.

TABLE 5

Mass spectral data of de-O-acetylated polysaccharide from *B. anthracis* Ames.

| Observed mass (m/z) | Proposed Composition |
|---|---|
| 2232 | $Gal_6GlcNAc_4ManNAc_2Na^+$ |
| 2069 | $Gal_5GlcNAc_4ManNAc_2Na^+$ |
| 1907 | $Gal_4GlcNAc_4ManNAc_2Na^+$ |
| 3327 | $Gal_9GlcNAc_6ManNAc_3Na^+$ |
| 3165 | $Gal_8GlcNAc_6ManNAc_3Na^+$ |
| 3003 | $Gal_7GlcNAc_6ManNAc_3Na^+$ |
| 4422 | $Gal_{12}GlcNAc_8ManNAc_4Na^+$ |
| 4260 | $Gal_{11}GlcNAc_8ManNAc_4Na^+$ |
| 4098 | $Gal_{10}GlcNAc_8ManNAc_4Na^+$ |
| 5517 | $Gal_{15}GlcNAc_{10}ManNAc_5Na^+$ |
| 5355 | $Gal_{14}GlcNAc_{10}ManNAc_5Na^+$ |
| 5193 | $Gal_{13}GlcNAc_{10}ManNAc_5Na^+$ |
| 6612 | $Gal_{18}GlcNAc_{12}ManNAc_6Na^+$ |
| 6450 | $Gal_{17}GlcNAc_{12}ManNAc_6Na^+$ |
| 6288 | $Gal_{16}GlcNAc_{12}ManNAc_6Na^+$ |

TABLE 6

$^1H$ and $^{13}C$ chemical shift values for the *B. anthracis* Ames cell wall polysaccharide.

| Residue | H1 (C1) | H2 (C2) | H3 (C3) | H4 (C4) | H5 (C5) | H6 (C6) |
|---|---|---|---|---|---|---|
| A. α-D-Gal | 5.64 | 3.82 | 3.74 | 4.00 | 3.84 | ≈3.76 |
| | (98.8) | (70.0) | (70.6) | (72.2) | (72.2) | (61.9) |
| B. α-D-Gal | 5.53 | 3.77 | 3.72 | 3.98 | 3.87 | ≈3.73 |
| | (100.3) | (70.3) | (70.6) | (70.3) | (72.2) | (61.9) |
| C. α-D-GlcNAc | 5.22 | 4.09 | 4.02 | 4.03 | 3.94 | 4.12/4.07 |
| | (99.7) | (54.1) | (76.3) | (77.5) | (71.9) | (68.1) |
| D. β-D-ManNAc | 4.91 | 4.51 | 4.10 | 3.74 | 3.51 | 3.84/3.77 |
| | (99.7) | (55.0) | (73.8) | (75.3) | (76.3) | (62.2) |
| E. β-D-GlcNAc | 4.67 | 3.92 | 3.92 | 4.10 | 3.54 | 3.84/3.77 |
| | (101.9) | (55.3) | (76.6) | (78.1) | (76.3) | (61.6) |
| F. β-D-Gal | 4.44 | 3.54 | 3.64 | 3.94 | 3.63 | 3.84/3.77 |
| | (104.1) | (72.5) | (73.8) | (70.0) | (73.8) | (61.9) |

Example 3

Synthesis and Antigenic Analysis of the BclA Glycoprotein Oligosaccharide from the *Bacillus anthracis* Exosporium The glycoprotein BclA is an important constituent of the exosporium of *B. anthracis*. This glycoprotein is substituted with an oligosaccharide composed of a 1,2-linked β-L-rhamnoside substituted with the previously unknown terminal saccharide, 2-O-methyl-4-(3-hydroxy-3-methylbutamido)-4,6-dideoxy-D-glucopyranose, also referred to as anthrose. Anthrose has not been found in spores of *B. cereus* and *B. thuringiensis*, making it a potential species-specific marker for *B. anthracis*. In order to study the antigenicity anthrose, efficient syntheses of an anthrose-containing trisaccharide and a series of structurally related analogs were developed. The analogs lacked either the methyl ether at C-2 or contained modified C-4 amino functionalities of anthrose. The synthetic compounds were equipped with an aminopropyl spacer to facilitate conjugation to the carrier proteins mcKHL and BSA. Serum of rabbits immunized with live or irradiated spores of *B. anthracis* Sterne $34F_2$ was able to recognize the synthetic trisaccharide-mcKLH conjugate. The specificity of the interaction was confirmed by a competitive inhibition assay with the free- and BSA-conjugated trisaccharides. Inhibition using the trisaccharide analogs demonstrated that the isovaleric acid moiety of anthrose is an important structural motif for antibody recognition. These data demonstrate that anthrose is a specific antigenic determinant of the *B. anthracis* Sterne spore, that this antigen is presented to the immune system of rabbits receiving the anthrax live-spore vaccine, and that synthetic analogues of the oligosaccharide retain the antigenic region is localized to specific terminal groups of the oligosaccharide. Collectively these data provide and important proof-of-concept step in the synthesis and development of spore-specific reagents for detection and targeting of non-protein structures in *B. anthracis.*

*B. anthracis* is a gram-positive, spore-forming bacterium that causes anthrax in humans and other mammals (Mock and Fouet, 2001, *Annu Rev Microbiol,* 55:647-671; Priest, 1993, *American Society for Microbiology*, Washington, D.C., p. 3-16). Because of the high resilience of *Bacillus anthracis* spores to environmental extremes they can persist for many years until encountering a signal to germinate. When spores of *B. anthracis* are inhaled or ingested they may germinate and establish populations of vegetative cells which release anthrax toxins, often resulting in the death of the host (Duesbery and Vande Woude, 1999, *Cell Mol Life Sci,* 55:1599-1609). The relative ease by which *B. anthracis* may be weaponized and the difficulty in early recognition of inhalation anthrax due to the non-specific nature of its symptoms were demonstrated by the deaths of four people who inhaled spores from contaminated mail. The source of infection for a fifth inhalation anthrax fatality during that outbreak remains unresolved (Jernigan et al., 2002, *Emerg Infect Dis,* 8:1019-1028; Jernigan et al., 2001, *Emerg Infect Dis,* 7:933-944; Webb, 2003, *Proc Natl Acad Sci USA,* 100:4355-4356). Consequently, considerable efforts are being directed towards the development of early disease diagnostics and a renewed interest in anthrax vaccines has emerged. Sterile, cell-free vaccines containing the protective antigen (PA) component of anthrax toxin have proven safe and effective (Friedlander et al., 1999, *JAMA,* 282:2104-2106; Joellenbeck et al., 2002, *The Anthrax vaccine: is it safe? Does it work?*, National Academy Press, Washington, D.C.). However, the anthrax vaccine that provides the most comprehensive protection is the *B. anthracis* Sterne $34F_2$ live-spore vaccine (Sterne, 1937, *Onderstepoort J. Vet. Sci. Anim. Ind.,* 9:49-67; Sterne, 1937, *Onderstepoort J. Vet. Sci. Anim. Ind.,* 8:271-349). Although not licensed for human use in the United States or Europe, the live-spore vaccine has proven highly efficacious as a veterinary vaccine and similar live-spore preparations have been used extensively in humans and animals in eastern Europe and Asia (Turnbull, 1991, *Vaccine,* 9:533-539). Although these live-spore vaccines may elicit lower anti-toxin antibodies than the licensed cell-free anthrax vaccines, their documented efficacy is attributed to additional adjuvant properties and as yet undefined protective epitopes contributed by the spores or outgrowing vegetative cells (Brossier et al., 2002, *Infect Immun,* 70:661-664). It is feasible, but as yet unexplored, that specific carbohydrate antigens may contribute to the enhanced efficacy of the live spore vaccines.

Figure 10:
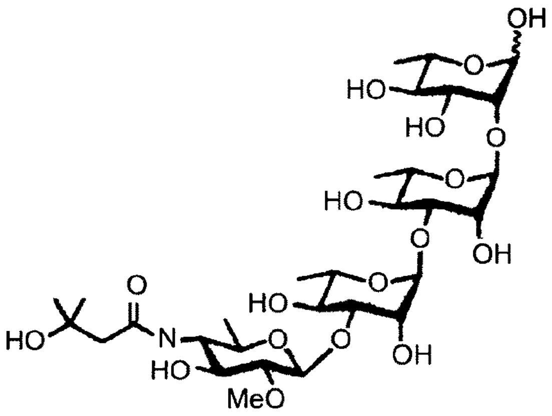
FIG. 10 shows the oligosaccharide of glycoprotein BclA and synthetic targets.
Figure 10:
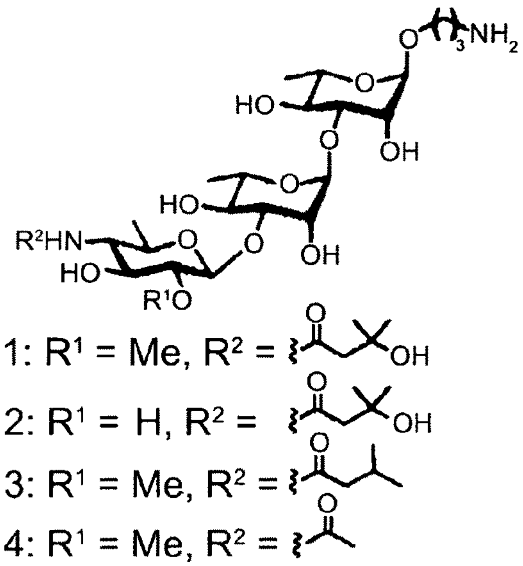

Spores of *B. anthracis* are enclosed by a prominent loose fitting layer called the exosporium, which consists of a paracrystalline basal layer composed of a number of different proteins and an external hair-like nap (Gerhardt, 1967, *Fed Proc,* 26:1504-1517; Gerhardt and Ribi, 1964, *J Bacteriol,* 88:1774-1789; Hachisuka et al., 1966, *J Bacteriol,* 91:2382-2384; Beaman et al., 1971, *J Bacteriol,* 107:320-324; and Kramer and Roth, 1968, *Can J Microbiol,* 14:1297-1299). The filaments of the nap are formed by the highly immunogenic glycoprotein BclA, which has a long, central collagen-like region containing multiple X-X-Gly repeats where X can be any amino acid (Sylvestre et al., 2002, *Mol Microbiol,* 45:169-178). Almost all of the repeating units contain a threonine (Thr) residue, which provides sites for potential glycosylation (Schmidt et al., 2003, *Trends Microbiol,* 11:554-561; Jentoft, 1990, *Trends Biochem Sci,* 15:291-294). Recently, it was shown that the BclA glycoprotein contains two O-linked saccharides, the structures of which were determined by a combination of NMR spectroscopy and mass spectrometry (Daubenspeck et al., 2004, *J Biol Chem,* 279:30945-30953). The oligosaccharides are probably attached to the protein through a GalNAc moiety, which was lost during the hydrazine-mediated release from the BclA glycoprotein (Daubenspeck et al., 2004, *J Biol Chem,* 279:30945-30953). The structure of the tetrasaccharide is depicted in FIG. 10. The previously unknown non-reducing terminal saccharide, 2-O-methyl-4-(3-hydroxy-3-methylbutamido)-4,6-dideoxy-D-glucopyranose, was named anthrose and has not been found in spores of *B. cereus* and *B. thuringiensis*, making it a potential species-specific marker for *B. anthracis*. It may also be a new target for therapeutic intervention or vaccine development (Daubenspeck et al., 2004, *J Biol Chem,* 279:30945-30953).

In this example, the synthesis of an anthrose-containing trisaccharide and a series of structurally related analogues are reported. In this example, 1-4 are as shown in FIG. 10, 5-13 are as shown in FIG. 11, and 14-25 are as shown in FIG. 12. This example demonstrates that serum of rabbits immunized by live or irradiated spores of *B. anthracis* Sterne $34F_2$ recognize the trisaccharide 1, which is derived from the glycoprotein BclA; that the antigenic nature of the trisaccharide can be altered by modification of specific side groups in the terminal glycosyl structure; and that a 3-methyl butyryl substituent is essential for recognition by anti-spore antiserum.

Experimental Section $^1$H-NMR spectra were recorded in $CDCl_3$ or $D_2O$ on Varian Merc-300 or Varian Inova-500 spectrometers equipped with Sun workstations at 300K. TMS ($\delta_H$ 0.00) or $D_2O$ ($\delta_H$ 4.67) was used as the internal reference. $^{13}$C-NMR spectra were recorded in $CDCl_3$ or $D_2O$ at 75 MHz on a Varian Merc-300 spectrometer, respectively using the central resonance of $CDCl_3$ ($\delta_C$ 77.0) as the internal reference. COSY, HSQC, HMBC and TOCSY experiments were used to assist assignment of the products. Mass spectra were obtained on Applied Biosystems Voyager DE-Pro MALDI-TOF (no calibration) and Bruker DALTONICS 9.4T (FTICR, external calibration with BSA). Optical rotatory power was obtained on JASCO P-1020 polarimeter at 300K. Chemicals were purchased from Aldrich or Fluka and used without further purification. DCM, acetonitrile and toluene were distilled from calcium hydride; THF from sodium; and MeOH from magnesium and iodine. Mariculture keyhole limpet hemocyanin (mcKLH), maleimide activated bovine serum albumin (BSA-MI), and succinimidyl 3-(bromoacetamido)propionate (SBAP) were purchased from Pierce Endogen, Rockford, Ill. Aqueous solutions are saturated unless otherwise specified. Molecular sieves were activated at 350° C. for three hours in vacuo. All reactions were performed under anhydrous conditions under argon and monitored by TLC on Kieselgel 60 F254 (Merck). Detection was by examination under UV light (254 nm) and by charring with 10% sulfuric acid in methanol. Silica gel (Merck, 70-230 mesh) was used for chromatographies. Iatrobeads 6RS-8060 was purchased from Bioscan.

General procedure for levulination. To a solution of 10 or 14 (1 equivalent (eq.)) and levulinic acid (10 eq.) in DCM (0.06 mol/L) was added a solution of DCC (6 eq.) and DMAP (0.015 eq.) in DCM under argon. The reaction mixture was stirred at room temperature for 2 hours, and then filtered through Celite. The filtrate was washed twice with water. The organic layer was dried ($MgSO_4$), filtered, and concentrated to dryness. Purification of the crude product by column chromatography on silica gel afforded the desired product 11 or 15.

General procedure for isopropylidene removal. A solution of 6 or 11 (1 eq.) in acetic acid/water (3:2, 0.5 mol/L) was refluxed at 90° C. for 15 minutes, and then concentrated to dryness. The residue was co-distilled with toluene twice. Purification of the crude product by column chromatography on silica gel afforded the desired product 7 or 12.

General procedure for introduction of the C-4 azide group. To a solution of 7 or 12 (1 eq.) in pyridine (10 eq.) and dry DCM (0.2 mol/L) at 0° C. was added trifluoromethanesulfonic anhydride (1.5 eq.) slowly. The reaction mixture was stirred at 0° C. for 1 hour, and then diluted with DCM. The solution was washed with $H_2O$ and saturated $NaHCO_3$. The organic layer was dried ($MgSO_4$), filtered, and concentrated to dryness. To a solution of this residue in DMF (0.08 mol/L) was added sodium azide (5 eq.). The reaction mixture was stirred at 40° C. overnight, and then concentrated to dryness. The residue was dissolved in ethyl acetate, and the solution was washed with saturated $NaHCO_3$ and brine. The organic layer was dried ($MgSO_4$), filtered, and concentrated to dryness. Purification of the crude product by column chromatography on silica gel afforded the desired product 8 or 13.

General procedure for cleavage of the levulinoyl ester. To a solution of 17 or 19 (1 eq.) in dry DCM (0.04 mol/L) was added a solution of hydrazine acetate (1 eq.) in dry MeOH (0.4 mol/L) under argon. The reaction mixture was stirred at room temperature for 4 hours, and then concentrated to dryness. The residue was dissolved in DCM, and then washed with water. The organic layer was dried ($MgSO_4$), filtered, and concentrated to dryness. Purification of the crude product by column chromatography on silica gel afforded the desired product 18 or 20.

General procedure for azide reduction and introduction of C-4" moiety. To a solution of 20 or 21 (1 eq.) and 1,3-propanedithiol (20 eq.) in pyridine (0.014 mol/L) and $H_2O$ (0.1 mol/L) was added TEA (15 eq.). The reaction mixture was stirred at room temperature overnight, and then concentrated to dryness. The residue was co-evaporated with toluene twice and ethanol twice. Purification of the crude product by column chromatography on silica gel (DCM/MeOH/TEA, 100:5:1, v:v:v) afforded the free amine compounds. β-hydroxyisovaleric acid or isovaleric acid (2 eq.) was activated by HOAt (4 eq.) and HATU (4 eq.) in DMF (0.01 mol/L) for 1 h, and then DIPEA (8 eq.) was added. The resulting yellow solution was added drop wise to the free amine compound (1 eq.) in DMF (0.02 mol/L). The reaction mixture was stirred at room temperature for 4 hours, and then concentrated to dryness. Purification of the crude product by column chromatography on silica gel afforded the desired product 22, 23 or 24. Alternatively, a solution of free amine (1 eq.) in $Ac_2O$ (2 eq.), pyridine (2 eq.) and DMAP (0.1 eq.) was stirred at room temperature overnight, and then concentrated to dryness. The residue was co-evaporated with toluene twice. Purification of the crude product by column chromatography on silica gel afforded the desired product 25.

General procedure for global deprotection. To a solution of 22, 23, 24 or 25 in dry MeOH (0.06 mol/L) was added NaOMe (pH=8-10). The reaction mixture was stirred at room temperature overnight, and then neutralized by the addition of Dowex 650H$^+$. The suspension was filtered through Celite, and washed with MeOH/DCM (1:1, v:v). The combined filtrates were concentrated to dryness. Purification of the crude product by column chromatography on silica gel afforded the desired deacetylated product. To a solution of the partially deprotected compound in tert-butanol/$H_2O$/AcOH (40:1:1, 0.01 mol/L) was added Pd/C (cat.) under an atmosphere of hydrogen. The reaction mixture was stirred at room temperature overnight, and then filtered through Celite. The filtrate was concentrated to dryness. Purification of the crude product by Iatro beads afforded the desired product 1, 2, 3 or 4.

Allyl 2-O-methyl-3,4-O-isopropylidene-α-D-fucopyranoside (6): To a solution of 5 (8.26 g, 33.81 mmol) in DMF (90 mL) was added NaH (3.25 g, 67.63 mmol, 50% in mineral oil). The reaction mixture was stirred at 0° C. for 1 hour, and then methyl iodide (4.21 mL, 67.62 mmol) was added drop wise. The reaction mixture was stirred at room temperature for 6 hours, and then poured into ice water. The solution was extracted with DCM (100 mL) and washed with water (100 mL). The organic layer was dried ($MgSO_4$), filtered, and concentrated to dryness. Purification of the crude product by column chromatography on silica gel (Hexane/EtOAc, 4:1, v:v) afforded the desired product 6 as colorless oil (8.66 g, 99%). $R_f$=0.74 (hexane/EtOAc, 2:1). $[\alpha]^{27}_D$=+67.7 ($CHCl_3$, c=36.4 mg/mL). $^1H$ NMR (300 MHz, $CDCl_3$): δ 1.26 (d, 3H, $J_{5,6}$=6.3 Hz, H-6), [1.29, 1.47 ($CH_3CCH_3$)], 3.30 (dd, 1H, $J_{1,2}$=3.6, $J_{2,3}$=8.1 Hz, H-2), 3.44 (s, 3H, $OCH_3$), 3.94-4.10 (m, 3H, H-4, H-5, $OCH_2CHCH_2$), 4.14 (dd, 1H, J=5.4, 12.9 Hz, $OCH'_2CHCH_2$), 4.18 (dd, 1H, $J_{2,3}$=8.1, $J_{3,4}$=5.7 Hz, H-3), 4.88 (d, 1H, $J_{1,2}$=3.6 Hz, H-1), 5.16 (dd, 1H, J=1.2, 10.2 Hz, $OCH_2CHCH_2$), 5.28 (dd, 1H, J=1.5, 17.1 Hz, $OCH_2CHCH_2$), 5.87 (m, 1H, $OCH_2CHCH_2$); $^{13}C$ NMR (75 MHz, $CDCl_3$): δ 16.2 (C-6), [26.3, 28.3 ($CH_3CCH_3$)], 58.5 ($OCH_3$), 63.1 (C-5), 68.2 ($OCH_2CHCH_2$), 75.7 (C-4), 76.0 (C-3), 79.1 (C-2), 95.3 (C-1), 108.7 ($CH_3CCH_3$), 117.9 ($OCH_2CHCH_2$), 133.6 ($OCH_2CHCH_2$); MALDI-TOF/MS: 171/z: found $[M+Na]^+$ 281.7. $C_{13}H_{22}O_5$ calcd for $[M+Na]^+$ 281.1365.

Allyl 2-O-Methyl-3-O-benzyl-α-D-fucopyranoside (7): Treatment of 6 (8.66 g, 33.53 mmol) in acetic acid/water (40.24 mL: 26.83 mL) as described in the general procedures gave the diol 7 as white solid (7.39 g, 33.86 mmol, quantitative). $R_f$=0.30 (DCM/MeOH, 19:1, v:v). $[\alpha]^{27}_D$=+4.9 ($CHCl_3$, c=25.9 mg/mL). $^1H$ NMR (300 MHz, $CDCl_3$): δ 1.21 (d, 3H, $J_{5,6}$=6.6 Hz, H-6), 2.56 (s, 1H, OH), 3.40 (s, 3H, $OCH_3$), 3.47 (dd, 1H, $J_{1,2}$=3.0, $J_{2,3}$=9.6 Hz, H-2), 3.75 (s, 1H, H-4), 3.89-3.97 (m, 2H, H-3, H-5), 4.00 (dd, 1H, J=6.3, 12.6 Hz, $OCH_2CHCH_2$), 4.14 (dd, 1H, J=3.6, 12.9 Hz, $OCH'_2CHCH_2$), 4.99 (d, 1H, $J_{1,2}$=3.0 Hz, H-1), 5.16 (d, 1H, J=10.5 Hz, $OCH_2CHCH_2$), 5.28 (d, 1H, J=17.1 Hz, $OCH_2CHCH'_2$), 5.87 (m, 1H, $OCH_2CHCH_2$); $^{13}C$ NMR (75 MHz, $CDCl_3$): δ 16.1 (C-6), 57.7 ($OCH_3$), 65.6 (C-5), 68.2 ($OCH_2CHCH_2$), 69.4 (C-3), 71.5 (C-4), 77.9 (C-2), 94.5

(C-1), 117.9 ($OCH_2CHCH_2$), 133.8 ($OCH_2CHCH_2$); MALDI-TOF/MS: m/z: found $[M+Na]^+$ 241.7. $C_{10}H_{18}O_5$ calcd for $[M+Na]^+$ 241.1052. To a solution of the diol (7.39 g, 33.8 mmol) in dry MeOH (300 mL) was added dibutyltin oxide (8.43 g, 33.86 mmol). The reaction mixture was refluxed until the solution became clear. After cooling to room temperature, the reaction mixture was concentrated to dryness. To a solution of the residue in DMF (130 mL) was added benzyl bromide (4.05 mL, 33.86 mmol) and CsF (5.15 g, 33.86 mmol.). The reaction mixture was stirred at room temperature overnight, and then concentrated to dryness. The residue was dissolved in DCM (100 mL), and the solution was washed with $H_2O$ (100 mL). The organic layer was dried ($MgSO_4$), filtered, and concentrated to dryness. Purification of the crude product by column chromatography on silica gel (Hexane/EtOAc, 3:1, v:v) afforded the desired product 7 as colorless oil (10.03 g, 32.53 mmol, 96%). $R_f$=0.34 (Hexane/EtOAc, 2:1, v:v). $[\alpha]^{27}_D$=+86.6 ($CHCl_3$, c=20.4 mg/mL). $^1H$ NMR (500 MHz, $CDCl_3$): δ 1.21 (d, 3H, $J_{5,6}$=6.5 Hz, H-6), 3.45 (s, 3H, $OCH_3$), 3.55 (dd, 1H, $J_{1,2}$=3.5, $J_{2,3}$=9.5 Hz, H-2), 3.59-3.78 (m, 2H, H-3, H-5), 3.86 (dd, 1H, $J_{2,3}$=7.0, $J_{3,4}$=7.0 Hz, H-4), 3.99 (dd, 1H, J=7.0, 13.0 Hz, $OCH_2CHCH_2$), 4.12 (dd, 1H, J=5.5, 13.0 Hz, $OCH'_2CHCH_2$), 4.61 (d, 1H, J=12.0 Hz, $PhCH_2$), 4.72 (d, 1H, J=12.0 Hz, $PhCH'_2$), 4.94 (d, 1H, $J_{1,2}$=3.5 Hz, H-1), 5.15 (d, 1H, J=100.5 Hz, $OCH_2CHCH_2$), 5.26 (d, 1H, J=17.0 Hz, $OCH_2CHCH'_2$), 5.89 (m, 1H, $OCH_2CHCH_2$), 7.19-7.29 (m, 5H, $H_{arom}$); $^{13}C$ NMR (75 MHz, $CDCl_3$): δ 16.1 (C-6), 58.9 ($OCH_3$), 65.3 (C-4), 68.2 ($OCH_2CHCH_2$), 70.2 (C-3), 72.7 ($PhCH_2$), 77.5 (C-2), 77.9 (C-5), 95.5 (C-1), 117.9 ($OCH_2CHCH_2$), [127.7, 127.8, 128.4, 133.9 ($C_{arom}$)], 138.3 ($OCH_2CHCH_2$); MALDI-TOF/MS: m/z: found $[M+Na]^+$ 331.2. $C_{17}H_{24}O_5$ calcd for $[M+Na]^+$ 331.1521.

Allyl 4-azido-2-O-methyl-3-O-benzyl-4,6-dideoxy-α-D-glycopyranoside (8): Treatment of 7 (10.03 g, 32.53 mmol) in pyridine (28.62 mL, 0.33 mol) and DCM (160 mL) with trifluoromethanesulfonic anhydride (8.22 mL, 48.66 mmol) followed by treatment of triflate residue in DMF (400 mL) with sodium azide (10.40 g, 0.16 mol) was performed according to the general procedure to give compound 8 as colorless oil (8.67 g, 80%). $R_f$=0.41 (Hexane/EtOAc, 5:1, v:v). $[\alpha]^{27}_D$=+130.5 ($CHCl_3$, c=23.8 mg/mL). $^1H$ NMR (500 MHz, $CDCl_3$): δ 1.30 (d, 3H, $J_{5,6}$=6.5 Hz, H-6), 3.02 (t, 1H, $J_{3,4}$=9.0, $J_{4,5}$=10.0 Hz, H-4), 3.27 (dd, 1H, $J_{1,2}$=3.5, $J_{2,3}$=90.5 Hz, H-2), 3.44 (s, 3H, $OCH_3$), 3.52 (m, 1H, H-5), 3.72 (t, 1H, $J_{2,3}$=9.5, $J_{3,4}$=9.0 Hz, H-3), 3.98 (dd, 1H, J=7.0, 13.0 Hz, $OCH_2CHCH_2$), 4.12 (dd, 1H, J=5.0, 13.0 Hz, $OCH'_2CHCH_2$), 4.72 (d, 1H, J=10.5 Hz, $PhCH_2$), 4.84 (d, 1H, J=10.5 Hz, $PhCH'_2$), 4.89 (d, 1H, $J_{1,2}$=3.5 Hz, H-1), 5.18 (d, 1H, J=10.5 Hz, $OCH_2CHCH_2$), 5.28 (d, 1H, J=17.5 Hz, $OCH_2CHCH'_2$), 5.87 (m, 1H, $OCH_2CHCH_2$), 7.19-7.35 (m, 5H, $H_{arom}$); $^{13}C$ NMR (75 MHz, $CDCl_3$): δ 18.4 (C-6), 58.7 ($OCH_3$), 66.1 (C-5), 67.9 (C-4), 68.2 ($OCH_2CHCH_2$), 75.5 ($PhCH_2$), 79.8 (C-3), 82.3 (C-2), 94.8 (C-1), 118.3 ($OCH_2CHCH_2$), [127.8, 128.2, 128.4, 133.6 ($C_{arom}$)], 138.2 ($OCH_2CHCH_2$); MALDI-TOF MS: m/z: found $[M+Na]^+$ 356.7. $C_{17}H_{23}N_3O_4$ calcd for $[M+Na]^+$ 356.16.

Ethyl 2-O-levulinoyl-3,4-O-isopropylidene-1-thio-α-D-fucopyranoside (11): Treatment of 10 (1.34 g, 5.40 mmol) and levulinic acid (5.53 mL, 54.00 mmol) in DCM (90 mL) with DCC (6.69 g, 32.42 mmol) and DMAP (9.90 mg, 0.081 mmol) in DCM (9 mL) according to the general procedure gave compound 11 as colorless oil (1.76 g, 94%). $R_f$=0.71 (Hexane/EtOAc, 1:1, v:v). $[\alpha]^{27}_D$=+1.3 ($CHCl_3$, c=7.0 mg/mL). $^1H$ NMR (500 MHz, $CDCl_3$): δ 1.19 (t, 3H, J=7.5 Hz, $SCH_2CH_3$), 1.28 (s, 3H, $CH_3$), 1.35 (d, 3H, $J_{5,6}$=7.0 Hz, H-6), 1.49 (s, 3H, $CH'_3$), 2.12 (s, 3H, $CH_3C(O)CH_2CH_2C(O)O$), 2.53-2.78 (m, 6H, $CH_3C(O)CH_2CH_2C(O)O$, $SCH_2CH_3$, $CH_3C(O)CH_2CH_2C(O)O$), 3.78-3.82 (m, 1H, H-5), 3.98 (dd, $J_{3,4}$=5.5, $J_{4,5}$=2.5 Hz, H-4), 4.06 (dd, 1H, $J_{2,3}$=7.5, $J_{3,4}$=5.5 Hz, H-3), 4.25 (d, 1H, $J_{1,2}$=10.0 Hz, H-1), 4.92 (dd, 1H, $J_{1,2}$=10.0, $J_{2,3}$=7.5 Hz, H-2); $^{13}C$ NMR (75 MHz, $CDCl_3$): δ 14.7 ($SCH_2CH_3$), 16.8 (C-6), [23.8, 26.4 ($CH_3$)], [27.8, 28.1 ($CH_3C(O)CH_2CH_2C(O)O$, $SCH_2CH_3$)], 29.8 ($CH_3C(O)CH_2CH_2C(O)O$), 38.0 ($CH_3C(O)CH_2CH_2C(O)O$), 71.8 (C-2), 72.7 (C-5), 76.4 (C-4), 77.2 (C-3), 82.2 (C-1), 171.7 ($CH_3C(O)CH_2CH_2C(O)O$), 206.3 ($CH_3C(O)CH_2CH_2C(O)O$); MALDI-TOF/MS: m/z: found $[M+Na]^+$ 369.5. $C_{16}H_{26}O_6S$ calcd for $[M+Na]^+$ 369.13.

Ethyl 2-O-levulinoyl-3-O-benzyl-1-thio-α-D-fucopyranoside (12): Treatment of 11 (1.75 g, 5.05 mmol) in acetic acid/water (6.06 mL: 4.04 mL) according to the general procedure for isopropylidene removal gave the diol 12 as white solid (1.55 g, quantitative). $R_f$=0.38 (DCM/MeOH, 19:1). $[\alpha]^{27}_D$=−3.5 ($CHCl_3$, c=12.0 mg/mL). $^1H$ NMR (300 MHz, $CDCl_3$): δ 1.19 (t, 3H, J=7.5 Hz, $SCH_2CH_3$), 1.28 (d, 3H, $J_{5,6}$=6.0 Hz, H-6), 2.13 (s, 3H, $CH_3C(O)CH_2CH_2C(O)O$), 2.51-2.86 (m, 6H, $CH_3C(O)CH_2CH_2C(O)O$, $SCH_2CH_3$, $CH_3C(O)CH_2CH_2C(O)O$), 3.57-3.68 (m, 2H, H-3, H-5), 3.75 (d, J=2.7 Hz, H-4), 4.32 (d, 1H, $J_{1,2}$=9.9 Hz, H-1), 4.98 (t, 1H, $J_{1,2}$=9.9, $J_{2,3}$=9.3 Hz, H-2); $^{13}C$ NMR (75 MHz, $CDCl_3$): δ 14.8 ($SCH_2CH_3$), 16.6 (C-6), 23.7 ($SCH_2CH_3$), 28.2 ($CH_3C(O)CH_2CH_2C(O)O$), 29.8 ($CH_3C(O)CH_2CH_2C(O)O$), 38.4 ($CH_3C(O)CH_2CH_2C(O)O$), [71.5, 71.8 (C-2, C-4)], 73.8 (C-3), 74.7 (C-5), 82.7 (C-1), 172.7 ($CH_3C(O)CH_2CH_2C(O)O$), 206.3 ($CH_3C(O)CH_2CH_2C(O)O$); MALDI-TOF/MS: m/z: found $[M+Na]^+$ 330.2. $C_{13}H_{22}O_6S$ calcd for $[M+Na]^+$ 329.10. To a solution of the diol (1.55 g, 5.06 mmol) in dry toluene (50 mL) was added dibutyl tin oxide (1.26 g, 5.06 mmol). The reaction mixture was refluxed with a Dean-Stark apparatus for 3 hours, and then cooled to 60° C. Benzyl bromide (0.60 mL, 5.06 mmol) and tetrabutylammonium iodide (1.68 g, 5.06 mmol) were added and the resulting reaction mixture was refluxed for 3 hours. After cooling to room temperature, the reaction mixture was concentrated to dryness. The residue was dissolved in EtOAc (50 mL), and the resulting solution was washed with $H_2O$ (50 mL). The organic layer was dried ($MgSO_4$) filtered, and concentrated to dryness. Purification of the crude product by column chromatography on silica gel (PE/EtOAc, 2:1, v:v) afforded the desired product 12 as colorless oil (1.04 g, 52%). $R_f$=0.43 (Hexane/EtOAc, 1:1, v:v). $[\alpha]^{27}_D$=−4.0 ($CHCl_3$, c=8.2 mg/mL). $^1H$ NMR (300 MHz, $CDCl_3$): δ 1.16 (t, 3H, J=7.5 Hz, $SCH_2CH_3$), 1.28 (d, 3H, $J_{5,6}$=6.3 Hz, H-6), 2.12 (s, 3H, $CH_3C(O)CH_2CH_2C(O)O$), 2.48-2.76 (m, 6H, $CH_3C(O)CH_2CH_2C(O)O$, $SCH_2CH_3$, $CH_3C(O)CH_2CH_2C(O)O$), 3.43-3.54 (m, 2H, H-3, H-5), 3.75 (d, J=3.0 Hz, H-4), 4.23 (d, 1H, $J_{1,2}$=9.9 Hz, H-1), 4.57 (d, 1H, J=12.0 Hz, $PhCH_2$), 4.61 (d, 1H, J=11.1 Hz, $PhCH'_2$), 5.14 (t, 1H, $J_{1,2}$=9.6, $J_{2,3}$=9.6 Hz, H-2), 7.19-7.31 (m, 5H, $H_{arom}$); $^{13}C$ NMR (75 MHz, $CDCl_3$): δ 14.7 ($SCH_2CH_3$), 16.6 (C-6), 23.4 ($SCH_2CH_3$), 28.1 ($CH_3C(O)CH_2CH_2C(O)O$), 29.9 ($CH_3C(O)CH_2CH_2C(O)O$), 37.9 ($CH_3C(O)CH_2CH_2C(O)O$), [69.1, 69.2 (C-2, C-4)], 71.7 ($PhCH_2$), 74.5 (C-3), 79.7 (C-5), 82.9 (C-1), [127.9, 128.1, 128.5, 137.5 ($C_{arom}$)], 171.7 ($CH_3C(O)CH_2CH_2C(O)O$), 206.3 ($CH_3C(O)CH_2CH_2C(O)O$); MALDI-TOF/MS: m/z: found $[M+Na]^+$ 419.5. $C_{20}H_{28}O_6S$ calcd for $[M+Na]^+$ 419.15.

Ethyl 4-azido-2-O-levulinoyl-3-O-benzyl-4,6-dideoxy-1-thio-α-D-glucopyranoside (13): Treatment of 12 (0.50 g, 1.26 mmol) in pyridine (1.02 mL, 12.61 mmol) and DCM (6.5 mL) with trifluoromethanesulfonic anhydride (0.32 mL, 1.90 mmol) followed by treatment of triflate residue in DMF (16 mL) with sodium azide (0.41 g, 6.31 mmol) according to the general procedure for introduction of the C-4 azide group gave compound 13 as colorless oil (0.42 g, 79%). $R_f$=0.32 (Hexane/EtOAc, 4:1, v:v). $[\alpha]^{27}_D$=+13.1 ($CHCl_3$, c=5.1 mg/mL). $^1$H NMR (300 MHz, $CDCl_3$): δ 1.67 (t, 3H, J=7.5 Hz, $SCH_2CH_3$), 1.30 (d, 3H, $J_{5,6}$=5.7 Hz, H-6), 2.10 (s, 3H, $CH_3C(O)CH_2CH_2C(O)O$), 2.44-2.49 (m, 2H, $CH_3C(O)CH_2CH_2C(O)O$), 2.57-2.67 (m, 4H, $SCH_2CH_3$, $CH_3C(O)CH_2CH_2C(O)O$), 3.11-3.24 (m, 2H, H-4, H-5), 3.48 (t, $J_{3,4}$=9.0, $J_{2,3}$=9.0 Hz, H-3), 4.27 (d, 1H, $J_{1,2}$=9.9 Hz, H-1), 4.68 (d, 1H, J=11.1 Hz, $PhCH_2$), 4.71 (d, 1H, J=11.1 Hz, $PhCH'_2$), 4.94 (dd, 1H, $J_{1,2}$=9.9, $J_{2,3}$=9.0 Hz, H-2), 7.22-7.29 (m, 5H, $H_{arom}$); $^{13}$C NMR (75 MHz, $CDCl_3$): δ 14.8 ($SCH_2CH_3$), 18.7 (C-6), 23.9 ($SCH_2CH_3$), 28.0 ($CH_3C(O)CH_2CH_2C(O)O$), 29.8 ($CH_3C(O)CH_2CH_2C(O)O$), 37.8 ($CH_3C(O)CH_2CH_2C(O)O$), 67.7 (C-4), 72.2 (C-2), 74.9 ($PhCH_2$), 75.1 (C-5), 82.3 (C-3), 83.2 (C-1), [127.9, 128.0, 128.2, 128.4, 137.5 ($C_{arom}$)], 171.5 ($CH_3C(O)CH_2CH_2C(O)O$), 206.1 ($CH_3C(O)CH_2CH_2C(O)O$); MALDI-TOF/MS: m/z: found $[M+Na]^+$ 444.1. $C_{20}H_{27}N_3O_5S$ calcd for $[M+Na]^+$ 444.15.

Ethyl 2-O-benzoyl-3-O-levulinoyl-4-O-benzyl-1-thio-α-L-rhamnopyranoside (15): Treatment of 14 (4.93 g, 12.25 mmol) and levulinic acid (12.54 mL, 122.50 mmol) in DCM (180 mL) with DCC (15.18 g, 73.57 mmol) and DMAP (22.45 mg, 0.18 mmol) in DCM (18 mL) according to the general procedure for levulination gave compound 15 as colorless oil (5.29 g, 86%). $R_f$=0.34 (Hexane/EtOAc, 3:1, v:v). $[\alpha]^{27}_D$=−18.9 ($CHCl_3$, c=26.5 mg/mL). $^1$H NMR (300 MHz, $CDCl_3$): δ 1.23 (t, 3H, J=7.2 Hz, $SCH_2CH_3$), 1.33 (d, 3H, $J_{5,6}$=6.0 Hz, H-6), 2.02 (s, 3H, $CH_3C(O)CH_2CH_2C(O)O$), 2.35-2.39 (td, 2H, J=6.9, 9.6 Hz, $CH_3C(O)CH_2CH_2C(O)O$), 2.46-2.72 (m, 4H, $SCH_2CH_3$, $CH_3C(O)CH_2CH_2C(O)O$), 3.58 (t, $J_{4,5}$=9.3, $J_{3,4}$=9.6 Hz, H-4), 4.18 (m, 1H, H-5), 4.59 (d, 1H, J=1.1 Hz, $PhCH_2$), 4.66 (d, 1H, J=11.1 Hz, $PhCH'_2$), 5.22 (s, 1H, H-1), 5.28 (dd, 1H, $J_{2,3}$=3.3, $J_{3,4}$=9.6 Hz, H-3), 5.51 (dd, 1H, $J_{1,2}$=1.5, $J_{2,3}$=3.3 Hz, H-2), 7.19-8.00 (m, 10H, $H_{arom}$); $^{13}$C NMR (75 MHz, $CDCl_3$): δ 14.9 ($SCH_2CH_3$), 18.0 (C-6), 25.4 ($SCH_2CH_3$), 27.9 ($CH_3C(O)CH_2CH_2C(O)O$), 29.7 ($CH_3C(O)CH_2CH_2C(O)O$), 37.8 ($CH_3C(O)CH_2CH_2C(O)O$), 68.3 (C-5), 72.5 (C-2), 72.6 (C-3), 74.9 ($PhCH_2$), 78.9 (C-4), 81.9 (C-1), [127.8, 127.9, 128.4, 128.5, 129.7, 129.8, 133.4, 137.9 ($C_{arom}$)], 165.5 (PhC(O)O), 171.7 ($CH_3C(O)CH_2CH_2C(O)O$), 206.2 ($CH_3C(O)CH_2CH_2C(O)O$); MALDI-TOF/MS: m/z: found $[M+Na]^+$ 524.1, MALDI-FTICR/MS: m/z: found $[M+Na]^+$ 523.1761. $C_{27}H_{32}O_7S$ calcd for $[M+Na]^+$ 523.1766.

3-[(N-benzyloxycarbonyl)amino]propyl 2-O-benzoyl-4-O-benzyl-α-L-rhamnopyranoside (16): Glycosyl donor 14 (3.79 g, 9.42 mmol), 3-(N-benzyloxycarbonyl)aminopropanol (3.94 g, 18.83 mmol) and 4 Å powdered molecular sieves (7.73 g) in DCM (150 mL) in the presence of NIS (2.33 g, 10.36 mmol) and TfOH (0.166 mL, 1.88 mmol) were reacted according to the general procedure for NIS glycosylation to give compound 16 as white solid (3.73 g, 72%). $R_f$=0.26 (Hexane/EtOAc, 2:1, v:v). $[\alpha]^{27}_D$=+11.3 ($CHCl_3$, c=18.0 mg/mL). $^1$H NMR (300 MHz, $CDCl_3$): δ 1.32 (d, 3H, $J_{5,6}$=6.0 Hz, H-6), 1.73 (m, 2H, $OCH_2CH_2CH_2NHZ$), 2.11 (d, 1H, J=4.5 Hz, OH), 3.24 (dd, 2H, J=6.3, 12.6 Hz, $OCH_2CH_2CH_2NHZ$), 3.36-3.45 (m, 2H, $OCH_2CH_2CH_2NHZ$, H-4), 3.65-3.75 (m, 2H, $OCH'_2CH_2CH_2NHZ$, H-5), 4.12 (dd, 1H, $J_{2,3}$=3.3, $J_{3,4}$=8.4 Hz, H-3), 4.69 (d, 1H, J=11.1 Hz, $PhCH_2$), 4.76 (s, 1H, H-1), 4.79 (d, 1H, J=11.1 Hz, $PhCH'_2$), 4.85 (broad, 1H, NH), 5.02 (s, 2H, $PhCH_2OC(O)$), 5.25 (dd, 1H, $J_{1,2}$=1.5, $J_{2,3}$=3.3 Hz, H-2), 7.18-7.99 (m, 15H, $H_{arom}$); $^{13}$C NMR (75 MHz, $CDCl_3$): δ 18.2 (C-6), 29.6 ($OCH_2CH_2CH_2NHZ$), 38.6 ($OCH_2CH_2CH_2NHZ$), 65.6 ($OCH_2CH_2CH_2NHZ$), 66.6 (C-5), 67.6 ($PhCH_2OC(O)$), 70.5 (C-3), 73.2 (C-2), 75.2 ($PhCH_2$), 81.6 (C-4), 97.5 (C-1), [127.9, 128.1, 128.4, 129.7, 129.9, 130.4, 133.3, 136.6, 138.1 ($C_{arom}$)], 156.3 ($PhCH_2OC(O)$), 166.3 (PhC(O)O); MALDI-TOF/MS: m/z: found $[M+Na]^+$ 572.9, MALDI-FTICR/MS: m/z: found $[M+Na]^+$ 572.2259. $C_{31}H_{35}NO_8$ calcd for $[M+Na]^+$ 572.2260.

3-[(N-benzyloxycarbonyl)amino]propyl O-(2-O-benzoyl-3-O-levulinoyl-4-O-benzyl-α-L-rhamnopyranosyl)-(1→3)-2-O-benzoyl-4-O-benzyl-α-L-rhamnopyranoside (17): Glycosyl donor 15 (3.04 g, 6.07 mmol), glycosyl acceptor 16 (3.03 g, 5.51 mmol) and 4 Å powdered molecular sieves (6.07 g) in DCM (100 mL) in the presence of NIS (1.51 g, 6.71 mmol) and TfOH (0.11 mL, 1.22 mmol) was treated according to the general procedure for the linker glycosylation to give compound 17 as colorless oil (4.26 g, 78%). $R_f$=0.34 (Hexane/EtOAc, 2:1, v:v). $[\alpha]^{27}_D$=+23.6 ($CHCl_3$, c=18.0 mg/mL). $^1$H NMR (300 MHz, $CDCl_3$): δ 1.11 (d, 3H, $J_{5,6}$=6.0 Hz, H-6b), 1.28 (d, 3H, $J_{5,6}$=6.0 Hz, H-6a), 1.72 (m, 2H, $OCH_2CH_2CH_2NHZ$), 1.99 (s, 3H, $CH_3C(O)CH_2CH_2C(O)O$), 2.32-2.39 (m, 2H, $CH_3C(O)CH_2CH_2C(O)O$), 2.50-2.67 (m, 2H, $CH_3C(O)CH_2CH_2C(O)O$), 3.22 (dd, 2H, J=6.0, 12.3 Hz, $OCH_2CH_2CH_2NHZ$), 3.39-3.49 (m, 2H, $J_{3,4}$=9.6, $J_{4,5}$=9.6 Hz, $OCH_2CH_2CH_2NHZ$, H-4b), 3.56 (t, $J_{3,4}$=9.3, $J_{4,5}$=9.3 Hz, H-4a), 3.62-3.72 (m, 2H, $OCH'_2CH_2CH_2NHZ$, H-5a), 3.84 (m, 1H, H-5b), 4.17 (dd, 1H, $J_{2,3}$=3.0, $J_{3,4}$=9.0 Hz, H-3a), 4.45 (d, 1H, J=11.4 Hz, $PhCH_2$), 4.50 (d, 1H, J=11.4 Hz, $PhCH'_2$), 4.66 (d, 1H, J=10.8 Hz, $PhCH''_2$), 4.80 (broad, 2H, H-1a, NH), 4.95 (d, 1H, J=10.8 Hz, $PhCH'''_2$), 4.99 (s, 2H, $PhCH_2OC(O)$), 5.06 (s, 1H, H-1b), 5.29 (d, 1H, $J_{2,3}$=3.3 Hz, H-2a), 5.32 (dd, 1H, $J_{2,3}$=3.0, $J_{3,4}$=9.6 Hz, H-3b), 5.52 (dd, 1H, $J_{1,2}$=1.8, $J_{2,3}$=3.0 Hz, H-2b), 7.05-8.00 (m, 25H, $H_{arom}$); $^{13}$C NMR (75 MHz, $CDCl_3$): δ 17.8 (C-6b), 18.2 (C-6a), 28.0 ($CH_3C(O)CH_2CH_2C(O)O$), 29.7 ($OCH_2CH_2CH_2NHZ$, $CH_3C(O)CH_2CH_2C(O)O$)), 37.8 ($CH_3C(O)CH_2CH_2C(O)O$), 38.5 ($OCH_2CH_2CH_2NHZ$), 65.6 ($OCH_2CH_2CH_2NHZ$), 66.5 ($PhCH_2OC(O)$), 67.9 (C-5a), 68.6 (C-5b), 70.7 (C-2b), 71.8 (C-3b), 72.7 (C-2a), [73.9, 75.8 ($PhCH_2$)], 78.2 (C-4b), 79.3 (C-3a), 79.8 (C-4a), 97.0 (C-1a), 99.7 (C-1b), [127.5, 127.7, 127.9, 128.2, 128.3, 128.4, 128.5, 129.5, 129.6, 129.7, 129.8, 133.4, 136.6, 137.9, 138.0 ($C_{arom}$)], 156.3 ($PhCH_2OC(O)$), [165.3, 166.1 (PhC(O)O)], 171.7 ($CH_3C(O)CH_2CH_2C(O)O$), 206.2 ($CH_3C(O)CH_2CH_2C(O)O$); MALDI-TOF/MS: m/z: found $[M+Na]^+$ 1011.6, MALDI-FTICR/MS: m/z: found $[M+Na]^+$ 1010.3932. $C_{56}H_{61}NO_{15}$ calcd for $[M+Na]^+$ 1010.3939.

3-[(N-benzyloxycarbonyl)amino]propyl O-(2-O-benzoyl-4-O-benzyl-α-L-rhamnopyranosyl)-(1→3)-2-O-benzoyl-4-O-benzyl-α-L-rhamnopyranoside (18): Treatment of 17 (4.26 g, 4.31 mmol) in DCM (100 mL) with hydrazine acetate (397 mg, 4.31 mmol) in MeOH (10 mL) according to the general procedure for cleavage of the levulinoyl ester gave compound 18 as white solid (3.56 g, 93%). $R_f$=0.42 (Hexane/EtOAc, 2:1, v:v). $[\alpha]^{27}_D$=+21.9 ($CHCl_3$, c=22.0 mg/mL). $^1$H NMR (300 MHz, $CDCl_3$): δ 1.17 (d, 3H, $J_{5,6}$=6.0 Hz, H-6b), 1.26 (d, 3H, $J_{5,6}$=6.0 Hz, H-6a), 1.72 (m, 2H, $OCH_2CH_2CH_2NHZ$), 3.22 (d, 2H, J=6.0 Hz, $OCH_2CH_2CH_2NHZ$), 3.30-3.41 (m, 2H, $J_{3,4}$=9.6, $J_{4,5}$=9.3 Hz, $OCH)CH_2CH_2NHZ$, H-4b), 3.54 (t, 1H, $J_{3,4}$=9.3, $J_{4,5}$=9.3 Hz, H-4a), 3.62-3.71 (m, 2H, $OCH'_2CH_2CH_2NHZ$, H-5a), 3.78 (dd, 1H, $J_{4,5}$=9.3 Hz, $J_{5,6}$=6.0 Hz, H-5b), 4.04 (dd, 1H, $J_{2,3}$=2.1, $J_{3,4}$=9.6 Hz, H-3b), 4.18 (dd, 1H, $J_{2,3}$=3.0, $J_{3,4}$=9.0 Hz, H-3a), 4.57-4.63 (m, 3H, $PhCH_2$), 4.77 (s, 1H, H-1a), 4.86 (d, 1H, J=10.8 Hz, $PhCH'_2$), 4.99 (s, 2H, $PhCH_2OC(O)$), 5.11 (s, 1H, H-1b), 5.28 (d, 1H, $J_{2,3}$=3.0 Hz, H-2a), 5.33 (dd, 1H, $J_{2,3}$=2.1 Hz, H-2b), 7.12-8.01 (m, 25H, $H_{arom}$); $^{13}$C NMR (75 MHz, $CDCl_3$): δ 17.9 (C-6b), 18.1 (C-6a), 29.5 ($OCH_2CH_2CH_2NHZ$), 38.5

$(OCH_2CH_2CH_2NHZ)$, 65.6 $(OCH_2CH_2CH_2NHZ)$, 66.5 $(PhCH_2OC(O))$, 67.9 (C-5a), 68.3 (C-5b), 69.8 (C-3b), 72.8 (C-2b), 73.1 (C-2a), [74.0, 75.6 $(PhCH_2)$], 77.6 (C-3a), 80.3 (C-4a), 81.1 (C-4b), 97.1 (C-1a), 99.5 (C-1b), [127.7, 127.8, 127.9, 128.2, 128.3, 128.4, 128.5, 129.6, 129.7, 129.8, 133.2, 133.3, 137.8, 138.1 $(C_{arom})$], 156.3 $(PhCH_2OC(O))$, [165.8, 165.9 (PhC(O)O)]; MALDI-TOF/MS: m/z: found $[M+Na]^+$ 913.5, MALDI-FTICR/MS: m/z: found $[M+Na]^+$ 912.3559. $C_{51}H_{55}NO_{13}$ calcd for $[M+Na]^+$ 912.3571.

3-[(N-benzyloxycarbonyl)amino]propyl O-(4-azido-2-O-levulinoyl-3-O-benzyl-4,6-dideoxy-β-D-glucopyranosyl)-(1→3)-O-(2-O-benzoyl-4-O-benzyl-α-L-rhamnopyranosyl)-(1→3)-2-O-benzoyl-4-O-benzyl-α-L-rhamnopyranoside (19): Glycosyl donor 13 (80 mg, 0.19 mmol), glycosyl acceptor 18 (151 mg, 0.17 mmol) and 4 Å powdered molecular sieves (0.23 g) in DCM (3 mL) in the presence of NIS (47 mg, 0.21 mmol) and TfOH (3 μL, 0.034 mmol) was treated according to the general procedure for the linker glycosylation to give compound 19 as colorless oil (161 mg, 76%). $R_f$=0.30 (Hexane/EtOAc, 2:1, v:v). $[\alpha]^{27}_D$=+ 15.3 $(CHCl_3$, c=7.7 mg/mL). $^1H$ NMR (500 MHz, $CDCl_3$): δ 0.89 (d, 3H, $J_{5,6}$=6.5 Hz, H-6c), 1.06 (d, 3H, $J_{5,6}$=6.5 Hz, H-6b), 1.27 (d, 3H, $J_{5,6}$=6.5 Hz, H-6a), 1.73 (m, 2H, $OCH_2CH_2CH_2NHZ$), 1.88 (s, 3H, $CH_3C(O)CH_2CH_2C(O)O$), 1.99-2.10 (m, 2H, $CH_3C(O)CH_2CH_2C(O)O$), 2.12-2.22 (m, 2H, $CH_3C(O)CH_2CH_2C(O)O$), 2.76 (m, 1H, H-5c), 2.91 (t, 1H, $J_{3,4}$=9.5, $J_{4,5}$=10.0 Hz, H-4c), 3.17-3.23 (m, 3H, $OCH_2CH_2CH_2NHZ$, H-3c), 3.41-3.44 (m, 2H, $OCH_2CH_2CH_2NHZ$, H-4a), 3.56 (t, 1H, $J_{3,4}$=9.5, $J_{4,5}$=9.5 Hz, H-4b), 3.66-3.74 (m, 3H, $OCH'_2CH_2CH_2NHZ$, H-5a, H-5b), 3.97 (dd, 1H, $J_{2,3}$=3.0, $J_{3,4}$=9.5 Hz, H-3a), 4.20 (m, 2H, H-1c, H-3b), 4.45 (d, 1H, J=12.0 Hz, $PhCH_2$), 4.53 (d, 1H, J=11.5 Hz, $PhCH'_2$), 4.61 (d, 1H, J=12.0 Hz, $PhCH''_2$), 4.63 (d, 1H, J=11.5 Hz, $PhCH'''_2$), 4.71 (d, 1H, J=11.5 Hz, $PhCH''''_2$), 4.77 (s, 1H, H-1a), 4.84 (m, 2H, NH, $PhCH'''''_2$), 4.95 (t, 1H, $J_{1,2}$=8.0, $J_{2,3}$=10.5 Hz, H-2c), 5.00 (s, 2H, $PhCH_2OC(O)$), 5.14 (s, 1H, H-1b), 5.30 (d, 1H, $J_{2,3}$=3.0 Hz, H-2a), 5.32 (d, 1H, $J_{2,3}$=3.0 Hz, H-2b), 7.13-8.05 (m, 30H, $H_{arom}$); $^{13}C$ NMR (75 MHz, $CDCl_3$): δ 17.7 (C-6c), 17.9 (C-6b), 18.1 (C-6a), 27.6 $(CH_3C(O)CH_2CH_2C(O)O)$, 29.6 $(CH_3C(O)CH_2CH_2C(O)O)$, 31.6 $(OCH_2CH_2CH_2NHZ)$, 37.3 $(CH_3C(O)CH_2CH_2C(O)O)$, 38.5 $(OCH_2CH_2CH_2NHZ)$, 65.6 $(OCH_2CH_2CH_2NHZ)$, 66.6 $(PhCH_2OC(O))$, 67.2 (C-4c), 67.8 (C-5a), 68.6 (C-5b), 70.6 (C-5c), 71.9 (C-2a), 72.7 (C-2b), [73.4, 74.3, 74.4 $(PhCH_2)$], 75.4 (C-2c), 77.2 (C-3b), 78.0 (C-3a), 79.6 (C-4a), 80.2 (C-4b), 80.9 (C-3c), 97.2 (C-1a), 98.8 (C-1b), 100.3 (C-1c), [127.0, 127.3, 127.8, 128.0, 128.1, 128.2, 128.3, 128.4, 128.5, 129.8, 129.9, 130.1, 133.0, 133.3, 133.4, 136.6, 137.5, 137.9, 138.6 $(C_{arom})$], 156.3 $(PhCH_2OC(O))$, [165.7, 165.8 (PhC(O)O)], 171.1 $(CH_3C(O)CH_2CH_2C(O)O)$, 206.1 $(CH_3C(O)CH_2CH_2C(O)O)$; MALDI-TOF/MS: m/z: found $[M+Na]^+$ 1271.7, MALDI-FTICR/MS: m/z: found $[M+Na]^+$ 1271.4893. $C_{69}H_{76}N_4O_{18}$ calcd for $[M+Na]^+$ 1271.5052.

3-[(N-benzyloxycarbonyl)amino]propyl O-(4-azido-3-O-benzyl-4,6-dideoxy-β-D-glucopyranosyl)-(1→3)-O-(2-O-benzoyl-4-O-benzyl-α-L-rhamnopyranosyl)-(1→3)-2-O-benzoyl-4-O-benzyl-α-L-rhamnopyranoside (20): Treatment of 19 (116 mg, 0.093 mmol) in DCM (2.3 mL) with hydrazine acetate (8.6 mg, 0.093 mmol) in MeOH (0.23 mL) according to the general procedure for cleavage of the levulinoyl ester gave compound 20 as white solid (100 mg, 93%). $R_f$=0.36 (Hexane/EtOAc, 2:1, v:v). $[\alpha]^{27}_D$=+ 11.0 $(CHCl_3$, c=0.6 mg/mL). $^1H$ NMR (500 MHz, $CDCl_3$): δ 0.88 (d, 3H, $J_{5,6}$=6.0 Hz, H-6c), 1.13 (d, 3H, $J_{5,6}$=6.0 Hz, H-6b), 1.26 (d, 3H, $J_{5,6}$=5.5 Hz, H-6a), 1.73 (m, 2H, $OCH_2CH_2CH_2NHZ$), 2.74 (m, 1H, H-5c), 2.83 (t, 1H, $J_{3,4}$=9.5, $J_{4,5}$=10.0 Hz, H-4c), 3.12 (t, 1H, $J_{2,3}$=9.0, $J_{3,4}$=9.5 Hz, H-3c), 3.22 (m, 2H, $OCH_2CH_2CH_2NHZ$), 3.30 (t, 1H, $J_{1,2=8.0}$, $J_{1,3}$=9.0 Hz, H-2c), 3.40 (m, 1H, $OCH_2CH_2CH_2NHZ$), 3.49 (t, 1H, $J_{3,4}$=9.0, $J_{4,5}$=0.0 Hz, H-4b), 3.54 (t, 1H, $J_{3,4}$=9.0, $J_{4,5}$=10.0 Hz, H-4a), 3.64-3.71 (m, 2H, $OCH_2CH_2CH_2NHZ$, H-5a), 3.78 (m, 1H, H-5b), 4.05 (dd, 1H, $J_{2,3}$=3.0, $J_{3,4}$=9.5 Hz, H-3b), 4.08 (d, 1H, $J_{1,2}$=8.0 Hz, H-1c), 4.21 (dd, 1H, $J_{2,3}$=3.0, $J_{3,4}$=9.0 Hz, H-3a), 4.56 (d, 1H, J=10.5 Hz, $PhCH_2$), 4.60 (d, 1H, J=10.5 Hz, $PhCH'_2$), 4.66 (d, 1H, J=11.0 Hz, $PhCH''_2$), 4.71 (d, 1H, J=12.0 Hz, $PhCH'''_2$), 4.75 (d, 1H, J=12.0 Hz, $PhCH''''_2$), 4.76 (s, 1H, H-1a), 4.83 (broad, 1H, NH), 4.92 (d, 1H, J=11.0 Hz, $PhCH'''''_2$), 5.00 (s, 2H, $PhCH_2OC(O)$), 5.12 (s, 1H, H-1b), 5.32 (d, 1H, $J_{2,3}$=3.0 Hz, H-2a), 5.36 (d, 1H, $J_{2,3}$=3.0 Hz, H-2b), 7.19-8.01 (m, 30H, $H_{arom}$); $^{13}C$ NMR (75 MHz, $CDCl_3$): δ 17.9 (C-6c), 18.1 (C-6a, C-6b), 29.6 $(OCH_2CH_2CH_2NHZ)$, 38.5 $(OCH_2CH_2CH_2NHZ)$, 65.6 $(OCH_2CH_2CH_2NHZ)$, 66.6 $(PhCH_2OC(O))$, 66.9 (C-5c), 67.9 (C-5a), 68.7 (C-5b), 70.6 (C-4c), 72.5 (C-2a, C-2b), 74.6 (C-2c), [74.7, 75.0, 75.3 $(PhCH_2)$], 75.4 (C-3b), 77.6 (C-3a), 80.1 (C-4a, C-4b), 82.2 (C-3c), 97.1 (C-1a), 99.0 (C-1b), 103.0 (C-1c), [127.8, 127.9, 128.0, 128.1, 128.2, 128.3, 128.4, 128.5, 128.6, 129.8, 130.0, 133.3, 133.4, 136.6, 137.8, 138.0 $(C_{arom})$], 156.4 $(PhCH_2OC(O))$, [165.6, 165.8 (PhC(O)O)]; MALDI-TOF/MS: m/z: found $[M+Na]^+$ 1172.7, MALDI-FTICR/MS: In/z: found $[M+Na]^+$ 1173.4588. $C_{64}H_{70}N_4O_{16}$ calcd for $[M+Na]^+$ 1173.4685.

3-[(N-benzyloxycarbonyl)amino]propyl O-(4-azido-2-O-methyl-3-O-benzyl-4,6-dideoxy-β-D-glucopyranosyl)-(1→3)-O-(2-O-benzoyl-4-O-benzyl-α-L-rhamnopyranosyl)-(1→3)-2-O-benzoyl-4-O-benzyl-α-L-rhamnopyranoside (21). Method A. To a solution of 8 (0.594 g, 1.78 mmol) in $AcOH/H_2O$ (9:1, v:v, 60 mL) was added sodium acetate (0.63 g, 7.68 mmol) and $PdCl_2$ (0.38 g, 2.14 mmol). The reaction mixture was stirred at room temperature overnight, and then filtered through celite. The filtrate was concentrated to dryness and the residue was co-evaporated with toluene (2×60 mL). Purification of the crude product by column chromatography on silica gel (Hexane/EtOAc, 2:1, v:v) afforded the hemiacetal compound. To a solution of this compound in DCM (30 mL) was added trichloroacetonitrile (1.79 mL, 17.85 mmol) and DBU (0.11 mL, 0.74 mmol). The reaction mixture was stirred at room temperature for 5 hours, and then concentrated to dryness. Purification of the crude product by column chromatography on silica gel (Hexane/EtOAc, 2:1, v:v, +0.5% TEA) afforded imidate donor 9 as an α/β mixture (9:1) (0.622 g, 85%). A mixture of acceptor 18 (1.22 g, 1.37 mmol), donor 9 (0.622 g, 1.51 mmol) and 4 Å powdered molecular sieves (1.85 g) in dry acetonitrile (23 mL) was stirred at 0° C. for 1 hour, and then cooled to −40° C. A solution of $BF_3$-etherate (0.28 mL, 2.27 mmol) was added slowly. The mixture was stirred at −40° C. for 1 hour, and then neutralized with triethylamine. The solution was filtered through Celite, washed with MeOH/DCM (5:95, v:v, 20 mL), and the combined filtrates were concentrated to dryness. Purification of the crude product by column chromatography (Hexane/EtOAc, 3:1, v:v) on silica gel afforded the desired product 21 as α/β (1:4) mixture (1.38 g, 86%). Method B. To a solution of 20 (93 mg, 0.08 mmol) in THF (2 mL) was added methyl iodide (0.20 mL, 3.24 mmol) and silver(I) oxide (0.37 g, 1.60 mmol). Dimethyl sulfide (1 μL, 0.014 mmol) was added as catalyst. The flask was wrapped by aluminum foil to exclude light. The reaction mixture was stirred at room temperature overnight, and then filtered through celite. The filtrate was concentrated to dryness. Purification of the crude product by column chromatography (Hexane/EtOAc, 3:1, v:v) on silica gel afforded the desired product 21 as colorless oil (48 mg, 51%). $R_f$=0.56 (Hexane/EtOAc, 2:1, v:v).

$[\alpha]^{27}_D$=+82.0 ($CHCl_3$, c=1.9 mg/mL). $^1H$ NMR (500 MHz, $CDCl_3$): δ 0.83 (d, 3H, $J_{5,6}$=6.0 Hz, H-6c), 1.12 (d, 3H, $J_{5,6}$=6.0 Hz, H-6b), 1.24 (d, 3H, $J_{5,6}$=5.5 Hz, H-6a), 1.73 (m, 2H, $OCH_2CH_2CH_2NHZ$), 2.74 (m, 1H, H-5c), 2.84 (t, 1H, $J_{3,4}$=10.5, $J_{4,5}$=10.0 Hz, H-4c), 2.91 (t, 1H, $J_{1,2}$=8.0, $J_{2,3}$=9.0 Hz, H-2c), 3.11 (t, 1H, $J_{2,3}$=9.0, $J_{3,4}$=9.5 Hz, H-3c), 3.22 (m, 2H, $OCH_2CH_2CH_2NHZ$), 3.36 (s, 3H, $OCH_3$), 3.39 (m, 1H, $OCH_2CH_2CH_2NHZ$), 3.50 (t, 1H, $J_{3,4}$=9.5, $J_{4,5}$=10.0 Hz, H-4b), 3.54 (t, 1H, $J_{3,4}$=9.5, $J_{4,5}$=10.0 Hz, H-4a), 3.67 (m, 2H, $OCH'_2CH_2CH_2NHZ$, H-5a), 3.76 (m, 1H, H-5b), 4.10 (dd, 1H, $J_{2,3}$=3.0, $J_{3,4}$=9.5 Hz, H-3b), 4.20 (dd, 1H, $J_{2,3}$=3.0, $J_{3,4}$=9.5 Hz, H-3a), 4.31 (d, 1H, $J_{1,2}$=8.0 Hz, H-1c), 4.52 (d, 1H, J=11.0 Hz, $PhCH_2$), 4.59 (d, 1H, J=10.5 Hz, $PhCH'_2$), 4.65 (d, 1H, J=11.0 Hz, $PhCH''_2$), 4.72 (d, 1H, J=11.5 Hz, $PhCH'''_2$), 4.75 (d, 1H, J=12.0 Hz, $PhCH''''_2$), 4.76 (s, 1H, H-1a), 4.80 (d, 1H, J=10.5 Hz, $PhCH'''''_2$), 4.82 (broad, 1H, NH), 5.00 (s, 2H, $PhCH_2OC(O)$), 5.14 (s, 1H, H-1b), 5.30 (d, 1H, $J_{2,3}$=3.0 Hz, H-2a), 5.38 (d, 1H, $J_{2,3}$=3.0 Hz, H-2b), 7.19-8.02 (m, 30H, $H_{arom}$); $^{13}C$ NMR (75 MHz, $CDCl_3$): δ 17.8 (C-6c), 18.0 (C-6b), 18.1 (C-6a), 29.6 ($OCH_2CH_2CH_2NHZ$), 38.5 ($OCH_2CH_2CH_2NHZ$), 60.4 ($OCH_3$), 65.6 ($OCH_2CH_2CH_2NHZ$), 66.6 ($PhCH_2OC(O)$), 67.3 (C-5c), 67.9 (C-5a), 68.6 (C-5b), 70.2 (C-4c), 72.7 (C-2a), 73.2 (C-2b), [74.2, 75.2, 75.5 ($PhCH_2$)], 75.9 (C-3b), 78.0 (C-3a), 80.0 (C-4a), 80.5 (C-4b), 82.5 (C-3c), 84.3 (C-2c), 97.1 (C-1a), 99.2 (C-1b), 102.9 (C-1c), [127.6, 127.8, 127.9, 128.0, 128.2, 128.3, 128.4, 128.5, 129.7, 129.8, 129.9, 130.1, 133.0, 133.3, 137.8, 137.9, 138.2 ($C_{arom}$)], 156.3 ($PhCH_2OC(O)$), [165.5, 165.8 (PhC(O)O)]; MALDI-TOF/MS: m/z: found $[M+Na]^+$ 1187.8, MALDI-FTICR/MS: m/z: found $[M+Na]^+$ 1187.4715. $C_{65}H_{72}N_4O_{16}$ calcd for $[M+Na]^+$ 1187.4841.

3-[(N-benzyloxycarbonyl)amino]propyl O-(4-(3-hydroxy-3-methylbutamido)-2-O-methyl-3-benzyl-4,6-dideoxy-β-D-glucopyranosyl)-(1→3)-O-(2-O-benzoyl-4-O-benzyl-α-L-rhamnopyranosyl)-(1→3)-2-O-benzoyl-4-O-benzyl-α-L-rhamnopyranoside (22). Treatment of 21 (0.71 g, 0.61 mmol), 1,3-propanedithiol (1.26 mL, 12.55 mmol) in pyridine (43 mL) and $H_2O$ (6.1 mL) with TEA (1.28 mL, 9.15 mmol) according to the general procedure for azide reduction and introduction of C-4" moiety gave free amine (0.69 g, 99%). Treatment of the free amine (0.47 g, 0.41 mmol) in DMF (20 mL) with β-hydroxyisovaleric acid (88 μL, 0.82 mmol) which was activated with HOAt (0.23 g, 1.64 mmol) and HATU (0.62 g, 1.64 mmol) in DMF (10 mL) for 1 h, and then added DIPEA (5.71 mL, 3.28 mmol) gave compound 22 as colorless oil (0.32 g, 63%) and its α-isomer (76 mg, 15%). $R_f$=0.26 (Hexane/EtOAc, 1:1, v:v). $[\alpha]^{27}_D$=+9.4 ($CHCl_3$, c=2.8 mg/mL). $^1H$ NMR (500 MHz, $CDCl_3$): δ 0.73 (d, 3H, $J_{5,6}$=5.5 Hz, H-6c), 1.09 (s, 3H, $(CH_3)_2C(OH)CH_2C(O)NH$), 1.12 (d, 3H, $J_{5,6}$=6.0 Hz, H-6b), 1.18 (s, 3H, $(CH'_3)_2C(OH)CH_2C(O)NH$), 1.24 (d, 3H, $J_{5,6}$=5.5 Hz, H-6a), 1.74 (m, 2H, $OCH_2CH_2CH_2NHZ$), 1.99 (d, 1H, J=15.0 Hz, $(CH_3)_2C(OH)CH_2C(O)NH$), 2.09 (d, 1H, J=15.0 Hz, $(CH_3)_2C(OH)CH'_2C(O)NH$), 2.91 (m, 1H, H-5c), 2.98 (t, 1H, $J_{1,2}$=8.0, $J_{2,3}$=8.5 Hz, H-2c), 3.15 (t, 1H, $J_{2,3}$=8.5, $J_{3,4}$=9.0 Hz, H-3c), 3.22 (m, 2H, $OCH_2CH_2CH_2NHZ$), 3.38 (s, 3H, $OCH_3$), 3.39 (m, 2H, $OCH_2CH_2CH_2NHZ$, H-4c), 3.52 (t, 1H, $J_{3,4}$=9.0, $J_{4,5}$=9.5 Hz, H-4b), 3.54 (t, 1H, $J_{3,4}$=9.0, $J_{4,5}$=9.5 Hz, H-4a), 3.67 (m, 2H, $OCH'_2CH_2CH_2NHZ$, H-5a), 3.76 (m, 1H, H-5b), 4.12 (dd, 1H, $J_{2,3}$=3.5, $J_{3,4}$=9.0 Hz, H-3b), 4.21 (dd, 1H, $J_{2,3}$=3.0, $J_{3,4}$=9.0 Hz, H-3a), 4.34 (d, 1H, $J_{1,2}$=8.0 Hz, H-1c), 4.48 (d, 1H, J=11.0 Hz, $PhCH_2$), 4.54 (d, 1H, J=11.0 Hz, $PhCH'_2$), 4.60 (d, 1H, J=10.5 Hz, $PhCH_2$), 4.71 (d, 1H, J=12.5 Hz, $PhCH'''_2$), 4.77 (s, 1H, H-1a), 4.83 (d, 1H, J=11.5 Hz, $PhCH''''_2$), 4.85 (broad, 1H, NH), 4.95 (d, 1H, J=11.0 Hz, $PhCH'''''_2$), 5.00 (s, 2H, $PhCH_2OC(O)$), 5.15 (s, 1H, H-1b), 5.30 (d, 1H, $J_{2,3}$=3.0 Hz, H-2a), 5.39 (d, 1H, $J_{2,3}$=3.5 Hz, H-2b), 7.14-8.00 (m, 30H, $H_{arom}$); $^{13}C$ NMR (75 MHz, $CDCl_3$): δ 17.7 (C-6c), 17.8 (C-6b), 18.1 (C-6a), 29.2 ($OCH_2CH_2CH_2NHZ$), [29.3, 29.7 ($(CH_3)_2C(OH)CH_2C(O)NH$)], 38.5 ($OCH_2CH_2CH_2NHZ$), 47.7 ($(CH_3)_2C(OH)CH_2C(O)NH$), 55.7 (C-4c), 60.3 ($OCH_3$), 65.6 ($OCH_2CH_2CH_2NHZ$), 66.6 ($PhCH_2OC(O)$), 67.9 (C-5a), 68.6 (C-5b), 69.4 ($(CH_3)_2C(OH)CH_2C(O)NH$), 70.6 (C-5c), 72.8 (C-2a), 73.1 (C-2b), [73.5, 74.1, 75.5 ($PhCH_2$)], 76.1 (C-3b), 78.1 (C-3a), 79.8 (C-3c), 80.0 (C-4a), 80.5 (C-4b), 84.4 (C-2c), 97.1 (C-1a), 99.2 (C-1b), 103.0 (C-1c), [127.5, 127.7, 127.8, 127.9, 128.0, 128.1, 128.2, 128.3, 128.4, 128.5, 129.7, 129.8, 129.9, 130.2, 133.0, 133.3, 137.9, 138.3, 138.5 ($C_{arom}$)], 156.4 ($PhCH_2OC(O)$), [165.6, 165.9 (PhC(O)O)], 172.2 ($(CH_3)_2C(OH)CH_2C(O)NH$); MALDI-TOF/MS: m/z: found $[M+Na]^+$ 1261.4, MALDI-FTICR/MS: m/z: found $[M+Na]^+$ 1261.5427. $C_{70}H_{82}N_2O_{18}$ calcd for $[M+Na]^+$ 1261.5460.

3-[(N-benzyloxycarbonyl)amino]propyl O-(4-(3-hydroxy-3-methylbutamido)-3-O-benzyl-4,6-dideoxy-β-D-glucopyranosyl)-(1×3)-O-(2-O-benzoyl-4-O-benzyl-α-L-rhamnopyranosyl)-(1→3)-2-O-benzoyl-4-O-benzyl-α-L-rhamnopyranoside (23). Treatment of 20 (21 mg, 0.018 mmol), 1,3-propanedithiol (0.04 mL, 0.40 mmol) in pyridine (1.28 mL) and $H_2O$ (0.92 mL) with TEA (0.03 mL, 0.27 mmol) according to the general procedure for azide reduction and introduction of C-4" moiety gave free amine (20 mg, 98%). Treatment the free amine (20 mg, 0.018 mmol) in DMF (2 mL) with β-hydroxyisovaleric acid (4 μL, 0.037 mmol) which was activated with HOAt (10 mg, 0.074 mmol) and HATU (28 mg, 0.074 mmol) in DMF (1 mL) for 1 h, and then added DIPEA (26 μL, 0.15 mmol) gave compound 23 as colorless oil (17 mg, 78%). $R_f$=0.61 (Hexane/EtOAc, 1:2, v:v). $^1H$ NMR (500 MHz, $CDCl_3$): δ 0.79 (d, 3H, $J_{5,6}$=6.5 Hz, H-6c), 1.11 (s, 3H, $(CH_3)_2C(OH)CH_2C(O)NH$), 1.12 (d, 3H, $J_{5,6}$=6.5 Hz, H-6b), 1.14 (s, 3H, $(CH_3)_2C(OH)CH_2C(O)NH$), 1.25 (d, 3H, $J_{5,6}$=5.5 Hz, H-6a), 1.74 (m, 2H, $OCH_2CH_2CH_2NHZ$), 2.06 (d, 1H, J=15.0 Hz, $(CH_3)_2C(OH)CH_2C(O)NH$), 2.14 (d, 1H, J=15.0 Hz, $(CH_3)_2C(OH)CH'_2C(O)NH$), 2.98 (m, 1H, H-5c), 3.21 (m, 3H, $OCH_2CH_2CH_2NHZ$, H-3c), 3.36-3.42 (m, 3H, $OCH_2CH_2CH_2NHZ$, H-2c, H-4c), 3.52 (t, 1H, $J_{3,4}$=9.0, $J_{4,5}$=9.5 Hz, H-4b), 3.54 (t, 1H, $J_{3,4}$=9.0, $J_{4,5}$=10.0 Hz, H-4a), 3.68 (m, 2H, $OCH'_2CH_2CH_2NHZ$, H-5a), 3.77 (m, 1H, H-5b), 4.08 (dd, 1H, $J_{2,3}$=3.0, $J_{3,4}$=9.0 Hz, H-3b), 4.14 (d, 1H, $J_{1,2}$=7.5 Hz, H-1c), 4.21 (dd, 1H, $J_{2,3}$=3.0, $J_{3,4}$=9.0 Hz, H-3a), 4.49 (d, 1H, J=11.0 Hz, $PhCH_2$), 4.57 (d, 1H, J=11.0 Hz, $PhCH'_2$), 4.60 (d, 1H, J=10.5 Hz, $PhCH''_2$), 4.67 (d, 1H, J=11.0 Hz, $PhCH'''_2$), 4.73 (d, 1H, J=11.0 Hz, $PhCH''''_2$), 4.77 (s, 1H, H-1a), 4.86 (broad, 1H, NH), 4.94 (d, 1H, J=10.5 Hz, $PhCH'''''_2$), 5.00 (s, 2H, $PhCH_2OC(O)$), 5.13 (s, 1H, H-1b), 5.32 (d, 1H, $J_{2,3}$=3.0 Hz, H-2a), 5.38 (d, 1H, $J_{2,3}$=3.5 Hz, H-2b), 5.43 (d, 1H, J=9.0 Hz, $(CH_3)_2C(OH)CH_2C(O)NH$), 7.19-8.02 (m, 30H, $H_{arom}$); $^{13}C$ NMR (75 MHz, $CDCl_3$): δ 17.7 (C-6c), 17.9 (C-6b), 18.1 (C-6a), [29.3, 29.4 ($(CH_3)_2C(OH)CH_2C(O)NH$)], 29.7 ($OCH_2CH_2CH_2NHZ$), 38.5 ($OCH_2CH_2CH_2NHZ$), 47.8 ($(CH_3)_2C(OH)CH_2C(O)NH$), 55.3 (C-4c), 65.6 ($OCH_2CH_2CH_2NHZ$), 66.6 ($PhCH_2OC(O)$), 67.9 (C-5a), 68.7 (C-5b), 69.5 ($(CH_3)_2C(OH)CH_2C(O)NH$), 70.9 (C-5c), 72.7 (C-2a), 72.8 (C-2b), [72.5, 74.6, 75.4 ($PhCH_2$)], 74.9 (C-2c), 77.2 (C-3b), 78.0 (C-3a), 79.6 (C-3c), 80.0 (C-4a), 80.1 (C-4b), 97.1 (C-1a), 99.1 (C-1b), 103.1 (C-1c), [127.8, 127.9, 128.0, 128.1, 128.2, 128.3, 128.4, 128.6, 129.7, 129.8, 130.0, 133.1, 133.3, 137.9, 138.0, 138.4 ($C_{arom}$)], 151.7 ($PhCH_2OC(O)$), [165.7, 165.9 (PhC(O)O)], 172.3 (($(CH_3)_2C(OH)CH_2C(O)NH$); MALDI-TOF/MS: m/z: found $[M+Na]^+$ 1249.7. $C_{69}H_{80}N_2O_{18}$ calcd for $[M+Na]^+$ 1247.5304.

3-[(N-benzyloxycarbonyl)amino]propyl O-(4-(3-methylbutamido)-2-O-methyl-3-O-benzyl-4,6-dideoxy-α-D-glucopyranosyl)-(1→3)-O-(2-O-benzoyl-4-O-benzyl-α-L-rhamnopyranosyl)-(1→3)-2-O-benzoyl-4-O-benzyl-α-L-rhamnopyranoside (24). The azide of compound 20 was reduced as described in the general procedures. Treatment of the free amine (0.12 g, 0.11 mmol) in DMF (5 mL) with DIPEA (0.15 mL, 0.86 mmol) and isovaleric acid (24 μL, 0.22 mmol) that was pre-activated with HOAt (57 mg, 0.42 mmol) and HATU (0.16 g, 0.42 mmol) in DMF (2.6 mL) for 1 hour, gave compound 24 as colorless oil (78 mg, 0.064 mmol, 61%) and its α-isomer (19 mg, 0.016 mmol, 15%). $R_f$=0.39 (Hexane/EtOAc, 1:1, v:v). $[\alpha]^{27}_D$=+ 18.3 ($CHCl_3$, c=6.0 mg/mL). $^1H$ NMR (300 MHz, $CDCl_3$): δ 0.73 (d, 3H, $J_{5,6}$=6.0 Hz, H-6c), 0.78 (s, 3H, $(CH_3)_2CHCH_2C(O)NH$), 0.82 (s, 3H, $(CH'_3)_2CHCH_2C(O)NH$), 1.12 (d, 3H, $J_{5,6}$=6.0 Hz, H-6b), 1.24 (d, 3H, $J_{5,6}$=5.5 Hz, H-6a), 1.71 (m, 2H, $OCH_2CH_2CH_2NHZ$), 1.80-1.98 (m, 3H, $(CH_3)_2CHCH_2C(O)NH$, $(CH_3)_2CHCH_2C(O)NH$), 2.92 (m, 1H, H-5c), 2.97 (t, 1H, $J_{1,2}$=7.8, $J_{2,3}$=9.0 Hz, H-2c), 3.15-3.23 (m, 3H, $OCH_2CH_2CH_2NHZ$, H-3c), 3.37 (s, 3H, $OCH_3$), 3.39 (m, 2H, $OCH_2CH_2CH_2NHZ$, H-4c), 3.51 (t, 1H, $J_{3,4}$=9.0, $J_{4,5}$=9.0 Hz, H-4b), 3.56 (t, 1H, $J_{3,4}$=9.0, $J_{4,5}$=9.0 Hz, H-4a), 3.66 (m, 2H, $OCH'_2CH_2CH_2NHZ$, H-5a), 3.76 (m, 1H, H-5b), 4.13 (dd, 1H, $J_{2,3}$=3.0, $J_{3,4}$=9.0 Hz, H-3b), 4.21 (dd, 1H, $J_{2,3}$=3.0, $J_{3,4}$=9.0 Hz, H-3a), 4.34 (d, 1H, $J_{1,2}$=7.8 Hz, H-1c), 4.48 (d, 1H, J=12.0 Hz, $PhCH_2$), 4.53 (d, 1H, J=10.8 Hz, $PhCH'_2$), 4.60 (d, 1H, J=10.8 Hz, $PhCH''_2$), 4.69 (d, 1H, J=12.0 Hz, $PhCH'''_2$), 4.77 (s, 1H, H-1a), 4.83 (d, 1H, J=10.88 Hz, $PhCH''''_2$), 4.85 (broad, 1H, NH), 4.96 (d, 1H, J=10.8 Hz, $PhCH'''''_2$), 5.00 (s, 2H, $PhCH_2OC(O)$), 5.15 (d, 1H, $J_{1,2}$=1.2 Hz, H-1b), 5.30 (dd, 1H, $J_{1,2}$=1.2, $J_{2,3}$=3.0 Hz, H-2a), 5.39 (dd, 1H, $J_{1,2}$=1.8, $J_{2,3}$=3.0 Hz, H-2b), 7.18-8.06 (m, 30H, $H_{arom}$); $^{13}C$ NMR (75 MHz, $CDCl_3$): δ 17.6 (C-6c), 17.8 (C-6b), 18.1 (C-6a), [22.4, 22.5 ($(CH_3)_2CHCH_2C(O)NH$)], 25.9 ($(CH_3)_2CHCH_2C(O)NH$), 29.5 ($OCH_2CH_2CH_2NHZ$), 38.4 ($OCH_2CH_2CH_2NHZ$), 46.2 ($(CH_3)_2CHCH_2C(O)NH$), 55.7 (C-4c), 60.3 ($OCH_3$), 65.6 ($OCH_2CH_2CH_2NHZ$), 66.5 ($PhCH_2OC(O)$), 67.8 (C-5a), 68.5 (C-5b), 70.7 (C-5c), 72.7 (C-2a), 73.1 (C-2b), [73.3, 74.1, 75.5 ($PhCH_2$)], 76.0 (C-3b), 78.2 (C-3a), 79.7 (C-3c), 79.8 (C-4a), 80.4 (C-4b), 84.3 (C-2c), 97.0 (C-1a), 99.2 (C-1b), 103.0 (C-1c), [127.5, 127.6, 127.7, 127.9, 128.0, 128.1, 128.2, 128.3, 128.4, 128.5, 129.7, 129.8, 129.9, 130.1, 133.0, 133.3, 136.6, 137.9, 138.3, 138.4 ($C_{arom}$)], 156.3 ($PhCH_2OC(O)$), [165.6, 165.9 ($PhC(O)O$)], 172.2 ($(CH_3)_2CHCH_2C(O)NH$); MALDI-TOF/MS: m/z: found $[M+Na]^+$ 1245.4, MALDI-FTICR/MS: m/z: found $[M+Na]^+$ 1245.5510. $C_{70}H_{82}N_2O_{17}$ calcd for $[M+Na]^+$ 1245.5511.

3-[(N-benzyloxycarbonyl)amino]propyl O-(4-acetamido-2-O-methyl-3-O-benzyl-4,6-dideoxy-β-D-glucopyranosyl)-(1→3)-O-(2-O-benzoyl-4-O-benzyl-α-L-rhamnopyranosyl)-(1→3)-2-O-benzoyl-4-O-benzyl-α-L-rhamnopyranoside (25). The azide of compound 20 was reduced as described in the general procedures. Treatment the free amine (94 mg, 0.083 mmol) with acetic anhydride (0.016 mL, 0.17 mmol) in pyridine (0.014 mL, 0.17 mmol) and DMAP (1 mg, 0.008 mmol) gave compound 25 as colorless oil (64 mg, 66%) and its α-isomer (17 mg, 17%). $R_f$=0.25 (Hexane/EtOAc, 2:3). $[\alpha]^{27}_D$=+7.2 ($CHCl_3$, c=4.0 mg/mL). $^1H$ NMR (500 MHz, $CDCl_3$): δ 0.72 (d, 3H, $J_{5,6}$=6.0 Hz, H-6c), 1.12 (d, 3H, $J_{5,6}$=6.0 Hz, H-6b), 1.23 (d, 3H, $J_{5,6}$=6.5 Hz, H-6a), 1.70 (s, 3H, $CH_3C(O)NH$), 1.73 (m, 2H, $OCH_2CH_2CH_2NHZ$), 2.90 (m, 1H, H-5c), 2.97 (t, 1H, $J_{1,2}$=8.0, $J_{2,3}$=8.5 Hz, H-2c), 3.12 (t, 1H, $J_{2,3}$=8.5, $J_{3,4}$=9.5 Hz, H-3c), 3.22 (m, 2H, $OCH_2CH_2CH_2NHZ$), 3.33 (t, 1H, $J_{3,4}$=9.5, $J_{4,5}$=10.0 Hz, H-4c), 3.38 (s, 3H, $OCH_3$), 3.39 (m, 1H, $OCH_2CH_2CH_2NHZ$), 3.51 (t, 1H, $J_{3,4}$=9.0, $J_{4,5}$=10.0 Hz, H-4b), 3.54 (t, 1H, $J_{3,4}$=9.5, $J_{4,5}$=8.5 Hz, H-4a), 3.67 (m, 2H, $OCH'_2CH_2CH_2NHZ$, H-5a), 3.75 (m, 1H, H-5b), 4.13 (dd, 1H, $J_{2,3}$=3.0, $J_{3,4}$=9.0 Hz, H-3b), 4.21 (dd, 1H, $J_{2,3}$=2.5, $J_{3,4}$=9.5 Hz, H-3a), 4.34 (d, 1H, $J_{1,2}$=8.0 Hz, H-1c), 4.48 (d, 1H, J=11.5 Hz, $PhCH_2$), 4.53 (d, 1H, J=11.0 Hz, $PhCH'_2$), 4.59 (d, 1H, J=10.5 Hz, $PhCH''_2$), 4.70 (d, 1H, J=12.0 Hz, $PhCH'''_2$), 4.77 (s, 1H, H-1a), 4.81 (d, 1H, J=11.0 Hz, $PhCH''''_2$), 4.83 (broad, 1H, NH), 4.95 (d, 1H, J=10.5 Hz, $PhCH'''''_2$), 5.00 (s, 2H, $PhCH_2OC(O)$), 5.15 (s, 1H, H-1b), 5.30 (d, 1H, $J_{2,3}$=2.5 Hz, H-2a), 5.40 (d, 1H, $J_{2,3}$=3.0 Hz, H-2b), 7.19-8.00 (m, 30H, $H_{arom}$); $^{13}C$ NMR (75 MHz, $CDCl_3$): δ 17.5 (C-6c), 17.8 (C-6b), 18.1 (C-6a), 23.5 ($CH_3C(O)NH$), 29.7 ($OCH_2CH_2CH_2NHZ$), 38.5 ($OCH_2CH_2CH_2NHZ$), 55.9 (C-4c), 60.3 ($OCH_3$), 65.6 ($OCH_2CH_2CH_2NHZ$), 66.6 ($PhCH_2OC(O)$), 67.8 (C-5a), 68.5 (C-5b), 70.7 (C-5c), 72.8 (C-2a), 73.1 (C-2b), [73.5, 74.2, 75.5 ($PhCH_2$)], 76.0 (C-3b), 78.3 (C-3a), 79.6 (C-3c), 79.8 (C-4a), 80.5 (C-4b), 84.5 (C-2c), 97.0 (C-1a), 99.3 (C-1b), 103.0 (C-1c), [127.6, 127.8, 127.9, 128.0, 128.2, 128.3, 128.4, 128.5, 129.7, 129.8, 129.9, 130.2, 133.0, 133.3, 136.6, 137.9, 138.3, 138.5 ($C_{arom}$)], 156.3 ($PhCH_2OC(O)$), [165.6, 165.9 ($PhC(O)O$)], 169.8 ($CH_3C(O)NH$); MALDI-TOF/MS: m/z: found $[M+Na]^+$ 1204.3, MALDI-FTICR/MS: m/z: found $[M+Na]^+$ 1203.5040. $C_{67}H_{76}N_2O_{17}$ calcd for $[M+Na]^+$ 1203.5042.

3-aminopropyl O-(4-(3-hydroxy-3-methylbutamido)-2-O-methyl-4,6-dideoxy-β-D-glucopyranosyl)-(1→3)-O-(α-L-rhamnopyranosyl)-(1→3)-α-L-rhamnopyranoside (1). Treatment of 22 (138.0 mg, 111.3 μmol) in MeOH/DCM (2 mL: 2 mL) with NaOMe (pH=8-10) according to the general procedure for global deprotection gave deacetylated product (110.1 mg, 96%). Treatment of the partially deprotected compound (110.1 mg, 106.7 μmol) in tert-butanol/$H_2O$/AcOH (10 mL:0.25 mL:0.25 mL) with a catalytic amount of Pd/C under an atmosphere of hydrogen gave compound 1 as white solid (65.5 mg, 98%). $R_f$=0.50 ($CH_3CN/H_2O$/AcOH, 40:20:1, v:v:v). $^1H$ NMR (500 MHz, $D_2O$): δ 1.13 (d, 3H, $J_{5,6}$=6.0 Hz, H-6c), 1.21 (broad, 12H, $(CH_3)_2C(OH)CH_2C(O)NH$, H-6a, H-6b), 1.92 (m, 2H, $OCH_2CH_2CH_2NH_2$), 2.36 (s, 2H, $(CH_3)_2C(OH)CH_2C(O)NH$), 3.00-3.15 (m, 4H, $OCH_2CH_2CH_2NH_2$, H-2c, H-4c), 3.42-3.52 (m, 5H, $OCH_2CH_2CH_2NH_2$, H-4a, H-4b, H-3c, H-5c), 3.53 (s, 3H, $OCH_3$), 3.61 (m, 1H, H-5a), 3.69-3.76 (m, 3H, H-3a, H-5b, $OCH'_2CH_2CH_2NH_2$), 3.90 (d, 1H, $J_{3,4}$=10.0 Hz, H-3b), 3.93 (s, 1H, H-2a), 4.17 (s, 1H, H-2b), 4.63 (d, 1H, $J_{1,2}$=8.0 Hz, H-1c), 4.65 (s, 1H, H-1a), 4.93 (s, 1H, H-1b); $^{13}C$ NMR (75 MHz, $D_2O$): δ [16.7, 16.8 (C-6a, C-6b)], 17.2 (C-6c), 26.8 ($OCH_2CH_2CH_2NH_2$), [28.2, 28.4 ($(CH_3)_2C(OH)CH_2C(O)NH$)], 37.6 ($OCH_2CH_2CH_2NH_2$), 49.0 ($(CH_3)_2C(OH)CH_2C(O)NH$), 56.7 (C-4c), 60.2 ($OCH_3$), 65.0 ($OCH_2CH_2CH_2NH_2$), 68.9 (C-5a), 69.4 (C-5b), 69.9 ($(CH_3)_2C(OH)CH_2C(O)NH$), 70.0 (C-2a), 70.3 (C-2b), [70.9, 71.2, 71.4, 72.9 (C-4a, C-4b, C-3c, C-5c)], 78.4 (C-3a), 79.7 (C-3b), 83.4 (C-2c), 99.8 (C-1a), 102.3 (C-1b), 103.8 (C-1c), 174.2 ($(CH_3)_2C(OH)CH_2C(O)NH$); MALDI-TOF/MS: m/z: found $[M+Na]^+$ 649.6, MALDI-FTICR/MS: m/z: found $[M+Na]^+$ 649.3156. $C_{27}H_{50}N_2O_{14}$ calcd for $[M+Na]^+$ 649.3160.

3-aminopropyl O-(4-(3-hydroxy-3-methylbutamido)-4,6-dideoxy-β-D-glucopyranosyl)-(1→3)-O-(α-L-rhamnopyranosyl)-(1→3)-α-L-rhamnopyranoside (2). Treatment of 23 (17.0 mg, 13.9 μmol) in MeOH/DCM (0.5 mL: 0.5 mL) with NaOMe (pH=8-10) according to the general procedure for global deprotection gave the deacetylated product (14.0 mg, 99%). Treatment of the partially deprotected compound (14.0 mg, 13.8 μmol) in tert-butanol/H—O/AcOH (2 mL:0.05 mL:0.05 mL) with a catalytic amount of Pd/C under an atmosphere of hydrogen gave compound 2 as white solid (8.1 mg, 96%). $R_f$=0.30 ($CH_3CN/H_2O$/AcOH, 40:20:1, v:v:v). $^1H$ NMR (300 MHz, $D_2O$): δ 1.11 (d, 3H, $J_{5,6}$=6.0 Hz, H-6c), 1.17 (broad, 12H, $(CH_3)_2C(OH)CH_2C(O)NH$, H-6a, H-6b), 1.84 (m, 2H, $OCH_2CH_2CH_2NH_2$), 2.33 (s, 2H, $(CH_3)_2C(OH)CH_2C(O)NH$), 2.96 (m, 2H, $OCH_2CH_2CH_2NH_2$), 3.11 (t, 1H, $J_{3,4}$=7.2, $J_{4,5}$=7.2 Hz, H-4c), 3.27 (t, 1H, $J_{1,2}$=7.8, $J_{2,3}$=8.4 Hz, H-2c), 3.36-3.60 (m, 6H, $OCH_2CH_2CH_2NH_2$, H-4a, H-5a, H-4b, H-3c, H-5c), 3.64-3.75 (m, 3H, H-3a, H-5b, $OCH'_2CH_2CH_2NH_2$), 3.86 (m, 2H, H-2a, H-3b), 4.14 (s, 1H, H-2b), 4.58 (d, 1H, $J_{1,2}$=7.8 Hz, H-1c), 4.63 (s, 1H, H-1a), 4.88 (s, 1H, H-1b); $^{13}C$ NMR (75 MHz, $D_2O$): δ [16.7, 17.2 (C-6a, C-6b, C-6c)], 27.1 ($OCH_2CH_2CH_2NH_2$), [28.2, 28.4 ($(CH_3)_2C(OH)CH_2C(O)NH$)], 37.6 ($OCH_2CH_2CH_2NH_2$), 49.0 ($(CH_3)_2C(OH)CH_2C(O)NH$), 56.7 (C-4c), 65.1 ($OCH_2CH_2CH_2NH_2$), 68.9 (C-5a), 69.1 (C-5b), 69.9 ($(CH_3)_2C(OH)CH_2C(O)NH$), 70.0 (C-2a), 70.3 (C-2b), [71.1, 71.3, 71.4, 73.5 (C-4a, C-4b, C-3c, C-5c)], 74.2 (C-2c), 78.4 (C-3a), 79.7 (C-3b), 99.8 (C-1a), 102.3 (C-1b), 103.6 (C-1c), 174.2 ($(CH_3)_2C(OH)CH_2C(O)NH$); MALDI-TOF/MS: m/z: found $[M+Na]^+$ 635.3, MALDI-FTICR/MS: m/z: found $[M+Na]^+$ 635.3000. $C_{26}H_{45}N_2O_{14}$ calcd for $[M+Na]^+$ 635.3003.

3-aminopropyl O-(4-(3-methylbutamido)-2-O-methyl-4,6-dideoxy-β-D-glucopyranosyl)-(1→3)-O-(α-L-rhamnopyranosyl)-(1→3)-α-L-rhamnopyranoside (3). Treatment of 24 (47.0 mg, 38.4 μmol) in MeOH/DCM (0.5 mL:0.5 mL) with NaOMe (pH=8-10) according to the general procedure for global deprotection gave the deacetylated product (39.0 mg, 100%). Treatment of the partially deprotected compound (39.0 mg, 38.4 μmol) in tert-butanol/$H_2O$/AcOH (4 mL:0.1 mL:0.1 mL) with a catalytic amount of Pd/C under an atmosphere of hydrogen gave compound 3 as white solid (22.1 mg, 94%). $R_f$=0.40 ($CH_3CN/H_2O$/AcOH, 60:20:1). $^1H$ NMR (500 MHz, $D_2O$): δ 0.77 (m, 6H, $(CH_3)_2CHCH_2C(O)NH$), 1.06 (d, 3H, $J_{5,6}$=6.0 Hz, H-6c), 1.14 (m, 6H, H-6a, H-6b), 1.84 (broad, 3H, $OCH_2CH_2CH_2NH_2$, $(CH_3)_2CHCH_2C(O)NH$), 1.99 (m, 2H, $(CH_3)_2CHCH_2C(O)NH$), 2.94-2.99 (m, 4H, $OCH_2CH_2CH_2NH_2$, H-2c, H-4c), 3.33-3.46 (m, 5H, $OCH_2CH_2CH_2NH_2$, H-4a, H-4b, H-3c, H-5c), 3.47 (s, 3H, $OCH_3$), 3.55 (m, 1H, H-5a), 3.63 (dd, 1H, $J_{2,3}$=3.5, $J_{3,4}$=9.5 Hz, H-3a), 3.69 (m, 2H, H-5b, $OCH'_2CH_2CH_2NHZ$), 3.83 (dd, 1H, $J_{2,3}$=3.0, $J_{3,4}$=10.0 Hz, H-3b), 3.87 (s, 1H, H-2a), 4.12 (s, 1H, H-2b), 4.57 (d, 1H, $J_{1,2}$=8.5 Hz, H-1c), 4.61 (s, 1H, H-1a), 4.86 (s, 1H, H-1b); $^{13}C$ NMR (75 MHz, $D_2O$): δ [16.7, 16.8 (C-6a, C-6b)], 17.2 (C-6c), [21.7, 21.8 ($(CH_3)_2CHCH_2C(O)NH$)], 22.3 ($CH_3COOH$), 26.2 ($(CH_3)_2CHCH_2C(O)NH$), 26.8 ($OCH_2CH_2CH_2NH_2$), 37.6 ($OCH_2CH_2CH_2NH_2$), 45.5 ($(CH_3)_2CHCH_2C(O)NH$), 56.7 (C-4c), 60.2 ($OCH_3$), 65.1 ($OCH_2CH_2CH_2NH_2$), 69.0 (C-5a), 69.4 (C-5b), 70.0 (C-2a), 70.1 (C-2b), [71.0, 71.3, 71.5, 73.0 (C-4a, C-4b, C-3c, C-5c)], 78.4 (C-3a), 79.8 (C-3b), 83.5 (C-2c), 99.9 (C-1a), 102.3 (C-1b), 103.8 (C-1c), 177.2 ($CH_3COOH$), 179.7 ($(CH_3)_2CHCH_2C(O)NH$); MALDI-TOF/MS: m/z: found $[M+Na]^+$ 633.2, MALDI-FTICR/MS: m/z: found $[M+Na]^+$ 633.3207. $C_{27}H_{50}N_2O_{13}$ calcd for $[M+Na]^+$ 633.3211.

3-aminopropyl O-(4-acetamido-2-O-methyl-4,6-dideoxy-β-D-glucopyranosyl)-(1→3)-O-(α-L-rhamnopyranosyl)-(1→3)-β-L-rhamnopyranoside (4). Treatment of 25 (27.2 mg, 23.0 μmol) in MeOH/DCM (0.5 mL:0.5 mL) with NaOMe (pH=8-10) according to the general procedure for global deprotection gave the deacetylated product (22.9 mg, quantitative). Treatment of the partially deprotected compound (22.9 mg, 23.5 μmol) in tert-butanol/$H_2O$/AcOH (4 mL:0.1 mL:0.1 mL) with a catalytic amount of Pd/C under an atmosphere of hydrogen gave compound 4 as white solid (12.1 mg, 92%). $R_f$=0.45 ($CH_3CN/H_2O$/AcOH, 40:20:1, v:v:v). $^1H$ NMR (500 MHz, $D_2O$): δ 1.04 (d, 3H, $J_{5,6}$=5.5 Hz, H-6c), 1.13 (d, 3H, $J_{5,6}$=6.5 Hz, H-6b), 1.16 (d, 3H, $J_{5,6}$=6.5 Hz, H-6a), 1.87 (s, 3H, $CH_3C(O)NH$), 1.89 (m, 2H, $OCH_2CH_2CH_2NH_2$), 2.93-3.08 (m, 4H, $OCH_2CH_2CH_2NH_2$, H-2c, H-4c), 3.34-3.46 (m, 5H, $OCH_2CH_2CH_2NH_2$, H-4a, H-4b, H-3c, H-5c), 3.47 (s, 3H, $OCH_3$), 3.55 (m, 1H, H-5a), 3.64-3.71 (m, 3H, H-3a, H-5b, $OCH'_2CH_2CH_2NHZ$), 3.83 (d, 1H, $J_{3,4}$=10.0 Hz, H-3b), 3.87 (s, 1H, H-2a), 4.12 (s, 1H, H-2b), 4.59 (d, 1H, $J_{1,2}$=8.0 Hz, H-1c), 4.61 (s, 1H, H-1a), 4.87 (s, 1H, H-1b); $^{13}C$ NMR (75 MHz, $D_2O$): δ [16.8, 17.0 (C-6a, C-6b, C-6c)], 22.3 ($CH_3COOH$), 26.3 ($CH_3C(O)NH$), 26.8 ($OCH_2CH_2CH_2NH_2$), 37.6 ($OCH_2CH_2CH_2NH_2$), 56.9 (C-4c), 60.2 ($OCH_3$), 65.1 ($OCH_2CH_2CH_2NH_2$), 68.2 (C-5a), 69.0 (C-5b), 69.4 (C-2a), 70.0 (C-2b), [71.0, 71.3, 71.5, 73.0 (C-4a, C-4b, C-3c, C-5c)], 78.4 (C-3a), 79.7 (C-3b), 83.3 (C-2c), 99.9 (C-1a), 102.3 (C-1b), 103.8 (C-1c), 174.8 ($CH_3C(O)NH$), 178.4 ($CH_3COOH$); MALDI-TOF/MS: m/z: found $[M+Na]^+$ 591.2, MALDI-FTICR/MS: m/z: found $[M+Na]^+$ 591.2737. $C_{24}H_{44}N_2O_{13}$ calcd for $[M+Na]^+$ 591.2741.

General procedure for S-acetylthioglycolylamido derivatization of the aminopropyl spacer. The oligosaccharide 1 (10 mg, 0.016 mmol) was slurried in dry DMF (500 μL) and SAMA-OPfp (7.2 mg, 0.024 mmol) was added followed by drop wise addition of DIPEA (5.6 μL, 0.032 mmol). After stirring at room temperature for 2 hours, the mixture was concentrated, co-evaporated twice with toluene and the residue purified by size-exclusion chromatography (Biogel P2 column, eluated with $H_2O$ containing 1% n-Butanol) to give, after lyophilization, the corresponding thioacetate 26 (10.6 mg, 0.0144 mmol, 90%) as a white powder. In this manner, the thioacetamido derivatives of compounds 1-4 were prepared in yields of 85-95%.

General procedure for S-deacetylation. 7% $NH_3$ (g) in DMF solution (200 μL) was added to a solution of the thioacetate derivative corresponding to trisaccharide 1 (2.6 mg, 3.5 μmol) in dd$H_2O$ (40 μL) and the mixture was stirred under argon atmosphere. The reaction was monitored by MALDI-TOF showing the product peak of [M+Na]. After 1 hour the solvent was dried off under high-vacuum and the thiol derivatized trisaccharide was then further dried under high vacuum for 30 minutes and then used immediately in conjugation without further purification.

General procedure for the conjugation of thiol derivatized trisaccharides to BSA-MI. The conjugations were performed as instructed by Pierce Endogen Inc. In short, the thiol derivative (2.5 equiv. excess to available MI-groups on the protein), deprotected just prior to conjugation as described above, was dissolved in dd$H_2O$ (100 μL) and added to a solution of maleimide activated protein (2 mg) in the conjugation buffer sodium phosphate pH 7.2 containing EDTA and sodium azide (200 μL). The mixture was incubated for 2 hours at room temperature and then purified by Millipore Centriplus centrifugal filter devices with a 10 KDa molecular cut-off. All centrifugations were performed at 8° C. for 25 minutes, spinning at 13×g. The reaction mixture was centrifuged off and the filter washed with 10 mM Hepes buffer pH 6.5 (3×200 μL). The conjugate was retrieved and taken up in sodium phosphate buffer pH 7.4, 0.15M sodium chloride (1 mL). This gave glycoconjugates with a carbohydrate/BSA ratio of 18/1 for trisaccharide 1, 10/1 for 2"-OH-trisaccharide 2, 9/1 for 4"-isovaleric acid trisaccharide 3 and 4/1 for trisaccharide 4"-HNAc-trisaccharide 4 as determined by Dubois' phenol-sulfuric acid total carbohydrate assay, quantitative monosaccharide analysis by HPAEC/PAD and Lowry protein concentration test.

Conjugation of thiol derivatized trisaccharide to KLH-BrAc. A solution of KLH (15 mg) in 0.1 M sodium phosphate buffer pH 7.2 containing 0.15 M NaCl (1.5 mL) was added to a solution of SBAP (6 mg) in DMSO (180 μL). The mixture was incubated for 2 hours at room temperature and then purified using Millipore Centriplus centrifugal filter devices with a molecular cut-off of 30 KDa. All centrifugations were performed at 8° C. for 25 minutes spinning at 3000 rpm. The reaction mixture was centrifuged off and the filter washed with conjugation buffer (2×750 μL). The activated protein was retrieved by spinning at 3000 rpm for 15 minutes at 8° C. and taken up in 0.1 mM sodium phosphate buffer pH 8.0 containing 5 mM EDTA (2 mL). The activated protein was added to a vial containing de-S-acetylated trisaccharide (2.6 mg) and the mixture was incubated at room temperature for 18 hours. Purification was achieved using centrifugal filters as described above for the BSA-MI-trisaccharide conjugates. This gave a glycoconjugate with 1042 trisaccharide residues/KLH molecule as determined by phenol-sulfuric acid total carbohydrate assay, quantitative monosaccharide analysis by HPAEC/PAD and Lowry protein concentration test.

Preparation of *Bacillus anthracis* Sterne $34F_2$ Spores. *Bacillus anthracis* Sterne $34F_2$ was obtained from the CDC culture collection. Spores of *B. anthracis* Sterne $34F_2$ were prepared from liquid cultures of PA medium (Green et al., Infect Immun 1985, 49:291-297) grown at 37° C., 200 rpm for six days. Spores were washed two times by centrifugation at 10,000×g in cold (4° C.) sterile deionized water, purified in a 50% Reno-60 (Bracco Diagnostics Inc., Princeton, N.J.) gradient (10,000×g, 30 min, 4° C.) and washed a further four times in cold sterile deionized water. After suspension in sterile deionized water, spores were quantified with surface spread viable cell counts on brain heart infusion (BHI) agar plates (BD BBL, Sparks, Md.). Spore suspensions were stored in water at −80° C.

For the preparation of killed spores, 500-μl aliquots of spore suspensions in water, prepared as described above and containing approximately $3\times10^8$ CFU, were irradiated in 200-ml Sarstedt freezer tubes (Sarstedt, Newton, N.C.) in a gamma cell irradiator with an absorbed dose of 2 million rads. Sterility after irradiation was monitored by spread-plating 10-μl aliquots of irradiated spore suspension on BHI agar plates. The plates were incubated for 72 hours at 37° C. and monitored for colony growth. Absence of growth was taken as an indicator of sterility.

Preparation of Anti-Live Spore Antiserum. All antisera were prepared in female New Zealand White rabbits (2.0-3.5 kg) purchased from Myrtle's Rabbitry (Thompson Station, Tenn.). For antiserum production each of two rabbits were inoculated intramuscularly at two sites in the dorsal hind quarters with 0.5 ml of washed live-spore or irradiated spore innoculum ($3\times10^6$ total spores). Rabbits were vaccinated at O, 14, 28, and 42 days. Serum was collected prior to the first immunization (pre-immune serum) and at 7 and 14 days after each injection of antigen. Terminal bleeds were collected 14 days after the last immunization. All animal protocols were approved by the CDC Animal Care and Use Committee (ACUC) and implemented under the direction of the CDC attending veterinarian.

Antibody Binding Analyses. Binding of rabbit anti-live spore antiserum to synthetic oligosaccharide conjugates was done by enzyme-linked immunosorbent assay (ELISA). Briefly, Immulon II-HB flat bottom 96-well microtiter plates (Thermo Labsystems, Franklin, Mass.) were coated with 100 μl per well of the KLH-BrAc-1 conjugate at a concentration of 0.03 μg/ml of carbohydrate content, corresponding to 0.5 μg/ml by protein content, or by the protein mcKLH by itself (0.5 μg/mL protein) in coating buffer (0.01M PBS, pH 7.4). Plates were washed three times in wash buffer (0.01M PBS, pH 7.4, 0.1% Tween-20) using an ELX405 microplate washer (BioTek Instruments Inc., Winooski, Vt.). Serial dilutions (100 μl per well) in blocking solution (0.01M PBS, pH 7.4, 5% skim milk, 0.5% Tween-20) of either rabbit anti-spore antiserum from the day 49 bleed or pre-immune serum were then added and plates were incubated for 1 hour 37° C. After incubation the plates were washed three times in wash buffer at which time a goat anti-rabbit IgG horseradish peroxidase conjugate (ICN Pharmaceuticals, Aurora, Ohio) was added (100 μl/well) and the incubation continued for 1 hour at 37° C. Plates were then washed three times in wash buffer and 100 μl per well of ABTS peroxidase substrate was added (KPL, Gaithersburg, Md.). Color development was stopped after 15 minutes at 37° C. by addition of 100 μl/well of ABTS peroxidase stop solution (KPL, Gaithersburg, Md.). Optical density (OD) values were read at a wavelength of 410 nm (490 nm reference filter) with a MRX Revelation microtiter plate reader (Thermo Labsystems, Franklin, Mass.).

To test for competitive inhibition, the rabbit anti-live spore antiserum or the rabbit anti-irradiated spore antiserum was added together with unconjugated trisaccharide in blocking solution at a 6-, 12-, 25-, 50-, 100-, or 200-fold weight excess compared to weight of carbohydrate used for coating. The negative control consisted of uncoated wells incubated with the respective antiserum plus trisaccharide 1 at a concentration corresponding to "200-fold excess" of trisaccharide.

To explore competitive inhibition by synthetic saccharide analogues conjugated to bovine serum albumin (BSA; Pierce Biotechnology, Rockford, Ill.), rabbit anti-live spore antiserum was diluted 1:1600 in blocking solution. For each well 100 μl of the serum were mixed with either 100 μl blocking solution or 100 μl of BSA-MI-conjugate in blocking solution with a concentration corresponding to a 2-, 4-, 8-, 16-, 32-, 64-, or 128-fold weight excess of carbohydrate compared to carbohydrate used for coating. The four conjugates tested were: BSA-MI-1, BSA-MI-2, BSA-MI-3, and BSA-MI-4. First the serum and then the BSA-saccharide conjugate solutions were added to an uncoated microtiter plate and mixed by pipetting up and down before the well contents were transferred to a coated plate. The microtiter plates were incubated and developed as described above. All ELISA experiments were repeated three times.

Results and Discussion

To study the immunological properties of the oligosaccharide of BclA, this example examined whether antisera from rabbits immunized with live or irradiated spores of *B. anthracis* Sterne $34F_2$ were able to recognize the synthetic anthrose-containing BclA oligosaccharide (Adamo et al., 2005, *Carbohydr Res,* 340:2579-2582; Saksena et al., 2006, *Bioorg Med Chem Lett,* 16:615-617; Saksena et al., 2005, *Carbohyr Res,* 340:1591-1600; and Werz and Seeberger, 2005, *Angew Chem Int Ed Engl,* 44:6315-6318) and selected analogues. Although challenging, chemical synthesis offers an opportunity to obtain almost every oligosaccharide target in sufficient quantity and purity for these biological studies. Furthermore, chemical synthesis has the advantage that a target compound can be equipped with an artificial spacer for convenient conjugation to a carrier protein, and offers opportunities for obtaining analogues for structure-activity relationship studies.

Compounds 1-4 (FIG. 10) were selected as targets for chemical synthesis. Compound 1 is derived from the oligosaccharide of BclA and contains an intact anthrose moiety. Compound 2 lacks the methyl ether at C-2 and derivatives 3 and 4 contain modified C-4 amino functionalities of anthrose. It was anticipated that compound 1 conjugated to BSA or KLH would be an attractive material for determining whether live or irradiated spores of *B. anthracis* Sterne $34F_2$ can induce an anti-carbohydrate antibody response, and derivatives 2-4 valuable to examine which chemical moieties of anthrose are critical for binding with antibodies.

Figure 11:
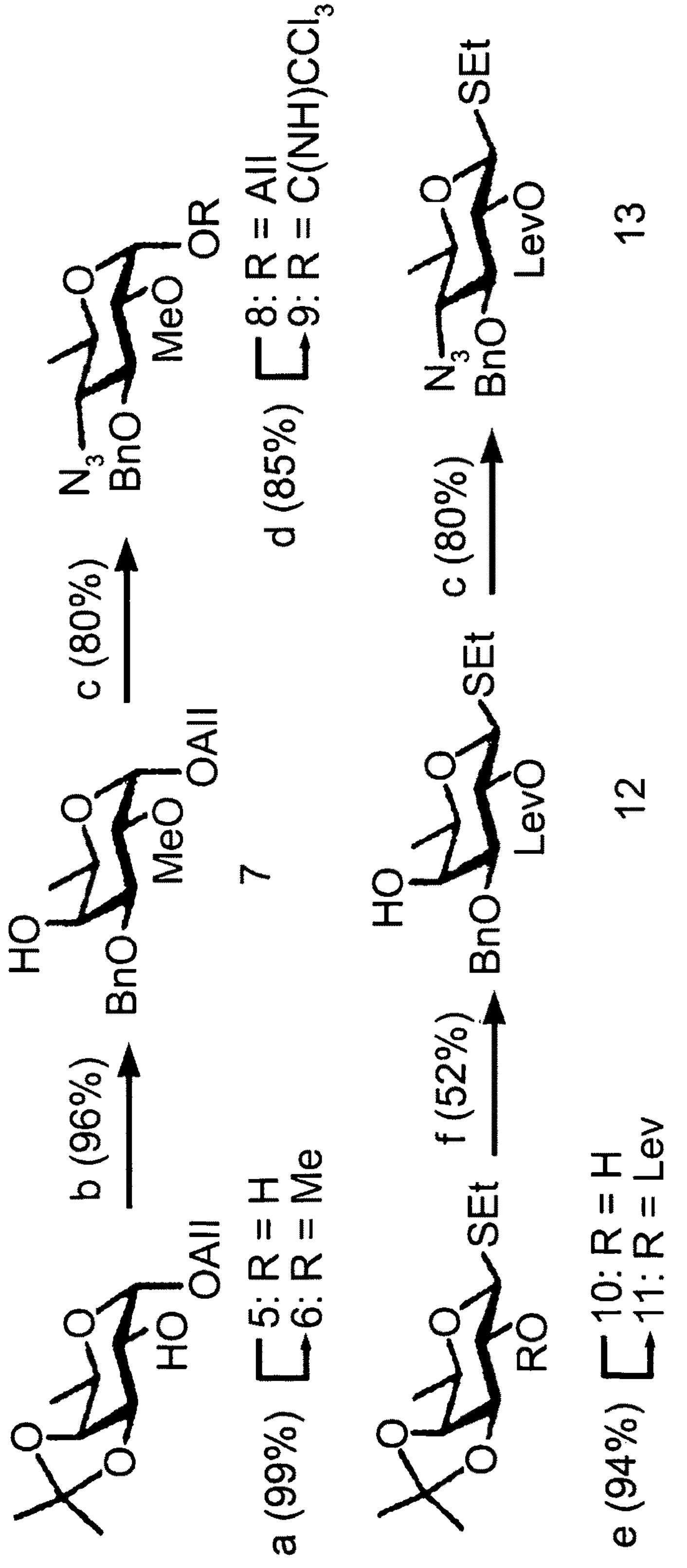
FIG. 11 presents synthetic Scheme 1. Reagents and conditions are as follows: a) MeI, NaH, DMF, rt; b) 1: 60% HOAc/$H_2O$, 90° C., 2: $Bu_2SnO$, MeOH, reflux, 3: CsF, BnBr, DMF, rt; c) 1: $Tf_2O$, pyridine, DCM, 0° C., 2:$NaN_3$, DMF, 40° C.; d) 1: $PdCl_2$, NaOAc, 90% HOAc/$H_2O$, rt, 2: trichloroacetonitrile, DBU, DCM, rt; e) Levulinic acid, DCC, DMAP, DCM, rt; f) 1: 60% aq. HOAc, 90° C., 2: $Bu_2SnO$, toluene, reflux, 3: $Bu_4NBr$, BnBr, toluene, reflux.
Figure 12:
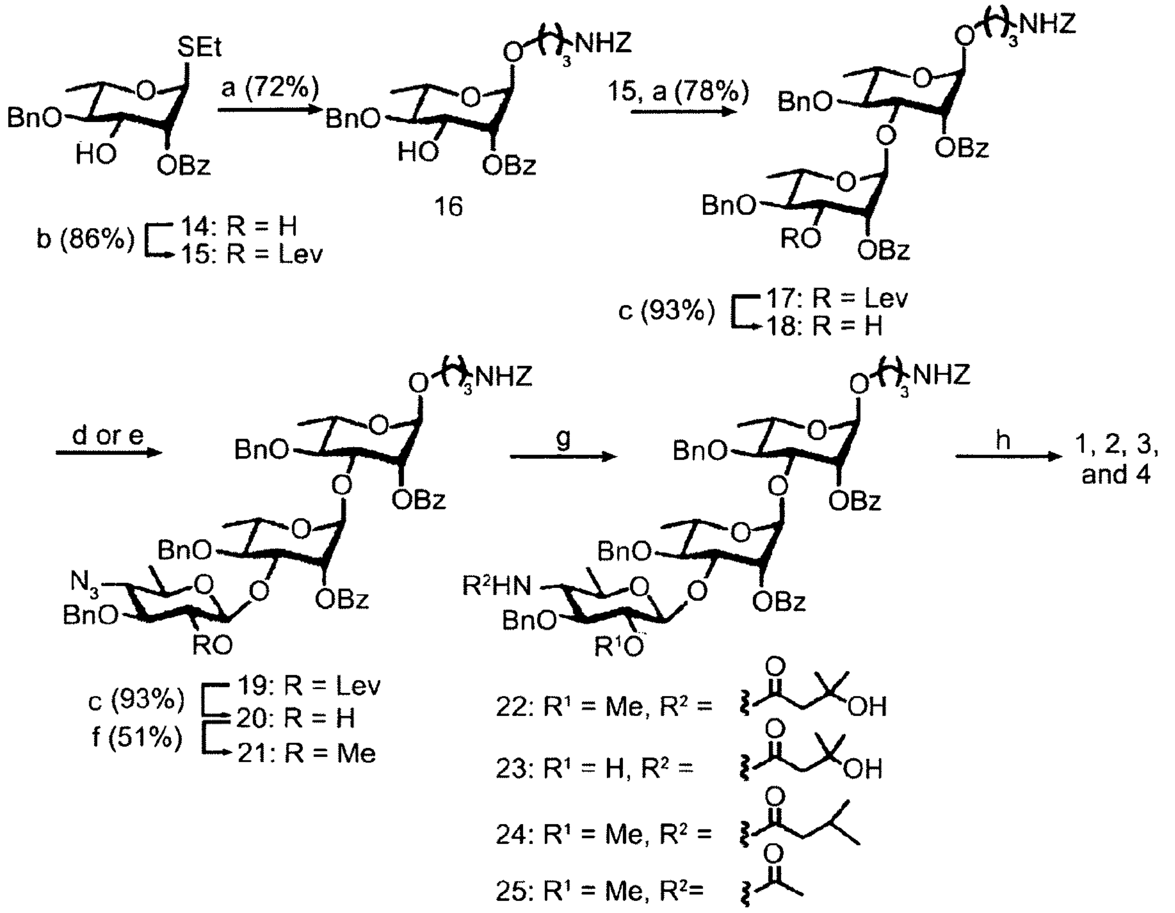
FIG. 12 presents synthetic Scheme 2. Reagents and conditions are as follows: a) NIS, TfOH, DCM, 0° C.; b) Levulinic acid, DCC, DMAP, DCM, rt; c) $NH_2NH_2$—HOAc, MeOH, DCM, rt; d) 13, NIS, TfOH, DCM, 0° C., 76%; e) 9, $BF_3$-Etherate, MeCN, −40° C., 86% α/β 1:4; f) MeI, $Ag_2O$, $Me_2S$, THF, rt; g) 1: 1,3-propanedithiol, TEA, pyridine, $H_2O$, 2: for 22, 23, 24, HOAt, HATU, DIPEA, rt, 61-76%, for 25, $Ac_2O$, pyridine, rt, 22: 63%, 23: 78%, 24: 61%, 25: 66%; h) 1: NaOMe, MeOH, rt, 2: Pd/C, $H_2$ (g), tert.-BuOH/$H_2O$/AcOH (40:1:1), rt, 1: 98%, 2: 96%, 3: 94%, 4: 92%.
Figure 13:
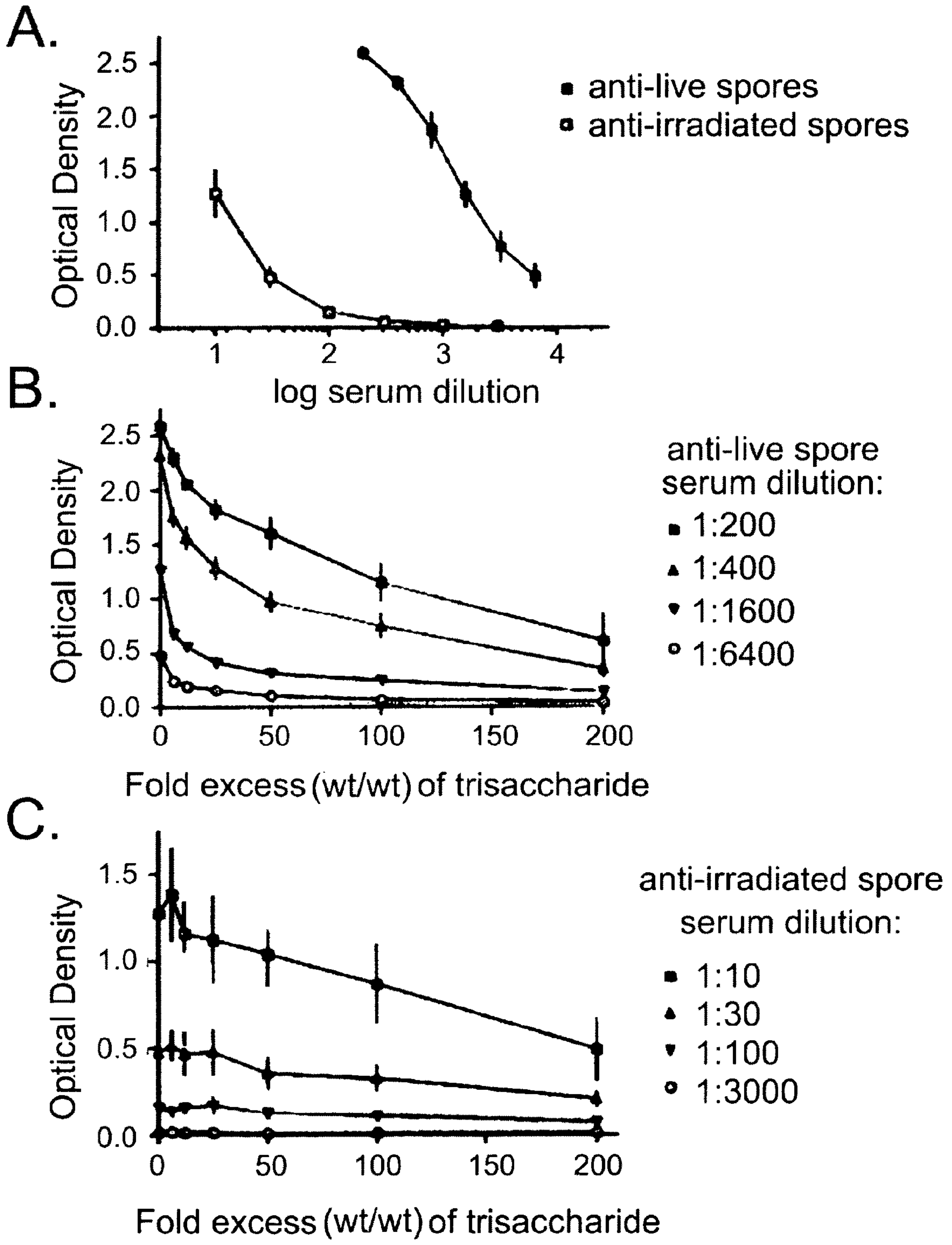
FIGS. 13A-13C show ELISA and competitive inhibition of anti-live and anti-irradiated spore anti-serum. Microtiter plates were coated with KLH-BrAc-1 conjugate (0.5 μg/mL conjugate, corresponding to 0.03 μg/mL trisaccharide). Rabbit anti-live (1:200-1:6400 diluted) or anti-irradiated (1:10-1:3000 diluted) spore *B. anthracis* Sterne $34F_2$ antiserum were applied to coated microtiter plates (FIG. 13A). For the inhibition assay the serum was first mixed with free trisaccharide 1 (structure 1 of FIG. 10) (0-200 fold excess, wt/wt) (FIGS. 13B and 13C). Unspecific binding was tested with uncoated wells with 200 fold "excess" trisaccharide or 200-fold "excess" KLH. The data are reported as the means±SD of triplicate measurements.

Compounds 1-4 were synthesized from monosaccharide precursors 14, 15 and 9 or 13 (Schemes 1 and 2, shown in FIGS. 11 and 12, respectively). Thus, glycosyl donor 14 can be coupled with a benzyloxycarbonyl protected amino propyl spacer to give compound 16, which immediately can be used in a subsequent glycosylation with rhamnoside 15 to give disaccharide 16. After removal of the levulinoyl (Lev) ester of 16, the resulting glycosyl acceptor can be coupled with an appropriately protected anthrose donor. The benzoyl ester at C-2 of 15 will ensure that only α-glycosides will be obtained during glycosylation due to neighboring group participation.

The anthrose moieties of target compounds 1-4 are linked through a β-glycoside to the C-3 hydroxyl of the rhamnoside. Thus, an obvious strategy to introduce this moiety would be the use of a glycosyl donor which carries a selectively removable ester at C-2. At a late stage of the synthesis, this protecting group can be removed to reveal an alcohol, which can then be methylated. However, this strategy is complicated by the fact that the methylation has to be performed under neutral or mildly acidic conditions due to the presence of a number of base sensitive ester protecting groups. In general, such procedures provide relatively low yields of product, especially when applied to a complex compound. Alternatively, the methyl ether can be introduced at the monosaccharide stage using strongly basic conditions; however, this approach may suffer from the formation of anomeric mixtures during the introduction of the anthrose glycoside. In order to examine both strategies, glycosyl donors 9 and 13 were prepared and coupled with glycosyl acceptor 18. Compounds 9 and 13 contain an azido moiety at C-4, which at a late stage of the synthesis can be reduced to an amine and then acylated with different reagents to provide compounds 1-4.

Glycosyl donor 9 was synthesized from selectively protected allyl galactoside 5 (Scheme 1) (Liu et al., 2000, *Carbohydr Res,* 329:745-754). Thus, methylation of the C-2 hydroxyl of 5 could easily be accomplished by treatment of 5 with methyl iodide in the presence of sodium hydride to give compound 6 in a yield of 99%. The 3,4-O-isopropylidene acetal of 6 could easily be removed using aqueous acetic acid to give a diol, which was selectively benzylated at C-3 to give compound 7, first by stannene acetal formation by reaction with dibutyltin oxide in refluxing methanol followed by treatment with benzyl bromide and CsF in DMF (David et al., 1981, *Journal of the Chemical Society-Perkin Transactions,* 1: 1796-1801; Qin and Grindley, 1996, *Journal of Carbohydrate Chemistry,* 15:95-108). Next, an azido group was introduced at C-4 with inversion of configuration to give compound 8 by conversion of the hydroxyl of 7 into a triflate by reaction with triflic anhydride and pyridine followed by displacement with sodium azide in DMF (Elchert et al., 2004, *Journal of Organic Chemistry,* 69:1513-1523). Fully protected 8 was converted into trichloroacetimidate 9 by removal of the anomeric allyl ether by treatment with $PdCl_2$ and NaOAc followed by reaction of the resulting lactol with trichloroacetonitrile in the presence of 1,8-diazabicyclo [5.4.0]undec-7-ene (DBU) (Schmidt, 1986, *Angew. Chem. Int. Ed. Engl.,* 25:212-235; Schmidt and Kinzy, 1994, *Advances in Carbohydrate Chemistry and Biochemistry,* 50:21-123).

Glycosyl donor 13 was synthesized from known thioglycoside 10 (Jiang et al., 2001, *Angewandte Chemie-International Edition,* 40:1502-1505). Thus, a levulinoyl (Lev) ester at C-2 of compound 10 was installed by treatment with levulinic acid, 1,3-dicyclohexylcarbodiimide (DCC), and 4-(dimethylamino)pyridine (DMAP) in DCM to give compound 11 in excellent yield (Zhu and Boons, 2001, *Chem. Eur. J.,* 7:2382-2389). Next, the isopropylidene acetal of 11 was removed by treatment with aqueous acetic acid to give the corresponding diol. Attempts to selectively benzylate the C-3 hydroxyl of this compound by intermediate stannene acetal formation, using conditions described for the preparation of 7, gave 12 in a low yield due to cleavage of the Lev ester.

However, a moderate yield of 12 was obtained when the stannene acetal formation was performed by refluxing the diol and dibutyltin oxide in toluene followed by treatment with benzyl bromide and tetrabutylammonium bromide ($Bu_4NBr$). Finally, triflation of 12 followed by nucleophilic displacement with sodium azide gave the required thioglycosyl donor 13.

Next, attention was focused on the preparation of rhamnosyl acceptor 18 and installment of the anthrose moiety. Thus, an N-iodosuccinimide/trifluoromethanesulfonic acid (NIS/TfOH) mediated glycosylation (Veeneman et al., 1990, *Tetrahedron Lett.,* 31:1331-1334) of thioglycosyl donor 14 with benzyl oxycarbonyl protected aminopropanol gave spacer modified 16 as only the α-anomer. No self-condensation of 14 was observed due to a much higher glycosyl acceptor reactivity of N-benzyloxycarbonyl amino propanol. Compound 16 was immediately used in a second glycosylation with glycosyl donor 15, using NIS/TfOH as the activator to give disaccharide 17 in a good yield. Next, the levolinoyl ester of 17 was selectively removed by treatment with hydrazine-acetate (Zhu and Boons, 2001, *Chem. Eur. J.,* 7:2382-2389), to afford glycosyl acceptor 18 in a yield of 93%. Coupling of trichloroacetimidate 9 with 18 in the presence of $BF_3$-etherate in acetonitrile at −40° C. gave trisaccharide 21 in a good yield (86%) as a ¼ mixture of α/β-anomers. In this case, the modest β-selectivity was achieved by the formation of an intermediate α-nitrilium ion (Braccini et al., 1993, *Carbohydrate Research,* 246: 23-41; Vankar et al., 1991, *Tetrahedron,* 47:9985-9992). Anomerically pure 22 was obtained after reduction of the azido-group of 21 to give an amine, which was acylated with 3-hydroxy-3-methyl-butyric acid using O-(7-azabenzotriazol-1-yl-N,N,N',N'-tetramethyluronium hexafluorophosphate/1-hydroxy-7-azabenzotriazole/diisopropylethylamine (HATU/HOAt/DIPEA) as the activating reagent.

As expected, an NIS/TfOH mediated coupling of thioglycosyl donor 13 with acceptor 18 gave trisaccharide 19 as only the β-anomer due to the neighboring group participating Lev ester at C-2. The Lev group of 19 was selectively removed by treatment with hydrazine-acetate (Zhu and Boons, 2001, *Chem. Eur. J.,* 7:2382-2389) and the hydroxyl of the resulting trisaccharide 20 was methylated by treatment with methyl iodide and freshly prepared $Ag_2O$ in the presence of dimethyl sulfide. Despite a prolonged reaction time, the product was obtained in a modest yield of 51%. Thus, the advantage of using glycosyl donor 13 in trisaccharide formation was offset by a low yielding methylation reaction.

Reduction of the C-4" azido moiety of 21 followed by the coupling with 3-hydroxy-3-methyl-butyric acid gave compound 22. Deprotection of 22 could easily be accomplished by a two-step procedure entailing removal of the benzoyl esters using sodium methoxide in methanol, followed by cleavage of the benzyl ethers and benzyloxycarbamate by hydrogenation over Pd/C in a mixture of t-butanol/water/acetic acid.

Analog 2, lacking a methyl ether at C-2, was prepared by reduction of the azido group of 20 followed by introduction of the 3-hydroxy-3-methyl-butyric acid moiety and deprotection using standard procedures. Compounds 3 and 4 were obtained by reduction of the azido moiety of 21 followed by acylation of the resulting amine using appropriate reagents to give compounds 24 and 25, which were deprotected using standard procedures.

Preparation of carbohydrate-protein conjugates. Trisaccharide 1, was linked to the carrier protein mcKLH for immunological evaluation. To this end, the amino functionality of trisaccharide 1 was derivatized with an acetyl thioacetic acid moiety by reaction with S-acetylthioglycolic acid pentafluorophenyl ester to afford the corresponding thioacetate derivative, which after purification by size-exclusion chromatography, was directly de-S-acetylated using 7% ammonia (g) in DMF just prior to conjugation. The de-S-acylation was performed under a strict argon atmosphere to prevent formation of the corresponding disulfide. KLH was activated with succinimidyl 3-(bromoacetamido) propionate (SBAP) in a sodium phosphate buffer (pH 7.2) containing 0.15 M sodium chloride and then purified by a centrifugal filter device with a nominal molecular-weight limit of 30 KDa. The bromoacetyl activated KLH (KLH-BrAc) was subsequently incubated with the thiolated trisaccharide in a 0.1 mM sodium phosphate buffer (pH 8.0) containing 5 mM ethylenediaminetetraacetate (EDTA). The afforded glycoconjugate (KLH-BrAc-1) carried 1042 copies of trisaccharide 1 per KLH molecule as determined by Lowry's protein concentration test and quantitative carbohydrate analysis by HPAEC-PAD. For the purpose of evaluating the binding specificity of antibodies raised against the *B. anthracis* spores, the thiol derivative of trisaccharide 1 was conjugated to maleimide activated BSA (BSA-MI, Pierce Endogen, Inc.) in a phosphate buffer (pH 7.2) containing sodium azide and EDTA. After a reaction time of 2 hours, the glycoprotein was purified using a centrifugal filter device with a nominal molecular weight cut-off of 10 KDa. The average number of trisaccharide copies per BSA molecule was determined to be 18/1. The same conjugation method and thiolated derivatives of trisaccharides 2, 3, and 4 were used to give the corresponding BSA-MI-2, BSA-MI-3, and BSA-MI-4 glycoconjugates with a sacchride/protein ratio of 10/1, 9/1, and 4/1, respectively.

Antibody Binding Analyses. To explore the immunogenicity of the saccharide moieties of BclA, rabbits were immunized four times at biweekly intervals with live or irradiated spores of *B. anthracis* Sterne $34F_2$. First, it was investigated whether the post-immune sera have the ability to recognize the synthetic anthrose-containing trisaccharide 1. For this purpose, an ELISA was performed whereby micro-titer plates were coated with the KLH-BrAc-1 conjugate and serial dilutions of sera added. An anti-rabbit IgG antibody labeled with horseradish peroxidase was employed as a secondary antibody for colorimetric detection (OD, optical density). Binding was observed between the anti-sera and KLH-trisaccharide conjugate whereas no interaction was detected for native KLH, indicating that the saccharide epitopes of BclA are antigenic (FIG. 13A). Rabbits immunized with irradiated Sterne $34F_2$ spores elicited lower but detectable titers of anti-saccharide antibodies. The fact that the irradiated spores elicited IgG antibodies indicates that the saccharide epitopes were not damaged during this process. Next, the specificity of the interaction of the antisera with the KLH-BrAc-1 conjugate was further investigated using a competitive inhibition ELISA. Thus, micro-titer plates were coated with the KLH-BrAc-1 conjugate, and serial dilutions of anti-sera mixed with free trisaccharide 1 were added. As depicted in FIG. 13B, a 6-fold excess of trisaccharide 1 (as compared to a concentration of trisaccharide used for coating microtiter wells), resulted in a significant drop in OD at all serum dilution tested. Also, increasing the excess of the competing trisaccharide 1 resulted in a further reduction in OD. It is evident that the inhibition is dose dependent, thus demonstrating that the interaction of the elicited antibodies with 1 is specific. The interaction of antisera from rabbits immunized with irradiated spores with 1 could also be inhibited in a dose response manner (FIG. 13C).

Figure 14:
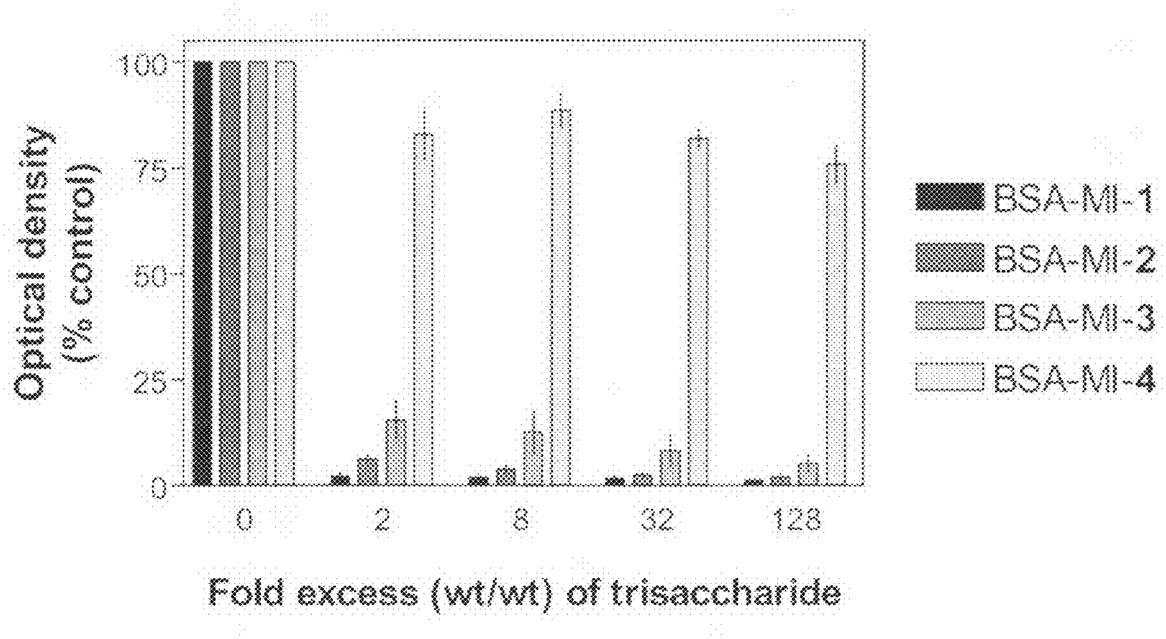
FIG. 14 demonstrates competitive inhibition of anti-live spore antiserum binding to synthetic anthrose-containing trisaccharide by synthetic analogue conjugates. Microtiter plates were coated with KLH-BrAc-1 conjugate (structure 1 of FIG. 10) (0.5 μg/mL conjugate corresponding to 0.03 μg/mL trisaccharide). Rabbit anti-live spore *B. anthracis* Sterne $34F_2$ antiserum (1:1600 dilute) was first mixed with BSA-trisaccharide conjugates (0-128 fold excess, wt/wt based on carbohydrate concentration) and then applied to the coated microtiter plate. Unconjugated BSA mixed with antiserum did not have any effect. OD values were normalized for the OD values obtained without BSA-trisaccharide conjugate (0 fold "excess", 100%). Non-specific binding was tested with uncoated wells containing antiserum and buffer. The data are reported as the means±SD of triplicate measurements.
Figure 15:
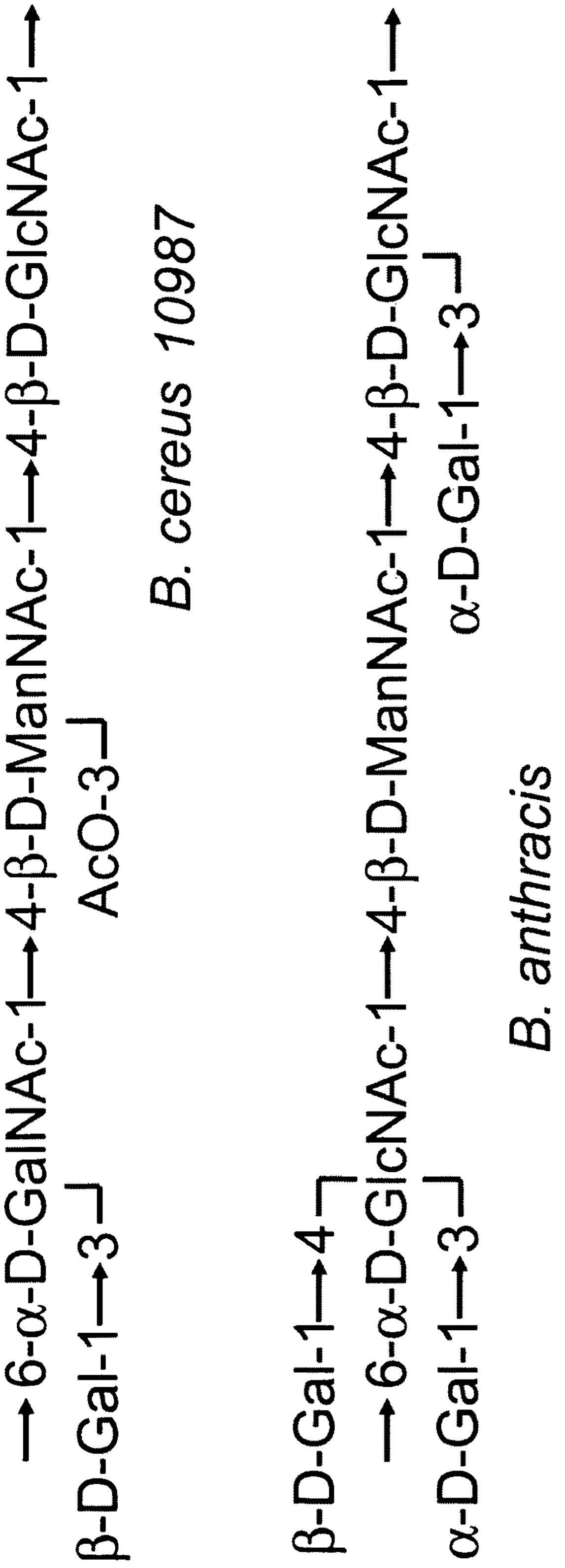
FIG. 15 shows the structure of HF-PS from *B. cereus* 10987 (top) compared with the structure of HF-PS from *B. anthracis* (bottom).

Having established that Sterne $34F_2$ spores are able to induce an anti-carbohydrate antibody response, this example sought to further evaluate which structural motifs of the anthrose moiety are critical for antibody recognition. To this end, the ability of BSA-MI-1 and BSA-MI-conjugates of the three structural analogs 2, 3, and 4 to inhibit the interaction of the antisera with KLH-BrAc-1 was determined (FIG. 14). For these experiments, BSA conjugates were employed in an effort to conserve synthetic material. Microtiter plates were again coated with the KLH-BrAc-1 conjugate and treated with an anti-sera dilution of 1:1600. The importance of the 2"-O-methyl ether of anthrose was established using the BSA-MI-2 conjugate. This conjugate carries trisaccharide analogue 2, which lacks the 2"-O-methyl ether but has an intact N-(3-hydroxy-3-methyl-butyryl) moiety at C-4" of anthrose. As shown in FIG. 14, this conjugate is a potent inhibitor of antibody binding with as low as a 2-fold weight excess eliciting >95% reduction in reporter signal. Compared to the BSA-MI-conjugate carrying the native trisaccharide 1, for which no significant difference in inhibition was observed in the concentration range investigated. These data indicate that the methyl ether is not critical for anti-spore antibody binding. To elucidate the importance of the 3-hydroxy-3-methyl-butyryl moiety of anthrose, conjugates BSA-MI-3 and BSA-MI-4 were prepared. Trisaccharide 3 carries a 3-methyl-butyryl moiety at the C-4", thus only lacking the hydroxyl group of the native C-4-moiety of the anthrose monosaccharide, whereas trisaccharide 4 is N-acetylated at the C-4", thus lacking most of the 3-hydroxy-3-methyl-butyryl moiety. Interestingly, a 2-fold excess of trisaccharide 3 reduced OD by 85% compared to the control. In contrast, a similar concentration of analogue 4 resulted in reduction in OD of only 17%. Very high concentrations of BSA-MI-4 were required to achieve considerable inhibition (a 500-fold excess of BSA-MI-4 resulted in a 50% drop in OD, data not shown). These results indicate that the 4"-(3-methylbutyryl)-moiety is an important structural motif of the authentic saccharide epitope on the surface of *B. anthracis* Sterne spores.

The significance of these observations is two-fold. First, this example demonstrates that, by using anti-live spore antisera and anti-irradiated spore antisera, the anthrose-containing trisaccharide of BclA is antigenic and exposed on the surface of *B. anthracis* Sterne $34F_2$ spores when presented in rabbits. Second, this example located an important antigenic component of this reactivity in the terminal 3-methyl-butyryl structures of the saccharide and confirmed its specificity using synthetic saccharide analogues. These data provide important information for the development of spore-specific reagents for detection and targeting of non-protein structures in *B. anthracis*. These structures may in turn provide a foundation for directing immune responses to spore structures during the early stages of the *B. anthracis* infection process.

Seeberger and co-workers have reported that the anthrax oligosaccharide conjugated to KLH could elicit antibodies that recognize *B. anthracis* spores (Tamborrini et al., 2006, *Angew Chem Int Ed Engl.,* 45(39):6581-2). The data of this example are complementary to these findings in that *B. anthracis* spores elicit anti-carbohydrate antibodies, which may be harnessed for diagnosis. Ongoing studies will demonstrate whether these and additional saccharide structures are present and accessible on the spores from other *B. anthracis* isolates, including the highly virulent *B. anthracis* Ames and other *B. anthracis* cured of virulence plasmids pXO1 and pXO2.

Example 4

Structure of *B. anthracis* Cell Wall Polysaccharide Compared to *B. cereus* Cell Wall Polysaccharide Composition and proton NMR analysis of the HF-PS from the closely related *B. cereus* strain ATCC10987 indicated that its structure was different from that of *B. anthracis*, and also different from the *B. cereus* type strain ATCC 14579 (Example 2 and Choudhury et al., 2006, *J. Biol. Chem.,* 281: 27932-27941). Strain ATCC10987 *B. cereus* contains a plasmid that is similar to pXO1 but lacks the pathogenicity island that encodes for the toxin components. The genome of *B. cereus* ATCC 10987 is 93.7% similar to *B. anthracis*, whereas it is 90.9% similar to *B. cereus* ATCC 14579 (Rasko et al., 2004, *Nucleic Acids Research,* 32:977-988). The structure of the HF-PS from *B. cereus* 10987 has now been completed (See FIG. 15, top structure). The repeating unit of this polysaccharide consists of an aminoglycosyl trisaccharide backbone of →6-α-GalNAc-1→4-β-ManNAc-1→4-β-GlcNAc-1→ in which the GalNAc residue is substituted at position 3 with a β-Gal and the ManNAc residue is O-acetylated at position 3. The data indicate that the repeat oligosaccharide of this polysaccharide, as with *B. cereus* 10987, also consists of a GalNAc-ManNAc-GlcNAc trisaccharide; however, it is substituted with Glc and GlcNAc rather than with Gal and an O-acetyl group.

That closely related members of the *B. cereus* group can differ significantly in the structures of their cell wall polysaccharides is also indicated by results of the glycosyl composition comparisons, shown in Table 7. These results, as indicated by the above structural analysis, clearly support the conclusion that even closely related members of the *B. cereus* group vary in the make-up of their polysaccharide components. Interestingly, the data shown in Table 7 indicate that three *B. cereus* strains, BB102, BB87, and G9241, contain cell wall glycosyl compositions that are quite close to those of *B. anthracis* cell walls. These *B. cereus* strains are also closely related by MLST to *B. anthracis* (Hoffmaster et al., 2006, *J. Clin. Microbiol.,* 44:3352-3360).

TABLE 7

Glycosyl composition of the cell walls from members of the *B. cereus* group relative to their MLST phylogenetic relatedness.
Table 1. Glycosyl composition of the cell walls from members of the *B. cereus* group relative to their MLST phylogenetic relatedness.

| MLST Clade. Lineage | Strain | Sugar composition Man | Glc | Gal | ManNAc | GlcNAc | GalNAc |
|---|---|---|---|---|---|---|---|
| Clade 1 Anthracis | *B. anthracis* Ames | n.d. | 5.3 ± 0.6 | 52 ± 8.7 | 13 ± 3.6 | 29 ± 5.3 | n.d. |
| Clade1 | *B. cereus* B5780 | 1.2 | 66 | 1.1 | 3.0 | 28 | n.d. |
| CereusIII | *B. cereus* BB102 | 0.8 | 4.2 | 55 | 14 | 26 | n.d. |
| Clade 1 | *B. cereus* F666 (ST92) | n.d. | 21 ± 4.2 | 11 ± 4.5 | 14 ± 3.0 | 35 ± 1.8 | 20 ± 4.3 |
| Cereus I | *B. cereus* ATCC 10987 | n.d. | 30 ± 40 | 22 ± 7.0 | 13 ± 4.2 | 18 ± 14 | 17 ± 15 |
| Clade 1 | *B. cereus* G9241 | n.d. | 2.3 | 64 | 8.9 | 25 | n.d. |
| Cereus IV | *B. cereus* BB87 | n.d. | 2.0 | 50 | 18 | 30 | n.d. |
| Clade2 Tolworthi | *B. cereus* ATCC 14579 | n.d. | 26 ± 2.5 | n.d. | 19 ± 2.5 | 40 ± 2.3 | 15 ± 1.3 |
| Clade 2 Kurstaki | *B. thuringiensis* ATCC 33679 | n.d. | 55 | n.d. | 7.2 | 30 | 7.7 |
| Clade 2 Sotto | *B. thuringiensis* ATCC 35646 | n.d. | 20 | n.d. | 15 | 49 | 17 |

[1]The composition of the cell envelopes from *B. anthracis* Pasteur is identical (within experimental error) to that of Ames, while the cell envelope of Sterne variably higher levels of glucose from batch to batch. This glucose is not present in the purified HF-PS obtained from the cell envelopes.

[2]Similarly the cell envelope of *B. cereus* ATCC 10987 contains batch variation in glucose content and glucose is not present in purified HF-PS. All members of Clade 1 are closely related to *B. anthracis.*

In addition, each of these strains causes severe human illness. Strain G9241 is an isolate obtained from a welder in Louisiana in 1994 that contracted severe pneumonia (see (Hoffmaster et al., 2006, *J. Clin. Microbiol.,* 44:3352-3360)), and strains BB87 and BB102 were obtained from two 2003 fatal cases of pneumonia in Texas metal workers from two different locations (see (Hoffmaster et al., 2006, *J. Clin. Microbiol.,* 44:3352-3360)). All of the *B. cereus* strains contained pXO1 genes with G9241 having almost a complete copy, and BB87 being virtually identical in this aspect to G9241 (Hoffmaster et al., 2006, *J. Clin. Microbiol.,* 44:3352-3360). These composition results show that *B. cereus* strains that are closely related to *B. anthracis* can have cell wall carbohydrates that vary from *B. anthracis* and from each other, and that closely related *B. cereus* strains that cause severe human illness (sometimes fatal) have cell wall glycosyl compositions that are very similar to that of *B. anthracis.*

Figure 16:
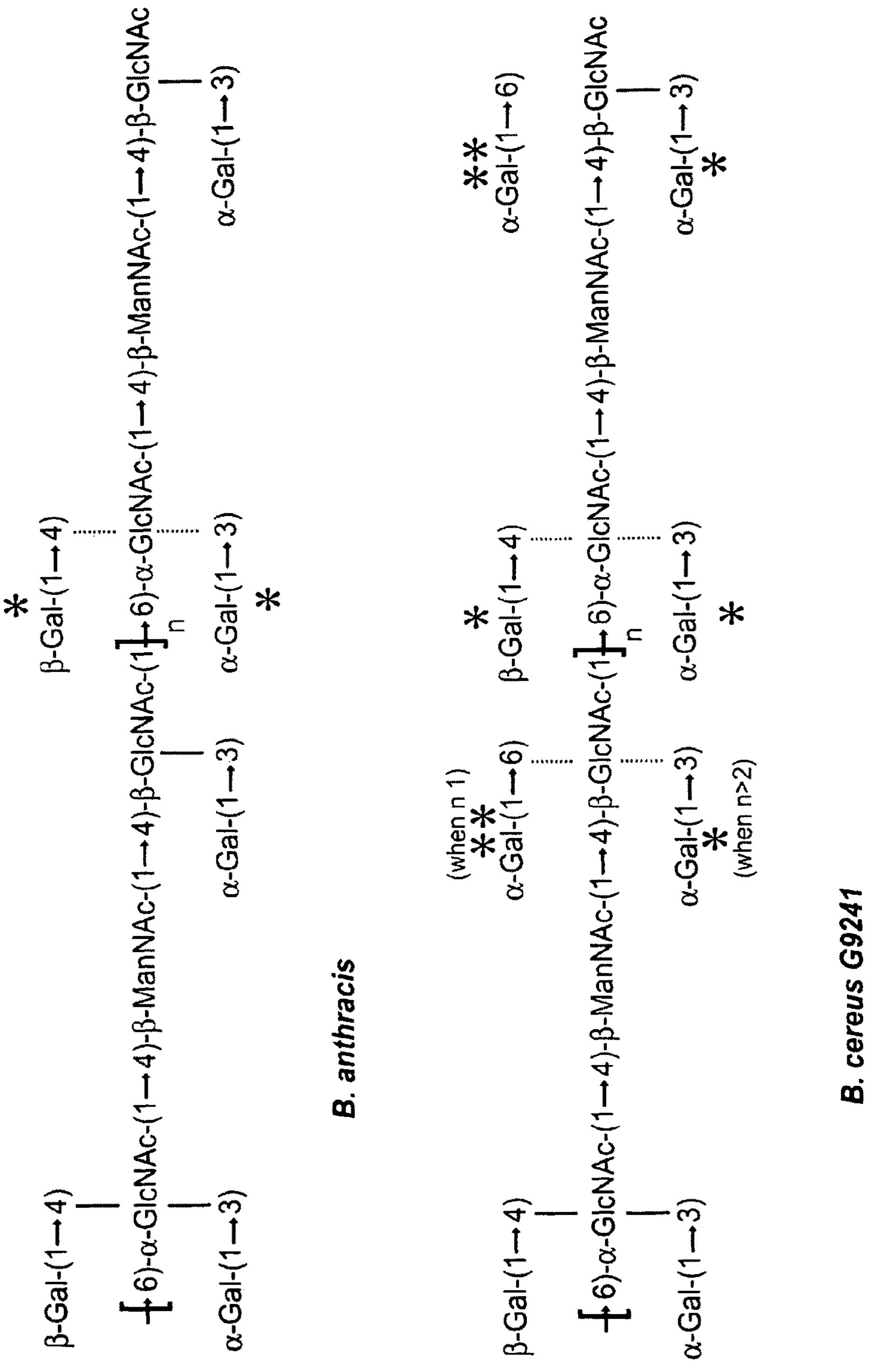
FIG. 16 shows the structure of HF-PS from *B. anthracis* (top) to the proposed structure for the HF-PS from *B. cereus* G9241 (bottom). The Gal residues designated by * indicate positions of heterogeneity, and the Gal residues designated by ** in the *B. cereus* structure indicate additional Gal substitutions for the *B. cereus* HF-PS that are not present in the *B. anthracis* HF-PS. In addition, mass spectrometry results show that that *B. cereus* HF-PS consists of 1-4 repeating units while that of *B. anthracis* consists of 2-6 repeating units.
Figure 17:
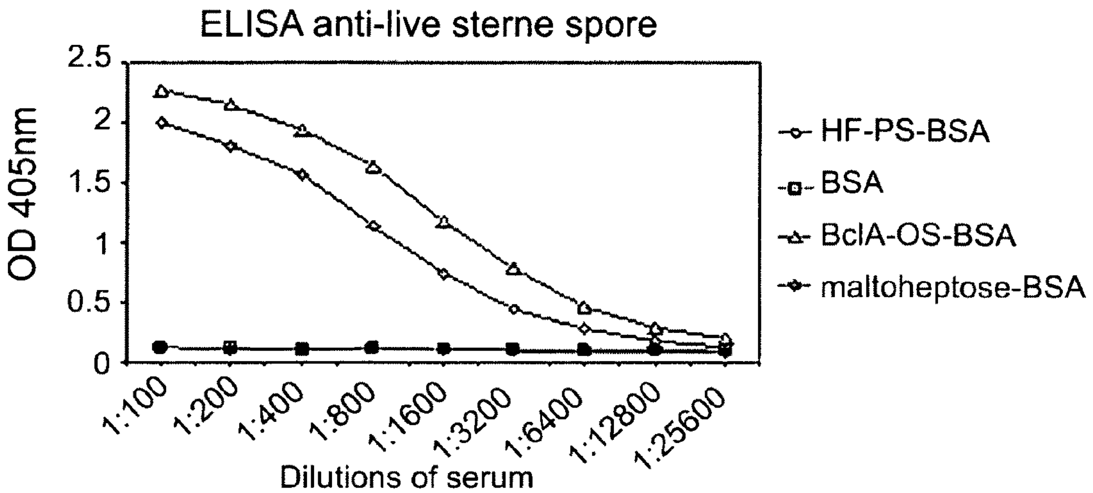
FIGS. 17A and 17B show the interaction of antiserum from rabbits inoculated with live (FIG. 17A) or irradiated (FIG. 17B) *B. anthracis* Sterne spores with the HF-PS-BSA conjugate from *B. anthracis*. The microtiter plates were coated with the conjugates indicated in the insert.
Figure 17:
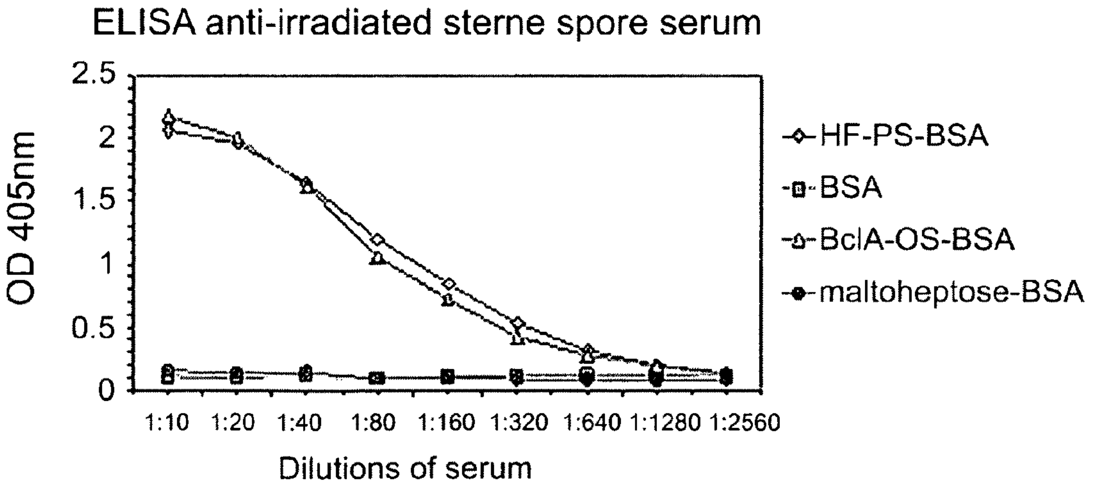

In order to determine the exact structural comparison between the HF-PSs of the *B. cereus* strains that cause severe human illness and that of *B. anthracis*, the structure of the HF-PS from strain G9241 was analyzed by glycosyl linkage analysis, NMR spectroscopy, and mass spectrometry. A comparison of the *B. anthracis* and *B. cereus* G9241 structures is shown in FIG. 16. These results suggest that the G9241 HF-PS contains the same trisaccharide backbone as that from *B. anthracis*, but that it is more extensively substituted by terminal Gal residues, that there is more heterogeneity in this substitution pattern, and that the HF-PS consists of a lower molecular weight distribution of molecules. Thus, unlike *B. cereus* 10987, the G9241 structure is very similar to that of *B. anthracis*, but is still structurally distinct.

This example also shows that the *B. anthracis* HF-PS is immunogenic, indicating that it is also immunochemically species-specific. Rabbits inoculated with purified *B. anthracis* spores produce antiserum that contains antibodies against the HF-PS. Polyclonal antiserum from a rabbit injected with either live or irradiated *B. anthracis* Sterne spores were tested for antibodies that would bind to the HF-PS purified from *B. anthracis*. The HF-PS from *B. anthracis* was conjugated to BSA, and this conjugate was used to coat microtiter plates, 32 μg/well. Control wells were coated with BSA, or with maltoheptaose conjugated to BSA. Wells coated with the chemically synthesized spore BclA-OS-BSA conjugate (Example 3 and Mehta et al., 2006, *Chemistry—A European Journal,* 12:9136-9149) were used as the positive control since it was known that these antiserum contain antibodies to this oligosaccharide (see below, Example 3, and Mehta et al., 2006, *Chemistry—A European Journal,* 12:9136-9149). Dilutions of polyclonal antiserum from rabbits injected with live spores, and from rabbits injected with irradiated spores were measured for their ability to bind the HF-PS-BSA conjugate. Detection was accomplished using a second goat anti-rabbit antibody conjugated to horse radish peroxidase and measuring peroxidase activity. The results show that both the live spore (FIG. 17A) and irradiated spore (FIG. 17B) antiserum contain antibodies that bind to the HF-PS purified from vegetative cells of *B. anthracis*. These results show that the animal's immune system recognizes the HF-PS structure as an antigen and makes antibodies against it. The finding of HF-PS antibodies in serum from rabbits inoculated with irradiated spores indicates that the HF-PS, or a structural component, is present in spore preparations.

Figure 18:
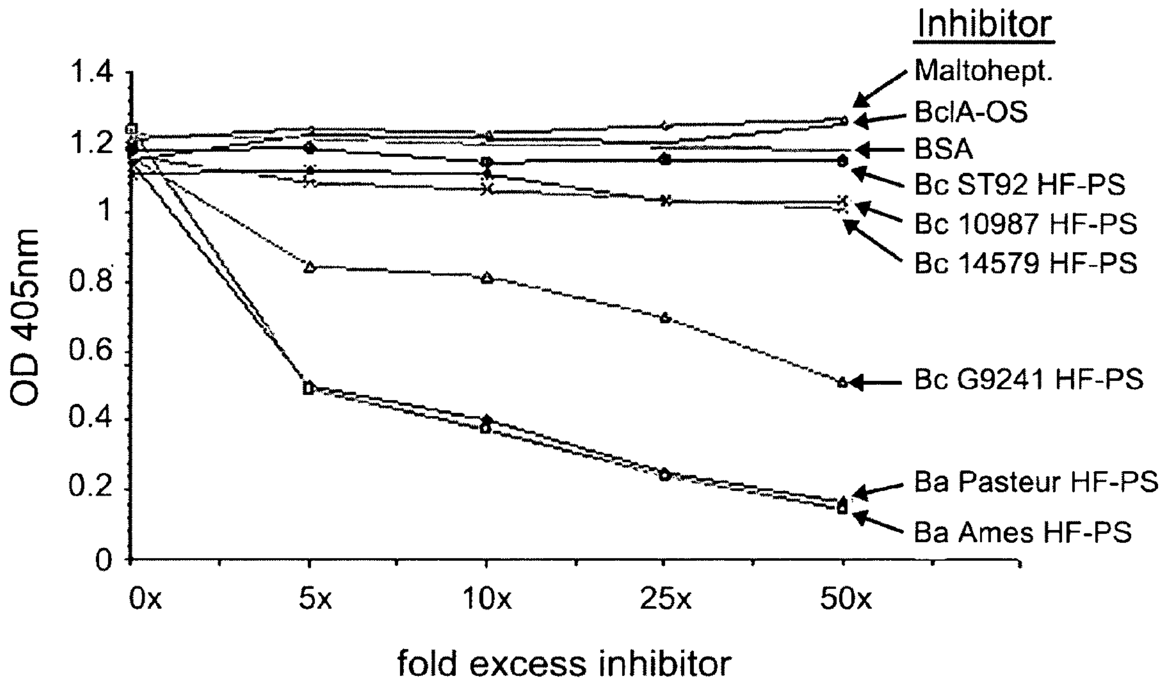
FIG. 18 shows the ability of the indicated polysaccharides to inhibit the binding of live spore antiserum to *B. anthracis* HF-PS-BSA conjugate (coated on the microtiter plate). The "fold excess inhibitor" refers to the ratio of the mass of polysaccharide used to the mass of *B. anthracis* HF-PS-BSA conjugated to each microtiter well (which is 0.32 μg/well).
Figure 19:
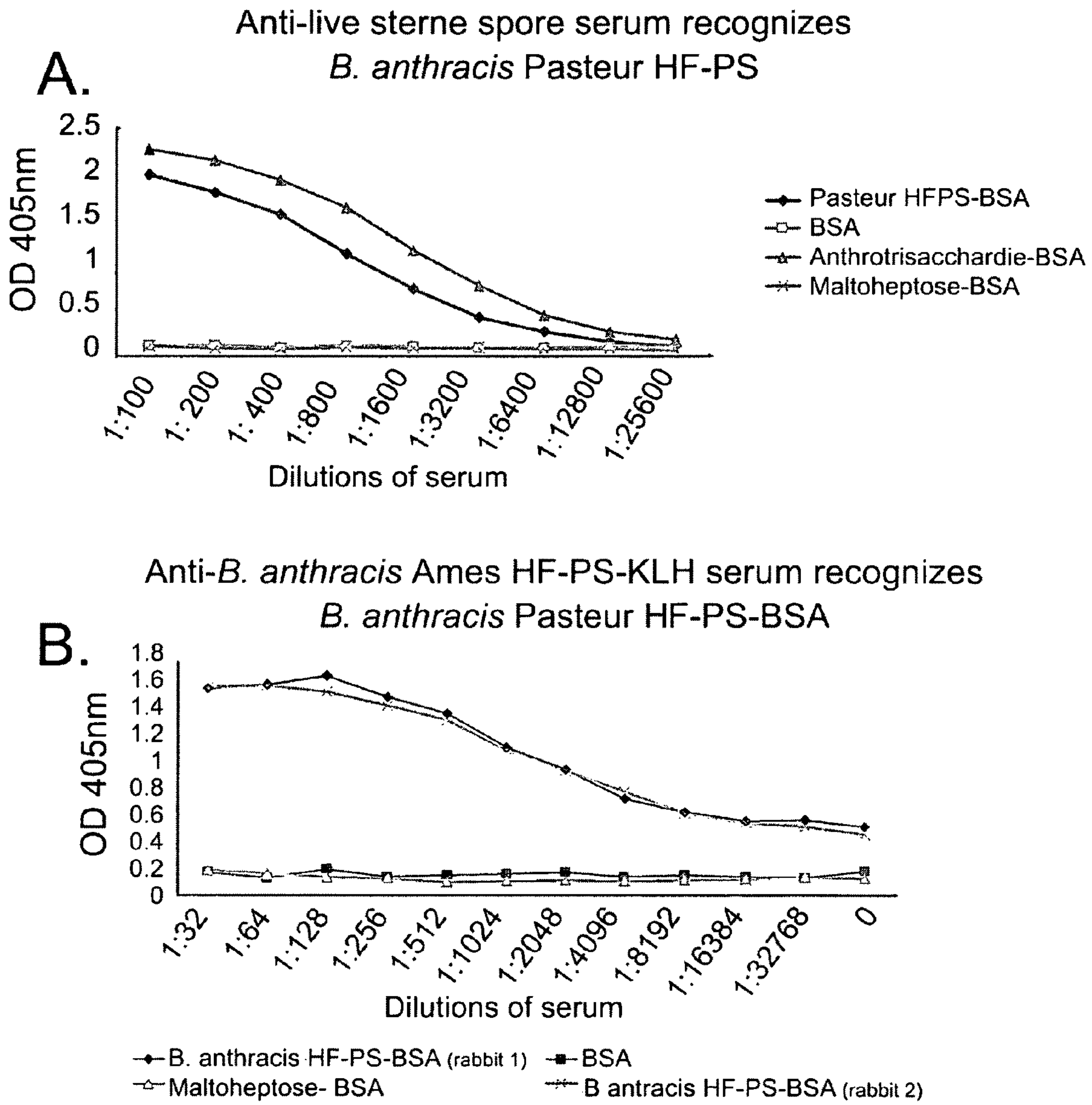
FIGS. 19A and 19B show the reactivity of using an indirect enzyme linked immunosorbent assay (ELISA) where *B. anthracis* HF-PS conjugated to BSA was used to coat the microtiter plate wells.

Next, ELISA-inhibition assays were used to test the varying abilities of polysaccharides from the different *B. anthracis* strains and from various *B. cereus* strains to inhibit binding of the antibodies to the HF-PS-BSA conjugate. In this experiment, a final dilution of rabbit anti-spore serum of 1/400 was used. The ability of this antiserum to bind to *B. anthracis* HF-PS-BSA was competitively inhibited by preincubating the antiserum with varying concentrations of unconjugated HF-PSs from *B. anthracis* strains, *B. cereus* ATCC14579 (the type strain), *B. cereus* ST92, *B. cereus* 10987, and *B. cereus* G9241. *B. cereus* strains ST92, 10987 and G9241 are all closely related to *B. anthracis*. The structures and/or glycosyl compositions are described above (FIGS. 15 and 16, and Table 7). In addition, inhibition by the synthetic BclA-OS (the spore oligosaccharide), and by maltoheptaose was determined. The concentration of each inhibitory polysaccharide was varied from 5- to 50-fold of the mass of the *B. anthracis* Pasteur HF-PS-BSA conjugate coated on the microtiter plates. The results shown in FIG. 18, show that the greatest inhibition occurs with HF-PSs from *B. anthracis* strains. This is expected since, as described above, the structures of the HF-PSs of all the *B. anthracis* strains are identical. There was very little, if any, significant inhibition by *B. cereus* 10987, *B. cereus* ST92 and 14579 HF-PSs. There was also no significant inhibition by the spore BclA-OS or by the negative control maltoheptaose. However, the HF-PS from the pathogenic *B. cereus* G9241 showed some inhibition. These results indicate that the polyclonal antiserum contains antibodies that are specific for the *B. anthracis*-specific HF-PS structure, with some cross-reactivity to the structurally related (see above FIG. 16) HF-PS from the closely related and pathogenic *B. cereus* G9241. The cross-reactivity with the G9241 HF-PS is almost certainly due to the very similar structure of this molecule to that of HF-PS.

In summary, this structural analysis shows that HF-PSs from different *B. anthracis* strains have the same structure, and that HF-PSs vary in structure among members of the *B. cereus* group, even those that are closely related to *B. anthracis*. These data show that *B. cereus* strains (BB87, BB102, and G9241) that are closely related to *B. anthracis* and cause severe human illness (pneumonia) have similar cell wall glycosyl compositions to those of *B. anthracis*; and the HF-PS from G9241 is closely related, but not identical, in structure to that of *B. anthracis*. These data show that *B. anthracis* HF-PS is immunogenic in that animals inoculated with live or dead spores produce antibodies that bind this molecule. The result with dead spores also indicates that the HF-PS structure is present in spore preparations. With regard to the *B. anthracis* HF-PS, HF-PS is immunochemically specific to *B. anthracis* strains since the antibodies in spore antiserum bind the *B. anthracis* molecule but not the HF-PS from closely related strains of *B. cereus*, except for some cross reaction with the structurally related HF-PS from the above pathogenic *B. cereus* G9241. At this time it is not known if there is a correlation between the structure of the HF-PS and the pathogenicity of *B. anthracis* and these *B. cereus* stains that cause human illness. These results strongly support the use of *B. anthracis*-specific HF-PS for diagnostic purposes; e.g. determining if clinical isolates are *B. anthracis*, and for detecting if individuals that are ill with anthrax-like symptoms contain antibodies to the *B. anthracis* HF-PS epitope. The fact that the HF-PS is immunogenic also supports the use of HF-PS-KLH or HF-PS-PA conjugates as protective vaccine antigens. While the HF-PS by itself may not be a powerful enough immunogen to provide protection, experience with other polysaccharides supports the possibility that protein conjugates could be effective protective antigens. In addition a PA conjugate may act as a divalent antigen by stimulating an immune response to both PA and to the HF-PS.

Example 5

The Immune Response to the Secondary Cell Wall Polysaccharide of *Bacillus anthracis* is Specific to these Bacteria As shown in Example 2, the structure of a *B. anthracis* polysaccharide (HF-PS) released from the bacterial cell wall through treatment with hydrofluoric acid has been determined. The structure was *B. anthracis*-specific and identical in all strains investigated (*B. anthracis* Ames, Pasteur and Sterne), but differed from the HF-PS isolated from closely related *B. cereus* strains (*B. cereus* 14579, 10987, F666). To investigate the immunogenicity of the HF-PS's, antisera were raised in rabbits against viable *B. anthracis* Sterne spores and against the *B. anthracis* Ames HF-PS conjugated to KLH. The reactivity of the derived antisera was tested using an indirect enzyme linked immunosorbent assay (ELISA) where *B. anthracis* HF-PS conjugated to BSA was used to coat the microtiter plate wells.

As shown by FIGS. 19A and 19B, both the anti-live sterne spore serum (FIG. 19A) and the anti-*B. anthracis* Ames HF-PS-KLH serum (FIG. 19B) showed specific binding to HF-PS-BSA coated microtiter plate wells. Serum reactivity was significantly reduced only by free unconjugated HF-PS from *B. anthracis*. The HF-PS from pathogenic *B. cereus* G9241 showed some cross reactivity indicating structural similarity to the *B. anthracis* HF-PS and structural investigations have confirmed similarities in the HF-PS's of these strains. BCL-A anthrose tetrasaccharide was the carbohydrate portion of *B. anthracis* spore surface glycoprotein and was used as a positive control. Maltoheptose was used as a negative carbohydrate control. BSA was also used as a negative control. See Examples 2 and 3 for more detail.

Monoclonal antibodies will be made against these HF-PS polysaccharides. The HF-PS carbohydrates of the present invention have use in both diagnostic tolls for the identification of *B. anthracis* and in carbohydrate based vaccines. Structural characterization of HF-PS's from pathogenic *B. cereus* strains will continue.

Example 6

Immunochemical Characterization of the BclA-OS Exosporium Oligosaccharide

Example 3 demonstrated the synthesis of the *B. anthracis* oligosaccharide BclA-OS, three structural analogs, and their protein conjugates Example 3 also showed that rabbits injected with live or dead *B. anthracis* spores produce antibodies against the synthetic BclA-OS structure showing that this structure is immunogenic. And, using synthetic analogs of BclA-OS, Example 3 showed that the immunodominant epitope of this structure is the isovaleryl portion of the BclA-OS glycosyl component known as anthrose (2-O-methyl-4-N-β-hydroxyisovaleryl-4,6-dideoxyglucose).

This example investigates whether there are anti-anthrose antibodies in the sera of vaccinated (AVA, BioThrax®, BioPort, Corp, Lansing Mich.) or non-vaccinated nonhuman primates (NHP, rhesus macaques) that survived inhalation anthrax. Six vaccinated and 4 four naïve animals were examined. The AVA-vaccinated and unvaccinated rhesus macaques were challenged with an aerosol of *B. anthracis* Ames spores, and at various times after the challenge the sera was examined for the presence of anti-anthrose antibodies using flat bottom 96-well microtiter plates coated with a KLH-conjugate of the synthetic anthrose trisaccharide (Structure 1 of FIG. 10) (KLH-A-3). The specificity of the binding was measured by the ability of the unconjugated anthrose-trisaccharide to inhibit the binding of antibodies. The binding and inhibition (ELISA) assay procedures were performed as described in Example 3 (see, also, Mehta et al., 2006, *Chemistry—A European Journal,* 12:9136-9149. The sera were drawn from individual nonhuman primates when they arrived at the facility (day 0), and 14 days post-challenge with *B. anthracis* Ames spores (day 14). In addition, pre-challenge sera drawn on week 30 from those animals receiving a full course of injections of the AVA was used. Pre-challenge sera for the unvaccinated animals were collected in week 50 or in week 128.

This example also studied the anti-anthrose and anti-PA IgG responses in post-infection sera from naive and AVA-vaccinated rhesus macaques who had survived exposure to spores of *B. anthracis* Ames were evaluated.

Aerosol challenge of nonhuman primates. Rhesus macaques were anesthetized prior to aerosol challenge with 200-400 LD50 equivalents of *B. anthracis* Ames strain. The animals were carefully monitored for clinical signs and symptoms.

Anti-PA ELISA. Quantitative measurement of anti-PA IgG was performed as previously described by Quinn et al. (Quinn et al., 2002, *Emerg Infect Dis* 8:1103-10).

Anti-anthrose ELISA. To specifically detect anti-anthrose antibodies in the sera, we coated flat-bottom 96-well microtiter dishes with the anthrose trisaccharide conjugated to the carrier protein KLH at a concentration of 0.5 μg/ml coating buffer. Control wells were coated with KLH (0.5 μg/ml). Serial dilutions of sera were added and an anti-rhesus IgG labeled with HRP was employed as a secondary antibody for colorimetric detection. There was no binding detected in wells coated with the carrier protein KLH by itself.

Figure 24:
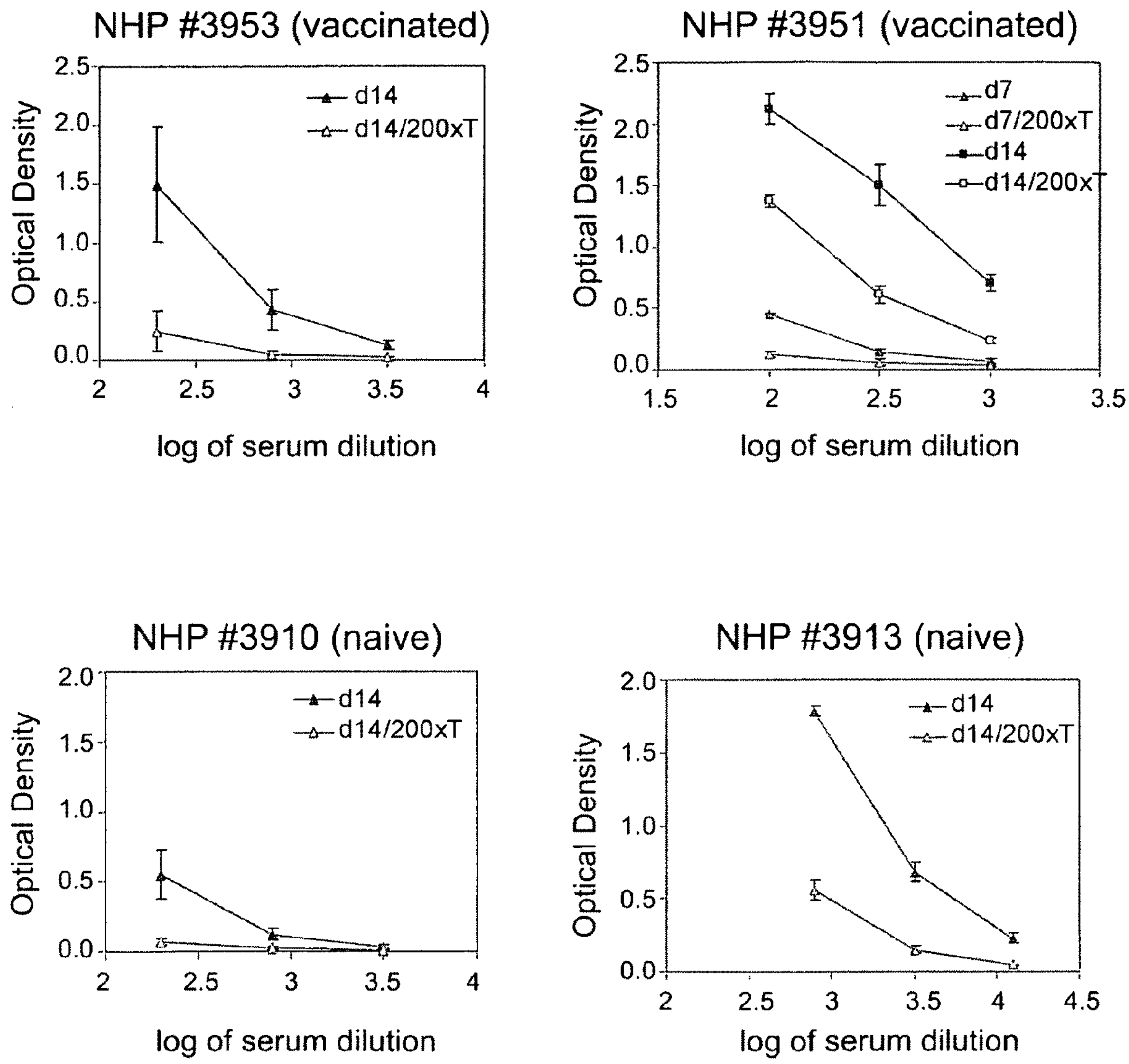
FIG. 24 shows the ability of unconjugated anthrose trisaccharide (Structure 1, FIG. 10) to inhibit the binding of sera from four representative individual rhesus macaques to the KLH-conjugate of the anthrose trisaccharide.

Competitive inhibition ELISA. The specificity of the interaction of the antisera with the anthrose trisaccharide conjugated to KLH was tested by adding a mixture of serum and free anthrose trisaccharide. A decrease in optical density (OD) as compared to wells to which only serum was added indicated that the competing free trisaccharide at a 200-fold weight excess (200×T) reduced the binding interaction between anti-anthrose IgG and immobilized KLH-conjugated anthrose trisaccharide. Assays were run in triplicate. Error bars indicate +/− one standard deviation (FIG. 24).

Figure 22:
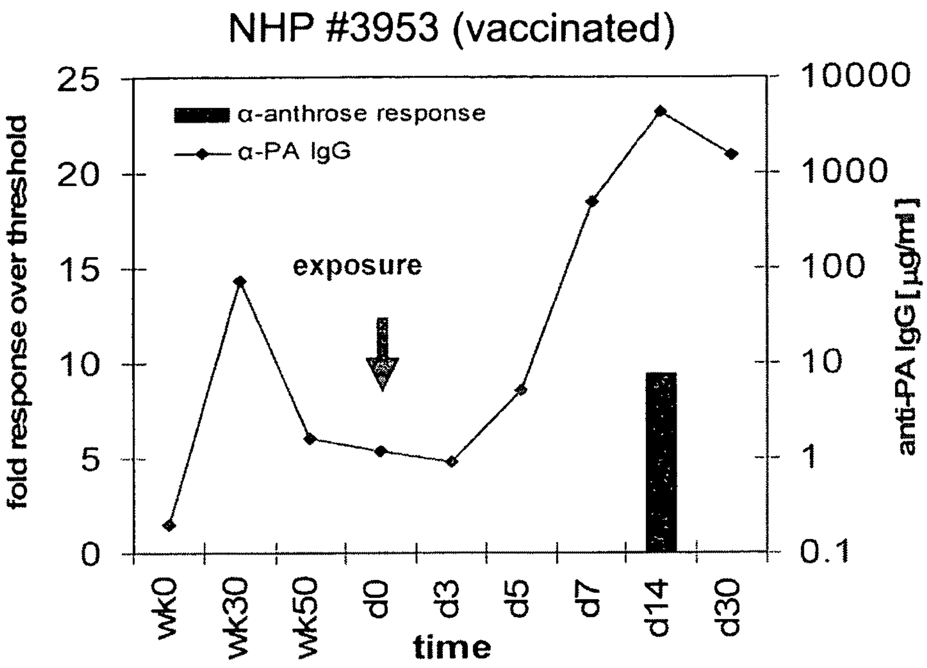
FIG. 22 shows anti-anthrose (structure 1 of FIG. 10) and anti-PA IgG responses of two representative AVA-vaccinated individual rhesus macaques. Animals were vaccinated at weeks 0, 4, and 26. Exposure to aerosols of 200-400 $LD_{50}$ equivalents of *B. anthracis* Ames took place at day 0, as indicated by the arrow.
Figure 22:
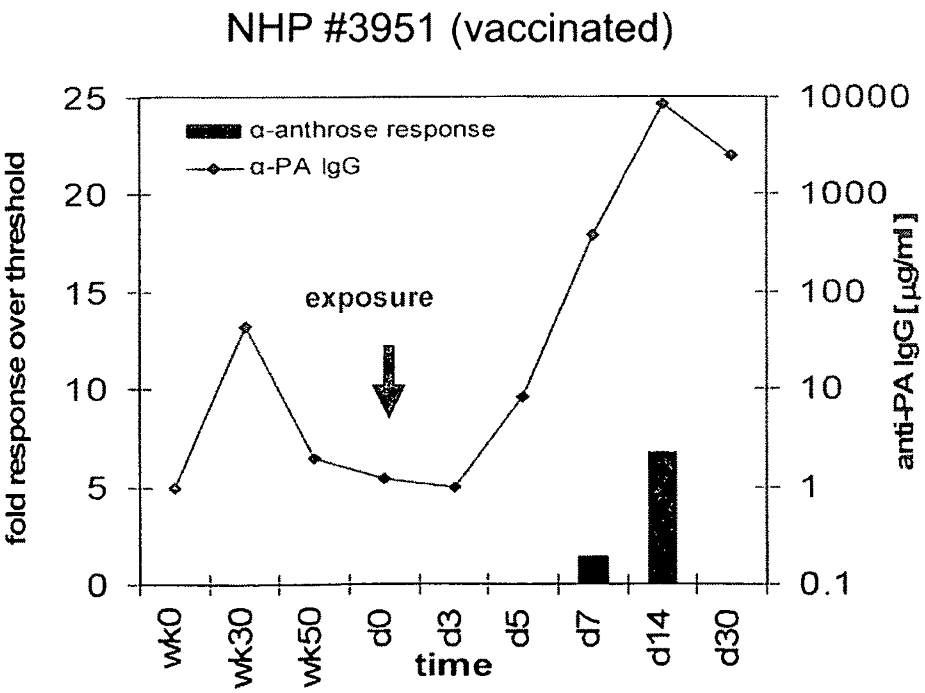
Figure 23:
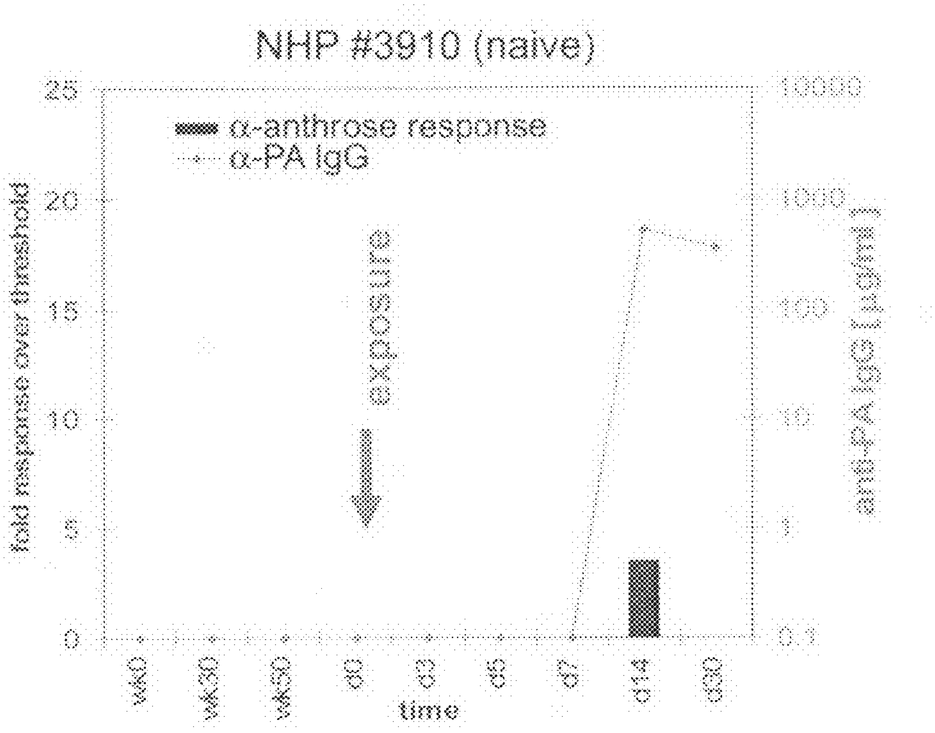
FIG. 23 shows anti-anthrose (structure 1 of FIG. 10) and anti-PA IgG responses of two representative naïve individual rhesus macaques.
Figure 23:
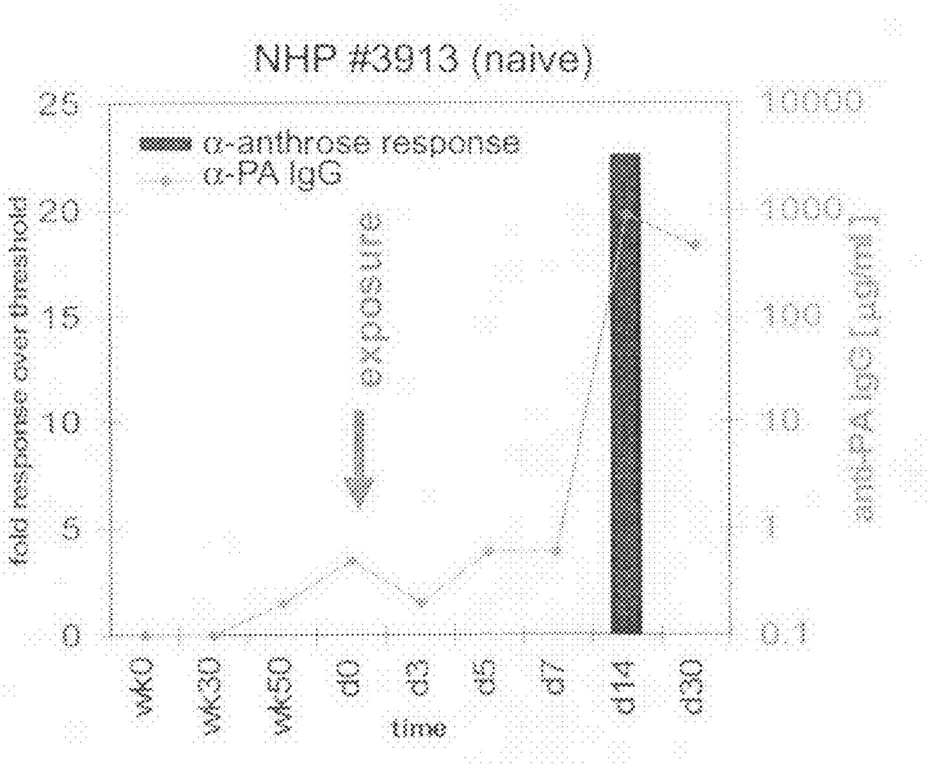

Threshold determination for the anti-anthrose response. A quantitative ELISA to measure the anti-anthrose IgG in nonhuman primate sera is not yet available. We decided to express the anti-anthrose IgG response as a fold increase over a threshold (FIGS. 22 and 23). The threshold value was determined by measuring the binding to anthrose trisaccharide conjugated to KLH for baseline serum samples of 113 naive rhesus macaques. Serum was drawn as the animals arrived at the facility. A 1/100 dilution of the baseline serum of each animal was tested twice and the mean OD for the two measurements was determined. For the 113 mean values average and standard deviation were calculated. The threshold was set by adding one standard deviation to the average.

Figure 20:
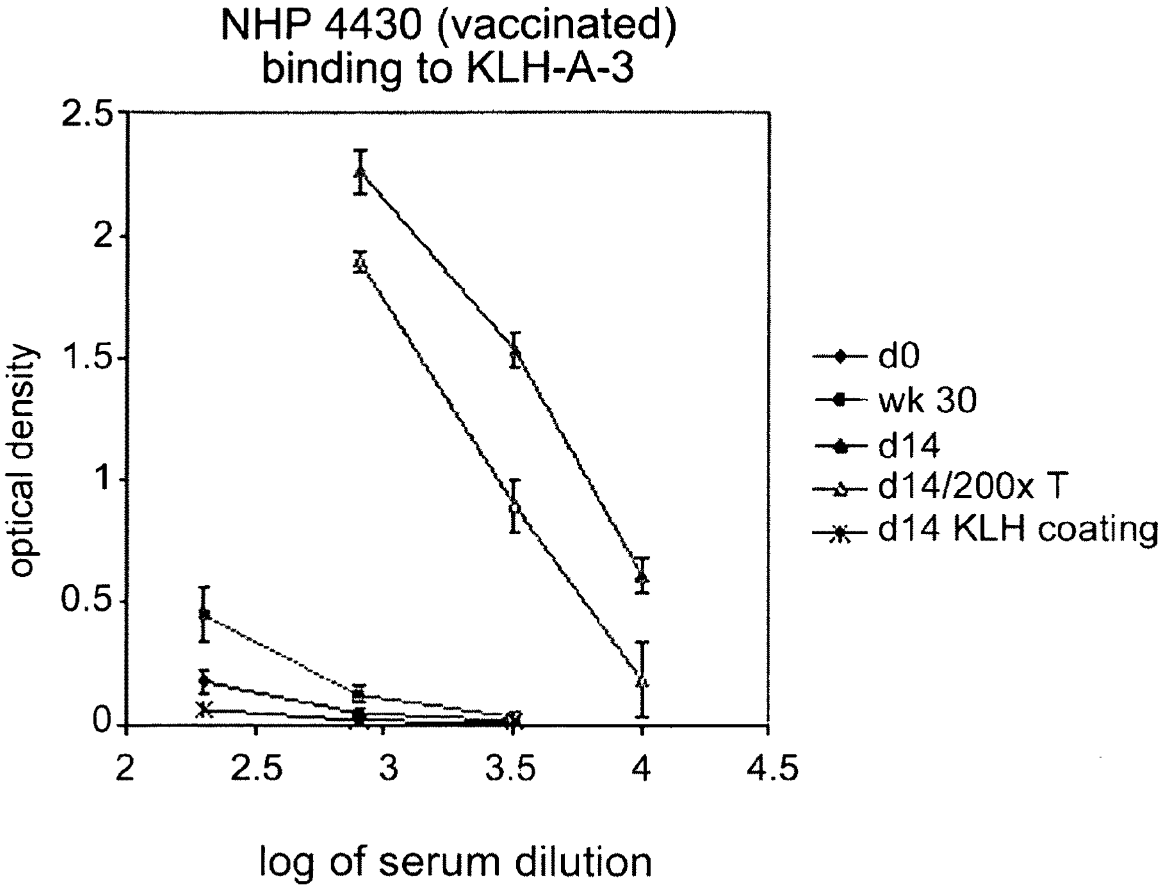
FIG. 20 shows binding of non-human primate (NHP) serum from an AVA vaccinated Rhesus macaque (NHP 4430) to the KLH-conjugated synthetic anthrose trisaccharide (structure 1 of FIG. 10) "KLH-A-3." "d0" represents serum from day 0 of challenge with *B. anthracis* Ames spores; "d14" represents serum from day 14 after challenge; "wk30" represents prechallenge serum from fully AVA vaccinated animal; "d14/200×T" represents inhibition of binding to post-challenge serum using a 200 fold concentration of free anthrose trisaccharide; and "d14KLH coating" represents binding to wells coated with KLH only.

FIG. 20 shows representative results for one of the vaccinated individuals. The assay was run in triplicate and error bars indicate +/− standard deviation. Binding of IgG from the post-challenge serum (day 14) to the KLH-A-3 plate coating was significantly higher than for the two pre-challenge time points (day 0, week 30). There was no binding detected in wells coated with the carrier protein KLH by itself. At all dilutions tested for the post-challenge serum (day 14), the addition of a 200-fold weight excess of the free trisaccharide inhibited binding to the KLH-A-3 plate coating which indicates that binding was specific for the anthrose trisaccharide portion of the conjugate. This result shows that aerosol exposure to *B. anthracis* Ames spores results in the production a quite large concentration of anti-anthrose antibodies. FIG. 20 also shows that there were lower concentrations of anti-anthrose antibodies in the day 0 serum as well as in the week 30 pre-challenge serum. Free trisaccharide also inhibited this binding. These results indicate that vaccination with AVA produces a slight immune response to the anthrose trisaccharide.

Figure 21:
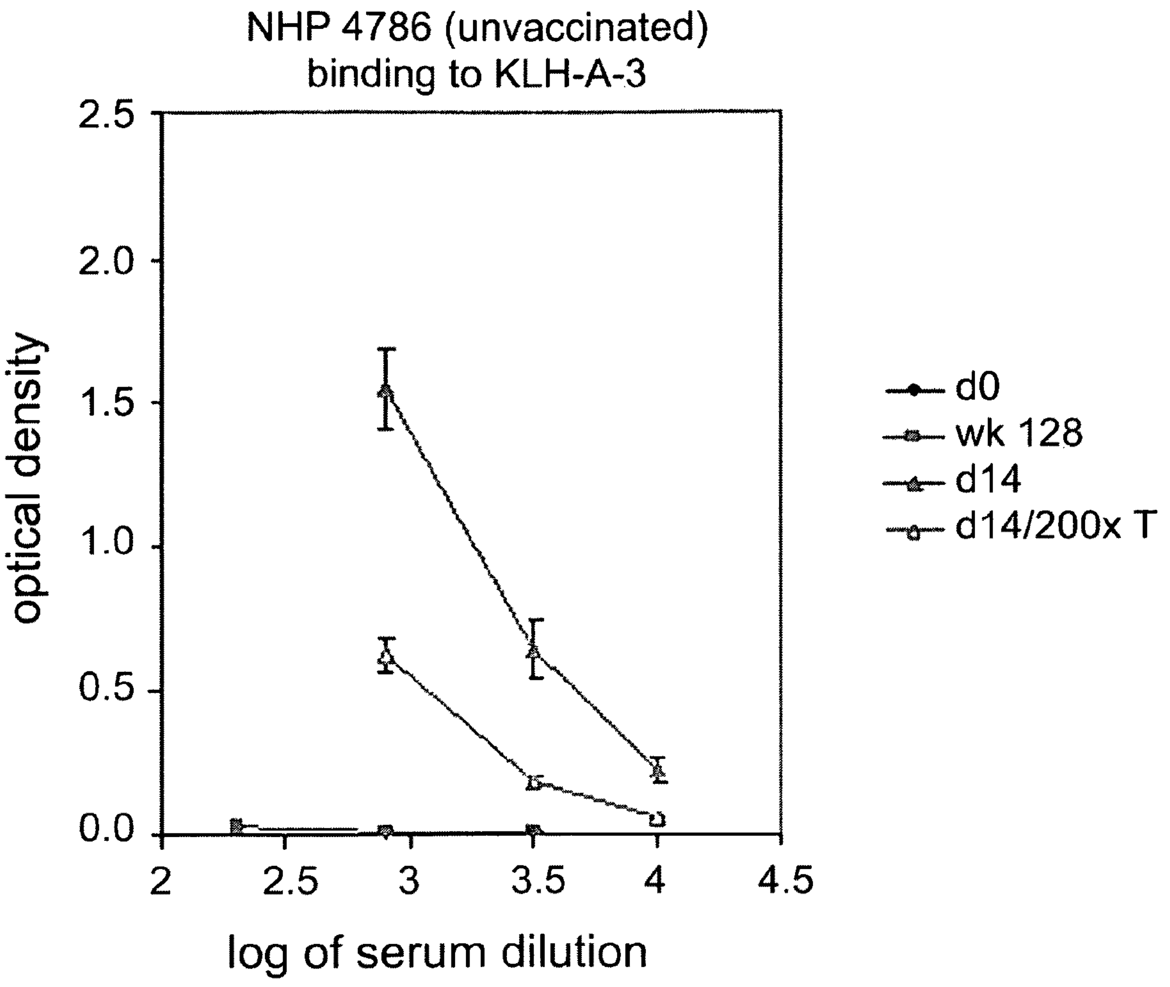
FIG. 21 shows binding of NHP serum from an unvaccinated Rhesus macaque (NHP 4786) to the KLH-conjugated synthetic anthrose trisaccharide (KLH-A-3). "d0" represents serum from day 0 of challenge with *B. anthracis* Ames spores; "d14" represents serum from day 14 after challenge; "wk128" represents prechallenge serum from the unvaccinated animal; and "d14/200×T" represents inhibition of binding to post-challenge serum using a 200 fold concentration of free anthrose trisaccharide.

FIG. 21 illustrates representative results for one of the unvaccinated nonhuman primates. No binding was detected for the pre-exposure time points (day 0, week 128) or the control wells which were coated with the carrier protein KLH alone. There was, however, significant binding for the post-exposure serum samples (day 14). Binding could be specifically inhibited by addition of a 200-fold weight excess of the free trisaccharide.

These results show that nonhuman primates that inhale aerosolized *B. anthracis* Ames spores mount an immune response that results in anti-anthrose antibodies. These results show that prior to inhalation of *B. anthracis* spores, vaccination with AVA produces a low level anti-anthrose immune response. These results also show that animals surviving inhalation anthrax may mount a specific antibody response to the anthrose oligosaccharide and support our conclusion that the BclA-OS structure is an antigen that has potential both as a marker of asymptomatic anthrax and as a tool in determining exposure to *B. anthracis* spores.

Further, this example evaluated by enzyme linked immunosorbent assay (ELISA) the anti-anthrose and anti-protective antigen (PA) IgG responses in post-infection sera from four naïve and six vaccinated rhesus macaques that had survived inhalation anthrax. Vaccinated animals received three intramuscular doses of anthrax vaccine adsorbed (AVA, BioThrax®, BioPort Corp, Lansing Mich.) at weeks 0, 4 and 26. Animals were exposed to aerosols of 200-400 LD50 equivalents of *B. anthracis* Ames strain at various time points after vaccination. Using a chemically synthesized anthrose trisaccharide conjugated to keyhole limpet hemocyanin (KLH) serum antibody responses at day 0 (baseline) and 14 days post-challenge were compared. Three of four naïve animals and six of six vaccinated animals mounted a measurable and specific antibody response to the synthetic oligosaccharide. All ten animals developed a post-challenge anti-PA IgG response indicating that they had been infected and recovered. None of the ten animals became moribund. Thus, animals surviving inhalation anthrax may mount a specific antibody response to the anthrose oligosaccharide and propose that this antigen has potential both as a marker of asymptomatic anthrax and as a tool in determining exposure to *B. anthracis* spores. Thus, vaccinated as well as naïve animals surviving inhalation anthrax mounted a specific antibody response to the anthrose oligosaccharide. The anti-anthrose response as measured by ELISA was specifically inhibited by addition of a 200-fold excess of the synthetic, anthrose-containing trisaccharide to the microtiter wells (FIG. 24). All animals, vaccinated (FIG. 22) as well as naïve (FIG. 23), were infected after exposure to *B. anthracis* Ames. They were not moribund and recovered from the infection. In the case of the vaccinated animals, the anti-PA IgG titers indicate an anamnestic response after spore exposure. The data indicate that while in vaccinated animals (FIG. 22) there was a measurable anti-PA response following the third injection of AVA in week 26, the anti-anthrose response was not triggered by the AVA but by exposure to spores of *B. anthracis* Ames. Thus, the anthrose antigen has potential as a marker of asymptomatic anthrax and as a tool for determining exposure to *B. anthracis* spores.

Example 7

The Evaluation of Spore Carbohydrate Antigens as Markers of Exposure and Infection by Aerosolized *Bacillus anthracis*

In the event of a bioterrorism *Bacillus anthracis* spore release, the first-line response will be administration of antibiotics to 'at risk' individuals as defined by the exposure zone. Defining the exposure zone however, remains difficult due to the potential for widespread dissemination of *B. anthracis* spores and the reliance of current diagnostics on either infection (culture isolation, immunohistochemistry and PCR) or seroconversion to anti-toxin antibody responses. By virtue of being a host systemic response, serologic responses have an important role in diagnosis particularly as they may be elicited by exposure to only low and transient levels of antigen. Where spore outgrowth occurs prior to onset of antibiotic activity it may increase the antigen levels presented to the host immune system thus increasing the potential for greater serological diagnostic sensitivity. Host responses to vegetative cell and toxin antigens are also confirmatory for infection versus exposure.

Nonetheless, a limitation of serologic responses to *B. anthracis* vegetative cell and or toxin antigens still require some level of spore outgrowth and toxin production, both of which may be limited by antibiotic intervention. In a recent study of immunological responses to *B. anthracis* it was reported that less than 40% of confirmed or high exposure risk individuals mounted immune responses to anthrax toxin and, where measurable, these responses were of low magnitude (Doolan et al., 2007, *J Infect Dis;* 195(2): 174-84). This example will show that immune responses to *B. anthracis* spore antigens are independent of germination and outgrowth and are therefore attractive candidates as markers of exposure and asymptomatic or aborted anthrax.

As discussed in more detail in Example 3, the *B. anthracis* Sterne spore surface carbohydrate 'anthrose' is a specific antigenic determinant of the *B. anthracis* Sterne spore, this antigen is presented to the immune system of rabbits receiving the anthrax live-spore vaccine, synthetic trisaccharide analogues of the oligosaccharide retain the antigenic structure and a *B. anthracis* specific antigenic region is localized to defined terminal groups of the oligosaccharide (see, also, Mehta et al., 2006, *Chemistry;* 12(36):9136-9149). In addition, as shown in Example 6, naïve and anthrax vaccine adsorbed (AVA) vaccinated rhesus macaques that have survived aerosol challenge with *B. anthracis* Ames also mount an immune response to the anthrose oligosaccharide.

This example will provide a serological demonstration that spore surface carbohydrates can be used as markers of *B. anthracis* exposure and infection. This example will complete mouse infection studies and obtain rabbit and nonhuman primate serum from post-exposure prophylaxis studies, respectively.

In vitro diagnostic assays have a critical role in defining the medical needs and expediting the appropriate prophylaxis of an exposed population following a bioterrorism (BT) event. In a BT event of unknown etiology or agent, two categories of diagnostic tests will have high priority; one, broad spectrum tests that detect onset of uncharacterized disease/infection in the exposed population and, two, agent specific diagnostics of high positive predictive value (PPV, 'rule in') and negative predictive value (NPV, 'rule out') for specific diseases in symptomatic and asymptomatic persons. These assays will be applied in conjunction to determine non-exposed, exposed and infected individuals and to triage the cohorts to the appropriate care for the BT agent.

This example will build on Examples 1-6 and demonstrate the use of *B. anthracis* spore carbohydrate antigens as markers of asymptomatic anthrax and thus as valuable tools in defining exposure zones and effective triaging of exposed individuals in an anthrax BT event. The mouse infection studies will also provide data on the potential of *B. anthracis* carbohydrate antigens as vaccine candidates.

With this example sera will be screened from an extended set of vaccinated and naïve rhesus macaques that have survived *B. anthracis* aerosol challenge for specific reactivity to the *B. anthracis* 'anthrose' oligosaccharide. A minimum oligosaccharide epitope (domain reduction) that is specifically recognized by rabbit anti-*B. anthracis* spore antiserum will be determined. It will be determined if 'Anthrose' seroreactivity is AVA mediated. It will also be determined whether protein conjugates of candidate *B. anthracis* spore and vegetative cell carbohydrate antigens have protective potential in a mouse model of anthrax. This example will also screen sera from studies on post-exposure prophylaxis in rabbits and non-human primates for specific reactivity to the *B. anthracis* 'Anthrose' oligosaccharide.

This example will synthesize and characterize the di- and monosaccharides containing the antigenic terminal 4"-(3-methylbutyryl)-moiety; prepare carrier protein conjugates of each of the domain reduction oligosaccharide moieties; evaluate sero-reactivity of oligosaccharide conjugates to rabbit anti-live spore antisera; evaluate sero-reactivity of oligosaccharide conjugates to rhesus macaque post-infection; evaluate antibody responses in rabbit serum from other collaborative studies on post-exposure prophylaxis for anthrax; and determine the potential for spore and cell wall carbohydrate conjugate vaccines to elicit specific antibody responses and to protect mice against *B. anthracis* aerosol challenge. Carbohydrates will be conjugated to Keyhole Limit Hemocyanin (KLH) and anthrax toxin protective antigen (PA) as carrier proteins.

Example 8

Secondary Cell Wall Polysaccharide Structure from *Bacillus anthracis* and Pathogenic *Bacillus cereus* are Closely Related

*Bacillus anthracis* (Ba), the causative agent of the disease anthrax is covered by a S-layer protein that is anchored to the cell-wall through a secondary cell-wall polysaccharide (Mesnage et al., 2000, *EMBO J;* 19:4473-4484). Example 2 presented the structure of the secondary cell-wall polysaccharide (HF-PS) that is unique to all Ba strains studied (see, also Choudhury et al., 2006, *JBC;* 281:27932-41) and differs from some non-pathogenic *B. cereus* (Bc) strains. This example expands the investigation to include HF-PS from recently isolated pathogenic Bc strains (BB-87, BB-102 and G-9241) which cause fatal pneumonia in humans. Interestingly, HF-PS isolated from these pathogenic Bc strains share the same amino-sugar backbone [→6)-α-D-GlcNAc-(1→4)-β-D-ManNAc-(1→4)-β-D-GlcNAc-(1→] as found in Ba. 2D NMR and mass spectrometric data along with composition and linkage of constituent sugar residues showed subtle differences in structures, with the HF-PS of the pathogenic Bc strains having more galactosyl residues attached to several positions of the amino-sugar back-bone in comparison to that of HF-PS from Ba strains. The immunochemical data with the HF-PS from different Bc strains also showed cross-reactivity with antiserum raised against Ba spores and HF-PS. Hence the HF-PS can be used as both a immunodiagnostic tool for the detection and differentiation of several pathogenic bacilli and as a vaccine component.

The composition analysis of HF-PS from different Bc strains in comparison to the Ba Ames strain is shown in Table 8. Three of the Bc strains (BB87, BB102 and G9241) showed very similar compositions to that of Ba Ames HF-PS with Gal, GlcNAc and ManNAc as the major component. However, HF-PS from Bc 10987 has GalNAc which is not found in the other Ba or Bc HF-PSs. The variable amounts of Glc were not the constituent of the HF-PS studied in above strains. The linkage analysis of purified HF-PS from Ba-Ames, showed the presence of terminal Gal, 3,4-linked GlcNAc, 3,4,6-linked GlcNAc and 4-linked ManNAc, however BB87, BB102 and G9241 showed the presence of same linkages along with higher amount of 3,4,6-linked GlcNAc and 3,4-linked ManNAc. Variation in the ratio of differently linked amino sugars indicated more heterogeneity in the HF-PS from different Bc strains studied.

Figure 25:
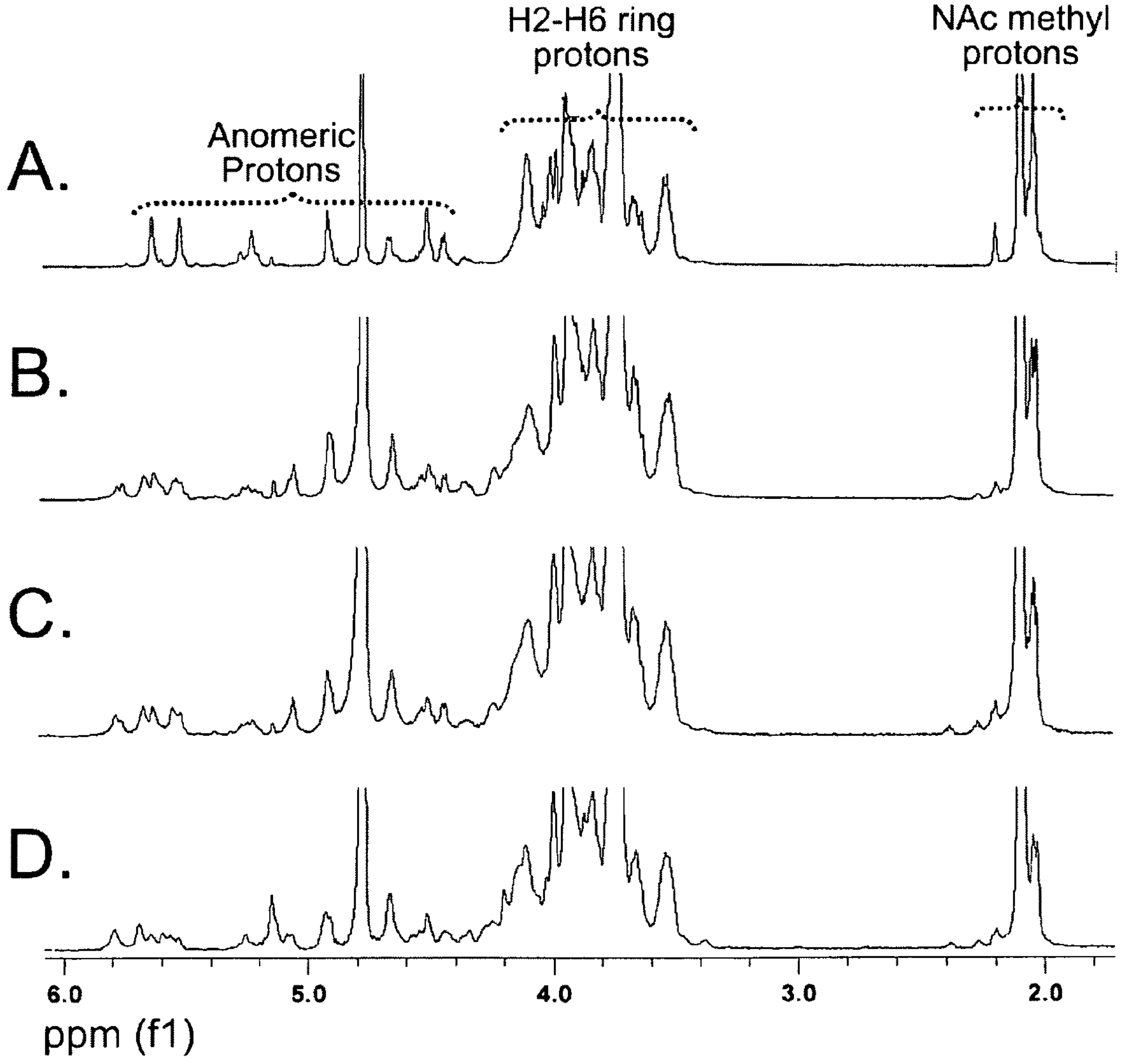
FIG. 25 presents $^{1}H$ NMR of HF-PS from Ba-Ames (A); Bc-G9241 (B); Bc-BB87 (C) and Bc-BB102 (D). One to two milligrams (mg) of each sample was exchanged three times with 99.9% $D_2O$ and finally dissolved in 0.6 ml of 100% $D_2O$ and taken in NMR-tube. All spectra were acquired at 25° C.
Figure 26:
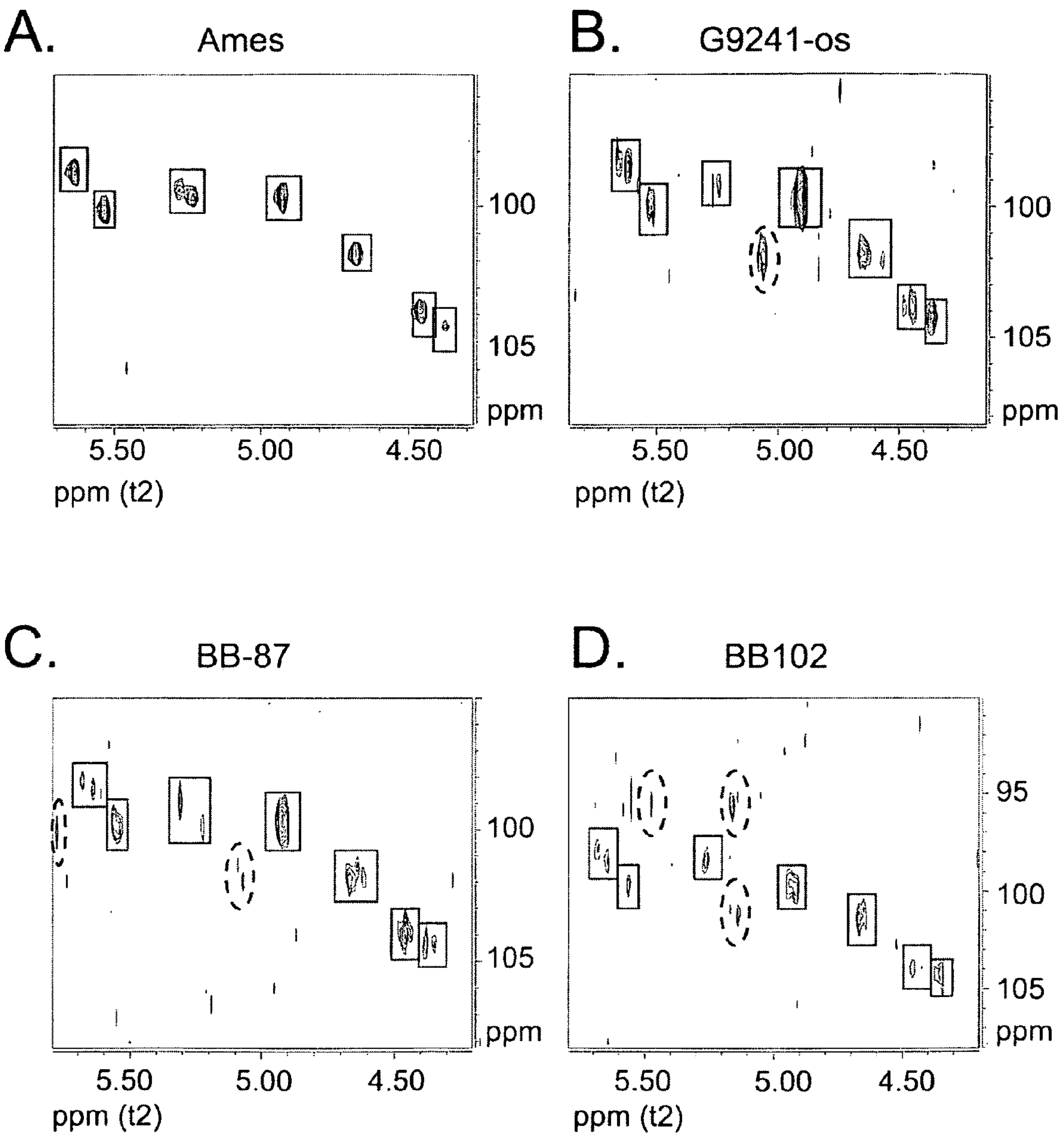
FIGS. 26A-26D present $^{1}H$-$^{13}C$ HSQC-NMR spectra showing the anomeric regions of HF-PS from Ba-Ames and several Bc strains.
Figure 27:
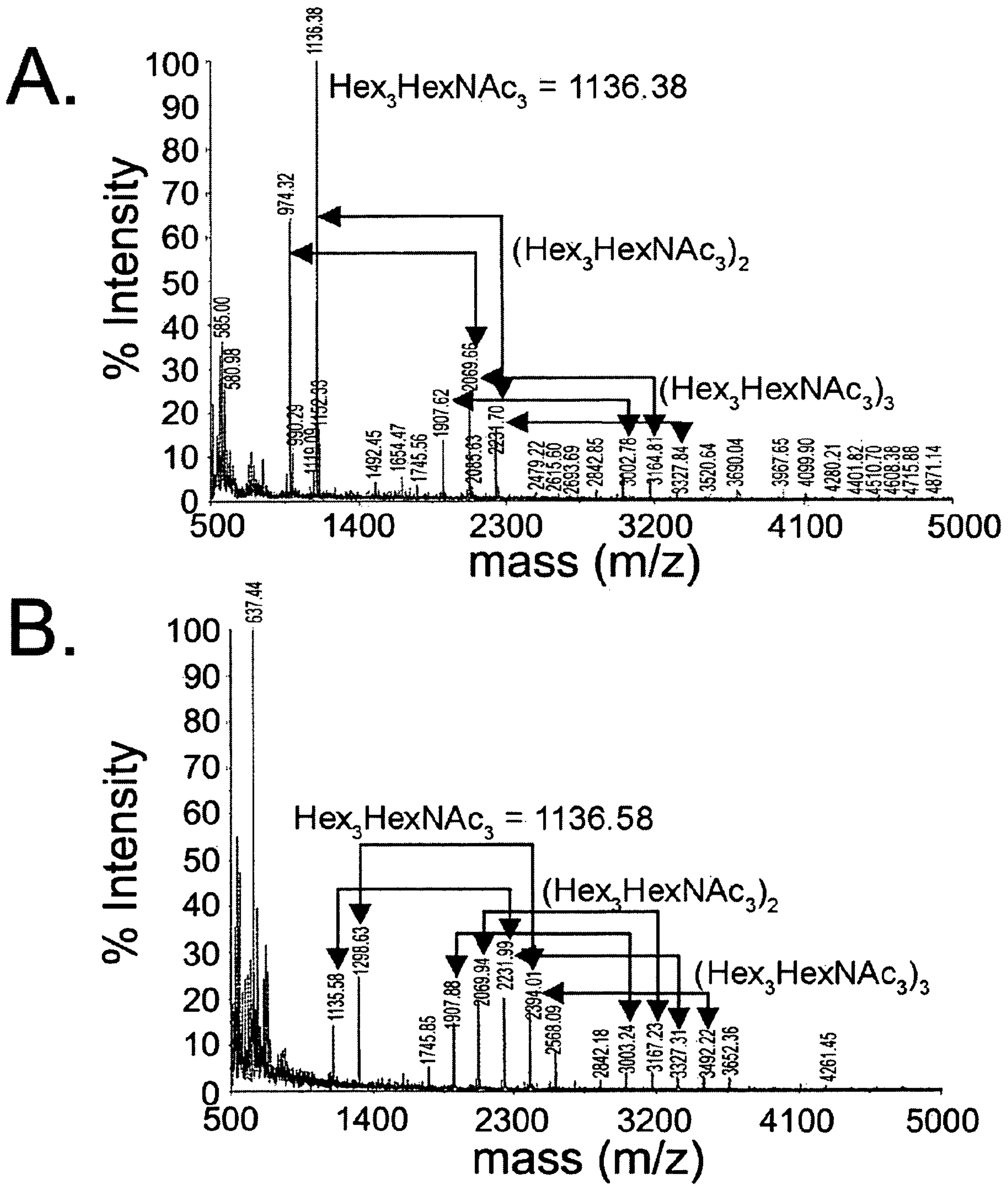
FIGS. 27A-27D present MALDI-TOF mass spectra of HF-PS of Ba-Ames and several Bc strains.
Figure 27:
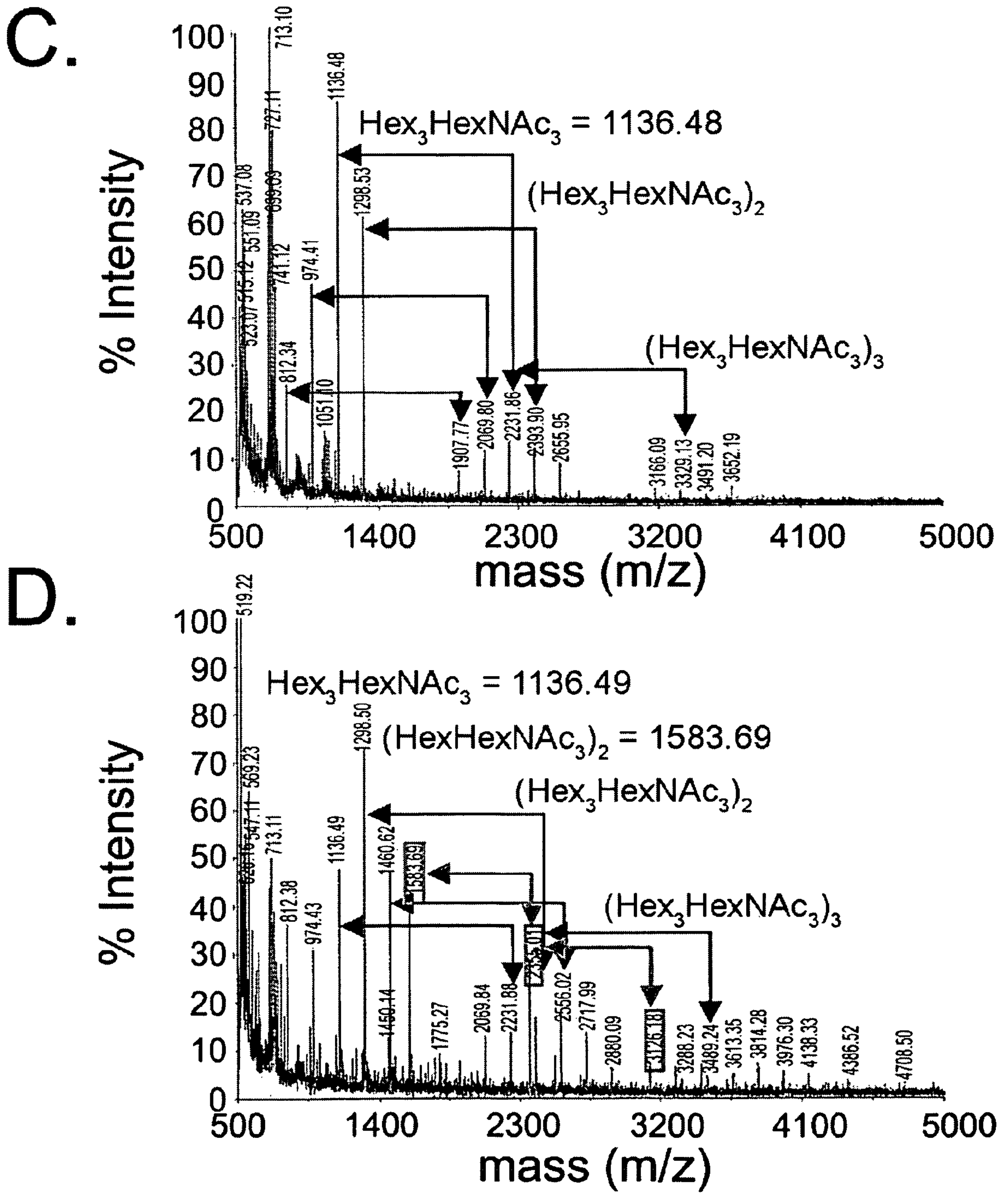

The 1H-NMR of HF-PS from Ba (Ames), Bc (BB87, BB102 and G9241) showed partial similarities in the anomeric, non-anomeric ring protons and N-Acetyl methyl protons (FIG. 25). However there are multiple signals lying between 5.4 to 5.8 ppm for all the Bc strains with respect to Ba. The expanded anomeric region of 2D-HSQC spectra (FIGS. 26A-26D) indicated the presence of multiple sugar residues in Bc strains (FIGS. 26B-26D). The anomeric signals similar for the Ba and Bc strains (shown by boxes) indicate the structural similarity of the HF-PS. However there are several anomeric signals found in all the Bc HF-PSs which were not detected in the Ba HF-PS (shown by ovals). Several different 2D NMR experiment showed that there are more than two anomeric Gal residues in comparison to Ba HF-PSI. Hence from the NMR spectra it was clear that HF-PS isolated from Bc strains had partial similarity with that from Ba-Ames.

The MALDI mass spectral analysis of the HF-PS from Ba Ames and the Bc strains are shown in FIGS. 27A to 27D. The molecular ion with mass of 1136 represents the sodiated molecular mass of hexasaccharide (Hex3HexNAc3). The molecular ion with mass of 974 indicates the presence of molecule with one hexose unit (here Gal) less. The next cluster of ions with mass 2232 represents the dimer of the hexasaccharide. The ions 2070 and 1908 are respectively one and two Gal unit less than the dimer. There are also ions seen for the trimer with more Gal differences. Interestingly, the HF-PS from all Bc strains showed the presence of similar ions to those for the Ba HF-PS indicating the presence of conserved structural features. However the presence of ions with more hexose substitutions were predominant in Bc HF-PSs compared to Ba HF-PS indicating more heterogeneity of this secondary cell wall structure. The HF-PS from BB102 had ions with m/z of 1298 and 1460 which are one and two Gal residues more than the observed for the mono repeat unit from Ba HF-PS. The ion with m/z of 1583 (indicated by box) was only seen in BB102 and was assigned with molecular composition of HexNAc4Hex2. The ion with mass of 2355 was also only present in BB102 the mass difference of 772 was assigned to a HexHexNAc3 composition and there were also ion observed with one more tetrasaccharide (shown by an arrow). Hence it is more likely that HF-PS from BB102 was more highly heterogeneous with respect Gal substitutions compared to other Bc and Ba HF-PSs.

Figure 28:
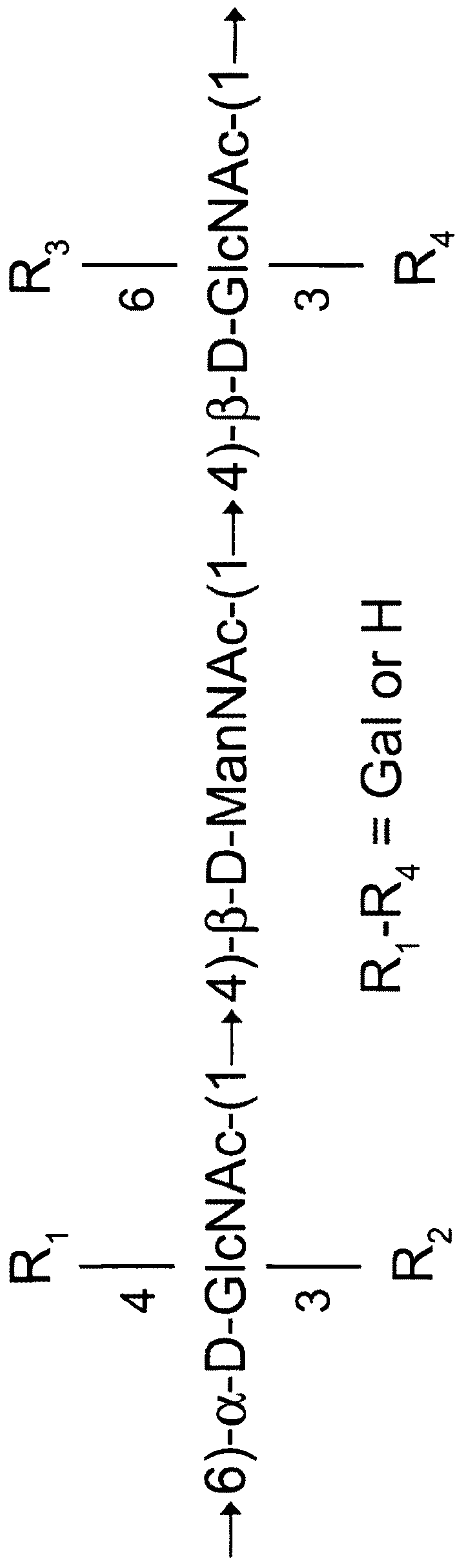
FIG. 28 shows the major amino-sugar backbone of HF-PS.

The immunochemical studies with antisera against KLH conjugated HF-PS from Ba showed cross reactivity with HF-PS from BB87, BB102 and G9241 strongly supporting the conserved structural motifs between Ba Ames and various pathogenic Bc strains. Hence it was concluded that HF-PS from Bc strains are structurally almost similar to the HF-PS from Ba, however with more hexose (Gal) distribution on the major amino-sugar backbone as shown in FIG. 28. This example presents a comparative structural study of predominant cell-wall carbohydrate from different strains of *Bacillus cereus* responsible for causing fatal pneumonia in patients in respect to *Bacillus anthracis*. It was interesting to observe the structural similarities between the isolated PSs from different strains. This conserved PS can be used as both a diagnostic tool and a successful vaccine candidate.

With this example, immunochemical data was also obtained, supporting the specificity of the Ba HF-PS in comparison to Bc HF-PSs using ELISA-inhibition assays. The Ba HF-PS-BSA conjugate was coated to the wells of a microtiter plate and the ability of antibodies to bind to this conjugate was competitively inhibited by pre-incubating the antiserum with varying concentrations of unconjugated HF-PSs. Besides the Ba HF-PS, only its structurally related HF-PS from strain Bc G9241 was able to competitively inhibit the reactivity of the antiserum. Overall, the HF-PS variability found in the various *B. cereus* strains indicates that these cell wall polysaccharides may be attractive targets for the development of diagnostic tools and, in case of *B. anthracis*, vaccine candidates.

TABLE 8

| Composition Analysis as TMS-glycosides | | | | | |
|---|---|---|---|---|---|
| FH-PS | Glc | Gal | ManNAc | GlcNAc | GalNAc |
| Ba-Ames | 1.6 | 54.2 | 16.2 | 28.0 | 0.0 |
| Bc-BB87 | 2.5 | 58.1 | 11.4 | 28.0 | 0.0 |
| Bc-BB102 | 5.1 | 61.6 | 10.3 | 23.0 | 0.0 |
| Bc-G9241 | 2.0 | 64.0 | 9.0 | 25.0 | 0.0 |
| Bc-10987 | 6.0 | 25.2 | 26.3 | 24.0 | 18.5 |

Example 9

*Bacillus anthracis* Carbohydrates Antigens for Vaccines and Diagnostics

This example has two overall aims. One, to use the *B. anthracis* BclA-OS and HF-PS for the preparation of vaccines that protect against infection. And, two, to use the *B. anthracis* BclA-OS and HF-PS structures to develop immunological detection methods. In order for a *B. anthracis* carbohydrate to be considered as a vaccine candidate it should be an antigen, it should show protective efficacy, antibodies to the carbohydrate should kill *B. anthracis* cells, and, it should offer added value compared to the current “PA-only” vaccines. The first aim of this example describes experiments that will determine these criteria for the BclA-OS and HF-PS carbohydrates. To evaluate the above criteria, minimal carbohydrate antigen structures needed for immunochemical reactivity and protective antibody development will be determined. This information could reveal that only small portions of the antigens are needed for raising protective antibody responses and will pave the way to the development of a fully synthetic vaccine and highly specific diagnostics. In addition, the protective efficacy of the carbohydrate-protein conjugates will be determined and compared with conventional PA-based *B. anthracis* vaccine. This example will also investigate whether derived polyclonal antiserum to BclA-OS and HF-PS mediate the opsonization and killing of *B. anthracis* cells.

Figure 29:
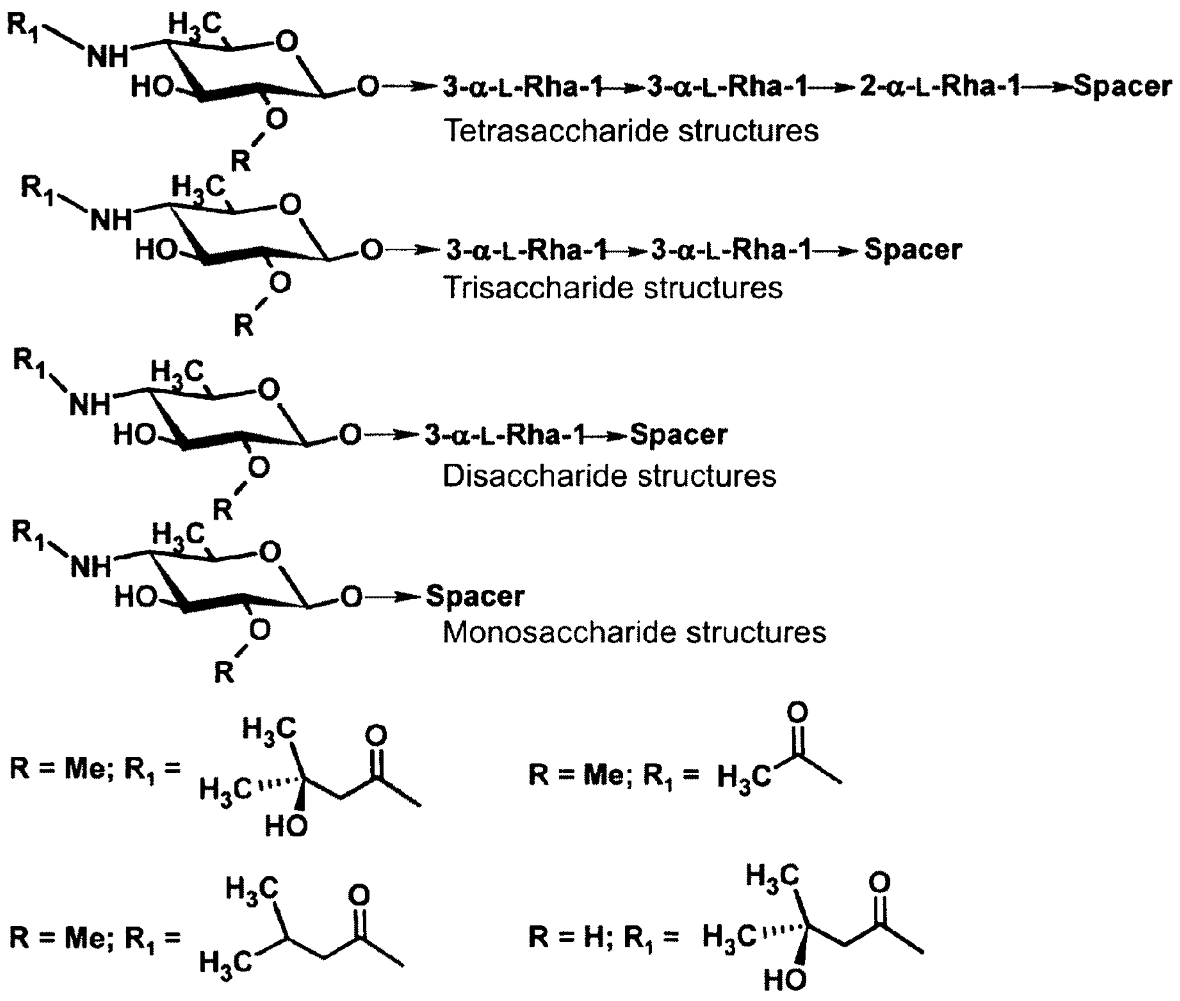
FIG. 29 shows the oligosaccharide structures that will be chemically synthesized to determine the immunodominant epitope of the BclA-OS.

The reactivity of each antigen with serum from animals inoculated with live-spore vaccine, animals that have survived inhalation anthrax, and human clinical serum will be determined. As shown in the previous examples, the BclA-OS structure and the HF-PS from *B. anthracis* are antigens since serum from rabbits inoculated with *B. anthracis* (Sterne) spores react with protein conjugates of these carbohydrates that are coated onto microtiter plates. With regard to synthetic trisaccharide analogues of the BclA-OS structure, the immunodominant epitope was identified in Example 3 as the isovaleryl portion of the anthrosyl β-hydroxylisolvaleryl substituent. However, in order to establish the minimal BclA-OS structural feature needed to bind and produce protective *B. anthracis* antibodies, this example will expand on these findings. The structures that will be chemically synthesized and evaluated as described below and as are shown in FIG. 29.

With regard to the HF-PS, there is considerable structural heterogeneity due to the number and location of terminal Gal residues attached to the trisaccharide amino sugar backbone of the repeating oligosaccharide (see Example 2). Therefore, the repeating oligosaccharide will be chemically synthesized together with structural analogs consisting of all the various combinations of these terminal Gal residues and these synthetic structures (shown in FIG. 30) will be used to determine the minimal HF-PS structural feature needed to bind and generate protective *B. anthracis* antibodies.

The minimal BclA-OS and HF-PS structures required for binding *B. anthracis* antibodies will be determined by ELISA inhibition analysis using procedures previously described in Example 3. Briefly, microtiter plates will be coated with either the BclA-OS-BSA (the BSA conjugate of structure 21 of Scheme 3 shown in FIG. 31) or the HF-PS (isolated)-BSA conjugate and the ability of the respective synthesized structures (FIGS. 29 and 30) to inhibit the binding of antiserum from a rabbit inoculated with *B. anthracis* spores will be measured by pre-incubating the antiserum with varying concentrations of the synthetic structures as described in Example 3. The results of this work will identify the optimal synthetic BclA-OS and HF-PS structures to use as synthetic vaccine antigens and for the development of diagnostic tools (i.e. detection of *B. anthracis* antibodies and the development of a MAb that can be used to identify *B. anthracis* spores and cells).

The reactivity with serum from animals that have survived inhalation anthrax and human clinical serum will be determined. Using the synthetic trisaccharide structure of BclA-OS, the previous examples showed that serum from non-human primates (NHP, Macaque monkeys) that have been vaccinated (with AVA) and from non-vaccined animals that survive exposure to an aerosol of *B. anthracis* spores produce antibodies that bind to this trisaccharide-KLH conjugate (coated to a microtiter plate). The ability of these sera to bind to the KLH conjugate of the synthesized BclA-OS tetrasaccharide structure will be examined, and also the conjugates of the isolated *B. anthracis* HF-PS. In addition, once the immunodominant synthetic minimal BclA-OS and HF-PS synthetic structures are identified (as described above), these sera will be examined for their ability to bind those structures. In addition to the NHS Rhesus Macaque sera, human clinical sera will be examined. These experiments will determine whether or not the BclA-OS and HF-PS are antigens in both NHP and humans that had been exposed to an aerosol of *B. anthracis* spores, and also if the minimal epitope structures are antigens for this type of exposure to *B. anthracis*. The experimental protocol will be to measure the ability of the sera to bind to microtiter plates that have been coated with either BSA- or KLH-conjugates of the BclA-OS or HF-PS structures. Methods as described in Example 3 will be used.

The protective efficacy of the *B. anthracis* BclA-OS and HF-PS structures as their KLH and PA conjugates and whether the PA-carbohydrate conjugates have added value compared to “PA-only” vaccines will be determined. The ability of the BclA-OS and HF-PS structures to protect against infection by *B. anthracis* will be determined using the mouse model. The structures that will be examined include KLH and PA conjugates of the chemically synthesized BclA-OS trisaccharide, the chemically synthesized BclA-OS tetrasaccharide, the BclA-OS minimal immunodominant epitope structure (as determined above), the isolated *B. anthracis* HF-PS, and the chemically synthesized minimal immunodominant HF-PS structure (as described above). The efficacy of these carbohydrate-conjugates will be compared to a "PA-only" vaccine.

The protective efficacy of the KLH and PA BclA-OS and HF-PS conjugates, as well as the recombinant PA vaccine will be examined and compared with each other in mice by intramuscular vaccination (twice at 10 intervals) followed 14 days later by subcutaneous challenge with *B. anthracis* Sterne. Briefly, evaluation of the protective efficacy of candidate PA-carbohydrate conjugate vaccines will be done in mice using the toxigenic ($pXO1^+$), non-capsulating ($pXO2^-$) *B. anthracis* Sterne. The spores of *B. anthracis* will be prepared from liquid cultures of PA medium (26) grown at 37° C., 200 rpm for four to six days. Female BALB/c mice (6-8 weeks of age) will be purchased (Harlan, Madison, Wis., or Jackson Laboratories, Bar Harbor, Me.) and maintained as specific pathogen free in the CDC SRP animal facility at Biosafety Level 2 with access to food and water ad libitum. Groups of 10 mice will be vaccinated with each test article to evaluate the protective efficacy of the carbohydrate moiety as a component of a protein conjugate. In the first instance an additional chemical adjuvant will not be used. If an adjuvant is required to obtain a detectable antibody response to PA or the PA-saccharide conjugate, a synthetic oligodeoxynucleotide (ODN) containing CpG motifs (CpG ODN) (Life Technologies, Grand Island, N.Y.) which have been demonstrated as effective intranasal and parenteral adjuvants in a variety of species including mice will be used (Klinman et al., 2004, *Vaccine* 22:2881-6). The test articles will be carrier protein alone, protein-saccharide conjugate, PA-saccharide conjugate and PA alone as a positive control. Each animal will be vaccinated with 2 intramuscular injections of test article at 10 day intervals. Mice will be challenged sub-cutaneously 14 days after the last vaccination with approximately 200 spores (~10 LD50 equivalents (Lyons et al., 2004, Infect. Immun. 72:4801-4809)). Protective efficacy will be reported as the geometric mean time to death (GMTD).

This example will also determine the ability of antibodies generated against the BclA-OS and HF-PS structures to opsonize *B. anthracis*. Rabbit polyclonal antiserum will be prepared using the KLH conjugates of the BclA-OS and HF-PS structures. The KLH conjugates of the BclA-OS chemically synthesized tetrasaccharide and the isolated *B. anthracis* HF-PS will be used to prepare rabbit polyclonal antisera. Rabbits will be injected with the relevant antigen at O, 14, 28, and 42 days. Serum will be collected prior to the first immunization (pre-immune serum) and at 7 and 14 days after each injection of antigen. Terminal bleeds will be collected 14 days after the last immunization. The ability of the polyclonal antiserum to opsonize *B. anthracis* cells will be determined. To determine whether the antibodies are functionally active against *B. anthracis* vegetative cells, opsonophagocytosis assays will be performed in which *B. anthracis* cells are incubated with various dilutions of the test sera in the presence of complement followed by addition of phagocytic effector cells (i.e. human HL-60 cells). A modification of the protocol described by Schneerson et al. will be used (Schneerson et al., 2003, *Proc. Natl. Acad. Sci.* 100: 8945-8950). Cells of the human cell line HL-60 (promyelocytic leukemia cells, CCL240, American Type Culture Collection, Rockville, Md.) will be used as effector cells. Differentiation will be carried out in cultures containing 100 mM dimethylformamide to 44% myelocytes and metamyelocytes and 53% band and polymorphonuclear leukocytes (PMN). PMN will be used in the assay at an effector/target cell ration of 400/1. PMN will be harvested by centrifugation (160×g, 10 min, room temperature) and the cell pellet will be resuspended in opsonophagocytosis buffer (Hank's buffer with $Ca^{2+}$, $Mg^{2+}$, and 0.1% gelatin; Life Technologies, Grand Island, N.Y.) to $2\times10^7$ cells per ml. The opsonophagocytosis assay will be carried out using either the unencapsulated *B. anthracis* strain Sterne $34F_2$ ($pXO1^+$, $pXO2^-$) or the encapsulated strain *B. anthracis* Pasteur ($pXO1^-$, $pXO2^+$). $5\times10^7$ spores will be added to 100 ml of brain heart infusion broth (BHI; BD Diagnostic Systems, Sparks, Md.) and incubated for 3 h at 37° C., shaking at 230 rpm, 20% $CO_2$ (for *B. anthracis* Pasteur) or air (for *B. anthracis* $34F_2$ Sterne). Before use the cultures will be diluted to approximately $5\times10^4$ colony forming units per ml. Test sera will be diluted 2-fold with opsonophagocytosis buffer and 50 μl added to the wells of a 24-well tissue culture plate (Falcon). To each well 20 μl of bacterial cell suspension containing approximately $10^3$ vegetative cells will be added. The plates will be incubated at 37° C., 5% $CO_2$ for 15 min. A 10-μL aliquot of colostrum-deprived baby calf serum (complement source) and 20 μl of HL-60 suspension containing $4\times10^5$ cells will be added to each well and incubated at 37° C. for 45 min, 5% $CO_2$, with mixing at 220 rpm in an incubator shaker. A 10-μl aliquot from each well will be spread-plated on brain heart infusion agar plates. The plates will be incubated over night at 37° C. and colony forming units counted the next morning. Opsonophagocytosis will be defined by ≧50% killing compared to growth from samples out of control wells (Romero-Steiner et al., 1997, *Clin. Diagn. Lab Immunol.* 4:415-422).

The second aim of this example is to develop immunological detection methods using the *B. anthracis* BclA-OS and HF-PS structures, to determine if either or both of the BclA-OS and HF-PS structures can be used to specifically detect *B. anthracis*-specific antibodies in serum, and to generate MAbs that will specifically bind *B. anthracis* cells and/or spores. The previous examples support the conclusion that the BclA-OS and HF-PS structures are *B. anthracis*-specific antigens, provide evidence that the HF-PSs from closely related strains of *B. cereus* have different structures, and show that *B. cereus* strains that have caused lethal pneumonia have HF-PS structures that closely resemble that of *B. anthracis* HF-PS. This example will fully evaluate the specificity of the structures and immunochemical reactivity of the BclA-OS and HF-PS from *B. anthracis* relative to those molecules from closely-related *B. cereus* strains, and to use BclA-OS and HF-PS structures to prepare MAbs that specifically bind *B. anthracis* cells and/or spores.

The ability of antibodies against *B. anthracis* BclA-OS and HF-PS to react with spores and cells of *B. cereus* strains that are closely related to *B. anthracis* will be determined. The previous examples indicate that the BclA-OS and HF-PS are specific to *B. anthracis* with regard to their structures and their immunochemical reactivity. With regard to the HF-PS, the previous examples showed that there was immunochemical cross-reactivity of *B. anthracis* anti-spore serum with the HF-PS from *B. cereus* strain G9241 that caused lethal pneumonia, but that the HF-PSs from several other closely related *B. cereus* strains were not reactive. In addition, the cross-reactive HF-PS from the *B. cereus* strain G9241 proved to be structurally similar to the *B. anthracis* HF-PS. With regard to the BclA-OS, the specificity of the structure and immunochemical reactivity has not been assessed with regard to the closely related *B. cereus* strains as determined by MLST. Therefore, this example will prepare polyclonal antiserum to *B. anthracis* BclA-OS and HF-PS protein conjugates and measure the cross-reactivity of each antiserum with spores and cells of closely related *B. cereus* strains. The closely related *B. cereus* strains indicated by MLST (Priest et al., 2004, *J. Bacteriol.* 186:7959-7970) plus other strains of interest, particularly those strains that cause severe human illness (Hoffmaster et al., 2006, *J. Clin. Microbiol.* 44:3352-3360), will be examined. For each strain that shows significant cross-reactivity, the BclA-OS or HF-PS will be isolated and structurally compared to the respective *B. anthracis* carbohydrate. Isolation and structural analysis will be done as described below.

BclA-OS and HF-PS antiserum will be prepared as described above. Screening of antigen availability on spores and vegetative cells will be done using immunoprecipitation techniques in which candidate antisera will be mixed with a known concentration of γ-irradiated spores, and vegetative cell chains. The availability of saccharide structures on the spore or vegetative cell surface will be visualized using indirect fluorescent antibody staining. The spores or vegetative cells will be prepared by suspending a pre-determined amount of culture biomass or spore number in 100 μl of 10 mM phosphate-buffered saline/0.3% Tween 20, pH 7.2 (PBST) and adjusting the concentration to ~$10^7$ colony forming units (CFU)/ml (De et al., 2002, *Emerg. Infect. Dis.* 8:1060). In this approach spores or cells of the *B. anthracis* strain will be mixed with a range of dilutions of rabbit anti-conjugate antiserum and subsequently, after washing, probed for bound rabbit antibody using a fluorescein isothiocyanate (FITC) labeled murine monoclonal anti-rabbit antibody according to the manufacturer's protocols (Molecular Probes, Eugene, Oreg.). The labeled cells/spores are visualized under oil on an epifluorescence microscope with a 40× or 100× objective. Spores or cells exhibiting whole-body bright green fluorescence against a dark background are considered to be a positive reaction. A negative reaction is characterized by cells that do not show fluorescence (De et al., 2002, *Emerg. Infect. Dis.* 8:1060). Together with appropriate controls for non-specific binding of rabbit antiserum these approaches will demonstrate the availability of saccharide structures on the surface of *B. anthracis* spores or vegetative cells.

Through chemical synthesis of structural analogues, the minimal BclA-OS and HF-PS structural epitope required to specifically bind *B. anthracis* antibodies will be characterized. The chemical synthesis of the BclA-OS and HF-PS structures are described below. Monoclonal antibodies (MAbs) that specifically bind *B. anthracis* spores or cells will be prepared. A B anthracis-specific MAb to the HF-PS and another to the BclA-OS would be very useful for several reasons. First, for the identification of clinical specimens from individuals that have developed anthrax-like symptoms; second, as research tools for in sits antigen localization and isolation of mutants with defects in HF-PS synthesis; and third, as an important step in the development of fully synthetic vaccines. The MAb production will include the immunization of mice with antigens, screening hybridoma cell lines for MAb production, cloning positive sibling cell lines, and bulking up MAb sera of interest.

For the development of MAbs specific for the HF-PS from *B. anthracis*, initial immunizations of mice will be with the KLH conjugated HF-PS isolated from *B. anthracis* described in Example 2. For antibody screening, ELISA assays will be employed. As a primary screen to identify candidate hybridoma cell lines producing *B. anthracis* HF-PS-related antibodies, hybridoma cell supernatants will be tested for their reactivity with cell walls isolated from *B. anthracis* Sterne. In this preparation the HF-PS polysaccharide structure is still bound the peptidoyglycan, and, therefore, the antigen conformation and presentation should more closely resemble that in intact *B. anthracis* vegetative cells. Those supernatants that positively react with the HF-PS will be, in turn, examined for their ability to react with the isolated HF-PS conjugated to BSA. If this approach does not yield the sought after MAb, crude cell wall preparations will be used as the immunization antigen. In case, primary screening of the hybridoma cell line supernatants will be done using the isolated HF-PS conjugated to BSA, and those that give a positive result will be tested for binding to the cell wall preparation of *B. anthracis.*

Once the supernatants of candidate hybridoma cell lines producing *B. anthracis*-binding MAbs have been obtained, additional screens of these supernatants will be performed using cell wall preparations from the closely related *B. cereus* strains, ATCC10987, and G9241. As described in the previous examples, the HF-PS from G9241 is structurally very similar to that from *B. anthracis* and polyclonal antibodies in animals inoculated with *B. anthracis* spores react to a certain extent with the G9241 HF-PS, as does a reported *B. anthracis* cell wall MAb (Hoffmaster et al., 2006, *J. Clin. Microbiol.* 44:3352-3360). Therefore, the inclusion of G9241 cell walls in this screen will allow identification of MAbs that specifically bind the HF-PS from *B. anthracis* but do not bind the structurally related HF-PS from G9241. This should identify a truly *B. anthracis*-specific MAb. Once the HF-PS *B. anthracis*-specific MAb has been identified, its epitope will be determined using the chemically synthesized structures in FIG. 30 using ELISA inhibition analysis. This will allow for the determination of the optimal structure which, in future work, can be developed into a fully chemically synthesized vaccine antigen or diagnostic.

To development of MAbs specific to the *B. anthracis* BclA-OS, mice will be immunized with a KLH-conjugated, synthetic tetrasaccharide antigen that will be prepared as described below. The antigenicity of the synthetic trisaccharide version of BclA-OS was established in Example 3 (see, also, Tamborrini et al., 2006, *Angew. Chem. Int. Ed.* 45:1-3). To identify hybridoma cell lines producing BclA-OS specific antibodies, hybridoma cell supernatants will be screened for reactivity with inactivated *B. anthracis* spores carrying the native BclA-OS on its exosporium and with synthesized BclA-OS tetrasaccharide conjugated to BSA. The BclA-OS-binding MAb will be used to investigate the BclA-OS structural conservation and occurrence using spores and vegetative cells from a range of different *B. anthracis* strains closely related strains of the *B. cereus* group. The MAb epitope structure will also be characterized with ELISA inhibition analysis using the structural analogs of the BclA-OS structure shown in FIG. 29.

Culturing the *Bacillus* strains will be performed in Biosafety Level 3 facilities in accordance with Select Agent rules and regulations. For Select Agents and non-pathogenic *Bacillus* strains alike, spores, cells, and cell extracts will be inactivated by either γ-irradiation or autoclaving. Potential residual viability will be monitored by culturing aliquots for 72 hours before the material is released from the BSL3 laboratory and shipped. All experiments requiring the use of live *B. anthracis* or *B. cereus* cells will be performed in accordance with Select Agent rules and regulations.

BclA-OS molecules will be isolated from *B. cereus* strains closely related to *B. anthracis*. Current evidence indicates that the BclA-OS is structurally specific to *B. anthracis*. However, the structures of analogous molecules from strains of *B. cereus* that are closely related to *B. anthracis* have not been fully characterized. Therefore, this example will examine the structures of these molecules from several closely related strains. These *B. cereus* strains include ATCC 10987, F666 (closely related to strain ATCC10987), and those strains which caused lethal pneumonia; i.e. BB87, BB102 and G9241. In addition to these strains, others that show cross-reactivity with antiserum to *B. anthracis* BclA-OS will be examined. Spores of these strains will be prepared, the BclA-OS molecules isolated, and their structures compared to that of the *B. anthracis* BclA-OS by glycosyl composition, linkage, mass spectrometric, and nuclear magnetic resonance spectroscopy analyses.

The spores of *B. anthracis* will be prepared from liquid cultures of PA medium (Green et al., 1985, *Infect. Immun.* 49:291-7) grown at 37° C., 200 rpm for four to six days. Spores will be washed two times by centrifugation at 10,000×g in cold (4° C.) sterile deionized water, purified twice in a 50% Reno-60 (Bracco Diagnostics Inc., Princeton, N.J.) gradient (10,000×g, 30 min, 4° C.) and washed a further four times in cold sterile deionized water. After suspension in sterile deionized water, spores will be quantified with surface spread viable cell counts on brain heart infusion agar plates (BD BBL, Sparks, Md.). Spore extracts will be prepared as previously described (Pitt et al., 2001, *Vaccine* 19:4768-73; Sylvestre et al., 2002, *Mol. Microbiol.* 45:169-178). Briefly, spores killed by γ-irradiation will be extracted by heating in buffer (50 mM Tris-HCl, pH 10, 8 M urea and 2% 2-mercaptoethanol; about 50 μl of buffer for every $10^9$ cells) for 15 minutes at 90° C. and centrifuging at 13,000×g for 10 minutes. The BclA-OS will be released from the intact spores of each strain by treatment with hydrazine as previously described (Daubenspeck et al., 2004, *J. Biol. Chem.* 279: 30945-30953). The various carbohydrates will be isolated using gel-filtration chromatography, HPLC and HPAEC as needed and structurally characterized as described below.

HF-PS molecules will be isolated from *B. cereus* strains closely related to *B. anthracis*. As shown in the previous examples, the HF-PSs from closely related members of the *B. cereus* group can vary significantly in their glycosyl residue compositions and are, therefore, structurally variable. Example 2 showed that the HF-PSs from strains of *B. anthracis* are identical in structure. Additionally, composition and structural data indicate that the HF-PSs from *B. cereus* strains that caused human fatal pneumonia are closely related in structure to that of the *B. anthracis* HF-PS. Therefore, this example will determine the exact structural relationship between the HF-PSs from these *B. cereus* strains (strains BB102, BB87, and G9241) with the HF-PS from *B. anthracis* and determine if there is a correlation between the structure of the HF-PS and the pathogenicity of these strains. In addition, the HF-PSs from other *B. cereus* strains that show cross-reactivity with the *B. anthracis* HF-PS antibodies will be examined.

Cell growth, killing of the cultures, and initial sample preparation will be done as described in Example 2. The HF-PS from each cell culture will be isolated from purified cell wall preparations as described in Example 2. Briefly, the cells will be grown to late exponential phase, killed by autoclaving, and harvested by centrifugation. The cell pellet will be washed by suspending in 0.05 M Tris-HCl, pH 7.5, followed by centrifugation. The washed cell pellet will be frozen at −20° C. The cells will then be suspended in cold (4° C.) deionized water at a concentration of 0.5 g/mL and disrupted by sonication. If necessary, cells can also be broken by passage through a French pressure cell. Unbroken cells are removed by low speed centrifugation, 5000×g, for 15 minutes. The pelleted unbroken cells will be subjected to a second sonication and centrifuged at 5000×g. The supernatants from the two low speed centrifugations will be combined and the cell walls will be sedimented by centrifugation at 48,000×g for 15 minutes. The resulting cell wall pellet will be washed several times by suspension in deionized water followed by centrifugation. Each cell wall preparation will be monitored to be sure that it is free of viable bacteria and contaminating nucleic acids. If nucleic acids are found, the preparation will be treated with DNase and RNase, dialyzed and freeze-dried. The HF-PS related carbohydrate components that are linked to the cell wall by phosphate diester bridges will be released by treatment with aqueous HF as previously described (Ekwunife et al., 1991, *FEMS Microbiol. Lett.* 82:257-262) and further purified by gel-filtration chromatography as described in Example 2.

Carbohydrate Structural Analysis. The techniques required to determine and compare the structures of the BclA-OS and HF-PS molecules from each bacterial strain will be the same as those described in Example 2. These techniques can be applied to both HF-PS and the BclA-OS preparations. Generally, structural elucidation of glycoconjugates requires determination of the following: 1) molecular size and heterogeneity, 2) glycosyl composition, 3) glycosyl linkage, 4) glycosyl sequence, 5) anomericity, and 6) analysis of other non-carbohydrate substituents (e.g., covalently attached amino acids, ester and ether substituents, etc.). Composition and linkage positions will be determined by combined gas chromatography-mass spectrometry (GC-MS) analysis (electron impact and chemical ionization) of derivatives such as trimethylsilyl (TMS) methyl glycosides, alditol acetates, or, in the case of methylation analysis, partially methylated alditol acetates (PMAAs) (York et al., 1985, *Meth. Enzymol.* 118:3-40), and by specific chemical degradations followed by GC-MS analysis (Carlson et al, 1992, *Carbohydr. Res.* 231:205-219; Forsberg et al., 2000, *J. Biol. Chem.* 275:18851-18863; and Gudlavalleti et al., 2003, *J. Biol. Chem.* 278:3957-3968). Glycosyl sequence information will be obtained using 2D NMR-based strategies, including sequential COSY, TOCSY, HSQC, HMBC, and NOESY analyses, alone and in combination with mass spectrometry and methylation analysis (Bhat et al., 1994, *J. Biol. Chem.* 269:14402-14410; Choudhury et al., 2005, *Carbohydr. Res.* 340:2761-2772; Choudhury et al., 2006, *J. Biol. Chem.* 281:27932-27941; Gudlavalleti et al., 2004, *J. Biol. Chem.* 279:42765-42773; Kahler et al., 2006, *J. Biol. Chem.* 281:19939-19948; Le Quere et al., 2006, *J. Biol. Chem.* 281:28981-28992; Le Quere et al., 2006, *J. Biol. Chem.* 281:28981-28992; Rahman et al., 2001, *Glycobiology* 11:703-709; and Tzeng et al., 2004, *J. Biol. Chem.*: M401-433200). The anomeric configuration of each glycosyl residue will also be revealed by these 1D and 2D NMR analysis experiments. Molecular mass analysis also yields sequence information and is performed by techniques such as electrospray ionization mass spectrometry (ESI-MS) or matrix assisted laser desorption time of flight mass spectrometry (MALDI-TOF MS). The types and locations of any non-carbohydrate components will be deduced from NMR analyses in combination with chemical analyses.

Chemical Synthesis of BclA-OS and HF-PS structures. In order to identify the minimal BclA-OS and HF-PS structures for *B. anthracis*-specific immunochemical reactivity and for use as a vaccine antigen, it is necessary to chemically synthesize structural analogues of these molecules for immunochemical evaluation. The identity of all synthetic structures and their intermediates will be confirmed by NMR spectroscopy and low- and high-resolution mass spectroscopy. NMR spectroscopy is a particularly powerful tool for the structural assignments of glycopeptides. Experiments that are particularly relevant to proton assignments are COSY, DQF-COSY, RELAY, TQF-COSY, TOCSY using HOHAHA transfer, NOESY, and ROESY. $^{13}C$ NMR spectroscopy is also a powerful assignment tool. Especially beneficial is the ability to correlate inversely $^{13}C$ chemical shifts with their attached protons shifts when sample amount is limited. HMQC/HMBC/HSQC experiments are particularly powerful in this respect for complete structural assignment. Mass spectroscopic techniques relevant to oligosaccharide analysis include electrospray-, and MALDI-TOF MS. The purity of the compounds will be evaluated by NMR spectroscopy and C/H/N determination by combustion analysis. Synthetic intermediates will be purified by silica gel column chromatography or Sephadex LH-20 size exclusion column chromatography. The final oligosaccharides will be purified by G-15 size exclusion column chromatography or P-2 Biogel desalting column chromatography. Compounds will be prepared in quantities of at least 15 mg and purity greater than 98%.

Synthesis of the *B. anthracis* BclA-OS and structural analogues. The BclA-OS tetrasaccharide (see structure 21 in Scheme 3, FIG. 31) and several part-structure analogues (shown FIG. 29) will be synthesized to establish the minimal structure that is necessary for binding to *B. anthracis* antibodies and can be used to generate protective anti-*B. anthracis* antibodies. The synthesis of trisaccharide 1 and its analogues 2, 3, and 4 (shown in FIG. 32) will follow procedures described in Example 3.

Figure 31:
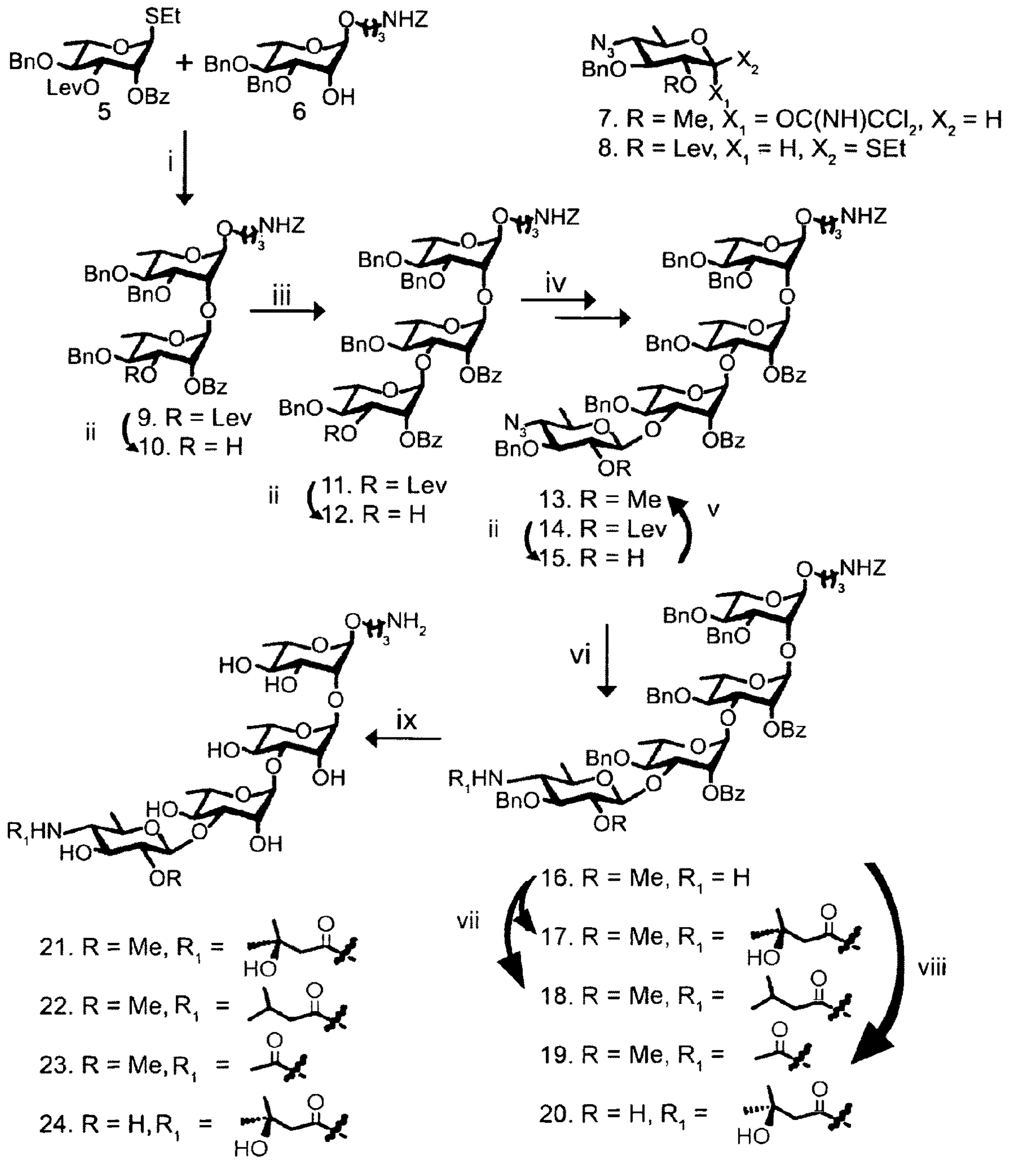
FIG. 31 presents Scheme 3 for the synthesis of the structural analogues of *B. anthracis* BclA-OS found in the exosporium. Reagents and conditions: i) NIS, TfOH, DCM; ii) NIS, TfOH, DCM; iii) $H_2NNH_2$—HOAc, DCM, MeOH; iv) 7, $BF_3$—$Et_2O$, MeCN, −40° C. or 8, NIS, TfOH, DCM; v) Mel, $Ag_2O$, $Me_2S$; vi) 1,3-propanedithiol, pyridine; vii) HO(O)$CCH_2COH(CH_3)_2$, DIC, HOAt, DMF; viii) $Ac_2O$, pyridine; ix) 1) NaOMe, 2) Pd/C, $H_2$, t-BuOH/$H_2O$/AcOH.

The spacer-containing tetrasaccharide 21 will be prepared from properly protected monosaccharide building blocks 5, 6, and 7 (Scheme 3, FIG. 31). Rhamnosides 5 and 6 will be prepared by routine protecting group manipulations (Pozsgay, 1998, *J. Org. Chem.* 63: 5983-5999). Anthrose donor 7 will be prepared as described in Example 3. The tetrasaccharide 21 will be assembled by a convergent approach as outlined in Scheme 3. The spacer equipped di-rhamnoside 9 will be prepared by NIS/TMSOTf (Veeneman et al., 1990, *Tetrahedron Lett.* 31:1331-1334) mediated activation of thioglycoside 5 in the presence of glycosyl acceptor 6, which has a C-2 hydroxyl. The benzoyl ester at C-2 of glycosyl donor 5 will perform neighboring group participation during the glycosylation leading to selective formation of an α-glycoside. Next, the levulinoyl ester (Lev) will selectively be removed by treatment with hydrazine acetate (Zhu and J. Boons, 2001, *Chemistry—a European Journal* 7:2382-2389) in a mixture of DCM and methanol to give glycosyl acceptor 10. Trisaccharide 11 will be prepared by glycosylation of glycosyl acceptor 10 with thioethyl donor 5. Thereafter, the Lev ester of 11 will be removed, which will provide tri-rhamnoside acceptor 12. Glycosylation of acceptor 12 with α-trichloroacetimidate donor 7 in a $BF_3$-$Et_2O$ mediated coupling at low temperature will provide tetrasaccharide 13 (Schmidt, 1986, *Angew. Chem. Int. Ed.* 25:212-235; Schmidt and Kinzy, 1994, *Method. Adv. Carbohydr. Chem. & Biochem.* 50:21-123). The anomeric selectivity of the glycosylation will be controlled by using acetonitrile as a participating solvent (Braccini et al., 1993, *Carbohydr. Res.* 246:23-41; Ratcliffe and Fraserreid, 1990, *J. Chem. Soc.-Perkin Trans.* 1:747-750), which will lead to the preferential formation of an equatorial glycoside. Also, thioethyl glycosyl donor 8, which carries a participating Lev ester at C-2, will be prepared and evaluated as a donor in this glycosylation. Anthrose derivative 8 can easily be prepared from ethyl 6-deoxy-3,4-isopropylidene thioglucoside following the synthetic route outlined for anthrose donor 7 (see Example 3). The C-2 Lev ester of 8 will lead to the β-anomer in the glycosylation to reach tetrasaccharide 14. Here, the C-2''' Lev ester will be removed followed by introduction of the methyl group by treatment with MeI in the presence of $Ag_2O$ and $Me_2S$, which will provide tetrasaccharide 13. Next, the azido moiety of 13 will be reduced to an amine (16) (Venot et al., 2004, *Chembiochem* 5:1228-1236), which subsequently will be acylated with 3-hydroxyl-3-methyl-butyric acid using DIC and HOAt as the activation reagents to give fully functionalized derivative 17. Deprotection of 17 can easily be accomplished by a two-step procedure entailing treatment with NaOMe in methanol followed by catalytic hydrogenation over Pd/C to give compound 21. The aminopropyl spacer of 21 will facilitate selective conjugation to various carrier proteins.

Also, as outlined in Scheme 3 (FIG. 31), the tetrasaccharide derivatives 15 and 16 will be employed for the synthesis of analogue structures of 21. The part-structures 22, 23, and 24 will be used for the preparation of glycoprotein conjugates and immunization studies. Furthermore, these derivatives will also be employed to determine which part of compound 21 that is recognized by antibodies raised against tetrasaccharide 21. Derivatives 22 and 23 can be synthesized from tetrasaccharide 16 using iso-valeric acid and acetic anhydride, respectively, as N-acylating reagents. Compounds 22 and 23 will help determine the importance of the 3-hydroxyl-3-methylbutamido-moiety. Compound 24, which lacks the C-2''' O-methyl group, can be synthesized from tetrasaccharide 15. After reduction of the azido-group of compound 15, a selective acylation with 3-hydroxy-3-methyl butyric acid will give, after deprotection, analogue structure 24. This derivative will provide a means to determine the importance of the O-methyl group of the *B. anthracis* tetrasaccharide.

In addition, building blocks 5, 6, 7, and 8 and the synthetic route outlined in Scheme 3 (FIG. 31) will be used to synthesize di- and trisaccharide part-structures, stemming both from the reducing and non-reducing end, of the BclA tetrasaccharide. Also, the anthrose monosaccharide as well as the 3-hydroxyl-3-methyl-butamido moiety will be equipped with an aminopropyl linker and conjugated to carrier proteins. All these synthetic analogues will aid in exploring the epitope requirements.

Synthesis of the *B. anthracis* HF-PS structure and analogues. The structure of the *B. anthracis*-specific HF-PS repeating unit and structural analogues will be synthesized as follows. All compounds will be equipped with an artificial aminopropyl spacer, which will facilitate a controlled conjugation to carrier proteins. The spacer-containing hexasaccharide 42 will be prepared from properly protected monosaccharide building blocks 25, 26, 27, 28, and 29 (Scheme 4, FIG. 32). These compounds will be prepared by routine procedures. The trisaccharide 35, which carries three orthogonal protecting groups allyloxycarbonyl (Alloc), Fmoc, and Lev at C-2, C-3'', and C-4'', respectively, will be a key-intermediate for the assembly of structural analogues exhibiting different galactosylation patterns. The selectively protected glucose acceptor 26 will be coupled with trichloroacetimidate donor 25 using TMSOTf as a promoter (Schmidt, 1986, *Angew. Chem. Int. Ed.* 25:212-235; Schmidt and Kinzy, 1994, *Method. Adv. Carbohydr. Chem. & Biochem.* 50:21-123) to give disaccharide 30. The anomeric thiophenyl group of 30 will then directly be activated using NIS/TMSOTf as promoter pair in the presence of spacer modified N-acetyl glucosamine acceptor 27 to give trisaccharide 31. To invert the hydroxyl at C-2' and thus reach a manno-configuration, the Lev ester of 31 will be removed by hydrazine acetate and the hydroxyl of the resulting compound 32 will be converted into a triflate, which will be displaced by sodium azide to obtain derivative 33 (Watt and Boons, 2004, *Carbohydr. Res.* 339: 181-193). Next, the benzylidene acetal of 33 will be regioselectively opened using triethylsilane and triflic acid (Sakagami and Hamana, 2000, *Tetra. Lett.* 41:5547-5551) to give derivative 34, which has a free hydroxyl at C-4''. Reaction of 34 with levulinic acid using dicylcohexylcarbodiimide as coupling reagent and in the presence of dimethylaminopyridine will furnish key building block 35. From this building block all part-structures exhibiting different galactosylation patterns, outlined in FIG. 30, can be reached by selective removal of any of the orthogonal protecting groups followed by galactosylation. To reach hexasaccharide 42 from trisaccharide 35, the Alloc ester at C-3 will first be selectively removed using $Pd(PPh_3)_4$ to give glycosyl acceptor 36. Glycosylation of this derivative with trichloroacetimidate donor 28 (Kim et al., 2005, *J. Am. Chem. Soc.* 127:12090-12097; Kim and Boons, 2005, *Angew. Chem. Int. Ed.* 44:947-949) using TMSOTf as activator will give tetrasaccharide 37. Here, it is to be expected that only the α-galactoside will be formed due to the participation of the (S)-(phenylthiomethyl)benzyl ether (Kim et al., 2005, *J. Am. Chem. Soc.* 127:12090-12097; Kim and Boons, 2005, *Angew. Chem. Int. Ed.* 44:947-949). Next, the Fmoc group will be removed using standard conditions (Zhu and J. Boons, 2001, *Chemistry—a European Journal* 7:2382-2389) and the resulting glycosyl acceptor 38 will be glycosylated with galactosyl donor 28 using TMSOTf as promoter. Again, it is to be expected that only the α-glycoside will be formed. After Lev group removal of 39 using standard conditions, the unveiled hydroxyl group of derivative 40 will be glycosylated with trichloroacetimidate donor 29 in the presence of TMSOTf. Global deprotection of derivative 41 in four steps using standard procedures will furnish target hexasaccharide 41.

Figure 32:
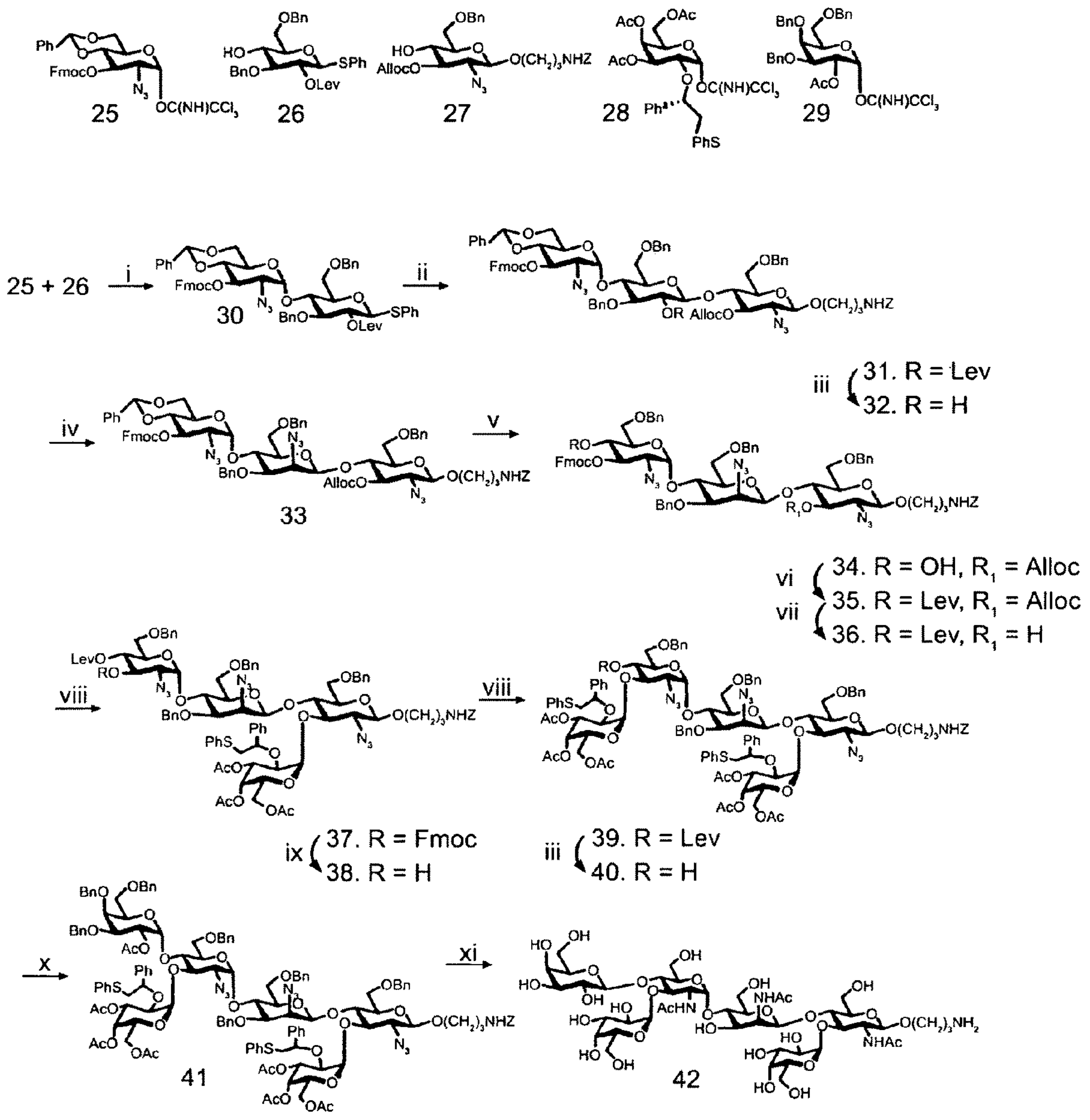
FIG. 32 presents Scheme 4 for the synthesis of *B. anthracis* HF-PS oligosaccharide repeating units and structural analogues. Reagents and conditions: i) TMSOTf, DCM, $Et_2O$, −20° C.; ii) 27, NIS, TMSOTf, DCM, 0° C.; iii) $H_2NNH_2$—AcOH, DCM, MeOH; iv) 1) $Tf_2O$, pyridine, DCM, 0° C., 2) $NaN_3$, DCM, 60° C.; v) $Et_3SiH$, TfOH, DCM, −78° C.; vi) LevOH, DCC, DMAP, DCM; vii) $BuNH_2$, HCOOH, pd$(PPh_3)_4$, THF; viii) 28, TMSOTf, DCM, −20° C.; ix) 1) $CH_3COSH$, DMF, 2) $BFD_3OET_2$, $Ac_2O$, 3) NaOMe, dioxane, 4) Pd/C, $H_2$, EtOH.

Several part-structures of hexasaccharide 41 (Scheme 4, FIG. 32) which are indicated in FIG. 30, will also be synthesized. In particular, compounds lacking one or both of the α- or β-galactosides are important since the heterogeneity of the oligosaccharide at these positions as described in Example 2. To this end, compounds 33, 38 and 40 will be deprotected to furnish three of the analogue structures. The remaining four structures can be reached using trisaccharide derivative 35 and the chemistry outlined in Scheme 4 (FIG. 32). These analogues will be used to determine, which part of hexasaccharide 41 is recognized by antibodies raised by this derivative. Protein conjugates of these oligosaccharides will also be prepared.

Conjugation of isolated and chemically synthesized carbohydrates to carrier proteins. A range of oligosaccharide-protein conjugates will be prepared for immunological characterization. The synthetic compounds described in above are equipped with an artificial aminopropyl spacer, which will allow a controlled conjugation to carrier proteins. The amino group of the spacer can be converted into a thioacetate functionality by treatment with S-acetylthioglycolic acid pentafluorophenylester (SAMA-OPfp). The thioacetyl group can be cleaved off to unmask the thiol group, which can be utilized for conjugations to a carrier protein that has been activated with, for example, a bromoacetyl group or a maleimide group. Alternatively, a "reverse approach" in which the amino group of the artificial aminopropyl linker is converted into a bromoacetyl or a maleimide group, which can be conjugated to a carrier protein that has been activated with 2-iminothiolane (Traut's reagent), can be employed. As carrier proteins, KLH will be used. Also, in order to make a divalent vaccine, the *B. anthracis* PA protein will be used for conjugation. Furthermore, BSA conjugates will be prepared for coating micro-titer plates to selectively determine antibody titers against the oligosaccharides.

Polysaccharides isolated from *B. anthracis* strains will also be conjugated with the carrier proteins. This will be done by direct activation of the polysaccharide with the cyanylating reagent, 1-cyano-4-dimethylaminopyridinium tetrafluoroborate (CDAP) followed by conjugation to the amine groups of the carrier protein (Bystrickýet al., 2000, *Glycoconj*. J. 17:677-680; Lees et al., 1996, *Vaccine* 14:190-198; and Shafer et al., 2000, *Vaccine* 18:1273-1281). Alternative protocols, if needed, include reductive amination (Mieszala et al., 2003, *Carbohydr. Res.* 338:167-175), and reductive amination after periodate activation (Guo, 2001, Methods in Molecular Medicine (Meningococcal Vaccines) 66:167-175). Conjugation procedures used will include the following:

De-S-acetylation of saccharide derivatives. 7% $NH_3$ (g) in DMF solution (200 μL) will be added to a solution of thioacetate derivatized oligosaccharide (5 mg) in dd$H_2O$ (50 μL) and the mixture will be stirred under an argon atmosphere. The reaction can be monitored by MALDI-TOF. When the de-S-acetylation is complete, the mixture will be concentrated under reduced pressure and the thiol dried in vacuo and then used immediately in conjugation without further purification to avoid formation of a disulfide.

Conjugation of oligosaccharide derivatives to BSA-maleimide. The sugar thiol (2-3 equiv. excess to available MI-groups on the protein), prepared as described in the preceding paragraph, will be deprotected just prior to conjugation as described above. The compound will be dissolved in dd$H_2O$ and added to a solution of maleimide activated BSA in PBS buffer pH 7.2 containing EDTA and sodium azide. The mixture will be incubated for 2 hours at room temperature and then purified by Millipore centrifugal filter device with a 10.000 Da molecular weight cut-off. The conjugate will be retrieved and taken up in 10 mM Hepes buffer pH 6.5 or PBS buffer. Alternatively, the conjugate can be purified by gel-filtration D-salt column using PBS buffer as eluant. The average number of saccharide copies attached to the BSA will be determined by quantitative monosaccharide analysis by HPAEC/PAD and/or GC-MS analysis and Lowry protein concentration test.

Conjugation of oligosaccharide derivative to bromoacetyl activated protein carriers. A solution of N-succinimidyl propionylbromoacetate (5 mg) in DMSO (40 μL) will be added to a solution of protein (2 mg) in 0.1 mM sodium phosphate buffer pH 8.0 containing 0.1 mM EDTA (200 μL). The mixture will be slowly stirred for one hour at room temperature and then purified using centrifugal filters with a molecular weight cut-off of 10.000 Da. The activated protein will be retrieved and taken up in a 0.1 mM sodium phosphate buffer pH 8.0 containing 0.1 mM EDTA (200 μL). A solution of thiol derivatized saccharide in the conjugation buffer will be added to the activated protein and the mixture will be incubated at room temperature overnight. Purification will be achieved using the centrifugal filters or D-salt gel-filtration column as described above for the BSA-maleimide conjugates. Sugar loading will be determined by quantitative monosaccharide analysis by HPAEC/PAD and/or GC-MS analysis and a Lowry protein concentration test.

Direct activation with a cyanylating reagent (Bystrickýet al., 2000, *Glycoconj. J.* 17:677-680; Lees et al., 1996, *Vaccine* 14:190-198; and Shafer et al., 2000, *Vaccine* 18:1273-1281). CDAP (4 mg) in acetonitrile (90 μL) will be added to isolated polysaccharide (1 mg) in HEPES buffer 0.15 M, pH 7.4 (90 μL) followed by addition of 0.3M TEA (120 μL). After two minutes the activated polysaccharide mixture will be added to the carrier protein (4 mg) in PBS buffer (0.1 M, pH 7.4 348 μL). The mixture will be incubated overnight at 4° C. Reaction will be quenched with 0.5 M ethanolamine in HEPES buffer (120 μL; 0.75 M; pH 7.4) and the glycoconjugate will then be purified by Millipore centrifugal filter device with a 30.000 Da molecular weight cut-off. The conjugate will be retrieved and taken up in dd$H_2O$ and lyophilized. The average number of saccharide copies attached to the protein will be determined by quantitative monosaccharide analysis by HPAEC/PAD and/or GC-MS analysis and Lowry protein concentration test.

Example 10

Chemical Synthesis and Immunological Properties of Oligosaccharides Derived from the Vegetative Cell Wall of *Bacillus anthracis*

*B. anthracis* is a Gram-positive, spore-forming bacterium that causes anthrax in humans and other mammals. The relative ease by which *B. anthracis* can be weaponized and the difficulty associated with the early recognition of inhalation anthrax due to the non-specific nature of its symptoms were underscored by the deaths of five people who inhaled spores from contaminated mail (Jernigan et al., 2001, *Emerging Infect. Dis;* 7:933-944; Jernigan et al., 2002, *Emerging Infect. Dis;* 8:1019-1028; and Webb, 2003, *Proc. Natl. Acad. Sci;* 100:4355-4356). As a result, there is a renewed interest in anthrax vaccines and early disease diagnostics (Bouzianas, 2007, *Expert Rev. Anti-Infective Ther;* 5:665-684). Anthrax vaccine adsorbed (AVA; BioThrax®, Emergent BioSolutions Inc.) is currently the only licensed anthrax vaccine in the US (Friedlander et al., 1999, *J. Am. Med. Assoc;* 282:2104-2106; and Joellenbeck et al., The Anthrax vaccine: is it safe? Does it work?, National Academy Press, Washington, D.C., 2002). The principal immunogen of AVA is anthrax toxin protective antigen (PA). Antibody responses against PA target and block the toxemia that is a necessary prerequisite of vegetative cell growth and bacteremia. Vaccines comprising additional *B. anthracis* specific antigens have been proposed as improvements to PA-only formulations as they have potential to target inclusively the toxemia and the vegetative cell or infectious spore (Schneerson et al., 2003, *Proc. Natl. Acad. Sci;* 100: 8945-8950; Chabot et al., 2004, Vaccine; 23:43-47; and Wang and Roehrl, 2005, *Med. Immunol;* 4:4). Recently described polysaccharides and glycoproteins of *B. anthracis* offer exciting new targets for vaccine formulations and for the development of improved diagnostics for *B. anthracis*. For example, an unusual oligosaccharide derived from the collagen-like glycoprotein BclA of the exosporium of *B. anthracis* has been characterized (Daubenspeck et al., 2004, *J. Biol. Chem;* 279: 30945-30953), chemically synthesized (Example 3, Werz et al., 2005, *Angew. Chem;* 117:6474-6476*; Angew. Chem. Int. Ed;* 44:6315-6318; Mehta et al., 2006, Chem. Eur. J; 12:9136-9149; Crich and Vinogradova, 2007, *J. Org. Chem;* 72:6513-6520; Guo et al., 2007, *Angew. Chem:* 119:5298-5300*; Angew. Chem. Int. Ed;* 46:5206-5208; Saksena et al., 2007, *Bioorg. Med. Chem;* 15, 4283-4310; and Werz et al., 2007, *Eur. J. Org. Chem;* 1976-1982), and immunologically evaluated. The latter studies demonstrated that the oligosaccharide is exposed to the immune system (Example 3, see also Mehta et al., 2006, Chem. Eur. J; 12:9136-9149) and has an ability to elicit relevant antibodies (Werz et al., 2005, *Angew. Chem;* 117:6474-6476*; Angew. Chem. Int. Ed;* 44:6315-6318).

The previous examples, including Examples 1 and 2, report the structure of a unique polysaccharide released from the vegetative cell wall of *B. anthracis*, which contains a →6)-α-D-GlcNAc-(1→4)-β-D-ManNAc-(1→4)-β-D-GlcNAc-(1→) backbone and is branched at C-3 and C-4 of α-D-GlcNAc with α-D-Gal and β-D-Gal residues, respectively and the β-GlcNAc substituted with α-Gal at C-3 (Scheme 1) (see also, Choudhury et al., 2006, *J. Biol. Chem;* 281:27932-27941; and Leoff et al., 2008, *J. Bacteriol;* 190:112-121). These positions are, however, only partially substituted leading to micro-heterogeneity.

Figure 34:
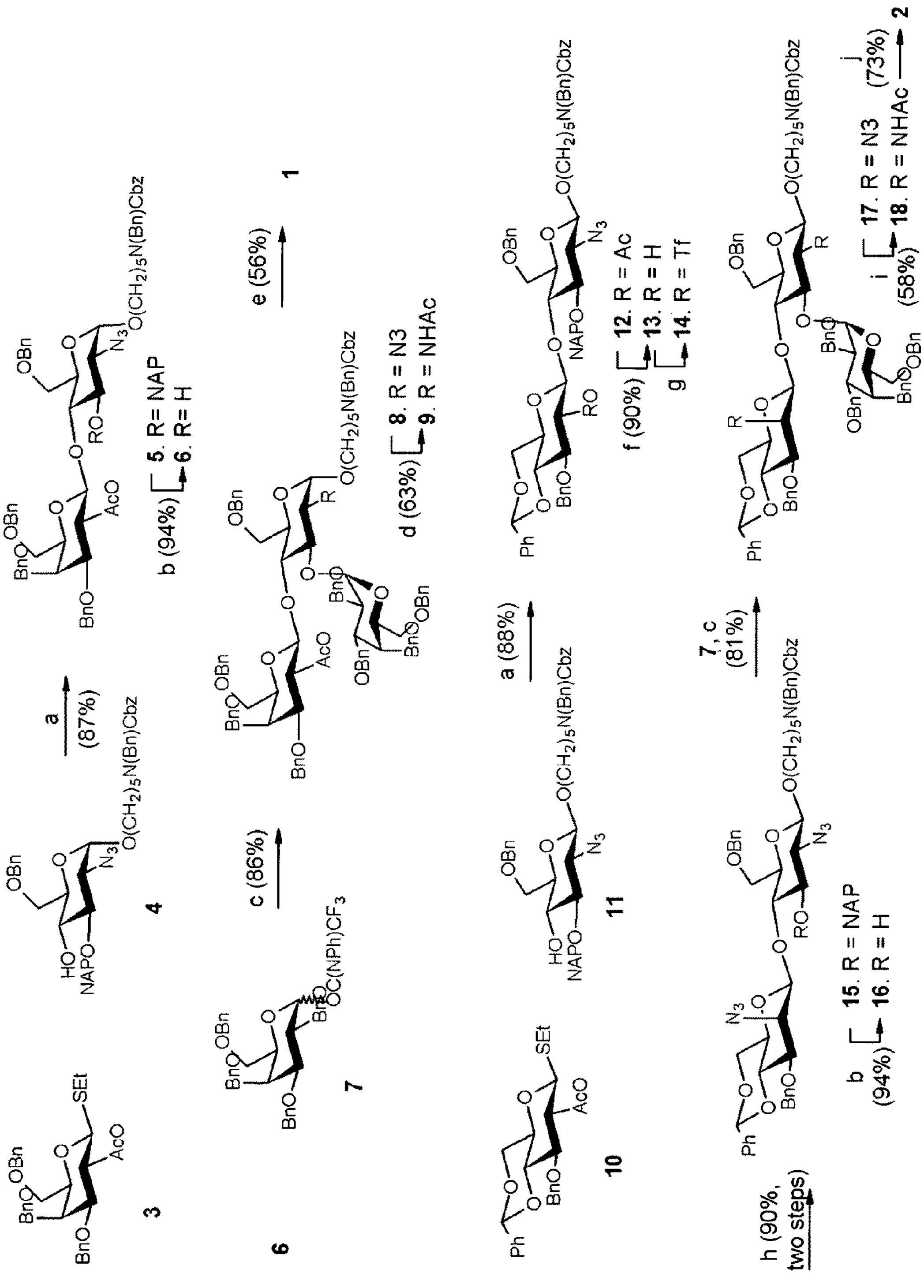
FIG. 34 presents Scheme 1 for compounds 1 and 2 of Example 10.

As part of a project to determine antigenic determinates of the polysaccharide of *B. anthracis* and to establish it as a diagnostic or vaccine candidate, this example reports the chemical synthesis and immunological properties of trisaccharides 1 and 2 (FIG. 33 and Scheme 1 of FIG. 34). These compounds, which are derived from *B. anthracis* polysaccharide, contain a 5-aminopentyl spacer for selective conjugation to carrier proteins required for enzyme linked immunosorbent assays (ELISA). It has been found that sera of rabbits exposed to live and irradiated-killed spores of *B. anthracis* Sterne $34F_2$ or immunized with polysaccharide conjugated to KLH recognize the isolated polysaccharide and the synthetic compounds 1 and 2. The data provide for the development of vegetative and spore-specific reagents for detection and targeting of non-protein structures of *B. anthracis.*

Compound 1 was conveniently prepared from monosaccharide building blocks 3, (Peters, 1991, *Liebigs Ann. Chem;* 135-141), 4, and 7 (Tanaka et al., 2005, *J. Am. Chem. Soc;* 127:1630-1631). Thus, a NIS/TMSOTf mediated glycosylation (Veeneman et al., 1990, *Tetrahedron Lett;* 31:1331-1334) of thioglycoside 3 with the C-4 hydroxyl of glycosyl acceptor 4 gave disaccharide 5 in a yield of 87% as only the β-anomer (Scheme 1 of FIG. 34). Interestingly, a lower yield of disaccharide was obtained when a glycosyl acceptor was employed that had a benzyloxycarbonyl-3-aminopropyl instead of a N-Benzyl-N-benzyloxycarbonyl-5-aminopropyl spacer (Mong et al., 2003, *Proc. Natl. Acad. Sci.;* 100:797-802). Next, the 2-naphthylmethyl ether (Gaunt et al., 19998, *J. Org. Chem;* 63:4172-4173; and Xia et al., 2000, *Tetrahedron Lett;* 41:169-17325) of 5 was removed by oxidation with DDQ in a mixture of dichloromethane and water to give glycosyl acceptor 6, which was used in a TMSOTf mediated glycosylation with (N-phenyl)trifluoracetimidate 7 (Gridley et al., 2000, *Chem. Soc., Perkin Trans;* 10:1471-1491; Yu and Tao, 2001, *Tetrahedron Lett;* 42:2405-2407; and Yu and Tao, 2002, *J. Org. Chem;* 67:9099-9102) to afford trisaccharide 8 in an excellent yield as only the α-anomer. The use of a conventional trichloroacetimidate as glycosyl donor (Schmidt and Kinzy, 1994, *Advances in Carbohydrate Chemistry and Biochemistry;* 50:21-123) led to a lower yield of product due to partial rearrangement to the corresponding anomeric amide. Target compound 1 was obtained by a three-step deprotection procedure involving reduction of the azide to an acetamido moiety by treatment with Zn/$CuSO_4$ (Winans et al., 1999, *Biochemistry;* 38:11700-11710) in a mixture of acetic anhydride, acetic acid, and THF, followed by saponification of the acetyl ester and reductive removal of benzyl ethers and benzyloxycarbamate by catalytic hydrogenation over Pd.

A challenging aspect of the preparation of target compound 2 is the installment of a β-mannosamine moiety (Gridley et al., 2000, *Chem. Soc., Perkin Trans;* 10:1471-1491). A strategy was adopted whereby a β-glucoside is initially installed using a glucosyl donor having a participating ester protecting group at C-2 to control beta-anomeric selectivity (Classon et al., 1991, *Carbohydr. Res;* 216:187-196). Next, the C-2 protecting group can be removed and the resulting hydroxyl triflated which can then be displaced by an azide to give a 2-azido-β-D-mannoside. Another strategic aspect of the synthesis of 2 was the use of an acetyl ester and 2-napthylmethyl ether (Gaunt et al., 19998, *J. Org. Chem;* 63:4172-4173; and Xia et al., 2000, *Tetrahedron Lett;* 41:169-17325) as a set of orthogonal protecting groups, which makes it possible to selectively modify C-2' of the β-glucoside and install an α-galactoside at C-3 of 2-azido-glucoside moiety. Thus, a NIS/TMSOTf mediated glycosylation (Veeneman et al., 1990, *Tetrahedron Lett;* 31:1331-1334) of thioglycoside 10 (Misra and Roy, 1998, *J. Carbohydr. Chem;* 17:1047-1056) with 11 gave disaccharide 12 in an excellent yield as only the β-anomer. The acetyl ester of 12 was saponified by treatment with sodium methoxide in methanol to give 13. Next, the alcohol of 13 was triflated by treatment with triflic anhydride in a mixture of pyridine and dichloromethane to afford triflate 14, which was immediately displaced with sodium azide in DMF at 50° C. to give mannoside 15. The 2-naphthylmethyl ether of 15 was removed by oxidation with DDQ (Xia et al., 2000, *Tetrahedron Lett;* 41:169-173) and the resulting glycosyl acceptor 16 was glycosylated with 7 in the presence of a catalytic amount of TMSOTf in a mixture of dichloromethane and diethyl ether to give anomerically pure trisaccharide 17. Deprotection of 17 was accomplished by reduction of the azides with trimethyl phosphine (Alper et al., 1998, *J. Am. Chem. Soc;* 120:1965-1978) followed by acetylation of the resulting amine with acetic anhydride in pyridine and then reductive removal of the benzyl ethers and benzyloxycarbamate by catalytic hydrogenation over Pd to give compound 2.

For immunological evaluations, trisaccharides 1 and 2 were conjugated to BSA by reaction with S-acetylthioglycolic acid pentafluorophenyl ester to afford the corresponding thioacetate derivatives, which after purification by size-exclusion chromatography were de-S-acetylated using 7% ammonia (g) in DMF and conjugated to maleimide activated BSA (BSA-MI, Pierce Endogen, Inc.) in a phosphate buffer (pH 7.2). After purification using a centrifugal filter device with a nominal molecular weight cut-off of 10 KDa, neoglycoproteins were obtained with an average of eleven and nineteen molecules of 1 and 2, respectively per BSA molecule as determined by Bradford's protein assay and quantitative carbohydrate analysis by high-performance anion-exchange chromatography with pulsed amperometric detection (HPAEC-PAD).

Next, conjugates of KLH and BSA to the polysaccharide of *B. anthracis* were prepared for immunizing rabbits and to examine anti-sera for anti-polysaccharide antibodies, respectively. To this end, the polysaccharide was treated with 1-cyano-4-dimethylaminopyridinium tetrafluoroborate (CDAP) (Shafer et al., 2000, *Vaccine;* 18:1273-1281) to form reactive cyanyl esters, which were condensed with free amines of BSA and KLH to give, after rearrangement of isourea-type intermediate, carbamate-linked polysaccharides. The KLH- and BSA-polysaccharide conjugate solutions were purified using centrifugal filter devices (Micron YM 30,000 Da) and then lyophilized. Saccharide loadings of 0.3 mg/mg BSA and 0.96 mg/mg KLH were determined by bicinchoninic acid (BCA; BSA-conjugate) and Bradford's (KLH-conjugate) protein assay and quantitative carbohydrate analysis by HPAEC-PAD. In addition, maltoheptaose was conjugated to BSA using CDAP to obtain a control conjugate to examine for the possible presence of anti-linker antibodies (Buskas et al., 2004, *Chem. Eur. J;* 10:3517-3524).

Figure 35:
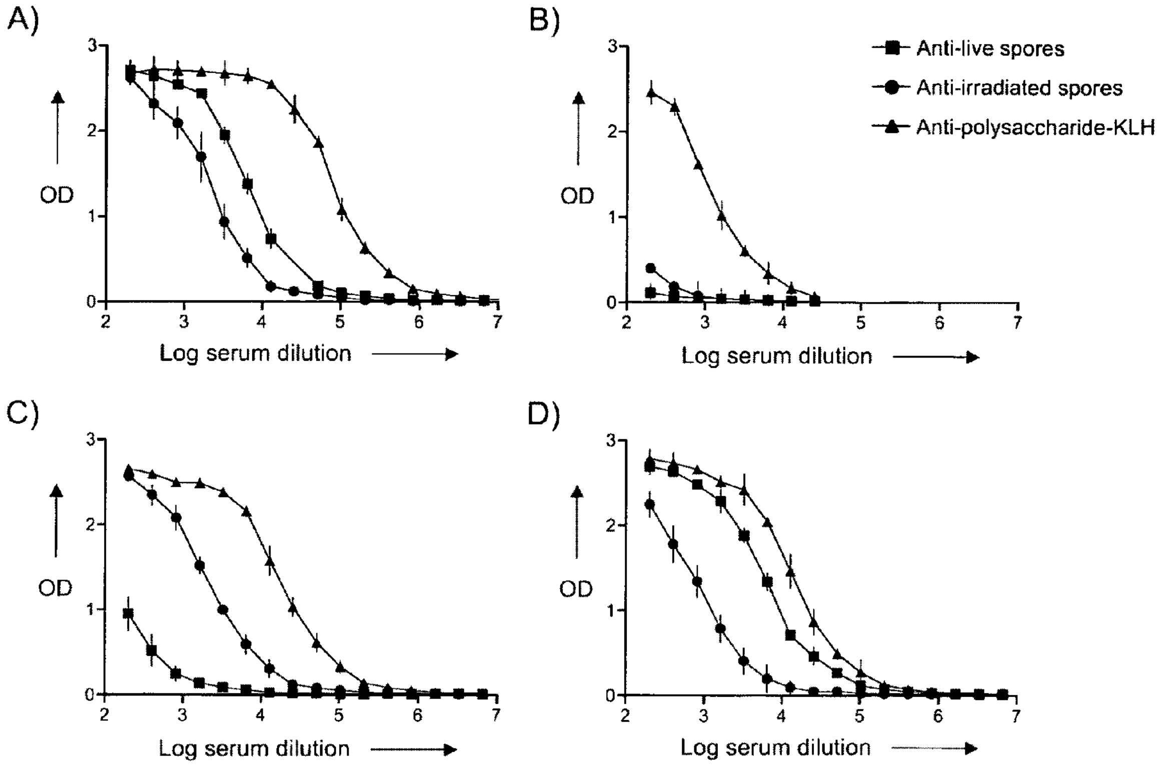
FIGS. 35A-35D demonstrate the immunoreactivity of polysaccharide and trisaccharides 1 and 2 to antisera elicited by *B. anthracis* Sterne live spores, irradiated-killed spores, and polysaccharide-KLH conjugate. Microtiter plates were coated with polysaccharide-BSA (FIG. 35A), maltoheptaose-BSA (FIG. 35B), 1-BSA (FIG. 35C), and 2-BSA (FIG. 35D) conjugates (0.15 μg $mL^{-1}$ carbohydrate). Serial dilutions of rabbit anti-live and anti-irradiated *B. anthracis* Sterne 34F2 spores antisera and rabbit anti-polysaccharide-KLH antiserum (starting dilution 1:200) were applied to coated microtiter plates. Serial dilutions of the pre-immune sera of the rabbits (starting dilution 1:200) did not show any binding to polysaccharide-BSA. Wells only coated with BSA at the corresponding protein concentration did not show binding to any sera. The optical density (OD) values are reported as the means±SD of triplicate measurements.

Rabbits were inoculated intramuscularly four times at biweekly intervals with live- or irradiated spores ($3\times10^6$ total spores) (Example 3; see also, Mehta et al., 2006, Chem. Eur. J; 12:9136-9149), or polysaccharide-KLH conjugate followed by the collection of terminal bleeds fourteen days after the last immunization. ELISA was used to examine the pre- and post-immune sera for polysaccharide recognition. Thus, microtiter plates were coated with the polysaccharide-BSA conjugate and serial dilutions of sera added. An anti-rabbit IgG antibody labeled with horseradish peroxidase was employed as a secondary antibody for detection purposes. High titers of anti-polysaccharide IgG antibodies had been elicited by the polysaccharide-KLH conjugate (see Table 9 and FIG. 35A). Furthermore, inoculation with live and irradiated spores resulted in the production of IgG antibodies that can recognize the polysaccharide. Antisera obtained from immunizations with polysaccharide-KLH conjugate showed recognition of maltoheptaose linked to BSA albeit at much lower titers than when polysaccharide linked to BSA was used as ELISA coating. This finding indicates that some anti-linker antibodies had been elicited (Buskas et al., 2004, *Chem. Eur. J;* 10:3517-3524). As expected, antisera from rabbits immunized with live and irradiated spores showed no reactivity towards the maltoheptaose conjugate (FIG. 35B).

TABLE 9

ELISA antibody titers after immunization with *B. anthracis* Sterne live spores, irradiated-killed spores, and polysacchride-KLH.

| | Immunization | | |
|---|---|---|---|
| Coating | live spores | irradiated spores | polysaccharide-KLH |
| polysaccharide-BSA | 18,500 | 6,100 | 239,700 |
| maltoheptaose-BSA | 0 | 0 | 3,600 |
| 1-BSA | 400 | 6,800 | 57,300 |
| 2-BSA | 18,700 | 2,600 | 46,700 |

ELISA plates were coated with BSA conjugates (0.15 μg $mL^{-1}$ carbohydrate) and titers determined by linear regression analysis, plotting dilution versus absorbance. Titers are defined as the highest dilution yielding an optical density of 0.5 or greater.

Next, the specificity of the anti-polysaccharide antibodies was investigated using synthetic trisaccharides 1 and 2 (FIG. 33) linked to BSA. Trisaccharides 1 and 2 were equally well recognized by IgG antibodies elicited by the polysaccharide-KLH conjugate and irradiated-killed spores (see Table 9, FIG. 35C and FIG. 35D). Surprisingly, antisera obtained after inoculation with live spores recognized trisaccharide 2 much better than trisaccharide 1.

Figure 36:
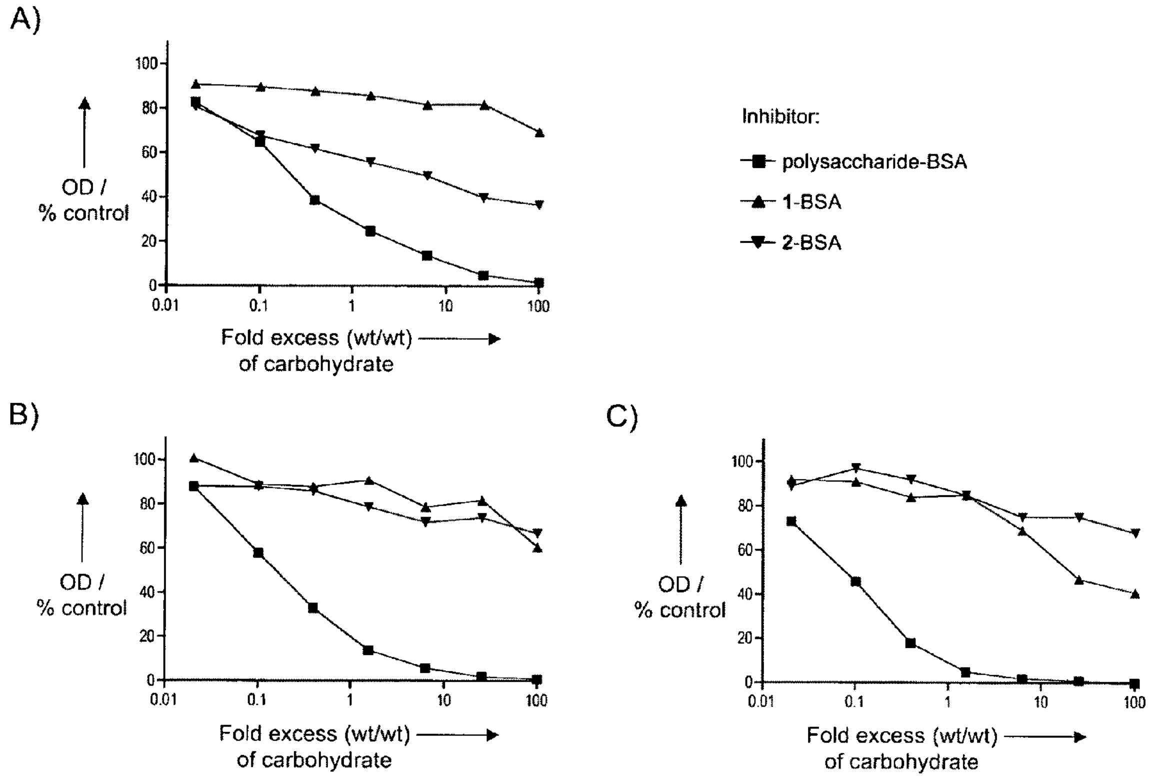
FIGS. 36A-36C present competitive inhibition ELISA. Microtiter plates were coated with polysaccharide-BSA conjugate (0.15 μg $mL^{-1}$ carbohydrate). Dilutions of rabbit anti-live (FIG. 36A) and anti-irradiated (FIG. 36B) *B. anthracis* Sterne 34F2 spores antisera and rabbit anti-polysaccharide-KLH antiserum (FIG. 36C) mixed with polysaccharide-BSA, 1-BSA, and 2-BSA (0-100-fold excess, wt/wt based on carbohydrate concentration) were applied to coated microtiter plates. Maltoheptaose-BSA conjugate and unconjugated BSA at corresponding concentrations mixed with antisera did not display inhibition. OD values were normalized for the OD values obtained in the absence of inhibitor (0-fold "excess", 100%).

To further study the antigenic components of the various antisera, inhibition ELISAs were performed by coating microtiters plates with polysaccharide-BSA conjugate and using 1-BSA, 2-BSA, and polysaccharide-BSA as inhibitors (FIGS. 36A-36C). As expected, for each anti-serum, the polysaccharide-BSA inhibitor could completely block the binding of IgG antibodies to immobilized polysaccharide, whereas only partial inhibition was observed for 1-BSA and 2-BSA. Furthermore, antibodies elicited by the live spore vaccine recognized trisaccharide 2 much better than 1, whereas the KLH-polysaccharide antiserum was better inhibited by 1. Antibodies elicited by the irradiated spore inoculum recognized 1 and 2 equally well. The partial inhibition by the synthetic compounds indicates that heterogeneous populations of antibodies have been elicited. Furthermore, the difference in antigenic component of the vaccines may be due to differences in presentation of the polysaccharide when part of vegetative cells, or attached to KLH, or when part of irradiated-killed spores.

The results presented here show that both live- and irradiated-killed *B. anthracis* spore inoculae and polysaccharide linked to the carrier protein KLH can elicit IgG antibodies that recognize isolated polysaccharide and the relatively small saccharides 1 and 2. Previously, the polysaccharide was identified as a component of the vegetative cell wall of *B. anthracis*, and thus, it was surprising that irradiated-killed spores could elicit anti-polysaccharide antibodies. It appears that not only vegetative cells but also *B. anthracis* spores express the polysaccharide. The implication of this finding is that a polysaccharide-based vaccine may provide immunity towards vegetative cells as well as spores. Thus, immune responses to dormant *B. anthracis* spores at the mucosal surface may inhibit spore uptake across the mucosa and may also target the susceptible emergent vegetative cell, thus preventing bacterial proliferation or enhancing bacterial clearance. Highly conserved integral carbohydrate components of the spore and vegetative cell structure are attractive vaccine candidate antigens because, unlike capsules, they are not sloughed off the replicating cell. Finally, this example has located important antigenic components of the various antisera using synthetic saccharides.

This example demonstrates the development of vegetative and spore-specific reagents for the detection and targeting of non-protein structures in *B. anthracis*. These structures may in turn provide a platform for directing immune responses to spore structures during the early stages of the *B. anthracis* infection process. Ongoing studies will demonstrate whether anti-polysaccharide antibodies can recognize *B. anthracis* spores including the highly virulent *B. anthracis* Ames and *B. anthracis* cured of virulence plasmids (pXO1 and pXO2). Examination of the cross reactivity of the antisera with cell wall polysaccharides from various *Bacillus* species and determination of antigenic responses against the synthetic oligosaccharides are also underway.

Materials and Methods

General chemical procedures. $^1$H-NMR spectra were recorded in $CDCl_3$ or $D_2O$ on a Varian Merc-300 or Varian Inova-500 spectrometers equipped with Sun workstations at 300 K. TMS ($\delta_H$ 0.00) or $D_2O$ ($\delta_H$ 4.67) was used as the internal reference. $^{13}$C-NMR spectra were recorded in $CDCl_3$ or $D_2O$ at 75 MHz on Varian Merc-300 spectrometer, respectively using the central resonance of $CDCl_3$ ($\delta_C$ 77.0) as the internal reference. COSY, HSQC, HMBC, and TOCSY experiments were used to assist assignment of the products. Mass spectra were obtained on Applied Biosystems Voyager DE-Pro MALDI-TOF (no calibration) and Bruker DALTONICS 9.4T (FTICR, external calibration with BSA). Optical rotary power was obtained on JASCO P-1020 polarimeter at 300 K. Chemicals were purchased from Aldrich or Fluka and used without further purification. DCM, acetonitrile, and toluene were distilled from calcium hydride; THF from sodium and MeOH from magnesium and iodine. Aqueous solutions are saturated unless otherwise specified. Molecular sieves were activated at 350° C. for 3 h in vacuo. All reactions were performed under anhydrous conditions under argon and monitored by TLC on Kieselgel 60 F254 (Merck). Detection was by examination under UV light (254 nm) and by charring with 10% sulfuric acid in methanol. Silica gel (Merck, 70-230 mesh) was used for chromatography. Iatrobeads 6RS-8060 was purchased from Bioscan. L denotes spacer.

Figure 37:
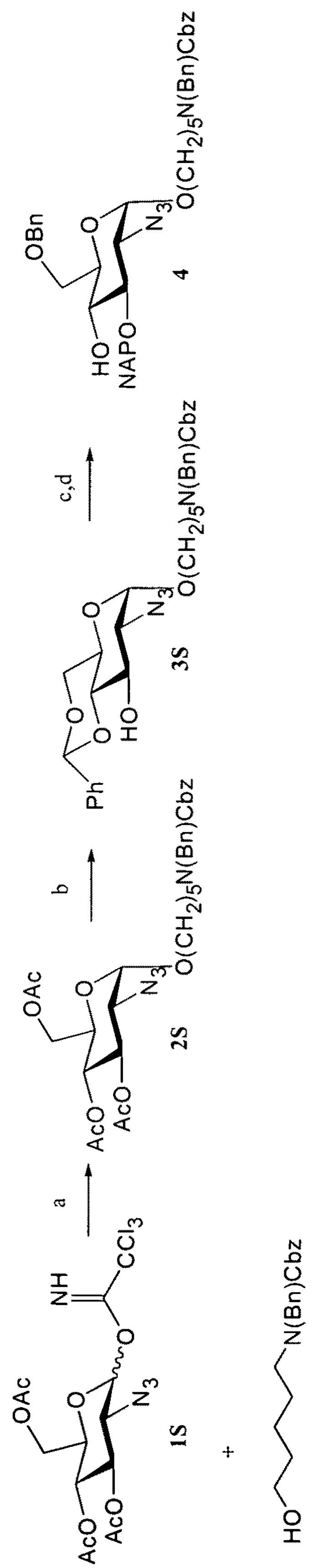
FIG. 37 presents Scheme 1S for the synthesis of compound 4 of Example 10. Reagents and conditions. a) NIS/TMSOTf, DCM 0° C.; b) DDQ, DCM, $H_2O$; c) TMSOTf, DCM, $Et_2O$, 50° C.; d) Zn/$CuSO_4$, AcOH, $Ac_2O$, THF; e) NaOMe, MeOH then $Pd(OH)_2$/C, $H_2$, AcOH, t-BuOH, $H_2O$; f) NaOMe, MeOH; g) $Tf_2O$, pyridine, DCM, 0° C.; h) $NaN_3$, DMF, 50° C.; i) $PMe_3$, THF, $H_2O$ then $Ac_2O$, pyridine; j) $Pd(OH)_2$/C, $H_2$, AcOH, t-BuOH, $H_2O$.

Preparation of Compounds (Scheme 1 of FIG. 34 and Scheme 1S of FIG. 37)

N-Benzyl-N-benzyloxycarbonyl-5-aminopentyl 3,4,6-tri-O-acetyl-2-azido-2-deoxy-<-D-glucopyranoside (2S). A mixture of glucosyl donor 1S (3.89 g, 8.2 mmol), N-benzyl-N-benzyloxy-carbonyl-5-aminopropanol (3.49 g, 10.0 mmol) was co evaporated with dry toluene (2×10 mL) and then dried in vacuo for 4 h. The dried compounds were dissolved in a mixture of DCM and diethyl ether (80 mL, ¼, v/v) and 4 Å MS was added. The mixture was stirred under an atmosphere of argon for 30 min and then cooled (0° C.). TMSOTf (74 µL, 0.41 mmol) was added and stirring was continued for 10 min and then the reaction mixture was quenched by the addition of pyridine (0.1 mL). The reaction mixture was filtered through celite and the filtrate concentrated in vacuo. The residue was purified by silica gel column chromatography (hexane/ethyl acetate, 3/1, v/v) to give 2S (4.2 g, 80%) as a clear oil. $R_f$=0.3 (hexane/ethyl acetate, 3/1, v/v). $^1$H (500 MHz, $CDCl_3$): δ=7.38-7.19 (m, 10H, aromatic), 5.48 (t, 1H, $J_{2,3}$=10.5 Hz, $J_{3,4}$=10.0 Hz, H-3), 5.21-5.17 (bd, 2H, $CH_2$, $L_{Bn}$), 5.05 (t, 1H, $J_{3,4}$=$J_{4,5}$=10.0 Hz, H-4), 4.96-4.29 (bd, 1H, H-1), 4.51 (bs, 2H, $CH_2$, $L_{Bn}$), 4.30-4.27 (m, 1H, H-6a), 4.10-4.06 (m, 1H, H-6b), 4.00 (m, 1H, H-5), 3.70-3.65 (m, 1H, CHH-L), 3.49-3.41 (m, 1H, CHH-L), 3.29-3.26 (dd, 1H, $J_{1,2}$=3.5 Hz, $J_{2,3}$=10.5 Hz), 3.22 (m, 1H, $CH_2$-L), 2.1-2.04 (s, 9H, 3×$COCH_3$), 1.65-1.53 (m, 4H, 2×$CH_2$-L), 1.38-1.25 (m, 2H, $CH_2$-L). $^{13}$C (75 MHz, $CDCl_3$): δ=170.79, 170.24, 170.21, 169.88, 169.82, 138.13, 128.76, 128.67, 128.15, 128.08, 127.53, 98.06 (C-1), 70.57, 68.87, 68.82, 68.67, 67.77, 67.39, 62.10, 61.03, 50.77, 50.50, 47.23, 46.35, 29.20, 23.52, 20.93, 20.83. HR-MALDI-TOF/MS (m/z) calcd for $C_{32}H_{40}N_4O_{10}$ $[M+Na]^+$: 663.2642. found: 663.2643.

N-Benzyl-N-benzyloxycarbonyl-5-aminopentyl 4,6-benzylidene-2-azido-2-deoxy-<-D-glucopyranoside (3S). Compound 2S (2.2 g, 3.43 mmol) was dissolved in methanol (15 mL) and sodium metal (79.0 mg, 0.34 mmol) was added and the resulting reaction mixture was stirred for 2 hours (h). The reaction mixture was then neutralized with weak acid resin (Amberlite IRC-50) and filtered. The filtrate was concentrated under reduced pressure and dried in vacuo. The resulting crude product was dissolved in acetonitrile (20 mL) and benzaldehyde dimethylacetal (0.78 mL, 5.15 mmol) was added followed by camphorsulfonic acid (55.7 mg, 0.24 mmol). The reaction mixture was stirred for 11 h and then quenched by addition of $Et_3N$ and concentrated in vacuo. The residue was purified by a silica gel column chromatography (hexane/ethyl acetate, 4/1, v/v) to give 3S (1.6 g, 83%) as a clear oil. $R_f$=0.25 (hexane/ethyl acetate, 4/1, v/v). $^1$H (500 MHz, $CDCl_3$): δ=7.51-7.19 (m, 15H, aromatic), 5.55 (s, 1H, >CHPh), 5.21-5.18 (bd, 2H, $CH_2$, $L_{Cbz}$), 4.89-4.86 (bd, 1H, H-1), 4.51 (bs, 2H, $CH_2$, $L_{Bn}$), 4.27-4.22 (m, 2H, H-6a, H-3), 3.85 (m, 1H, H-5), 3.76-3.67 (t, 1H, $J_{5,6a}$=$J_{6a,6b}$=10.0 Hz, H-6b) 3.67 (m, 1H, CHH-L), 3.52 (t, 1H, $J_{3,4}$=$J_{4,5}$=9.5 Hz, H-4), 3.45-3.39 (m, 1H, CHH-L), 3.30-3.23 (m, 3H, H-2, $CH_2$-L), 2.78 (s, 1H, OH), 1.66-1.59 (m, 4H, 2×$CH_2$-L), 1.39-1.34 (m, 2H, $CH_2$-L). $^{13}$C (75 MHz, $CDCl_3$): δ=138.14, 137.13, 129.59, 129.32, 128.77, 128.68, 128.61, 128.14, 128.08, 127.53, 126.48, 102.29 (>CHPh), 98.80 (C-1), 82.13, 69.08, 68.89, 68.67, 67.41, 63.26, 62.67, 50.81, 47.30, 29.30, 28.08, 23.53. HR-MALDI-TOF/MS (m/z) calcd for $C_{33}H_{38}N_4O_7$ $[M+Na]^+$: 625.2638. found: 625.2639.

N-Benzyl-N-benzyloxycarbonyl-5-aminopentyl 2-azido-6-O-benzyl-2-deoxy-3-O-(2-napthyl-methyl)-<-D-glucopyranoside (4). Compound 3S (0.5 g, 0.83 mmol) was dissolved in DMF (6 mL) and after cooling (0° C.), 60% NaH (60.0 mg, 1.5 mmol) was added and the resulting mixture was stirred under an atmosphere of argon for 20 min. 2-Naphthylmethyl bromide (0.24 g, 1.08 mmol) was added and the reaction mixture was stirred for 3 h and then quenched by the addition of methanol (0.5 mL). The reaction mixture was diluted with DCM (15 mL) and washed with aqueous solution of $NaHCO_3$ (sat., 10 mL) and brine (10 mL). The organic layer was dried ($MgSO_4$), filtered and the filtrate concentrated in vacuo. The residue was purified by silica gel column chromatography (hexane/ethyl acetate, 4/1, v/v) to give N-benzyl-N-benzyloxycarbonyl-5-aminopentyl 4,6-benzylidene-3-O-(2-napthylmethyl)-2-azido-2-deoxy-<-D-glucopyranoside (0.60 g, 98%) as a clear oil. $R_f$=0.35 (hexane/ethyl acetate, 4/1, v/v). $^1$H (500 MHz, $CDCl_3$): δ=7.84-7.20 (m, 22H, aromatic), 5.64 (s, 1H, >CHPh), 5.22-5.19 (bd, 2H, $CH_2$, $L_{Cbz}$), 5.13 (d, 1H, $J_{HaHb}$=11.5 Hz, $CH_aH_b$, napthylmethyl), 5.00 (d, 1H, $J_{HaHb}$=11.0 Hz, $CH_aH_b$, napthylmethyl), 4.90-4.87 (bd, 1H, H-1), 4.54-4.52 (bd, 2H, $CH_2$, $L_{Bn}$), 4.31-4.30 (m, 1H, H-6a), 4.15 (t, 1H, $J_{2,3}$=$J_{3,4}$=9.0 Hz, H-3), 3.91 (m, 1H, H-5), 3.81-3.67 (m, 3H, H-6b, H-4, CHH-L), 3.50-3.46 (m, 1H, CHH-L), 3.41-3.86 (dd, 1H, $J_{1,2}$=3.5 Hz, $J_{2,3}$=10.0 Hz, H-2), 3.31-3.23 (m, 2H, $CH_2$-L), 1.67-1.55 (m, 4H, 2×$CH_2$-L), 1.42-1.29 (m, 2H, $CH_2$-L). $^{13}$C (75 MHz, $CDCl_3$): δ=138.14, 137.43, 135.63, 133.52, 133.31, 129.30, 128.77, 128.67, 128.55, 128.41, 128.20, 128.14, 128.07, 127.88, 127.51, 127.14, 126.30, 126.27, 126.21, 126.10, 101.72 (>CHPh), 98.78 (C-1), 83.08, 76.36, 75.27, 69.17, 68.60, 67.40, 63.29, 62.96, 50.80, 47.31, 29.28, 23.52. HR-MALDI-TOF/MS (m/z) calcd for $C_{44}H_{46}N_4O_7$ $[M+Na]^+$: 765.3264. found: 765.3262.

The above compound (0.55 g, 0.74 mmol) was dissolved in DCM (7 mL) and 4 Å MS (1.0 g) was added and the resulting mixture stirred under an atmosphere of argon for 30 min. The mixture was cooled (−78° C.) and $Et_3SiH$ (0.3 mL, 1.85 mmol) was added followed by TfOH (0.16 mL, 1.85 mmol). The reaction mixture was stirred for 30 min and then quenched with MeOH (1 mL) and $Et_3N$ (1 mL) and diluted with DCM (7 mL). The reaction mixture was filtered through celite and the filtrate washed with aqueous solution of $NaHCO_3$ (sat., 7 mL) and brine (7 mL). The organic layer was dried ($MgSO_4$) and concentrated in vacuo. The residue was purified by silica gel column chromatography (hexane/ethyl acetate, 4/1, v/v) to give 4 (0.48 g, 87%) as a clear oil. $R_f$=0.25 (hexane/ethyl acetate, 4/1, v/v). $^1H$ (500 MHz, $CDCl_3$): δ=7.88-7.19 (m, 22H, aromatic), 5.22-5.17 (bd, 2H, $CH_2$, $L_{Cbz}$), 5.09 (d, 1H, $J_{HaHb}$=11.0 Hz, $CH_aH_b$, napthylmethyl), 5.02-4.99 (m, 1H, $CH_aH_b$, napthylmethyl), 4.91-4.89 (bd, 1H, H-1), 4.64-4.51 (m, 4H, $CH_2$, OBn, $CH_2$, $L_{Bn}$), 3.93-3.91 (m, 1H, H-3), 3.80-3.71 (m, 5H, H-4, H-5, H-6a,b, CHH-L), 3.47-3.41 (m, 1H, CHH-L), 3.34-3.21 (dd, 1H, $J_{1,2}$=3.0 Hz, $J_{2,3}$=10.0 Hz, H-2), 3.28-3.23 (m, 2H, $CH_2$-L), 1.59-1.54 (m, 4H, $2\times CH_2$-L), 1.42-1.28 (m, 2H, $CH_2$-L). $^{13}C$ (75 MHz, $CDCl_3$): δ=138.09, 135.85, 133.56, 133.31, 128.78, 128.67, 128.22, 128.16, 128.05, 127.92, 127.90, 127.54, 127.06, 126.34, 126.19, 126.13, 98.14 (C-1), 80.02, 75.28, 73.91, 72.62, 70.48, 70.02, 68.27, 67.44, 63.01, 50.63, 29.14, 23.52. HR-MALDI-TOF/MS (m/z) calcd for $C_{44}H_{48}N_4O_7$ $[M+Na]^+$: 767.3421. found: 767.3450.

N-Benzyl-N-benzyloxycarbonyl-5-aminopentyl 2-O-acetyl-3,4,6-tri-O-benzyl-β-D-galacto-pyranosyl-(1→4)-2-azido-6-O-benzyl-2-deoxy-3-O-(2-naphthylmethyl)-α-D-glucopyrano-side (5). A mixture of galactosyl donor 3 (0.18 g, 0.35 mmol), glucosyl acceptor 4 (0.20 g, 0.27 mmol), and 4 Å MS (0.4 g) in dichloromethane (5 mL) was stirred at room temperature under an atmosphere of argon for 30 min. The reaction mixture was cooled (0° C.) and then NIS (78.7 mg, 0.35 mmol) and TMSOTf (7.0 μL, 0.035 mmol) were sequentially added. The reaction mixture was stirred for 10 min and then quenched with pyridine (50 μL). The reaction mixture was diluted with dichloromethane (5 mL) filtered through celite and washed with aqueous solution of $Na_2S_2O_3$ (15%, 10 mL), $NaHCO_3$ (sat., 7 mL), and water (7 mL). The organic layer was dried ($MgSO_4$), filtered and the filtrate concentrated in vacuo. The residue was purified by silica gel column chromatography (hexane/ethyl acetate, 4/1, v/v) to give 5 (0.28 g, 87%) as a clear oil. $R_f$=0.35 (hexane/ethyl acetate, 4/1, v/v). $[\alpha]^{25}_D$=+46.3 (c 1.05, $CHCl_3$); $^1H$ (500 MHz, $CDCl_3$): δ 7.69-6.92 (m, 37H, aromatic), 5.28 (dd, 1H, $J_{1,2}$=8.0 Hz, $J=_{2',3'}$=8.5 Hz, H-2'), 5.19 (d, 1H, $J_{HaHb}$=11.0 Hz, $CH_aH_b$, napthylmethyl), 5.11-5.08 (bd, 2H, $CH_2$-$L_{Cbz}$), 4.86 (d, 1H, CHH, OBn), 4.74-4.72 (bd, 2H, $CH_aH_b$, napthylmethyl, H-1), 4.63-4.55 (dd, 2H, $CH_2$, OBn), 4.44-4.42 (bd, 2H, $CH_2$-$L_{Bn}$), 4.37-4.31 (dd, 3H, $CH_2$, OBn), 4.28 (d, 1H, $J_{1,2}$=8.0 Hz, H-1'), 3.89-3.81 (m, 5H, H-4', H-3, H-4, $CH_2$, OBn), 3.69-3.67 (m, 1H, H-5'), 3.59-3.50 (m, 3H, H-5, H-6a, b), 3.23-3.14 (m, 6H, H-2, H-3', H-6'a,b, 3×CHH-L), 3.04-3.02 (m, 1H, CHH-L), 1.88 (s, 3H, $COCH_3$), 1.52-1.48 (m, 4H, $2\times CH_2$-L), 1.27-1.18 (m, 2H, $CH_2$-L). $^{13}C$ (75 MHz, $CDCl_3$): δ 169.55, 138.97, 138.27, 138.19, 138.05, 136.62, 133.53, 133.10, 128.77, 128.68, 128.65, 128.52, 128.47, 128.28, 128.24, 128.15, 128.10, 128.07, 127.95, 127.92, 127.82, 127.80, 127.76, 127.51, 126.51, 125.82, 101.03 (C-1'), 97.99 (C-1), 80.70, 78.01, 77.68, 77.46, 77.26, 76.83, 75.21, 74.84, 73.81, 73.54, 73.35, 72.74, 72.17, 71.89, 70.82, 68.42, 68.04, 67.80, 67.39, 63.23, 29.24, 23.52, 21.32. HR-MALDI-TOF/MS (m/z) calcd for $C_{73}H_{78}N_4O_{13}[M+Na]^+$: 1241.5455. found: 1241.5457.

N-Benzyl-N-benzyloxycarbonyl-5-aminopentyl 2-O-acetyl-3,4,6-tri-O-benzyl-β-D-galacto-pyranosyl-(1→4)-6-O-benzyl-2-azido-2-deoxy-α-D-glucopyranoside (6). DDQ (49.0 mg, 0.21 mmol) was added to a solution of compound 5 (0.22 g, 0.18 mmol) in a mixture of dichloromethane and water (2.2 mL, 10/1, v/v). The reaction mixture was stirred vigorously at room temperature for 2 h in the dark and then quenched with an aqueous mixture of citric acid, ascorbic acid, and NaOH (0.1 mL, 1.2%, 1.0%, 0.92% w/v). The mixture was diluted with ethyl acetate (15 mL) and washed with aqueous $NaHCO_3$ (sat., 5 mL). The organic layer was dried ($MgSO_4$) and filtered, and the filtrate concentrated in vacuo. The residue was purified by silica gel column chromatography (hexane/ethyl acetate, 4/1, v/v) to give 6 (0.18 g, 94%) as a clear oil. $R_f$=0.30 (hexane/ethyl acetate, 4/1, v/v). $[\alpha]^{25}_D$=+66.0 (c 0.87, $CHCl_3$); $^1H$ (500 MHz, $CDCl_3$): δ 7.41-7.30 (m, 30H, aromatic), 5.38 (dd, 1H, $J_{1',2'}$=8.0 Hz, $J_{2',3'}$=8.5 Hz, H-2'), 5.20 (bd, 2H, $CH_2$-$L_{Cbz}$), 4.93 (d, 1H, CHH—OBn), 4.83-4.81 (bd, 1H, H-1), 4.70-4.66 (dd, 2H, $CH_2$, OBn), 4.58-4.42 (m, 8H, 5×CHH, OBn, $CH_2$-$L_{Bn}$), 4.34 (d, 1H, $J_{1',2'}$=8.0 Hz, H-1'), 4.11 (t, 1H, $J_{2,3}$=9.5 Hz, $J_{3,4}$=9.0 Hz, H-3), 3.89-3.88 (bd, 1H, H-4'), 3.73-3.60 (m, 7H, H-4, H-6a,b, H-5', H-6'a,b, H-5), 3.47-3.43 (m, 2H, H-3', CHH-L), 3.29-3.22 (m, 3H, 3×CHH-L), 3.16-3.13 (dd, 1H, $J_{2,3}$=9.5 Hz, $J_{1,2}$=3.5 Hz, H-2), 1.96 (s, 3H, $COCH_3$), 1.61-1.54 (m, 4H, $CH_2$-L), 1.36-1.27 (m, 2H, $CH_2$-L). $^{13}C$ (75 MHz, $CDCl_3$): δ169.45, 138.39, 138.18, 137.88, 137.55, 128.76, 128.73, 128.64, 128.54, 128.45, 128.22, 128.18, 128.07, 128.04, 127.94, 127.91, 127.72, 127.49, 101.80 (C-1'), 98.10 (C-1), 81.47, 80.47, 76.83, 74.71, 74.21, 74.00, 73.79, 72.40, 72.29, 71.40, 69.80, 69.56, 68.68, 68.40, 68.30, 67.36, 62.59, 29.26, 23.49, 21.21. HR-MALDI-TOF/MS (m/z) calcd for $C_{62}H_{70}N_4O_{13}[M+Na]^+$: 1101.4829. found: 1101.4831.

N-Benzyl-N-benzyloxycarbonyl-5-aminopentyl 2-O-acetyl-3,4,6-tri-O-benzyl-β-D-galacto-pyranosyl-(1→4)-[2,3,4,6-tetra-O-benzyl-α-D-galactopyranosyl-(1→3)]-6-O-benzyl-2-azido-2-deoxy-α-D-glucopyranoside (8). A mixture of 6 (0.098 g, 0.14 mmol) and 7 (0.1 g, 0.092 mmol) was co-evaporated with dry toluene (3×7 mL) and dried in vacuo for 4 h. The dried compounds were dissolved in a mixture of diethyl ether and dichloromethane (7 mL, 5/1, v/v) and 4 Å MS (0.28 g) was added. The mixture was stirred under an atmosphere of argon for 30 min and then cooled (−50° C.). TMSOTf (2.5 μL, 0.014 mmol) was added and the reaction mixture was allowed to reach 0° C. gradually over a period of 1 h. The reaction was then quenched by the addition of pyridine (20 μL), diluted with dichloromethane (7 mL), and filtered through celite. The filtrate was washed with aqueous $NaHCO_3$ (sat., 7 mL) and the organic layer was dried ($MgSO_4$) and filtered, and the filtrate was concentrated in vacuo. The residue was purified by silica gel column chromatography (hexane/ethyl acetate, 4/1, v/v) to give 8 (0.13 g, 86%) as a clear oil. $R_f$=0.35 (hexane/ethyl acetate, 4/1, v/v). $[\alpha]^{25}_D$=+59.4 (c 1.72, $CHCl_3$); $^1H$ (500 MHz, $CDCl_3$): δ 7.35-7.14 (m, 50H, aromatic), 5.76 (d, 1H, $J_{1,2}$=3.0 Hz, H-1"), 5.28 (t, 1H, $J_{2,3}$=9.5 Hz, $J_{1,2}$=8.0 Hz, H-2'), 5.18-5.16 (bd, 2H, $CH_2$-$L_{Cbz}$), 4.89-4.84 (m, 2H, CHH, OBn, H-1), 4.80-4.71 (dd, 3H, 3×CHH, OBn), 4.68-4.62 (m, 5H, 3×CHH, OBn, H-1'), 4.54-4.39 (m, 8H, $3\times CH_2$, OBn, $CH_2$-$L_{Bn}$), 4.35-4.24 (m, 3H, CHH, OBn, H-3, H-5"), 4.18-4.04 (m, 5H, $CH_2$, OBn, H-4, H-3", H-2"), 3.99 (bs, 1H, H-4"), 3.84 (bs, 1H, H-4'), 3.80-3.74 (m, 2H, H-6a, H-5), 3.65-3.51 (m, 4H, H-6b, H-6'a, H-6"a,b), 3.44-3.30 (m, 5H, $CH_2$-L, H-2, H-5', H-6'), 3.23-3.17 (m, 3H, $CH_2$-L, H-3'), 1.90 (s, 3H, $COCH_3$), 1.51-1.46 (m, 4H, $2\times CH_2$-L), 1.26-1.20 (m, 2H, $CH_2$-L). $^{13}C$ (75 MHz, $CDCl_3$): δ 169.26, 139.36, 139.18, 138.70, 138.28, 138.24, 138.15, 138.12, 137.08, 128.77, 128.68, 128.63, 128.59, 128.48, 128.42, 128.37, 128.36, 128.34, 128.29, 128.05, 127.95, 127.93, 127.82, 127.80, 127.70, 127.60, 127.53, 127.41, 127.35, 127.30, 99.64 (C-1'), 97.63 (C-1), 96.22 (C-1"), 81.04, 78.64, 76.84, 76.51, 76.28, 75.54, 74.92, 74.68, 73.68, 73.58, 73.45, 73.23, 72.51, 72.40, 72.19, 71.96, 70.49, 70.16, 69.17, 68.76, 68.33, 68.22, 67.37, 62.64, 53.66, 29.13, 23.41, 21.26. HR-MALDI-TOF/MS (m/z) calcd for $C_{96}H_{104}N_4O_{18}$[M+Na]$^+$: 1623.7246. found: 1623.7242.

N-Benzyl-N-benzyloxycarbonyl-5-aminopentyl 2-O-acetyl-3,4,6-tri-O-benzyl-β-D-galacto-pyranosyl-(1→4)-[2,3,4,6-tetra-O-benzyl-α-D-galactopyranosyl-(1→3)]-2-acetamido 6-O-benzyl-2-deoxy-α-D-glucopyranoside (9). Compound 8 (75 mg, 0.047 mmol) was dissolved in a mixture of THF, acetic anhydride, and acetic acid (2.0 mL/1.3 mL/0.7 mL, v/v/v). Zinc powder (40 mg, 0.61 mmol) was added followed by an aqueous solution of copper sulfate (sat., 60 μL) and the resulting reaction mixture was vigorously stirred for 20 min and then filtered through celite. The filtrate was concentrated in vacuo and the residue was purified by silica gel column chromatography (hexane/ethyl acetate, 1/1, v/v) to give 9 (47 mg, 63%) as a clear oil. $R_f$=0.6 (hexane/ethyl acetate, 1/1, v/v). $^1H$ (500 MHz, $CDCl_3$): δ 7.28-7.09 (m, 50H, aromatic), 6.29 (d, 1H, NHAc, $J_{NHAc,2}$=8.5 Hz), 5.22-5.19 (m, 2H, H-1", H-2'), 5.08-5.07 (bd, 2H, $CH_2$-$L_{Cbz}$), 4.76 (bs, 1H, H-1), 4.66-4.54 (m, 6H, 3×$CH_2$, OBn), 4.50-4.44 (m, 4H, CHH, OBn, $CH_2$-$L_{Bn}$, H-1'), 4.40-4.27 (m, 9H, 9×CHH, OBn), 4.17-4.08 (m, 2H, H-2, H-5"), 3.96-3.95 (m, 2H, H-3, H-2"), 3.88 (m, 1H, H-4), 3.80 (m, 2H, H-4', H-4"), 3.75-3.69 (m, 3H, H-5, H-3", H-6"a), 3.63-3.59 (t, 1H, $J_{6a,6b}$=$J_{5,6a}$=9.5 Hz, H-6a), 3.49-3.37 (m, 3H, H-6'a,b, H-6b, 6"b), 3.29-3.26 (m, 1H, H-5), 3.21-3.19 (m, 2H, H-3', CHH-L), 3.12-3.04 (m, 3H, 3×CHH-L), 1.96 (s, 3H, $COCH_3$), 1.86 (s, 3H, $NHCOCH_3$), 1.5-1.42 (m, 4H, 2×$CH_2$-L), 1.26-1.20 (m, 2H, $CH_2$-L). $^{13}C$ (75 MHz, $CDCl_3$): δ 170.58, 169.78, 155.15, 151.23, 150.32, 149.83, 145.13, 142.29, 141.97, 140.39, 139.31, 138.94, 138.86, 138.60, 138.37, 138.24, 138.12, 138.02, 134.75, 134.47, 133.58, 131.44, 131.09, 129.98, 128.76, 128.65, 128.61, 128.60, 128.58, 128.46, 128.40, 128.38, 128.14, 128.11, 128.05, 128.03, 127.90, 127.87, 127.82, 127.74, 127.67, 127.49, 126.88, 126.06, 124.94, 100.05 (C-1"), 97.50 (C-1"), 95.70 (C-1), 80.67, 78.20, 76.83, 75.91, 74.74, 73.97, 73.86, 73.77, 73.58, 73.44, 72.93, 72.50, 72.08, 71.22, 69.39, 68.56, 68.28, 67.37, 67.18, 51.83, 50.39, 47.27, 46.33, 29.93, 29.32, 23.47, 23.23, 21.31. HR-MALDI-TOF/MS (m/z) calcd for $C_{98}H_{108}N_2O_{19}$ [M+Na]$^+$: 1639.7436. found: 1639.7439.

5-Aminopentyl-β-D-galactopyranosyl-(1→4)-[α-D-galactopyranosyl-(1→3)]-2-acetamido-2-deoxy-α-D-glucopyranoside (1). Compound 9 (35 mg, 21.6 μmol) was dissolved in a mixture of methanol and dichloromethane (0.5 mL, 4:1, v/v). Sodium metal (1.0 mg) was added and stirred overnight. The reaction mixture was neutralized with weak acid resin (Amberlite IRC-50) and filtered. The filtrate was concentrated in vacuo and the residue purified by silica gel column chromatography (hexane/ethyl acetate 1/1, v/v) to give deacetylated product (13.0 mg, 90%) as a clear oil. $R_f$=0.5 (hexane/ethyl acetate, 1/1, v/v). $^1H$ (500 MHz, $CDCl_3$): δ 7.24-7.06 (m, 50H, aromatic), 6.21 (bs, 1H, NHAc), 5.48 (bs, 1H, H-1"), 5.08-5.06 (bs, 2H, $CH_2$-$L_{Cbz}$), 4.77-4.75 (m, 2H, H-1, CHH, OBn), 4.70-4.64 (m, 3H, 3×CHH OBn), 4.56-4.53 (m, 3H, H-1', $CH_2$, OBn,), 4.47-4.34 (m, 10H, 4×$CH_2$, OBn, $CH_2$-$L_{Bn}$), 4.23-4.12 (m, 5H, $CH_2$, OBn, H-2, H-5", H-3), 4.02-4.01 (m, 2H, H-2", 4"), 3.85-3.84 (m, 2H, H-4, H-6a), 3.76-3.56 (m, 3H, H-3", H-2', H-4'), 3.62-3.56 (m, 3H, H-6"a, H-6b, H-5), 3.44-3.34 (m, 3H, H-6'a,b, H-6"b), 3.28-3.26 (m, 1H, H-5'), 3.15-3.02 (m, 4H, 2×$CH_2$-L), 2.83-2.80 (m, 1H, H-3'), 1.76 (s, 3H, $NHCOCH_3$), 1.37-1.28 (m, 4H, 2×$CH_2$-L), 1.14-1.03 (m, 2H, $CH_2$-L). $^{13}C$ (75 MHz, $CDCl_3$): δ170.37, 139.25, 138.99, 138.81, 138.72, 138.18, 138.08, 128.77, 128.63, 128.60, 128.53, 128.49, 128.47, 128.34, 128.27, 128.19, 128.06, 128.03, 127.97, 127.90, 127.79, 127.65, 127.60, 127.46, 101.90 (C-1'), 97.69 (C-1"), 96.93 (C-1), 82.33, 82.19, 78.93, 76.82, 75.96, 75.87, 74.94, 74.71, 73.99, 73.87, 73.70, 73.52, 73.20, 73.04, 72.76, 72.56, 72.21, 70.99, 70.65, 69.98, 69.21, 68.57, 67.92, 67.39, 52.79, 50.42, 29.93, 29.19, 29.05, 23.48, 23.32. HR MALDI-TOF/MS: Calcd for $C_{96}H_{106}N_2O_{18}$: 1597.7331. found: 1597.7336 [M+Na]$^+$. The above compound (10.0 mg, 6.35 μmol) was dissolved in a mixture of AcOH, t-BuOH, and $H_2O$ (0.64 mL, 0.3 mL, 0.06 mL, 10:5:1, v/v/v) and placed under argon atmosphere. $Pd(OH)_2/C$ (15.0 mg) was added and the reaction mixture was degassed and placed under $H_2$ atmosphere and stirred for 16 h. The reaction mixture was filtered through a PTFE (polytetrafluoroethylene filter, Fischerbrand, 0.2 μm) filter and the residue washed with acetic acid (2.0 mL). The combined filtrates were concentrated in vacuo and the residue was purified over Iatrobeads (iPrOH/$NH_4OH$/$H_2O$, 3/2/1, v/v/v) to give 1 (2.5 mg, 63%) as a white solid. $R_f$=0.25 (iPrOH/$NH_4OH$/$H_2O$, 3/2/1, v/v/v). $^1H$ (500 MHz, $D_2O$): δ 5.33 (d, 1H, H-1", $J_{1,2}$=3.5 Hz), 4.68 (d, 1H, H-1, $J_{1,2}$=3.0 Hz), 4.39 (d, 1H, $J_{1,2}$=8.0 Hz, H-1'), 3.96-3.84 (m, 4H), 3.65-3.51 (m, 14H), 3.40-3.33 (m, 2H, H-2', CHH-L), 3.85 (t, 2H, $CH_2$-L), 1.90 (s, 3H, $NHCOCH_3$), 1.57-1.51 (m, 4H, 2×$CH_2$-L), 1.32-1.28 (m, 2H, $CH_2$-L). $^{13}C$ (125 MHz, $CDCl_3$): δ 102.95 (C-1"), 99.95 (C-1), 97.18 (C-1), 76.28, 76.17, 75.84, 74.78, 71.46, 71.24, 69.16, 69.71, 69.38, 68.94, 68.06, 61.27, 60.94, 60.07, 53.05 (C-2'), 39.67, 28.51, 27.15, 22.52, 22.38. HR-MALDI-TOF/MS (m/z) calcd for $C_{25}H_{46}N_2O_{16}$[M+Na]$^+$: 653.6255. found: 653.6257.

N-Benzyl-N-benzyloxycarbonyl-5-aminopentyl 2-O-acetyl-3-O-benzyl-4,6-O-benzylidene-2-deoxy-β-D-glucopyranosyl-(1→4)-2-azido-6-O-benzyl-2-deoxy-3-(2-napthylmethyl)-β-D-glucopyranoside (12). A mixture of galactosyl donor 10 (0.41 g, 0.93 mmol), glucosyl acceptor 11 (0.53 g, 0.72 mmol), and 4 Å MS (1.0 g) in dichloromethane (10 mL) was stirred at room temperature under an atmosphere of argon for 30 min. The reaction mixture was cooled (0° C.) and then NIS (0.21 g, 0.93 mmol) and TMSOTf (16.0 μL, 0.09 mmol) were sequentially added. The reaction was stirred for 10 min and then quenched with pyridine (50 μL). The reaction mixture was diluted with dichloromethane (10 mL), filtered through celite, and washed with an aqueous solution of $Na_2S_2O_3$ (15%, 7 mL), $NaHCO_3$ (sat., 7 mL), and water (7 mL). The organic layer was dried ($MgSO_4$) and filtered, and the filtrate concentrated in vacuo. The residue was purified by silica gel column chromatography (hexane/ethyl acetate, 4/1, v/v) to give 12 (0.69 g, 88%) as a white solid. $R_f$=0.35 (hexane/ethyl acetate, 4/1, v/v). $[Q]^{25}_D$=−15.4 (c 2.75, $CHCl_3$); $^1H$ (500 MHz, $CDCl_3$): δ 7.87-7.81 (m, 4H, aromatic), 7.55-7.16 (m, 33H, aromatic), 5.34 (s, 1H, >CHPh), 5.18-5.15 (bd, 2H, $CH_2$-$L_{Cbz}$), 5.03 (d, 1H, $J_{Ha,Hb}$=11.0 Hz, $CH_aH_b$— napthylmethyl), 4.97 (dd, 1H, $J_{1',2'}$=8.0 Hz, $J_{2,3}$=8.5 Hz, H-2'), 4.93 (d, 1H, $J_{Ha,Hb}$=11.0 Hz, $CH_aH_b$— napthylmethyl), 4.84 (d, 1H, CHH, OBn), 4.72 (d, 1H, CHH, OBn), 4.62 (d, 1H, CHH, OBn) 4.52 (d, 1H, $J_{1,2}$=8.0 Hz, H-1'), 4.49-4.47 (bd, 2H, $CH_2$-$L_{Bn}$), 4.42 (d, 1H, CHH, OBn), 4.15-4.12 (m, 1H, H-1), 4.10-4.07 (dd, 1H, $J_{6'a,6'b}$=$J_{5,6a}$=10.0 Hz, H-6'a), 3.96 (m, 1H, H-4), 3.85-3.83 (m, 1H, CHH-L), 3.73-3.65 (m, 2H, H-6a,b), 3.59 (t, 1H, $J_{3'4'}$=9.0 Hz, $J_{4'5'}$=9.5 Hz, H-4'), 3.50 (t, 1H, $J_{2'3'}$=9.5 Hz, $J_{3'4'}$=9.0 Hz, H-3), 3.40-3.25 (m, 7H, $CH_2$-L, H-2, H-4, H-3, H-5, H-6'b), 3.19 (m, 1H, CHH-L), 3.14-3.09 (m, 1H, H-5), 1.93 (s, 3H, $COCH_3$), 1.58-1.51 (m, 4H, $CH_2$-L), 1.38-1.25 (m, 2H, L-$CH_2$). $^{13}C$ (75 MHz, $CDCl_3$): δ 169.34, 138.52, 138.17, 37.99, 137.42, 136.08, 133.50, 133.26, 129.27, 128.76, 128.68, 128.57, 128.49, 128.29, 128.26, 128.17, 128.13, 128.05, 127.98, 127.91, 127.50, 126.89, 126.89, 126.37, 126.30, 126.24, 126.04, 102.25 (C-1), 101.38 (>CHPh), 100.83 (C-1'), 81.83, 81.21, 78.68, 76.58, 75.64, 75.12, 74.27, 73.90, 73.55, 70.11, 68.69, 67.70, 67.37, 66.17, 66.07, 29.39, 23.41, 21.11. HR-MALDI-TOF/MS (m/z) calcd for $C_{66}H_{70}N_4O_{13}$[M+Na]$^+$: 1149.4837. found: 1149.4839.

N-Benzyl-N-benzyloxycarbonyl-5-aminopentyl 3-O-benzyl-4,6-O-benzylidene-β-D-glucopy-ranosyl-(1→4)-2-azido-6-O-benzyl-2-deoxy-3-(2-napthylmethyl)-β-D-glucopyranoside (13). Compound 12 (0.48 g, 0.42 mmol) was dissolved in a mixture of methanol and dichloromethane (7 mL, 3:1, v/v) and sodium metal (10 mg) was added. The reaction mixture was stirred for 18 h and then neutralized with weak acid resin (Amberlite IRC-50) and filtered. The filtrate was concentrated in vacuo and the residue was purified by silica gel column chromatography (hexane/ethyl acetate, 4/1, v/v) to give 13 (0.41 g, 90%) as a clear oil. $R_f$=0.30 (hexane/ethyl acetate, 4/1, v/v). $[\alpha]^{25}_D$=−11.9 (c 6.85, $CHCl_3$); $^1H$ (500 MHz, $CDCl_3$): δ 7.90-7.17 (m, 37H, aromatic), 5.40 (s, 1H, >CHPh), 5.20-5.17 (bd, 2H, $CH_2$—$N_{Cbz}$), 5.06 (d, 1H, $J_{HaHb}$=11.4 Hz, $CH_aH_b$-napthylmethyl), 4.98-4.93 (dd, 2H, $CH_aH_b$— napthylmethyl, CHH, OBn), 4.76 (d, 1H, CHH, OBn), 4.70-4.68 (d, 1H, CHH, OBn), 4.61 (d, 1H, $J_{1'2'}$=6.6 Hz, H-1'), 4.55-4.49 (m, 3H, $CH_2$—$N_{Bn}$, CHH, OBn), 4.22-4.21 (m, 1H, H-1), 4.06-4.03 (m, 2H, H-6'a, H-4), 3.99-3.97 (dd, 1H, $J_{6a,6b}$=$J_{H5,6a}$=10.8 Hz, H-6a), 3.94-3.86 (m, 1H, CHH-L), 3.77 (bd, 1H, H-6b), 3.56 (t, 1H, $J_{3'4'}$=$J_{4'5'}$=9.0 Hz, H-4'), 3.52-3.42 (m, 7H, H-6'b, H-2', H-3, H-5, CHH-L, H-2, H-3'), 3.29-3.22 (m, 2H, $CH_2$-L), 3.15-3.09 (m, 1H, H-5'), 1.65-1.52 (m, 4H, 2×$CH_2$-L), 1.39-1.33 (m, 2H, $CH_2$-L). $^{13}C$ (75 MHz, $CDCl_3$): δ 138.68, 138.20, 137.93, 137.51, 136.10, 133.52, 133.26, 129.24, 128.79, 128.71, 128.70, 128.47, 128.30, 128.27, 128.23, 128.20, 128.17, 128.13, 128.09, 128.06, 128.03, 127.54, 126.41, 126.30, 126.10, 125.98, 103.50 (C-1'), 102.45 (C-1), 101.42 (>CHPh), 81.94, 81.52, 80.60, 75.47, 75.23, 74.90, 74.76, 73.82, 70.15, 68.82, 68.38, 67.41, 66.54, 66.36, 29.45, 23.46. HR-MALDI-TOF/MS (m/z) calcd for $C_{64}H_{68}N_4O_{12}$[M+Na]$^+$: 1107.4732. found: 1107.4739.

N-Benzyl-N-benzyloxycarbonyl-5-aminopentyl 2-azido-3-O-benzyl-4,6-O-benzylidene-2-deoxy-β-D-mannopyranosyl-(1→4)-2-azido-6-O-benzyl-2-deoxy-3-(2-napthylmethyl)-β-D-glucopyranoside (15). Compound 13 (0.23 g, 0.21 mmol) was dissolved in a mixture of dichloromethane and pyridine (7.2 mL, 5/1, v/v). The mixture was cooled (0° C.) and $Tf_2O$ (0.18 mL, 1.06 mmol) was added slowly over 5 min. The reaction mixture was stirred under argon for 5 h, diluted with dichloromethane (10 mL) and washed with aqueous $NaHCO_3$ (sat., 10 mL). The organic layer was dried ($MgSO_4$) and filtered, and the filtrate concentrated to dryness and further dried in vacuo for 2 h. $NaN_3$ (60 mg, 0.92 mmol) was added to the crude product 14 dissolved in dry DMF (8 mL). The resulting mixture was heated at 50° C. for 6 h, after which it was cooled to room temperature, diluted with ethyl acetate (15 mL), and washed with water (7 mL). The organic layer was dried ($MgSO_4$), concentrated in vacuo and the residue was purified by silica gel column chromatography (hexane/ethyl acetate, 4/1 v/v) to give 15 (0.17 g, 70%) as a clear oil. $R_f$=0.50 (hexane/ethyl acetate, 4/1 v/v). $[\alpha]^{25}_D$=−43.8 (c 2.75, $CHCl_3$); $^1H$ (500 MHz, $CDCl_3$): δ 7.87-7.15 (m, 37H, aromatic), 5.41 (s, 1H, >CHPh), 5.17-5.14 (bd, 2H, $CH_2$—$N_{Cbz}$), 5.11 (d, 1H, $J_{HaHb}$=10.5 Hz, $CH_aH_b$-napthylmethyl), 4.93 (d, 1H, $J_{HaHb}$=10.5 Hz, $CH_aH_b$-napthylmethyl), 4.74 (d, 1H, CHH, OBn), 4.67-4.65 (d, 1H, CHH, OBn), 4.61-4.59 (d, 2H, H-1, CHH, OBn), 4.48-4.69 (bd, 2H, $CH_2$—$N_{Bn}$), 4.39 (d, 1H, CHH, OBn), 4.19-4.18 (m, 1H, H-1), 4.00-3.95 (m, 2H, H-6'a, H-5'), 3.90 (t, 1H, $J_{1'2'}$=9.5 Hz, $J_{2'3'}$=9.5 Hz, H-2'), 3.87-3.83 (m, 1H, CHH, L), 3.78 (m, 1H, H-4), 3.71-3.64 (m, 2H, H-6a,b), 3.47-3.37 (m, 6H, H-3, CHH-L, H-6'b, H-3', H-2, H-5), 3.26-3.19 (m, 2H, $CH_2$-L), 3.01-2.97 (m, 1H, H-4'), 1.61-1.50 (m, 4H, 2×$CH_2$-L), 1.36-1.30 (m, 2H, CHH-L). $^{13}C$ (75 MHz, $CDCl_3$): δ 138.18, 138.14, 137.83, 137.52, 136.03, 133.50, 133.29, 129.23, 128.84, 128.77, 128.71, 128.45, 128.39, 128.22, 128.16, 128.09, 128.07, 128.00, 127.74, 127.53, 127.00, 126.41, 126.29, 126.08, 102.37 (C-1), 101.73 (>CHPh), 100.19 (C-1'), 81.49, 78.63, 75.55, 74.51, 73.94, 73.06, 70.19, 68.67, 68.51, 67.44, 67.39, 66.23, 63.87, 29.41, 23.42. HR-MALDI-TOF/MS (m/z) calcd for $C_{64}H_{67}N_7O_{11}$[M+Na]$^+$: 1132.4797. found: 1132.4797.

N-Benzyl-N-benzyloxycarbonyl-5-aminopentyl 2-azido-3-O-benzyl-4,6-O-benzylidene-2-deoxy-β-D-mannopyranosyl-(1→4)-2-azido-6-O-benzyl-2-deoxy-β-D-glucopyranoside (16). DDQ (22 mg, 0.09 mmol) was added to compound 15 (67.0 mg, 0.06 mmol) in a mixture of dichloromethane and water (3.3 mL, 10/1, v/v) and stirred vigorously in the dark for 2 h. The reaction mixture was then quenched with an aqueous mixture of citric acid, ascorbic acid, and NaOH (0.1 mL, 1.2%, 1.0%, 0.92% w/v). The reaction mixture was diluted with ethyl acetate (15 ml) and washed with aqueous $NaHCO_3$ (sat., 5 mL). The organic solvents were dried ($MgSO_4$) and filtered, and the filtrate concentrated in vacuo. The residue was purified by silica gel column chromatography (hexane/ethyl acetate, 4/1, v/v) to give 16 (0.054 g, 94%) as a clear oil. $R_f$=0.40 (hexane/ethyl acetate, 4/1, v/v). $[\alpha]^{25}_D$=−20.2 (c 1.24, $CHCl_3$); $^1H$ (600 MHz, $CDCl_3$): δ 7.40-7.09 (m, 30H, aromatic), 5.48 (s, 1H, >CHPh), 5.11-5.08 (bd, 2H, $CH_2$—$N_{Cbz}$), 4.77 (d, 1H, CHH, OBn), 4.64-4.60 (m, 2H, $CH_2$, OBn), 4.43-4.41 (bd, 2H, $CH_2$—$N_{Bn}$), 4.33 (s, 1H, H-1'), 4.29 (d, 1H, CHH, OBn), 4.23-4.21 (dd, 1H, $J_{6'a,6'b}$=$J_{5',6'}$=10.8 Hz, H-6'a), 4.17-4.15 (m, 1H, H-1), 3.88 (t, 1H, $J_{3'4'}$=$J_{4'5'}$=9.0 Hz, H-4'), 3.81-3.78 (m, 1H, CHH-L), 3.74 (t, 1H, $J_{6'a,6'b}$=$J_{5',6'b}$=10.2 Hz H-6'b), 3.63-3.58 (m, 3H, H-6a,b, H-4), 3.46-3.38 (m, 4H, H-2', H-3', H-3, H-5), 3.36 (m, 1H, CHH-L), 3.24-3.18 (m, 3H, H-2, H-5', CHH-L), 3.13 (m, 1H, CHH-L), 1.56-1.44 (m, 4H, 2×$CH_2$-L), 1.32-1.23 (m, 2H, $CH_2$-L). $^{13}C$ (75 MHz, $CDCl_3$): δ 138.14, 137.95, 137.90, 137.17, 129.35, 128.83, 128.76, 128.68, 128.52, 128.50, 128.20, 128.14, 128.06, 127.74, 127.51, 126.22, 102.29 (C-1), 101.88 (>CHPh), 100.96 (C-1'), 81.12, 78.35, 76.55, 73.82, 73.53, 73.41, 73.38, 70.30, 68.13, 67.53, 67.38, 65.52, 63.60, 29.39, 23.40. HR-MALDI-TOF/MS (m/z) calcd for $C_{53}H_{59}N_7O_{11}$ [M+Na]$^+$: 992.4171. found: 992.4174.

N-Benzyl-N-benzyloxycarbonyl-5-aminopentyl 2-azido-3-O-benzyl-4,6-O-benzylidene-2-deoxy-β-D-mannopyranosyl-(1→4)-[2,3,4,6-tetra-O-benzyl-β-D-galactopyranosyl-(1→3)]-2-azido-6-O-benzyl-2-deoxy-β-D-glucopyranoside (17). A mixture of 7 (0.068 g, 0.096 mmol) and 16 (0.042 g, 0.043 mmol) was co-evaporated with dry toluene (3×5 mL) and then further dried in vacuo for 4 h. The mixture was dissolved in diethyl ether and dichloromethane (4 mL, 5:1, v/v) and 4 Å MS (0.18 g) was added. The mixture was stirred under an atmosphere of argon for 30 min and then cooled (−50° C.). TMSOTf (1.7 μL, 4.6 μmol) was added and the reaction mixture was allowed to reach 0° C. gradually over a period of 1 h. The reaction was quenched by the addition of pyridine (20 μL), diluted with dichloromethane (7 mL) and filtered through celite. The filtrate was washed with aqueous $NaHCO_3$ (sat., 5 mL) and the organic layer was dried ($MgSO_4$) and filtered after which the filtrate was concentrated in vacuo. The residue was purified by silica gel column chromatography (hexane/ethyl acetate, 4/1, v/v) to give 17 (0.052 g, 81%) as a clear oil. $R_f$=0.35 (hexane/ethyl acetate, 4/1, v/v). $^1H$ (500 MHz, $CDCl_3$): δ 7.36-7.05 (m, 45H, aromatic), 5.57 (d, 1H, $J_{1'',2''}$=3.5 Hz, H-1"), 5.31 (s, 1H, >CHPh), 5.10-5.07 (bd, 2H, $CH_2$—$N_{Cbz}$), 4.83 (d, 1H, CHH, OBn), 4.75-4.38 (m, 10H, 7×CHH, OBn, H-1', $CH_2$—$N_{Bn}$), 4.42-4.38 (m, 4H, 2×$CH_2$, OBn), 4.09-4.08 (m, 1H, H-1), 4.04-4.00 (m, 2H, H-2", H-4") 3.97-3.89 (m, 4H, H-6'a, H-3, H-4, H-3'), 3.84-3.75 (m, 2H, CHH-L, H-4'), 3.68-3.65 (m, 3H, H-6a,b, H-2'), 3.61-3.59 (m, 2H, H-6"a,b), 3.52-3.36 (m, 4H, H-6'b, CHH-L, H-2, H-5), 3.29-3.27 (m, 2H, H-5", H-3"), 3.19-3.12 (m, 2H, $CH_2$-L), 2.80-2.75 (m, 1H, H-5'), 1.55-1.44 (m, 4H, 2×$CH_2$-L), 1.30-1.21 (m, 2H, $CH_2$-L). $^{13}C$ (125 MHz, $CDCl_3$): δ 128.98, 128.05, 126.26, 102.53 (C-1), 101.56 (>CHPh), 97.76 (C-1"), 95.99 (C-1"), 79.01, 78.48, 77.24, 76.62, 76.00, 75.65, 74.85, 75.03, 74.50, 73.88, 73.79, 73.53, 73.35, 73.44, 73.09, 72.82, 70.08, 69.72, 69.55, 69.49, 68.28, 67.43, 67.34, 65.57, 63.36, 50.53, 29.48, 23.54, 21.27. HR-MALDI-TOF/MS (m/z) calcd for $C_{87}H_{93}N_7O_{16}[M+Na]^+$: 1514.6577. found: 1514.6578.

N-Benzyl-N-benzyloxycarbonyl-5-aminopentyl 2-acetamido-3-O-benzyl-4,6-O-benzylidene-2-deoxy-β-D-mannopyranosyl-(1→4)-[2,3,4,6-tetra-O-benzyl-α-D-galactopyranosyl-(1→3)]-2-acetamido-6-O-benzyl-2-deoxy-β-D-glucopyranoside (18). Compound 17 (12.0 mgs, 8.04 μmol) was dissolved in THF (0.5 mL) and $H_2O$ (30 μL) and then $PMe_3$ (1M in THF, 50 μL) was added. After stirring the reaction mixture for 4-5 h, the solvents were evaporated and the residue was dissolved in pyridine (1 mL) and acetic anhydride (0.2 mL) and stirring was continued for 8 h. The solvents were then removed in vacuo and the residue purified by silica gel column chromatography (MeOH/DCM, 1/100, v/v) to give 18 (7.0 mgs, 58%) as a clear oil. $R_f$=0.35 (MeOH/DCM, 1/100, v/v). $^1H$ (500 MHz, $CDCl_3$): δ 7.39-7.12 (m, 45H, aromatic), 6.43-6.40 (bd, 1H, NHAc), 5.69-5.67 (bd, 1H, NH'AC), 5.34 (s, 1H, >CHPh), 5.09-5.07 (bd, 3H, $CH_2$—$N_{Cbz}$, H-1"), 4.82-4.80 (d, 2H, H-1', CHH, OBn), 4.70-4.57 (m, 6H, 2×$CH_2$, OBn, H-2', H-1), 4.47-4.34 (m, 9H, 7×CHH, OBn, $CH_2$—$N_{Bn}$), 4.08-3.83 (m, 7H, H-2', H-2, H-6'a, H-3, H-4, H-4', H-5'), 3.72-3.45 (m, 8H, H-6a,b, H-2", H-6'b, H-5", H-3", H-6"a,b), 3.40-3.26 (m, 2H, $CH_2$-L), 3.13-3.07 (m, 3H, $CH_2$-L, H-5'), 1.88 (s, 3H, $NHCOCH_3$), 1.73 (s, 3H, $NH'COCH_3$), 1.47-1.42 (m, 4H, 2×$CH_2$-L), 1.23-1.18 (m, 2H, $CH_2$-L). $^{13}C$ (125 MHz, $CDCl_3$): δ 128.43, 102.31 (>CHPh), 100.54 (C-1), 98.59 (C-1"), 98.03 (C-1'), 79.11, 78.84, 77.39, 76.34, 75.94, 75.19, 75.02, 75.04, 74.63, 74.35, 74.23, 73.87, 73.80, 73.52, 72.68, 72.13, 72.11, 70.00, 69.61, 68.68, 67.36, 67.39, 55.62, 51.23, 47.70, 46.65, 29.80, 29.02, 24.10, 23.58. HR-MALDI-TOF/MS (m/z) calcd for $C_{91}H_{101}N_3O_{18}[M+Na]^+$: 1546.6978. found: 1546.6980.

5-Aminopentyl-2-acetamido-2-deoxy-β-D-mannopyranosyl-(1→4)-[α-D-galactopyranoside-(1→3)]-2-acetamido-2-deoxy-β-D-glucopyranoside (2). Compound 18 (8.5 mg, 5.6 μmol) was dissolved in a mixture of t-BuOH, AcOH, and $H_2O$ (1.5 mL, 0.2 mL, 0.05 mL, 5/10/1, v/v/v) under an atmosphere of argon. $Pd(OH)_2/C$ (15.0 mg) was added and the mixture was degassed and placed under an atmosphere of $H_2$ and stirred for 16 h. The reaction mixture was filtered through a polytetrafluoroethylene (PTFE) filter (Fischerbrand, 0.2 μm) and the residue was washed with acetic acid (3 mL). The combined filtrates were concentrated in vacuo and the residue was purified over Iatrobeads ($iPrOH/NH_4OH/H_2O$, 3/2/1, v/v/v) to give 2 (2.7 mgs, 73%) as a white solid. $R_f$=0.25 ($iPrOH/NH_4OH/H_2O$, 3/2/1, v/v/v). $^1H$ (500 MHz, $CDCl_3$): δ 5.43 (d, 1H, $J_{1'',2''}$=4.0 Hz, H-1"), 4.76 (s, 1H, H-1'), 4.42-4.41 (m, 2H, H-1, H-2'), 3.93 (t, 1H, H-5"), 3.86 (m, 1H, H-4), 3.80-3.60 (m, 9H, CHH-L, H-6'a, H-2, H-2", H-6a,b, H-3, H-5, H-4"), 3.49-3.38 (m, 5H, CHH-L, H-6'b, H-6"a,b, H-3"), 3.28-3.25 (m, 1H, H-5'), 2.85 (t, 2H, $CH_2$-L), 1.96 (s, 3H, $NHCOCH_3$), 1.90 (s, 3H, $NH'COCH_3$), 1.57-1.45 (m, 4H, 2×$CH_2$-L), 1.29-1.23 (m, 2H, $CH_2$-L). $^{13}C$ (125 MHz, $CDCl_3$): δ 101.18 (C-1), 98.79 (C-1'), 98.11 (C-1"), 76.87, 74.86, 72.01, 71.12, 70.37, 69.44, 69.25, 68.95, 66.70, 60.95, 60.35, 60.32, 60.16, 54.74, 53.39. HR-MALDI-TOF/MS (m/z) calcd for $C_{27}H_{49}N_3O_{16}[M+Na]^+$: 694.3011. found: 694.3012.

Reagents for conjugation and immunological evaluation. 1-Cyano-4-dimethylaminopyridinium tetrafluoroborate (CDAP), bovine serum albumine (BSA), galactose (Gal), N-glucosamine (GlcNAc), N-acetylmannosamine (ManNAc), glucosamine ($GluNH_2$), mannosamine ($ManNH_2$), acetonitrile (HPLC grade), triethylamine (TEA), and HEPES buffer were obtained from Sigma. Keyhole Limpet Hemocyanin (KLH) was purchased from Pierce Chemicals. Trifluoracetic acid (TFA) was obtained from Aldrich. Nanopure water was obtained from B. Braun Medical, sodium hydroxide, 50% (w/w) solution was from J. T. Baker, sodium acetate anhydrous was from Fluka, Slide-A Lyzer Dialysis Cassette (MWCO 30,000; 1-3 mL) were from Thermo Scientific, centrifugal filter devices (Centriplus YM-30,000) were from Millipore, siliconized skirted-bottom tubes with screw caps were from Fisher Scientific, and Sep-Pak® PLUS $C_{18}$ cartridge was from Waters. The polysaccharide from *Bacillus anthracis* sterne was isolated as reported previously (Choudhury et al., *J. Biol. Chem.*, 2006, 281, 27932-27941).

CDAP-polysaccharide activation. Polysaccharide and maltoheptaose (1 mg) were dissolved in HEPES buffer (90 μL, 0.15 M; pH 7.4) and a solution of CDAP (4 mg) in acetonitrile (90 μL) was slowly added while stirring to avoid precipitation. After 30 sec, aqueous triethylamine solution (120 μL, 0.3 M) was added and after another 150 sec, the pH was readjusted and protein (4 mg BSA or KLH) in PBS buffer (0.1 M, pH 7.4; 100 μL and 348 μL, respectively) added. After stirring at 4° C. for 18 h, the reaction was quenched by the addition of 0.5 M ethanolamine in HEPES buffer (120 μL; 0.75 M; pH 7.4). No gelling was observed indicating that no excessive cross-linking of protein with polysaccharides had occurred. The polysaccharide-BSA, polysaccharide-KLH, and maltoheptaose-BSA conjugates were dialyzed against nanopure water (2×3 L) at 4° C. followed by isolation using centrifugal filter devices (Centriplus YM 30,000). Briefly, a solution of the polysaccharide-protein conjugate solution (3 mL) was transferred to a centrifugal filter tube with a cellulose membrane and centrifuged at 3,000 rpm at 4° C. for 1 h followed by addition of nanopure water (2×2 mL) and centrifuged for 2 h at 4° C. The filtrate was removed. The concentrate (polysaccharide-protein conjugate) remaining on a cellulose membrane in centrifugal filter tube was inverted to another assembly and further centrifugation at 2,000 rpm at 4° C. for 4 min followed by lyophilization gave polysaccharide-BSA (3.2 mg), polysaccharide-KLH (4.3 mg), and maltoheptaose-BSA (4.0 mg) conjugates as white foams. Each conjugate was dissolved in PBS buffer at a concentration of 1 mg $mL^{-1}$ and stored at 4° C. The amount of polysaccharide in polysaccharide-protein conjugate products was determined by HPAEC-PAD. Thus, solutions of polysaccharide-BSA, polysaccharide-KLH, maltoheptaose-BSA, and trisaccharide conjugates (50 μL) in screw-capped siliconized skirted-bottom tubes were treated with 2 M aqueous TFA (200 μL) and placed in a heating block at 100° C. for 4 h to cleave all glycosidic linkages. Next, the samples were cooled and the solvents removed by centrifugal vacuum evaporation (Speed-vac) at 40° C. During the acid hydrolysis GlcNAc and ManNAc are quantitatively de-N-acetylated giving $GlcNH_2$ and $ManNH_2$, respectively. Therefore, Gal, $GlcNH_2$, and $ManNH_2$ were employed as reference compounds and treated under the same condition as described for the conjugates. The dried samples were re-dissolved in nanopure water (500 μL) and passed through a SepPak® CIS cartridge. Briefly, before sample loading, a SepPak® $C_{18}$ cartridge was activated by subsequent washing with MeOH (5 mL), water (5 mL), and aqueous acetic acid (5%, 5 mL). The hydrolyzed samples (500 μL) were consequently loaded on activated SepPak® $C_{18}$ cartridges and eluted with nanopure water (3 mL). The concentrates containing respective hydrolyzed monosaccharides were lyophilized and re-dissolved in nanopure water (50 μL) and the resulting solutions analyzed by 817 Bioscan Metrohm HPAEC-PAD equipped with a Metrohm-Peak Gradient 709° C. Pump Module, an 812 Valve Unit with a 50 μL Rheodym loop, a 762° C. interface and an analytical (4×250 mm) Dionex CarboPac PA10 column with a CarboPac PA10 guard column (3×30 mm). A flow rate of 0.9 mL $min^{-1}$ at 32° C. and the following gradient program were used: t=0 min, E1=97.5%, E2=2.5%; t=10 min, E1=97.5%, E2=2.5%; t=25 min, E1=97.5%, E2=2.5%; t=27 min, E1=0%, E2=100%; t=37 min, E1=0%, E2=100%; t=39 min, E1=97.5%, E2=2.5%, t=50 min, E1=97.5%, E2=2.5%. Eluent 1 (E1) is nanopure water and eluent 2 (E2) is 200 mM NaOH. All eluents were degassed before use for 1 h. (Hardy and Townsend *Methods in Enzymology* 1994, 230, 208-225).

General procedure for S-acetylthioglycolylamido derivatization of the aminopropyl spacer. The oligosaccharide 1 (2.0 mg, 3.17 μmol) was slurried in dry DMF (300 μL) and SAMA-OPfp (1.43 mg, 4.76 μmol) was added followed by addition of DIPEA (1.6 μL, 9.51 μmol). After stirring at room temperature for 1.5 h, the mixture was concentrated, co-evaporated twice with toluene and the residue purified by size-exclusion chromatography (Biogel P2 column, eluted with $H_2O$ containing 1% n-Butanol) to give, after lyophilization, the corresponding thioacetate (1.98 mg, 84%) as a white powder. In a similar manner, the thioacetamido derivative of compound 2 was prepared in a yield of 86%.

General procedure for S-deacetylation. 7% $NH_3$ (g) in DMF solution (200 μL) was added to the thioacetate derivative corresponding to trisaccharide 2 (1.98 mg, 2.66 μmol) and the mixture was stirred under argon atmosphere. The reaction was monitored by MALDI-TOF showing the product peak of $[M+Na]^+$. After 1 h the solvent was dried under high-vacuum and the thiol derivatized trisaccharide was then further dried in vacuo for 30 min and immediately used in conjugation without further purification.

General procedure for the conjugation of thiol derivatized trisaccharides to BSA-MI. The conjugations were performed as instructed by Pierce Endogen Inc. In short, the thiol derivative (2.5 equiv. excess to available MI-groups on BSA), deprotected just prior to conjugation as described above, was dissolved in the conjugation buffer (sodium phosphate, pH 7.2 containing EDTA and sodium azide; 100 μL) and added to a solution of maleimide activated BSA (2.4 mg) in the conjugation buffer (200 μL). The mixture was incubated at room temperature for 2 h and then purified by a D-Salt™ Dextran de-salting column (Pierce Endogen, Inc.), equilibrated, and eluted with sodium phosphate buffer, pH 7.4 containing 0.15 M sodium chloride. Fractions containing the glycoconjugate were identified using the BCA protein assay and combined to give glycoconjugates with a carbohydrate/BSA molar ratio of 11/1 for trisaccharide 1, and 19/1 for trisaccharide 2 as determined by quantitative monosaccharide analysis by HPAEC/PAD and Bradford's protein assay.

Preparation of *Bacillus anthracis* Sterne $34F_2$ spores. Spores of *B. anthracis* Sterne $34F_2$ were prepared from liquid cultures of PA medium grown at 37° C., 200 rpm for six days. Spores were washed two times by centrifugation at 10,000×g in cold (4° C.) sterile deionized water, purified in a 50% Reno-60 (Bracco Diagnostics Inc.) gradient (10,000×g, 30 min, 4° C.) and washed further four times in cold sterile deionized water. After suspension in sterile deionized water, spores were quantified with surface spread viable cell counts on brain heart infusion agar plates (BD BBL). Spore suspensions were stored in water at −80° C.

For the preparation of killed spores, 500 μL aliquots of spore suspensions in water, prepared as described above and containing approximately $3\times10^8$ CFU, were irradiated in 200-mL Sarstedt freezer tubes (Sarstedt) in a gammacell irradiator with an absorbed dose of 2 million rads. Potential residual viability after irradiation was monitored by spread-plating 10 μL aliquots of irradiated spore suspension on BHI agar plates. The plates were incubated at 37° C. for 72 h and monitored for colony growth.

Preparation of antisera. All antisera were prepared in female New Zealand White rabbits (2.0-3.5 kg) purchased from Myrtle's Rabbitry (Thompson Station, Tenn.). For antiserum production each of two rabbits were inoculated intramuscularly at two sites in the dorsal hind quarters with 0.5 mL of washed live-spore, irradiated spore inoculum ($3\times10^6$ total spores). Rabbits were immunized at O, 14, 28, and 42 days. Antiserum to *B. anthracis* polysaccharide-KLH conjugate was prepared by a primary injection with polysaccharide-KLH conjugate (500 μg) and the MPL, TDM, CWS adjuvant system (0.5 mL). Booster immunizations were administered at 14, 28, and 42 days using the polysaccharide-KLH conjugate (250 μg) and the MPL, TDM, CWS adjuvant system (0.5 mL). Terminal bleeds were collected 14 days after the last immunization. The CDC animal facilities are approved by the Association for Assessment and Accreditation of Laboratory Animal Care. All animal protocols were approved by the CDC Animal Care and Use Committee and implemented under the direction of the CDC attending veterinarian.

Antibody-binding analyses. Binding of rabbit antisera to saccharide conjugates was performed by enzyme-linked immunosorbent assay (ELISA). Briefly, Immulon II-HB flat bottom 96-well microtiter plates (Thermo Labsystems) were coated overnight at 4° C. with 100 μL per well of polysaccharide-BSA, 1-BSA, 2-BSA, or maltoheptaose-BSA conjugate at a concentration of 0.15 μg $mL^{-1}$ of carbohydrate content, or with the carrier protein BSA by itself at corresponding protein content in coating buffer (0.2 M borate buffer, pH 8.5 containing 75 mM sodium chloride). Plates were washed three times in wash buffer (0.05% Tween-20 in PBS, pH 7.4) using an automatic microplate washer (DYNEX Technologies, Inc.). After blocking the plate for 1 h with blocking buffer (PBS containing 1% BSA; 200 μL/well) and washing three times in wash buffer, serial dilutions in diluent buffer (PBS, pH 7.4 containing 1% BSA and 0.5% Tween-20) of either rabbit antisera from the terminal bleed or pre-immune sera were then added (100 μL/well) and plates were incubated for 2 h. After incubation the plates were washed three times in wash buffer and a goat anti-rabbit IgG, Fc fragment specific, horseradish peroxidase conjugated antibody (Pierce Biotechnology) was added (0.16 μg $mL^{-1}$; 100 μL/well) for 2 h. Plates were then washed three times in wash buffer and ABTS (2,2'-azino-di(3-ethylbenthiazoline-6-sulfonate)) peroxidase substrate was added (100 μL/well; KPL, Kirkegaard & Perry Laboratories, Inc). Color development was stopped after 25 min by addition of ABTS peroxidase stop solution (100 μL/well; KPL). Optical density (OD) values were measured at a wavelength of 410 nm (490 nm reference filter) using a microplate reader (BMG Labtech) and reported as the means±SD of triplicate measurements. Titers are determined by linear regression analysis, plotting dilution versus absorbance. Titers are defined as the highest dilution yielding an optical density of 0.5 or greater.

To explore competitive inhibition of the binding of sera to polysaccharide-BSA conjugate by polysaccharide-BSA, 1-BSA, and 2-BSA, rabbit antisera were diluted in diluent buffer in such a way that, without inhibitor, expected final OD values were approximately 1. For each well 60 μL of the diluted sera were mixed in an uncoated microtiter plate with either 60 μL diluent buffer or 60 μL BSA-conjugates (polysaccharide-BSA, 1-BSA, and 2-BSA and as controls maltoheptaose-BSA and unconjugated BSA) in diluent buffer with a final concentration corresponding to a 0.02-, 0.1-, 0.4-, 1.6-, 6.3-, 25-, or 100-fold weight excess of carbohydrate compared to carbohydrate used for coating. After incubation at room temperature for 2 h, 100 μL of the mixtures were transferred to a plate coated with polysaccharide-BSA. The microtiter plates were incubated and developed as described above.

Example 11

Secondary Cell Wall Polysaccharides of *Bacillus anthracis* and *Bacillus cereus* Strains are Antigens that Display Both Common and Strain-Specific Antigenicity The immunoreactivities of hydrogen fluoride (HF) released cell wall polysaccharides (HF-PSs) from selected *Bacillus anthracis* and *B. cereus* strains were compared using antisera against live and killed *B. anthracis* spores. These antisera bound to the HF-PSs from *B. anthracis* and from three clinical *B. cereus* isolates (G9241, 03BB87 and 03BB102) obtained from cases of severe or fatal human pneumonia but did not bind the HF-PSs from the closely related *B. cereus* ATCC 10987 or from *B. cereus* type strain ATCC 14579. Antiserum against a keyhole limpet hemocyanin conjugate of the *B. anthracis* HF-PS (HF-PS-KLH) also bound HF-PSs and cell walls from *B. anthracis* and the three clinical *B. cereus* isolates, and *B. anthracis* spores. These results indicate that the *B. anthracis* HF-PS is an antigen in both *B. anthracis* cell walls and spores, and that it shares cross-reactive, and possibly pathogenicity-related, epitopes with three clinical *B. cereus* isolates that caused severe disease. The anti-HF-PS-KLH antiserum cross-reacted with the bovine serum albumin (BSA)-conjugates of all *B. anthracis* and all *B. cereus* HF-PSs tested, including those from non-clinical *B. cereus* ATCC 10987 and ATCC 14579 strains. Finally, the serum of vaccinated (anthrax vaccine adsorbed [AVA]) Rhesus macaques that survived inhalation anthrax contained IgG antibodies that bound the *B. anthracis* HF-PS-KLH conjugate. These data indicate that HF-PSs from the cell walls of the bacilli tested here are antigens that contain a potentially virulence-associated carbohydrate antigen motif, and another antigenic determinant that is common to *B. cereus* strains.

Anthrax is primarily a disease of herbivores although humans can also be infected. The etiologic agent of anthrax is *B. anthracis*. Systemic anthrax, secondary to any of its associated routes of entry (such as cutaneous, gastrointestinal and inhalations) if untreated, potentially fatal. The potential for using *B. anthracis* as a weapon has been widely reported (Baillie, 2005, *Lett. Appl. Microbiol;* 41:227-229; and Hilleman, 2002, *Vaccine;* 20:3055-3067). In particular since the anthrax bioterrorism events in 2001 there has been a renewed interest in effective diagnostic tools and medical countermeasures. The carbohydrate antigens of *B. anthracis* have not been extensively investigated. This example demonstrates that carbohydrates on *B. anthracis* spores or vegetative cells were antigenic and had structural or immunochemical properties that may make them suitable for the development of improved diagnostic methods and new or improved vaccines. In Example 2 and 3, two *B. anthracis* carbohydrate antigens demonstrating this potential were identified (see also, Daubenspeck et al. 2004, *J. Biol. Chem;* 279:30945-30953; Mehta et al., 2006, *Chemistry;* 12:9136-9149; and Choudhury et al., 2006, *J. Biol. Chem;* 281:27932-27941). One of these carbohydrates is an oligosaccharide that is part of the collagen-like protein, BclA, on the spore exosporium (Example 3, see also, Daubenspeck et al. 2004, *J. Biol. Chem;* 279:30945-30953; and Mehta et al., 2006, *Chemistry;* 12:9136-9149, and the second is a non-classical secondary cell wall polysaccharide found in the vegetative cell wall Example 2, see also, Choudhury et al., 2006, *J. Biol. Chem;* 281:27932-27941).

Figure 38:
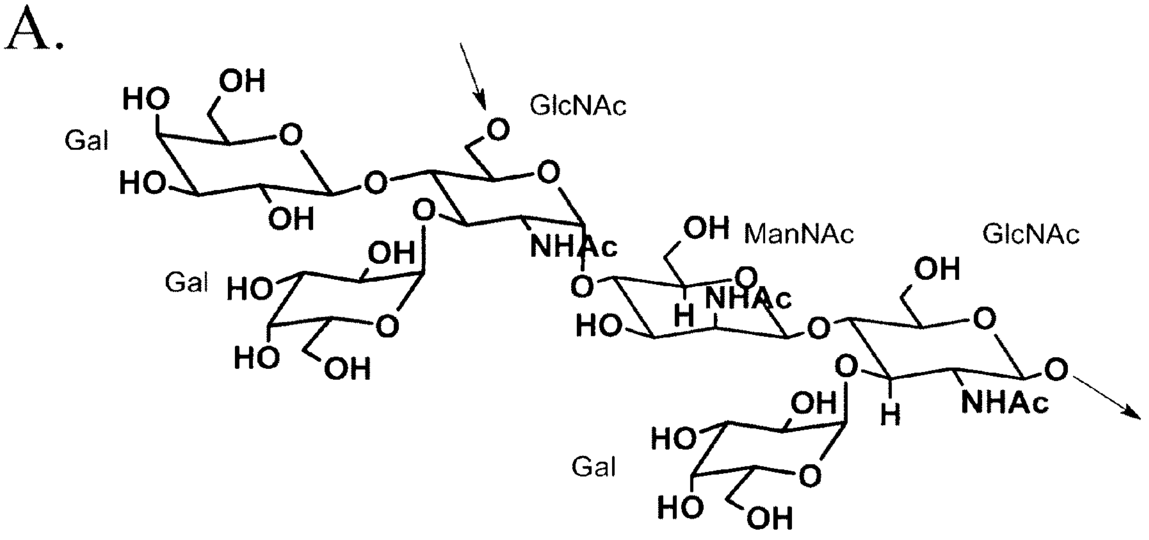
FIGS. 38A and 38B show the repeating unit structure of the HF-PS from *B. anthracis* Sterne, Pasteur, and Ames (FIG. 38A) and the consensus structure that is indicated for the HF-PS from members of the *B. cereus* group (FIG. 38B). This consensus repeating unit structure can be substituted by Gal, Glc, as well as by acetyl groups (indicated by "X").

This example focuses on the secondary cell wall polysaccharide that is released from the *B. anthracis* cell wall by aqueous hydrogen fluoride (HF-PS). For *B. anthracis*, it was shown that the HF-PS anchors cell surface proteins, such as S-layer proteins, to the peptidoglycan (Mesnage et al., 2000, *EMBO J;* 19:4473-4484). It is thought that the HF-PS is the ligand for the carbohydrate-binding SLH-domain of the surface protein while a HF-labile phosphate bond anchors the PS to the peptidoglycan. A recent report identified 23 *B. anthracis* genes that encode proteins with SLH-domains and, further, demonstrated that one of these genes, bslA, is present on the pXO1 pathogenicity island and that its product is necessary for adherence of *B. anthracis* to host cells (Kern and Schneewind, 2008, *Mol. Microbiol;* 68:504-515). As shown in Examples 1 and 2, by examining the cell walls of *B. anthracis* and related *B. cereus* strains, that *B. anthracis* produces a specific HF-PS structure that is identical in the investigated *B. anthracis* strains; i.e. Ames, Sterne, and Pasteur; but different from that of *B. cereus* cell walls (see also, Choudhury et al., 2006, *J. Biol. Chem;* 281:27932-27941; Leoff et al., 2008, *J. Bacteriol;* 190:112-121; and Leoff et al., 2008, *J. Biol. Chem;* 283:29812-29821). As shown in FIG. 38, the *B. anthracis* HF-PS is comprised of an amino sugar backbone of →6)-α-GlcNAc-(1→4)-β-ManNAc-(1→4)-β-GlcNAc-(1→ in which the α-GlcNAc residue is substituted with α-Gal and β-Gal at O3 and O4, respectively, and the β-GlcNAc substituted with α-Gal at O3 (see Example 2; see also, Choudhury et al., 2006, *J. Biol. Chem;* 281:27932-27941). In comparison, the HF-PS from the closely related *B. cereus* ATCC 10987 consists of a →6)-α-GalNAc-(1→4)-β-ManNAc-(1→4)-β-GlcNAc-(1→ backbone in which the α-GalNAc is substituted at O3 with a β-Gal residue and the β-ManNAc is acetylated at O3 (Leoff et al., 2008, *J. Biol. Chem;* 283:29812-29821). To date, structural investigations into the *B. cereus* HF-PSs from *B. cereus* ATCC 10987 and into the HF-PS from the more distantly related *B. cereus* type strain ATCC 14579, revealed a common structural theme in the HF-PSs (see FIG. 38) consisting of a HexNAc-ManNAc-GlcNAc backbone that is substituted with terminal galactosyl (Gal) or glucosyl (Glc) residues or non-carbohydrate substituents such as acetyl groups.

This example shows that the HF-PS from *B. anthracis* is antigenic in that anti-HF-PS IgG antibodies are found in the antisera from rabbits inoculated with *B. anthracis* live or killed spores. In addition, this example demonstrates that HF-PS from pathogenic *B. cereus* clinical isolates of human patients suffering from severe or fatal pneumonia (Avashia et al., 2007, *Clin. Infect. Dis;* 44:414; Hoffmaster et al., 2006, *J. Clin. Microbiol;* 44:3352-3360; and Hoffmaster et al., 2004, *Proc. Natl. Acad Sci;* 101:8449-8454), i.e. *B. cereus* strains G9241, 03BB87, and 03BB102, share carbohydrate antigen epitopes with *B. anthracis* and that these epitopes are not found on the non-pathogenic *B. cereus* ATCC 10987 and *B. cereus* type strain ATCC 14579. This example shows, using antisera against a keyhole limpet hemocyanin (KLH) conjugate of *B. anthracis* HF-PS, that the five *B. cereus* and three *B. anthracis* strains tested share a common epitope in their HF-PS-BSA conjugates. Finally, using antisera from Rhesus macaques that survived inhalation anthrax, this example demonstrates that the HF-PS antigen is expressed during *B. anthracis* infection in vivo.

Materials and Methods

Bacterial strains and culture conditions. The strains/isolates used in this work and their phylogenetic relatedness are listed in Table 10. All *B. anthracis* strains were obtained from the CDC culture collection. Cells cultured over night in brain heart infusion medium (BHI) (BD BBL, Sparks, Md.) containing 0.5% glycerol were used to inoculate four 250 milliliter (mL) volumes of BHI medium in 2 liter (L) Erlenmeyer flasks the next morning. Cultures were grown at 37° C. (*B. anthracis*) or 30° C. (*B. cereus*) with shaking at 200 rpm. Growth was monitored by measuring the optical density of the cultures at 600 nm. In mid-log phase, cells were harvested by centrifugation (8,000×g, 4° C., 15 min), washed two times in sterile saline, enumerated by dilution plating on BHI agar plates, and then autoclaved for 1 hour (h) at 121° C. before further processing.

TABLE 10

*Bacillus anthracis* and *B. cereus* group strains used in this study.

| Strain | MLST Clade, Lineage[1,2] | Clinical Information | Source/ Provider | Reference |
|---|---|---|---|---|
| *B. anthracis* Ames | Clade 1 *Anthracis* | Veterinary isolate | Bovine anthrax isolate (1981, Texas) | Van Ert et al.[4] |
| *B. anthracis* 34F$_2$ Sterne | | Veterinary vaccine strain | Bovine anthrax isolate (1930s, South Africa) | Sterne[5] |
| *B. anthracis* 4229 Pasteur | | Veterinary vaccine strain (Italy) | Unknown, 1880's | Green[6] |
| *B. cereus* ATCC 10987 | Clade 1, *Cereus* I | n/a[3] | Dairy isolate (1930) | Smith[7] |
| *B. cereus* 03BB102 | Clade 1, *Cereus* III | Fatal pneumonia | Human blood isolate (2003, Texas) | Hoffmaster et al.[8] |
| *B. cereus* G9241 | Clade 1, *Cereus* IV | Severe pneumonia | Human blood isolate (1994, Louisiana) | Hoffmaster et al.[9] |
| *B. cereus* 03BB87 | | Fatal pneumonia | Human blood isolate (2003, Texas) | Hoffmaster et al.[8] |
| *B. cereus* ATCC 14579 | Clade 2 Tolworthii | n/a[3] | *B. cereus* type strain; possibly dairy isolate (1916) | Ford and Lawrence[10] |

[1]The phylogenetic relatedness of strains on the basis of multi locus sequence typing (MLST) was adopted from Priest et al. (29) with modifications.
[2]The classification of these strains in *Cereus* IV is proposed (Hoffmaster et al., 2008, *BMC Microbiology*; 8: 191-200).
[3]n/a = not available.
[4]Van Ert et al., 2007, *J. Clin. Microbiol*; 45(1): 47-53.
[5]Sterne, 1937, Onderstepoort *J. Vet. Sci Anim. Ind*; 9: 49-67.
[6]Green et al., 1985, *Infect. Immun*; 49: 291-297.
[7]Smith, 1952, *US Dep. Agric. Monogr*; 16: 1-148.
[8]Hoffmaster et al., 2006, *J. Clin. Microbiol*; 44: 3352-3360.
[9]Hoffmaster et al., 2004, *Proc.Natl. Acad Sci*; 101: 8449-8454.
[10]Ford and Lawrence, 1916, *J. Bacteriol*; 1: 277-320.

Preparation of bacterial cell walls. Bacterial cell walls were prepared from previously enumerated autoclaved bacterial cells ($3\times10^8$ to $3\times10^9$ CFU/mL) that were disrupted in 40 ml sterile saline on ice by four 10 min sonication cycles. The complete or near complete disruption of cells was checked microscopically. Unbroken cells were removed by a low speed centrifugation run (8,000×g, 4° C., 15 min). The separated pellet and supernatant fractions were stored at −70° C. The cell walls were separated from the low speed supernatants by ultracentrifugation at 100,000×g, 4° C. for 4 h. The resulting cell wall pellets were washed by suspension in cold, deionized water followed by an additional ultracentrifugation at 100,000×g, 4° C. for 4 h, and lyophilized.

Release of phosphate-bound polysaccharides from the cell wall. Phosphate-bound polysaccharides were released from the cell walls by treatment with aqueous HF according to a modification of the procedure described by Ekwunife et al., (Ekwunife et al., 1991, *FEMS Microbiol. Lett;* 82:257-262). Briefly, the cell walls were subjected to 47% HF under stirring at 4° C. for 48 h. The reaction mixture was neutralized with $NH_4OH$, subjected to a 10 min low speed centrifugation, and the supernatant with the released polysaccharides lyophilized, redissolved in deionized water and subjected to a chromatographic size separation on a BioGel P2 column (Bio-Rad). The fractions eluting from the BioGel P2 column were monitored using a refractive index detector. Polysaccharide-containing fractions were pooled, lyophilized and analyzed by gas chromatography-mass spectrometry as previously described (Example 2; see also, Choudhury et al., 2006, *J. Biol. Chem;* 281:27932-27941).

Preparation of Spores. Spores of *B. anthracis* were prepared from liquid cultures of phage assay (PA) medium (Green et al., 1985, *Infect. Immun;* 49:291-297) grown at 37° C., 200 rpm for six days. Spores of *B. cereus* ATCC 14579 were prepared from liquid cultures of PA medium grown at 30° C., 200 rpm for six days. Spores were harvested by centrifugation and washed two times by suspension in cold (4° C.) sterile deionized water followed by centrifugation at 10,000×g. They were then purified in a 50% Reno-60 (Bracco Diagnostics Inc., Princeton, N.J.) gradient (10,000×g, 30 min, 4° C.) and washed a further four times in cold sterile deionized water. After suspension in sterile deionized water, spores were quantified by surface spreading on brain heart infusion (BHI) agar plates (BD BBL, Sparks, Md.) and counting the colony forming units (cfu). Spore suspensions were stored in water at −80° C.

For the preparation of killed spores, 500 μL aliquots of spore suspensions in water, prepared as described above and containing approximately $3\times10^8$ CFU/mL, were irradiated in 2 mL Sarstedt freezer tubes (Sarstedt, Newton, N.C.) in a gamma cell irradiator with an absorbed dose of 2 million rads. Sterility after irradiation was confirmed by spread-plating 10 μL aliquots of irradiated spore suspension on BHI agar plates. The plates were incubated for 72 h at 37° C. and monitored for colony growth. Absence of growth was taken as an indicator of sterility.

Preparation of rabbit anti-spore antiserum and Rhesus macaque infection sera. Anti-spore antiserum against spores of *B. anthracis* Sterne and *B. cereus* ATCC 14579 were prepared in female New Zealand White rabbits (2.0-3.5 kg) purchased from Myrtle's Rabbitry (Thompson Station, Tenn.). Each of two rabbits were inoculated intramuscularly at two sites in the dorsal hind quarters with 0.5 mL of washed live-spore or killed-spore inoculum ($3\times10^6$ total spores). Rabbits were vaccinated at 0, 14, 28, and 42 days. Serum was collected prior to the first immunization (pre-immune serum) and at day 7 and day 14 after each injection of antigen. Terminal bleeds were collected on day 14 after the last immunization. All animal protocols were approved by the CDC Animal Care and Use Committee (ACUC) and implemented under the direction of the CDC attending veterinarian. Rhesus macaque sera were made available from anthrax correlates of protection studies at CDC.

Conjugation of HF-PS to BSA or KLH. Conjugation was performed by modification of a previously described method (Shafer et al., 2000, *Vaccine;* 18:1273-1281; and Bystricky et al., 2000, *Glycoconj*. J; 17:677-680). Approximately 1 mg of freeze dried polysaccharide was dissolved in 90 μL of 0.15 M HEPES buffer, pH 7.4. While stirring, 4 mg of 1-cyano-4-dimethylaminopyridinium tetrafluoroborate (CDAP) in acetonitrile (90 μL) were slowly added to a solution of the polysaccharide to avoid precipitation. After activation of the polysaccharide (30 sec), aqueous triethylamine (120 μL of 0.3 M triethylamine) was added and stirred for 2 min. Finally, 4 mg of bovine serum albumin (BSA; Sigma, St. Louis, Mo.) or keyhole limpet hemocyanin (KLH; Sigma, St. Louis, Mo.) were dissolved in 348 μL 0.01 M phosphate buffered saline (PBS), pH 7.4 and added to the reaction mixture. After stirring for 18 h at 4° C., the reaction mixture was quenched with addition of 120 μL of 0.5 M ethanolamine in 0.75 M HEPES buffer, pH 7.4. After 15-20 min of stirring, the unconjugated sugars in the mixture were separated from the protein-polysaccharide conjugate by centrifugation at 3200×g using a centrifugal filter device (Centriplus YM-10, Millipore, Billerica, Mass.). The conjugate was lyophilized and stored at room temperature. The percentage of sugars in the conjugates was determined by the preparation and GC-MS analysis of trimethylsilyl methyl glycosides (York et al., 1985, *Meth. Enzymol;* 118:3-40). Briefly, 200 μg of the HF-PS-KLH or -BSA conjugate were methanolyzed in methanolic 1 M HCl, derivatized into trimethylsilyl ethers and analyzed by GC-MS. Using this procedure the percent mass of hexose and the amount of carbohydrate in the HF-PS-protein conjugates was determined from the known hexose percent present in the unconjugated HF-PS; e.g. based on Gal for *B. anthracis*, and on Glc for *B. cereus* ATCC 14579 HF-PS-protein conjugates.

Preparation of antiserum to the *B. anthracis* HF-PS-KLH conjugates. *Bacillus anthracis* Pasteur HF-PS was conjugated to KLH as described above and used for the preparation of anti-HF-PS antiserum. For antiserum production each of two female (2.0-3.5 kg) New Zealand White rabbits (Myrtle's Rabbitry, Thompson Station, Tenn.) were inoculated intramuscularly at two sites in the dorsal hind quarters. For the primary injection 1.0 mL of MPL+TDM+CWS Adjuvant System (Sigma, St. Louis, Mo.) with 500 μg of the HF-PS-KLH conjugate were divided into two injections per rabbit. For the booster shots 1.0 mL of MPL+TDM+CWS Adjuvant System with 250 μg of the HF-PS-KLH conjugate were used. Rabbits were immunized at 0, 14, 28, and 42 days. Serum was collected prior to the first immunization (pre-immune serum) and at day 7 and day 14 after each injection of antigen. Terminal bleeds were collected 14 days after the last immunization.

Enzyme linked immunosorbent assay (ELISA) determination of IgG binding to *B. anthracis* and *B. cereus* HF-PS-protein conjugates. The immunochemical reactivity of serum from rabbits inoculated with *B. anthracis* spores and of serum from Rhesus macaques that survived inhalation anthrax were tested against protein conjugated HF-PS extracts from *B. anthracis* Ames and *B. cereus* ATCC 14579 by enzyme linked immunosorbent assay (ELISA). Slightly different protocols were used to examine these antisera.

The rabbit anti-*B. anthracis* spore antisera were assayed using the wells of a 96 well microtiter plate (Immulon II-HB, Thermo Labsystems, Franklin, Mass.) in which each well was coated with the 100 μL of a 5 μg/mL solution of HF-PS-BSA conjugate in 100 μL of 0.01 M PBS, pH 7.4 and incubated over night at 4° C. The next day, the plates were washed 3 times with wash buffer (0.01 M PBS, pH 7.4, 0.1% Tween-20) followed by blocking buffer (5% non fat dry milk in 0.01 M PBS, pH 7.4, 0.5% Tween-20) for 1 h at room temperature. The plates were then washed again, and serial dilutions (100 μL per well) of spore rabbit antiserum in blocking buffer were added and the plates incubated for 1 h at room temperature. The plates were then washed three times with wash buffer. Horseradish peroxidase (HRPO) labeled goat anti-rabbit IgG, 1:5000 dilution, was added (100 μL/well) and incubated for 1 h at room temperature. Plates were washed five times with wash buffer before adding 100 μL of ABTS/$H_2O_2$ peroxidase substrate (KPL, Gaithersburg, Md.) for 10 min. The color development was stopped with the addition of 100 μL of ABTS peroxidase stopping solution (KPL, Gaithersburg, Md.) and the optical density of each well was read at a wavelength of 405 nm with a microtiter plate reader (Bio-Rad Laboratories, Hercules, Calif.).

The Rhesus macaque sera were assayed as described above with the exception that *B. anthracis* HF-PS-KLH conjugate rather than the BSA conjugate was used to coat the microtiter plates. Samples were tested three times and average OD and standard deviation were calculated. Anti-HF-PS IgG responses were expressed as a "fold response" over a reactivity threshold (RT) value. The RT was determined from the average OD value plus two standard deviations (SD) from the sera of 88 true negative Rhesus macaques tested against HF- PS-KLH by ELISA. Each sample was tested twice at a 1:100 dilution in dilution buffer. The RT was calculated as an OD value of 0.22.

Figure 40:
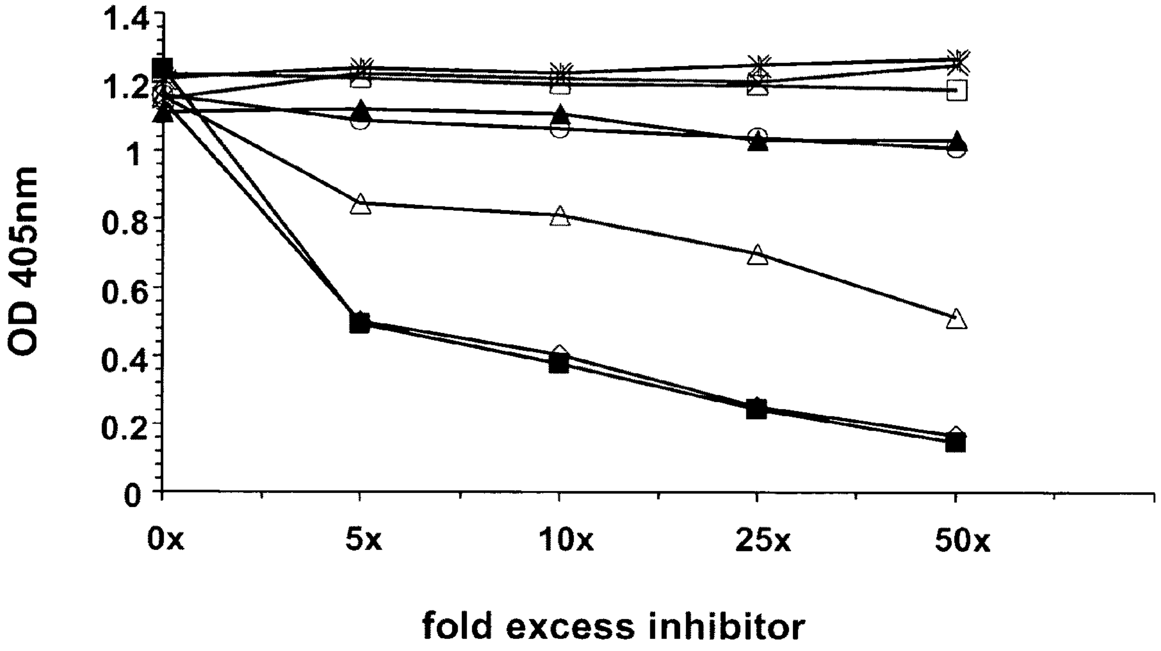
FIG. 40 shows an ELISA inhibition assay showing the ability of various HF-PSs to inhibit the binding of antiserum to live *B. anthracis* spores to the HF-PS-BSA conjugate of *B. anthracis* Pasteur. The microtiter plates were coated with the HF-PS-BSA and the ability to bind antiserum that had been incubated with various concentrations of the different HF-PS preparation was determined. *B. anthracis* Pasteur HF-PS (◊); *B. anthracis* Ames HF-PS (■); *B. cereus* G9241 HF-PS (Δ); *B. cereus* ATCC 14579 HF-PS (○); *B. cereus* ATCC 10987 HF-PS (▲); AntRha$_2$ (●); maltoheptaose (x); BSA (□).

Specificity of Anti-spore antisera for HF-PS. Specificity analyses were done by inhibition ELISAs using various unconjugated HF-PSs and evaluating their ability to block the binding of anti-*B. anthracis* spore antiserum IgG to the *B. anthracis* Pasteur HF-PS-BSA conjugate. The HF-PS samples tested for inhibition were: *B. anthracis* Pasteur HF-PS, *B. anthracis* Ames HF-PS, *B. cereus* ATCC 10987 HF-PS, *B. cereus* ATCC 14579 HF-PS, and *B. cereus* G9241 HF-PS. BSA was used as the inhibition negative control. For analysis, rabbit anti-live spore serum was diluted 1:1600 in ELISA blocking buffer to obtain an OD of approximately 1.0 for the positive control HF-PS-BSA conjugate (FIG. 40). Subsequently, 100 μL of diluted serum were added to the coated microtiter plate wells together with 0-, 5-, 10-, 25-, or 50-fold excess unconjugated HF-PS (i.e. fold excess relative to the 0.35 μg of carbohydrate equivalent of the *B. anthracis* HF-PS-BSA conjugate coating each well of the microtiter plate). Each HF-PS inhibitor was diluted in blocking buffer. Inhibitor and serum were briefly mixed in an uncoated microtiter plate followed by immediate transfer to the coated plate. Plates were incubated for 1 h at room temperature followed by washing with wash buffer three times. The microtiter plates were incubated with horseradish peroxidase labeled anti-rabbit IgG and developed as described above.

Reactivity of anti-HF-PS-KLH antiserum with cells, cell walls, and spores of *B. anthracis* and *B. cereus* strains. Immuno-dot blot assays were used to measure the binding of various antiserum preparations to cells, cell walls and spores. Cells, cell walls, or spores were suspended in distilled water and blotted onto a nitrocellulose membrane. The spore suspension had an optical density of 0.56 at 600 nm. Samples with a volume >5 μL were taken from 1 mg/mL of cell or cell wall stock preparations, dried in a speed-vac and re-dissolved in 3 μL of distilled water before they were blotted onto the membrane. Samples with volumes <5 μL were taken from the above mentioned stock preparations and directly blotted onto the membrane without prior reduction of the volume. BSA, maltoheptaose, and chemically synthesized *B. anthracis* BclA $AntRha_2$ trisaccharide were blotted as controls. The membrane was allowed to dry over night before blocking with blocking buffer for 1 h. The membrane was then incubated at room temperature for 1 h with antiserum to *B. anthracis* HF-PS-KLH conjugate that had been diluted 1:1600 in blocking buffer. After washing three times with wash buffer the membrane was incubated with a 1:1000 dilution of mouse anti-rabbit IgG linked to alkaline phosphatase in 0.01 M PBS buffer, pH 7.4 for 1 h at room temperature. After washing five times, the membrane was developed using Nitro Blue Tetrazolium (0.3 mg/mL in 0.1 M NaCl, 0.1 M trishydroxymethylaminomethane (Tris), 5 mM $MgCl_2$, of 0.15 mg/mL of 5-bromo-4-chloro-indolyl-phosphate, pH 9.0). The reaction was stopped by washing in tap water.

As used herein, "Ant" represents (4-N-β-hydroxyisovalyerl-4,6-dideoxy-D-glucose) and "Rha" represents rhamnose.

Results

Figure 39:
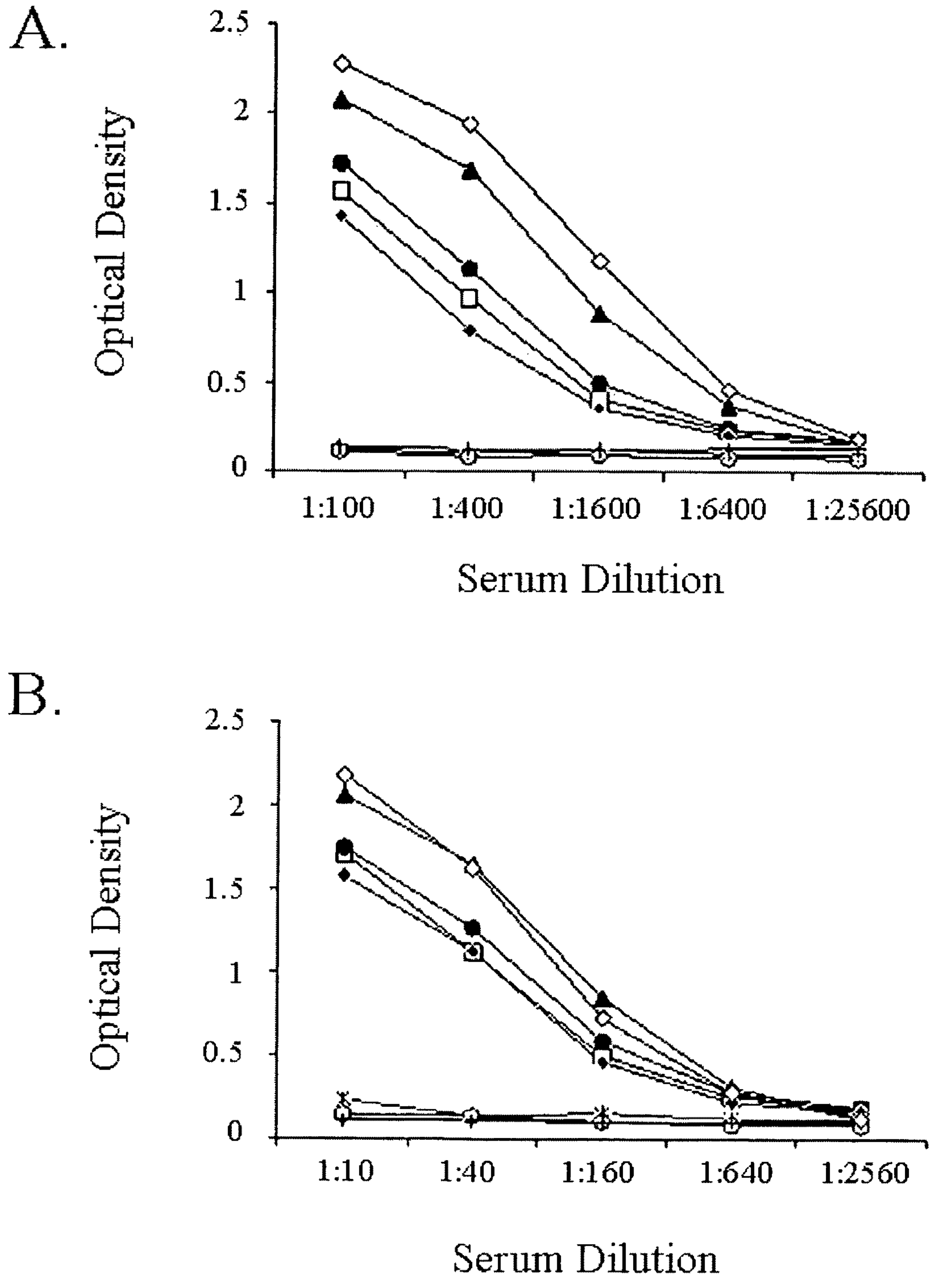
FIGS. 39A-39C present the immunoreactivity of the HF-PSs to antisera raised in rabbits against *B. anthracis* Sterne (FIG. 39A) live spores and (FIG. 39B) killed spores, and to (FIG. 39C) *B. cereus* ATCC 14579 spores. The ELISA microtiter plate wells were coated with *B. anthracis* Pasteur HF-PS-BSA (▲), *B. cereus* G9241 HF-PS-BSA (□), *B. cereus* 03BB87 HF-PS-BSA (●), *B. cereus* 03BB102 HF-PS-BSA (♦), *B. cereus* ATCC 14579 HF-PS (x), the chemically synthesized AntRha$_2$-BSA conjugate was used as a positive control (◊), and maltoheptaose-BSA (○) and BSA (|) alone as negative controls. Even though the antisera were raised against spores from *B. anthracis* Sterne and the HF-PS-BSA conjugate was prepared from *B. anthracis* Pasteur HF-PS, it should be noted that the HF-PSs from *B. anthracis* Ames, Pasteur, and Sterne all have identical structures.
Figure 39:
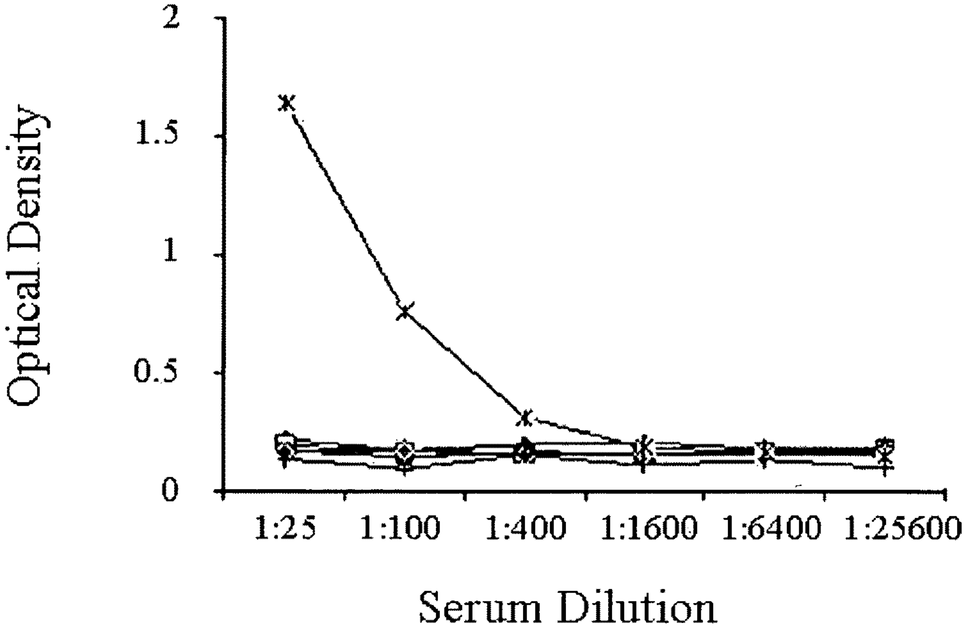

Reactivity of anti-spore antisera with HF-PS from *B. anthracis* and *B. cereus* strains. Immunoreactivity of HF-PS extracts from selected *B. anthracis* and *B. cereus* strains was evaluated by ELISA. Antiserum to both live and killed *B. anthracis* spores contained IgG antibodies that bound conjugates of the HF-PSs from *B. anthracis* and the *B. cereus* clinical isolates, G9241, 03BB87, and 03BB102, isolated from cases of severe or fatal pneumonia (FIGS. 39A and 39B). In contrast however, these antisera did not bind the *B. cereus* ATCC 14579 HF-PS-BSA conjugate. Binding of anti-*B. anthracis* spore antisera to the synthetic $AntRha_2$-BSA conjugate was also observed, as previously reported (Schaffer et al., 1999, *Microbiol;* 145:1575-1583). There was no detectable binding of these antisera to the negative control BSA or maltoheptaose-BSA conjugate. Furthermore, anti-*B. cereus* ATCC 14579 spore antiserum bound to a *B. cereus* ATCC 14579 HF-PS-BSA conjugate but not to the HF-PS-BSA conjugates from *B. anthracis*, or the *B. cereus* G9241, 03BB87, and 03BB102 clinical isolates (FIG. 39C). These data indicate that the *B. anthracis* HF-PS contains epitopes that are present on *B. anthracis* spores and that cross-reactive epitopes exist between *B. anthracis* spore HF-PS antigen and the HF-PSs from the three clinical *B. cereus* isolates that caused severe or fatal pneumonia.

The specificity of the antibody binding to the HF-PSs from *B. anthracis* and *B. cereus* was further evaluated using inhibition ELISAs where *B. anthracis* Pasteur HF-PS-BSA conjugate was used as the capture antigen and unconjugated HF-PSs from *B. anthracis* Pasteur HF-PS, *B. anthracis* Ames, *B. cereus* ATCC 10987, *B. cereus* ATCC 14579, and *B. cereus* G9241 were used as the inhibitors (FIG. 40). The data show that the HF-PS from *B. anthracis* Pasteur and *B. anthracis* Ames were effective inhibitors and that the *B. cereus* G9241 HF-PS was able to inhibit binding but to a lesser extent; 50% inhibition required a 10-fold greater concentration of HF-PS compared to *B. anthracis* HF-PS. The HF-PSs from *B. cereus* isolates 03BB87 and 03BB102 were not examined by ELISA inhibition; however, the results described above and shown in FIG. 39 as well as immuno dot-blot results described below clearly show that these HF-PSs also contain cross-reactive epitopes to the *B. anthracis* HF-PS. In contrast to these HF-PSs, the HF-PSs from *B. cereus* ATCC 14579 and from the closely related *B. cereus* ATCC 10987 were not effective inhibitors, even when presented at 50-fold excess (wt/wt). Also, no inhibition was observed when using the chemically synthesized spore $AntRha_2$ trisaccharide indicating that the reactivity to HF-PS is due to epitopes different from those on $AntRha_2$.

Figure 41:
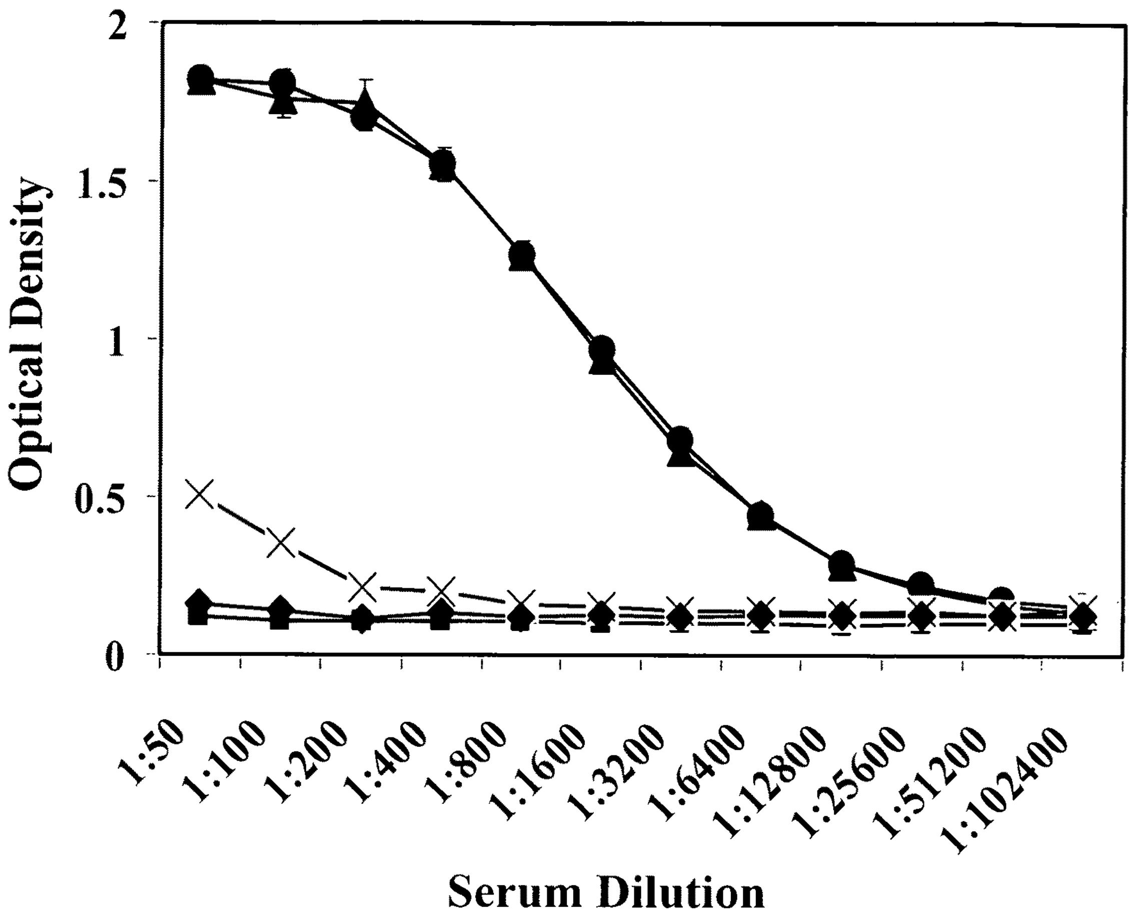
FIG. 41 shows the reactivity of rabbit anti-*B. anthracis* HF-PS-KLH antiserum with HF-PS from other species. ELISA microtiter plates were coated with the various HF-PS- BSA conjugates and the ability of the HF-PS-KLH antiserum to bind these conjugates was determined as described in the Materials and Methods section. *B. anthracis* HF-PS-BSA (●); *B. cereus* ATCC 14579 HF-PS-BSA (▲); chemically synthesized AntRha$_2$ trisaccharide-BSA (♦); maltoheptaose-BSA (x); and BSA only (■).

Reactivity of anti-*B. anthracis* HF-PS-KLH conjugate antisera with HF-PS from *B. anthracis* and *B. cereus*. Rabbit anti-*B. anthracis* HF-PS-KLH conjugate antiserum reacted to similar levels in ELISA with HF-PS-BSA conjugates of *B. anthracis* and *B. cereus* ATCC 14579 extracts indicating the presence of common cross-reactive epitopes in these HF-PS-protein conjugates (FIG. 41). The presence of these common cross-reactive epitopes in the HF-PS-protein conjugates of all the *B. anthracis* and *B. cereus* strains was further examined by immuno-dot blot assays which are described below. A low level of binding to a maltoheptaose-BSA conjugate was observed but this occurred only at the highest serum concentration and was at the assay threshold of 0.5 OD units. In contrast, no binding to the $AntRha_2$-BSA conjugate was observed indicating, again, that the cross reactive epitopes to the HF-PS are not present on this spore carbohydrate.

Figure 42:
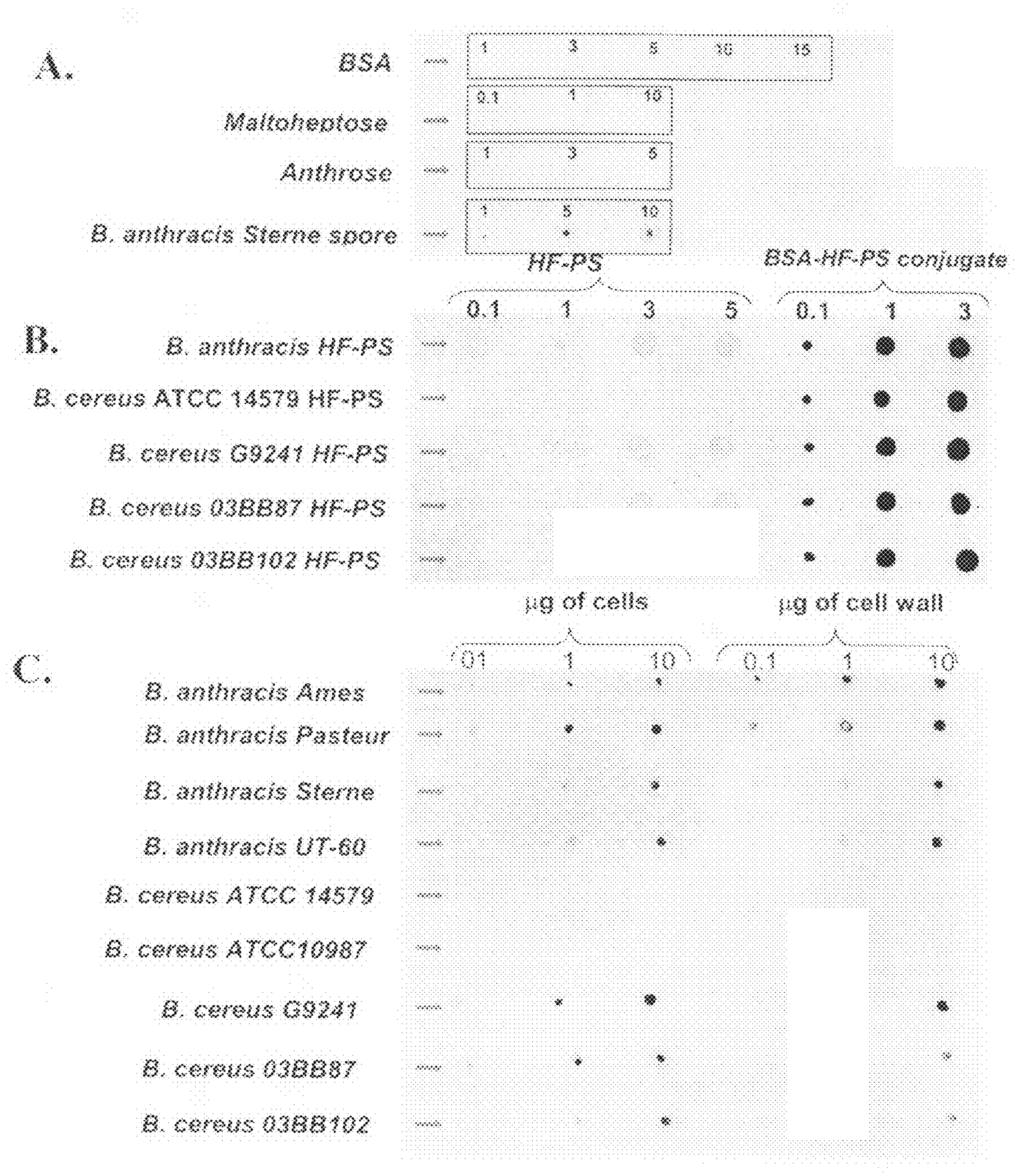

The ability of rabbit anti-*B. anthracis* HF-PS-KLH conjugate to bind *B. cereus* and *B. anthracis* HF-PSs, HF-PS-BSA conjugates, cells and cell walls, and to *B. anthracis* spores was explored further using an immuno-dot blot assay. In this assay, at a serum dilution of 1:1600, antibody binding was observed to *B. anthracis* Sterne spores, but not to the $AntRha_3$ trisaccharide or to the maltoheptaose or BSA controls (FIG. 42A). This result indicates that the $AntRha_2$ trisaccharide is a distinct antigen from the HF-PS and, also, that one or more structural motifs of HF-PS are present as antigens in spores. FIG. 42B shows that the binding of rabbit anti-*B. anthracis* HF-PS-KLH antiserum to unconjugated HF-PSs could be observed down to a threshold level of 0.1 μg for the *B. anthracis* HF-PS, 1 to 3 μg for the HF-PSs from the three *B. cereus* clinical isolates G9241, 03BB87, and O3 BB102, and no detectable binding for up to 5 μg of the HF-PS from non-clinical *B. cereus* ATCC 14579 type strain. However, a different reactivity pattern was observed with the HF-PS-BSA conjugate antigens for which antiserum against *B. anthracis* HF-PS-KLH reacted strongly to the HF-PS-BSA conjugates from all species and strains, including that from *B. cereus* ATCC 14579 (FIG. 42B). This latter result indicates that conjugation to protein produces or exposes an antigenic determinant that is common to protein conjugates of the HF-PSs from all of the *B. cereus* strains used in this study.

FIG. 42C shows that rabbit anti-*B. anthracis* HF-PS-KLH antiserum was reactive against whole cells and cell walls of all *B. anthracis* strains used in this assay, as well as whole cells and cell wall extracts from *B. cereus* clinical isolates G9241, 03BB87, and 03BB102. The detection threshold limit for binding the cell walls of the *B. anthracis* strains was 0.1 μg. In comparison, this threshold limit for binding the cell walls from the *B. cereus* clinical isolates G9241 and 03BB87 was increased to about 1.0 μg, and even greater for the clinical isolate 03BB102 requiring 10 μg. No binding of this antiserum to the cells and cell walls of *B. cereus* ATCC 14579 and *B. cereus* ATCC 10987 was observed, a result which is consistent with the data described above showing that anti-*B. anthracis* spore antiserum binds the HF-PSs from *B. anthracis* and the three *B. cereus* clinical isolates, but not the HF-PS from these latter two *B. cereus* strains. This cross-reactivity of the *B. anthracis* HF-PS with the HF-PS from *B. cereus* clinical isolates that caused fatal pneumonia is intriguing and indicative of a shared structural epitope among these pathogenic bacilli, a conclusion that is consistent with the similar glycosyl compositions of these HF-PSs.

Figure 43:
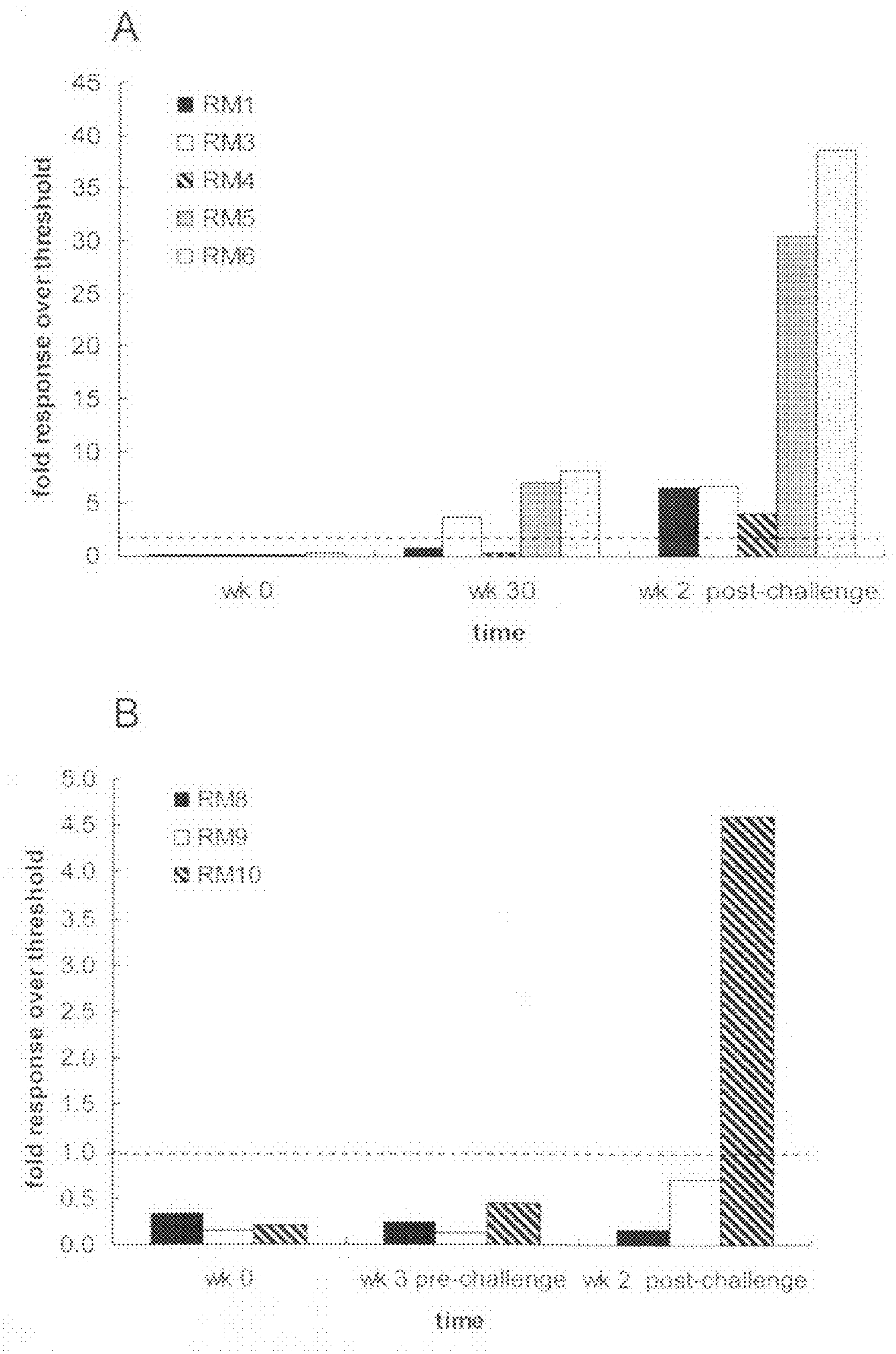
FIGS. 43A and 43B show the reactivity of Rhesus macaque sera with *B. anthracis* HF-PS. Pre- and post-exposure sera from five AVA-vaccinated (FIG. 43A) and three naïve (FIG. 43B) animals were tested with ELISA for the presence of anti-HF-PS IgG on plates coated with the *B. anthracis* Pasteur HF-PS conjugated to KLH. The dashed line indicates the reactivity threshold (RT), corresponding to the value 1, which was determined by testing the sera from 88 true negative Rhesus macaques (RM). Based on the RT, OD values were transformed to represent the fold rise over the RT. For all animals baseline sera drawn in week 0 were tested. For the vaccinated animals (FIG. 43A) sera from week 30, after a course of three AVA shots, and 14 days after exposure to *B. anthracis* Ames spores were tested. For the naïve Rhesus macaques (FIG. 43B) pre-exposure sera drawn three weeks before exposure and post-exposure sera from day 14 were tested.

Reactivity of Rhesus macaque (*Macacca mulata*) anti-AVA and post-infection sera with *B. anthracis* HF-PS. The presence of IgG antibodies that bind the *B. anthracis* HF-PS in animals inoculated with *B. anthracis* spores prompted an examination of available antiserum from naïve and anthrax vaccine adsorbed (AVA) vaccinated Rhesus macaques that had survived aerosol challenge with *B. anthracis*. Pre-challenge and convalescent sera were obtained from five anthrax-vaccinated (RM1, RM3, RM4, RM5, RM6) and three naïve (RM8, RM9, RM10) Rhesus macaques. Vaccinated animals had received three doses (week 0, 4, 26) of a 1:10 (RM4), 1:20 (RM1, RM3, RM6) or 1:40 (RM5) dilution of anthrax vaccine adsorbed (AVA), and survived aerosol challenge with 20-422 $LD_{50}$ equivalents ($7\times10^5$-$4\times10^6$ CFUs) of *B. anthracis* Ames strain at week 52 or week 132 (RM10 only). Sera were evaluated by ELISA using the *B. anthracis* Pasteur HF-PS-KLH conjugate as the capture antigen (FIG. 43). None of the animals showed a pre-vaccination response (week 0). Three of the five vaccinated animals (RM3, RM5, RM6) had an above-threshold response at week 30 and all of the vaccinated animals responded above the threshold on day 14 post-exposure at levels much greater than those in naïve animals indicating that AVA may contain HF-PS (FIG. 43A). None of the naïve animals had a detectable pre-exposure response above the threshold and only one of the three unvaccinated animals (RM10) mounted an immune response above the threshold on day 14 post exposure (FIG. 43B). All animals mounted an anti-protective antigen (PA) IgG response post-exposure, confirming that they had been infected with *B. anthracis.*

Discussion

This example demonstrates that the major polysaccharides released from the cell walls of a selection of *B. anthracis* and *B. cereus* strains by aqueous HF are antigenic and animals exposed to spores of these strains generated anti-polysaccharide IgG antibodies to *B. anthracis* and *B. cereus*, respectively. Post-infection Rhesus macaque serum also reacted to *B. anthracis* HF-PS indicating that this antigen is expressed during infection, and the presence of anti-HF-PS antibodies in the serum from vaccinated animals prior to spore exposure indicated that HF-PS is likely present in the AVA. Further, immunochemical analysis of these polysaccharide antigens showed that they contain both common and strain-specific epitopes depending on the antiserum-antigen combination used for investigation.

Common cross-reactive epitopes were demonstrated by reaction of a rabbit anti-*B. anthracis* HF-PS-KLH antiserum with the HF-PS-BSA conjugate antigens from all *B. anthracis* and *B. cereus* strains investigated. This antiserum reacted strongly with the BSA-conjugates of the HF-PSs from *B. cereus* strains ATCC 10987, ATCC 14579 as well as with these same antigens from *B. anthracis* and the three clinical *B. cereus* isolates that caused severe or fatal pneumonia. The identity of the structural features on the HF-PSs responsible for the observed common cross-reactive epitopes is unknown, but this cross-reactivity depended on conjugation of the isolated HF-PSs to a protein. This dependence suggests that the common cross-reactive epitopes are normally cryptic and not exposed in the cells, cell walls, or unconjugated HF-PSs. One possible explanation is that the combination of releasing the HF-PS from the cell wall with conjugation to a protein exposes a common structural feature that becomes immunoreactive. The present invention indicate that the HF-PS from *B. anthracis* and all of the *B. cereus* strains examined here have a backbone repeating unit structure that is rich in aminoglycosyl residues (FIG. 38), of which two residues are GlcNAc and ManNAc with another being either GlcNAc or GalNAc, and that this backbone structure is substituted with Gal or Glc residues or non-carbohydrate groups such as acetyl substituents (Leoff et al., 2008*, J. Biol. Chem;* 283:29812-29821). It may be that conjugation to proteins involves a ManNAc-GlcNAc-common structural motif in these HF-PSs that, when conjugated to protein, becomes a more accessible epitope for the host's immune response and for antibody binding. A second possible explanation is that a common structural motif may be present in the form of a highly conserved linkage group between these HF-PSs and the peptidoglycan (PG); e.g., if the HF-PSs of all of these *B. anthracis* and *B. cereus* strains were attached to the PG via the same -HexNAc-P(P)-PG glycosyl-phosphate (or pyrophosphate) bridge. In the cell wall, such a common -HexNAc-P(P)-PG region in each of the polysaccharides would be in the innermost portion of the cell wall and not directly accessible to the host's immune system while the structurally variable portion of the polysaccharide is more exposed and accessible. However, when the polysaccharides are released by HF cleavage of the phosphate bridge, the common structural region that was linked to the PG is "uncovered" and, therefore, more accessible to the host's immune system. Conjugation of the isolated HF-PS to the protein may enhance this accessibility and result in the observed cross-reactivity between anti-*B. anthracis* HF-PS-KLH antiserum and all of the HF-PS-BSA conjugates. At this time, it is not known if all of these HF-PSs have a common structural region at their reducing ends (i.e. the end that would have been attached to the PG via a phosphate bridge). There is evidence however, that cell wall teichoic acid polymers of certain bacilli are linked to the peptidoglycan through a common -ManNAc-GlcNAc-P(P)-PG linkage (Bhavsar et al., 2004, *J Bacteriol;* 186:7865-7873; Freymond et al., 2006, *Microbiology;* 152:1709-1718; and Ginsberg et al., 2006*, ACS Chem. Biol;* 1:25-28). It has also been shown that other secondary cell wall polysaccharides from several bacilli are linked from a GlcNAc residue to the PG muramic acid residue via phosphate or pyrophosphate (Schaffer et al., 1999, *Microbiol;* 145:1575-1583; Schaffer et al., 2000, *Glycoconj. J;* 17:681-690; and Steindl et al., 2005, *Carbohydr. Res;* 340:2290-2296). Investigation into the existence and structures of the PG linkage region of the *B. anthracis* and *B. cereus* HF-PSs is underway.

Specific epitopes were demonstrated by the reaction of antiserum raised against live or killed *B. anthracis* spores with the isolated HF-PS or HF-PS-BSA conjugate antigens from *B. anthracis* strains. Also, these antisera reacted, at a reduced level, with HF-PS-BSA conjugate antigens from the clinical *B. cereus* isolates that caused fatal or severe pneumonia. However, no reaction was observed with the HF-PS-BSA conjugate from the *B. cereus* type strain ATCC 14579. Likewise, antiserum to the spores from *B. cereus* ATCC 14579 only reacted with the HF-PS-BSA conjugate of that strain. Also demonstrated is the existence of specific epitopes in cells, cell walls, and isolated but unconjugated HF-PSs from *B. anthracis* strains and from the three clinical *B. cereus* isolates through their reactivity with an antiserum raised against the *B. anthracis* HF-PS-KLH conjugate. This antiserum did not react with the same extracts from *B. cereus* strains ATCC 14579 or ATCC 10987. It was also observed that this anti-*B. anthracis* HF-PS antiserum reacted with *B. anthracis* spores. Thus, in addition to its specificity, the reactivity of the anti-HF-PS-KLH antiserum with *B. anthracis* spores, as well as the presence of anti-HF-PS IgG antibodies in antiserum generated against *B. anthracis* killed spores, indicating that this HF-PS structure is a spore antigen or a component of these spore preparations, as well as a vegetative cell wall antigen.

With this example, cross-reactive epitopes that bound *B. anthracis* spore antiserum were present in the HF-PSs from three clinical isolates of *B. cereus* that caused severe or fatal pneumonia; G9241, 03BB87, and 03BB102 were also observed, indicating structural conservation or relatedness in the HF-PS antigens of these strains to that from *B. anthracis*. The cross-reactive epitopes were not observed in the HF-PSs from the closely-related *B. cereus* ATCC 10987 strain or the ATCC 14579 type strain. The lack of cross-reactive epitopes on these latter two *B. cereus* HF-PSs is likely due to the fact that the structures of these molecules differ significantly from the *B. anthracis* HF-PS (see Examples 1, 2; see also Choudhury et al., 2006, *J. Biol. Chem;* 281:27932-27941; Leoff et al., 2008, *J. Bacteriol;* 190:112-121; and Leoff et al., 2008, *J. Biol. Chem;* 283:29812-29821). On the other hand, the cross-reactive epitopes on the HF-PSs from the three clinical *B. cereus* isolates are most likely due to the similarity in their structures to that of the *B. anthracis* HF-PSs. These HF-PSs are very similar in glycosyl residue composition to the *B. anthracis* HF-PSs (Example 1; see also Leoff et al., 2008, *J. Bacteriol;* 190:112-121). It seems unlikely that all three investigated HF-PSs from *B. cereus* strains that were clinically isolated from human cases of fatal pneumonia coincidentally have HF-PS structures that are immunochemically cross-reactive with the *B. anthracis* HF-PS. These results indicate the existence of pathogenicity-related conserved structural elements in these cell wall antigens, and these cross-reactive structural features in the HF-PSs will be particularly useful for the development of multivalent vaccines that would be effective against both *B. anthracis* as well as against *B. cereus* strains that cause severe illness.

While the details of the relationship between pathogenicity and HF-PS structures are not yet known, it is likely that the HF-PS has important functions for growth and/or pathogenicity, e.g. involving the carbohydrate binding domain (CBD) of cell surface proteins. It is known that surface proteins in *B. anthracis*, S-layer proteins and others, have a CBD. This CBD, e.g. in the *B. anthracis* S-layer proteins Sap and EA1, is a protein domain that is normally comprised of three short amino acid stretches with a motif known as the SLH motif (for S-layer homology) (Zona and Janeek, 2005, *Biologia* (*Bratisl*); 60 (Suppl. 16):115-121). In the case of Sap and EA1 from *B. anthracis*, their export and anchoring to the cell wall is mediated by the SLH domain to form a crystalline array in the surface of the cell (Mesnage et al., 2000, *EMBO J;* 19:4473-4484) and it is thought that the SLH protein domain binds to the HF-PS which, in turn, is covalently bound via a phosphate bridge to the PG of the cell wall. In addition to Sap and EA1, it was recently reported that another surface protein, BslA, that is encoded on the pXO1 plasmid contains a SLH domain and is responsible for adherence of *B. anthracis* to host cells (Kern and Schneewind, 2008, *Mol. Microbiol;* 68:504-515). Thus, the HF-PS of pathogenic strains could be involved in exporting/anchoring proteins, such as BslA, that are necessary for virulence.

Finally, this example shows that sera from all vaccinated Rhesus macaques that were exposed to *B. anthracis* spores contain IgG antibodies that bind the *B. anthracis* HF-PS. This result supports the use of the HF-PS-conjugates to detect exposure of primates to *B. anthracis*, and use as an alternative antigen component for the development or improvement of anthrax vaccines.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified. Unless otherwise specified, "a," "an," "the," and "at least one" are used interchangeably and mean one or more than one.

For any method disclosed herein that includes discrete steps, the steps may be conducted in any feasible order. And, as appropriate, any combination of two or more steps may be conducted simultaneously.

What is claimed is:

1. An isolated oligosaccharide having the formula

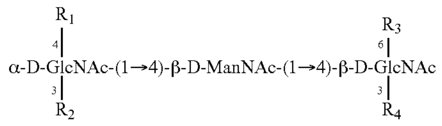

wherein $R_1$ to $R_4$ are independently Gal or H.

2. A composition comprising the isolated oligosaccharide of claim 1.

3. A diagnostic kit comprising the isolated oligosaccharide of claim 1.

4. The diagnostic kit of claim 3 further comprising an isolated anthrose oligosaccharide comprising 2-O-methyl-4-

N-β-hydroxyisovaleryl-4,6-dideoxyglucose, or an isolated anthrose trisaccharide having the formula

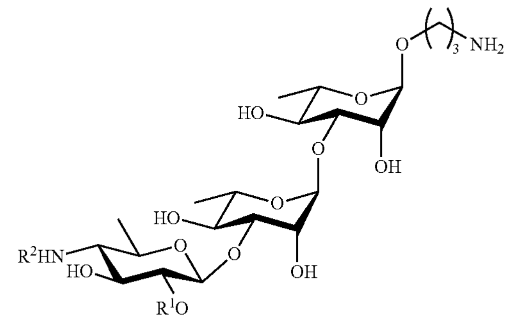

wherein

1. $R^1$ = Me, $R^2$ = 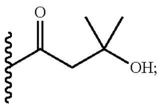

2. $R^1$ = H, $R^2$ = 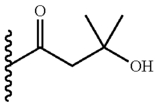 (anthrose variant 2);

3. $R^1$ = Me, $R^2$ = 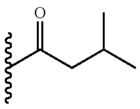 (anthrose variant 3); or

4. $R^1$ = Me, $R^2$ = 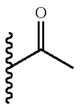 (anthrose variant 4).

5. The diagnostic kit of claim 3 further comprising an isolated anthrose oligosaccharide comprising 2-O-methyl-4-N-β-hydroxyisovaleryl-4,6-dideoxyglucose, an isolated monosaccharide, an isolated disaccharide, or an isolated trisaccharide, the isolated monosaccharide having the formula:

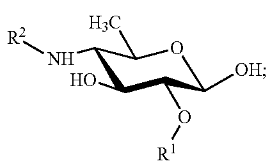

the isolated disaccharide having the formula:

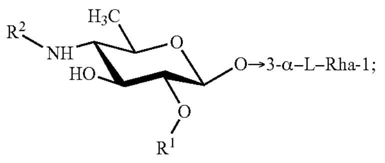

and the isolated trisaccharide having the formula:

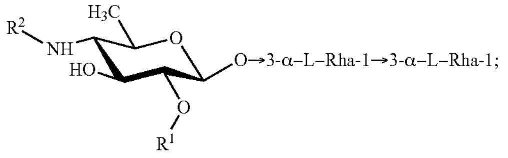

wherein

1. $R^1$ = Me, $R^2$ = 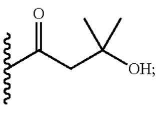

2. $R^1$ = H, $R^2$ = 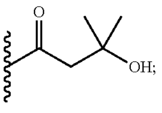

3. $R^1$ = Me, $R^2$ = 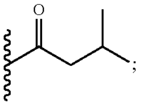 or

4. $R^1$ = Me, $R^2$ = 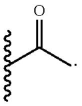

6. An isolated oligosaccharide polypeptide conjugate, the isolated oligosaccharide polypeptide conjugate comprising an isolated oligosaccharide having the formula

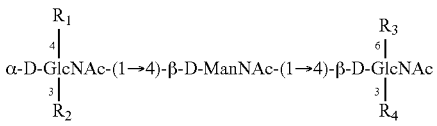

wherein $R_1$ to $R_4$ are independently Gal or H, and wherein the isolated oligosaccharide is further conjugated to a polypeptide.

7. The isolated oligosaccharide polypeptide conjugate of claim 6 wherein the polypeptide is selected from the group consisting of keyhole limpet hemacyanin (KLH), protective antigen (PA), tetanus toxoid (TT), and bovine serum albumin (BSA).

8. A composition comprising the isolated oligosaccharide polypeptide conjugate of claim 6.

9. An isolated oligosaccharide conjugate, the isolated oligosaccharide conjugate comprising an isolated oligosaccharide having the formula

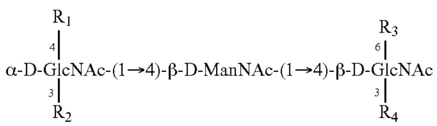

wherein $R_1$ to $R_4$ are independently Gal or H, and wherein the isolated oligosaccharide is further conjugated to an artificial spacer at the anomeric position.

10. A diagnostic kit, wherein the diagnostic kit comprises an isolated oligosaccharide having the formula

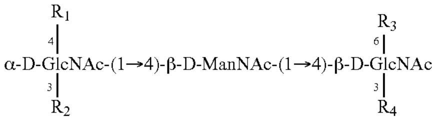

wherein $R_1$ to $R_4$ are independently Gal or H, and wherein the isolated oligosaccharide is further bound to a solid substrate.

11. An isolated detectably labeled oligosaccharide, the isolated detectably labeled oligosaccharide comprising an isolated oligosaccharide having the formula

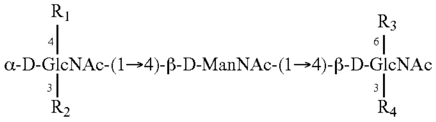

wherein $R_1$ to $R_4$ are independently Gal or H, and wherein one or more saccharide moiety is further labeled with a detectable marker.

12. A method of detecting exposure to or infection with *Bacillus anthracis* in a subject, the method comprising detecting the presence of an antibody that binds to the isolated oligosaccharide of claim 1 in a sample from the subject.

13. The method of claim 12, wherein the exposure is asymptomatic or aborted anthrax.

14. The method of claim 12, wherein post exposure antibiotic prophylaxis has been administered.

* * * * *